US011008564B2

(12) United States Patent
Puckette et al.

(10) Patent No.: US 11,008,564 B2
(45) **Date of Patent: *May 18, 2021**

(54) PROCESSING ENGINEERED FMDV P1 POLYPEPTIDE USING AN ALTERNATIVE TEV PROTEASE

(71) Applicant: The Government of the United States of America, as represented by the Secretary of Homeland Security, Washington, DC (US)

(72) Inventors: Michael Puckette, Waterford, CT (US); Max Rasmussen, Guilford, CT (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/364,633

(22) Filed: Mar. 26, 2019

(65) Prior Publication Data

US 2019/0211321 A1 Jul. 11, 2019

Related U.S. Application Data

(63) Continuation of application No. 15/407,982, filed on Jan. 17, 2017, now Pat. No. 10,308,927.

(51) Int. Cl.

| | |
|---|---|
| ***C07K 14/005*** | (2006.01) |
| ***C12N 7/00*** | (2006.01) |
| ***C12N 9/50*** | (2006.01) |
| ***A61K 39/12*** | (2006.01) |
| ***C12N 9/96*** | (2006.01) |
| ***A61P 31/14*** | (2006.01) |
| *A61K 39/00* | (2006.01) |

(52) U.S. Cl.

CPC ................ *C12N 9/96* (2013.01); *A61K 39/12* (2013.01); *A61P 31/14* (2018.01); *C07K 14/005* (2013.01); *C12N 7/00* (2013.01); *C12N 9/506* (2013.01); *C12Y 304/22044* (2013.01); *A61K 2039/523* (2013.01); *A61K 2039/5254* (2013.01); *A61K 2039/5258* (2013.01); *C12N 2770/32122* (2013.01); *C12N 2770/32123* (2013.01); *C12N 2770/32134* (2013.01); *C12N 2770/32151* (2013.01)

(58) Field of Classification Search

None

See application file for complete search history.

(56) References Cited

U.S. PATENT DOCUMENTS

| | | | |
|---|---|---|---|
| 5,965,124 A | 10/1999 | Feinberg et al. | |
| 8,846,051 B2 | 9/2014 | Kew et al. | |
| 2012/0295330 A1 | 11/2012 | Ghanshani et al. | |
| 2018/0066235 A1 | 3/2018 | Puckette et al. | |
| 2019/0211321 A1 * | 7/2019 | Puckette | A61K 39/12 |

FOREIGN PATENT DOCUMENTS

| | | | |
|---|---|---|---|
| WO | WO 2011/048353 | * | 4/2011 |

OTHER PUBLICATIONS

Shaw, SEQ ID No. 26 alignment with Geneseq database access No. ARL79834, Jul. 2008.

SEQ ID No. 22 Alignment with Geneseq database access No. AYN45447 by Maree et al., Mar. 2011.

SEQ ID No. 2 Alignment with Geneseq database access No. Q6PMY7_9PICO, Jul. 2004.

Veerapen et al., "Novel expression of immunogenic foot-and-mouth disease virus-like particles in Nicotiana benthamiana", (Virus Research, 2018; 244: 213-217).

Birtley et al., "Crystal Structure of Foot-and-Mouth Disease Virus 3C Protease", Journal of Biological Chemistry, vol. 280, No. 12, pp. 11520-11527, Mar. 25, 2005.

Phan et al., "Structural Basis for the Substrate Specificity of Tobacco Etch Virus Protease", Journal of Biological Chemistry, vol. 277, No. 52, pp. 50564-50572, Dec. 27, 2002.

Grubman et al., "Foot-and-Mouth Disease", Clinical Microbiology Reviews, vol. 17, No. 2, pp. 465-493, Apr. 2004.

Sweeney et al., "Structural and Mutagenic Analysis of Foot-and-Mouth Disease Virus 3C Protease Reveals the Role of the β-Ribbon in Proteolysis", Journal of Virology, vol. 81, No. 1, pp. 115-124, Jan. 2007.

Zunszain et al., "Insights into Cleavage Specificity from the Crystal Structure of Foot-and-Mouth Disease Virus 3C Protease Complexed with a Peptide Substrate", Journal of Molecular Biology, 395 pp. 375-389, 2010.

Ghanshani et. al., sequence alignment of instant SEQ 82 with SEQ ID 30, Jul. 2012.

Liu et. al. (Derwent abstract of CN 105056227, published Nov. 2015).

(Continued)

*Primary Examiner* — Shanon A. Foley

(74) *Attorney, Agent, or Firm* — Lavanya Ratnam; Kelly G. Hyndman

(57) ABSTRACT

Polynucleotide constructs that express an engineered foot-and-mouth disease (FMDV) P1 precursor protein and a non-FMDV TEV protease and methods for safe and efficient recombinant production of FMDV antigens and immunogens. Recombinant production of FMDV antigens avoids the need to culture highly-infectious FMDV, while conventional culture methods for producing FMDV antigens rely on the native FMDV 3C protease which exerts toxic effects on host cells. The inventors have developed a new system that efficiently and safely processes FMDV P1 precursor without the FMDV 3C protease, thus avoiding the toxic effects associated with use of the 3C protease. The invention is also directed to the FMDV antigens and virus-like particles produced by this system as well as to FMDV vaccines, diagnostics and other biologics.

20 Claims, 14 Drawing Sheets

Specification includes a Sequence Listing.

(56) References Cited

OTHER PUBLICATIONS

Verhoeven et al., Applied biochemistry and biotechnology, 166, 5, pp. 1340-1354, 2012.
Potyvirus NIa protease (NIa-pro) domain, https://www.ebi.ac.uk/interpro/entry/InterPro/IPR001730, (last accessed Aug. 24, 2016).
Puigbo, P., Optimizer: A web server utility that optimize a DNA or Protein sequence, Evolutionary Genomics Group Biochemistry and Biotechnology Department Universitat Rovira i Virgili (URV), Tarragona, Spain, 2005.
Codon Usage Database, www._kazusa.or.jp/codon,(last accessed Feb. 5, 2016), Kazusa DNA Research Institute, Chiba, Japan.
Office NA. The 2001 outbreak of foot and mouth disease. National Audit Office, London. 2002; Available at: www.nao.org.uk/publications/0102/the_2001_outbreak_of foot_and.aspx.
Donnelly ML, Luke G, Mehrotra A, Li X, Hughes LE, Gani D, et al. Analysis of the aphthovirus 2A/2B polyprotein cleavage mechanism indicates not a proteolytic reaction, but a novel translational effect: a putative ribosomal 'skip'. The Journal of general virology. 2001;82:1013-25.
Vakharia VN, Devaney MA, Moore DM, Dunn JJ, Grubman MJ. Proteolytic processing of foot-and-mouth disease virus polyproteins expressed in a cell-free system from clone-derived transcripts. Journal of virology. 1987;61:3199-207.
Bablanian GM, Grubman MJ. Characterization of the foot-and-mouth disease virus 3C protease expressed in *Escherichia coli*. Virology. 1993;197:320-7.
Harber JJ, Bradley J, Anderson CW, Wimmer E. Catalysis of poliovirus VP0 maturation cleavage is not mediated by serine 10 of VP2. Journal of virology. 1991;65:326-34.
Lee WM, Monroe SS, Rueckert RR. Role of maturation cleavage in infectivity of picornaviruses: activation of an infectosome. Journal of virology. 1993;67:2110-22.
Curry S, Fry E, Blakemore W, Abu-Ghazaleh R, Jackson T, King A, et al. Dissecting the roles of VP0 cleavage and RNA packaging in picornavirus capsid stabilization: the structure of empty capsids of foot-and-mouth disease virus. Journal of virology. 1997;71:9743-52.
Zhou Z, Mogensen MM, Powell PP, Curry S, Wileman T. Foot-and-mouth disease virus 3C protease induces fragmentation of the Golgi compartment and blocks intra-Golgi transport. Journal of virology. 2013;87:11721-9.
Armer H, Moffat K, Wileman T, Belsham GJ, Jackson T, Duprex WP, et al. Foot-and-mouth disease virus, but not bovine enterovirus, targets the host cell cytoskeleton via the nonstructural protein 3Cpro. Journal of virology. 2008;82:10556-66.
Belsham GJ, McInerney GM, Ross-Smith N. Foot-and-mouth disease virus 3C protease induces cleavage of translation initiation factors eIF4A and eIF4G within infected cells. Journal of virology. 2000;74:272-80.
Falk MM, Grigera PR, Bergmann IE, Zibert A, Multhaup G, Beck E. Foot-and-mouth disease virus protease 3C induces specific proteolytic cleavage of host cell histone H3. Journal of virology. 1990;64:748-56.
Lawrence P, Schafer EA, Rieder E. The nuclear protein Sam68 is cleaved by the FMDV 3C protease redistributing Sam68 to the cytoplasm during FMDV infection of host cells. Virology. 2012;425:40-52.
Wang D, Fang L, Li K, Zhong H, Fan J, Ouyang C, et al. Foot-and-mouth disease virus 3C protease cleaves NEMO to impair innate immune signaling. Journal of virology. 2012;86:9311-22.
Kapust RB, Tozser J, Fox JD, Anderson DE, Cherry S, Copeland TD, et al. Tobacco etch virus protease: mechanism of autolysis and rational design of stable mutants with wild-type catalytic proficiency. Protein engineering. 2001;14:993-1000.
Lucast LJ, Batey RT, Doudna JA. Large-scale purification of a stable form of recombinant tobacco etch virus protease. BioTechniques. 2001;30:544-6, 8, 50 passim.
Dougherty WG, Carrington JC, Cary SM, Parks TD. Biochemical and mutational analysis of a plant virus polyprotein cleavage site. The EMBO journal. 1988;7:1281-7.
Gullberg M, Polacek C, Botner A, Belsham GJ. Processing of the VP1/2A junction is not necessary for production of foot-and-mouth disease virus empty capsids and infectious viruses: characterization of "self-tagged" particles. Journal of virology. 2013;87:11591-603.

* cited by examiner

Gel Layout

Lane 1: VP0J

Lane 2: VP0J + 3C(C163A)

Lane 3: pOM

Lane 4: pOM + 3C(C163A)

Lane 5: O1P1 – 3C (positive control)

Lane 6: 2A - SGluc pSNAP TEVpro 500 nm scale bar. Image taken on a Hitachi 7600 TEM at 80kV.

pSNAP OM 500 nm scale bar. Image taken on a Hitachi 7600 TEM at 80kV.

pSNAP TEVpro 100 nm scale bar. Image taken on a Hitachi 7600 TEM at 80kV.

pSNAP OM 100 nm scale bar. Image taken on a Hitachi 7600 TEM at 80kV.

FIG. 8

| | GI | Nucleotide Start | Nucleotide End |
|---|---|---|---|
| Habenaria Mosaic Virus | 928505223 | 6151 | 6876 |
| Moroccan Watermelon Mosaic Virus | 1031417576 | 6400 | 7116 |
| Zucchini Shoestring Virus | 1032966039 | 6988 | 7704 |
| Daphnea Virus Y | 1011326778 | 6198 | 6926 |
| Potato Virus Y | 887496652 | 6235 | 6966 |
| Catharanthus Mosaic Virus | 807068454 | 6245 | 6973 |
| Lupine Mosaic Virus | 317010281 | 6797 | 7525 |
| Leek Yellow Stripe Virus | 452888437 | 6628 | 7353 |
| Turnip Mosaic Virus | 124507406 | 6479 | 7207 |
| Zucchini Yellow Mosaic Virus | 84993541 | 6263 | 6991 |

SEQUENCE LISTING

```
<160> NUMBER OF SEQ ID NOS: 136

<210> SEQ ID NO 1
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: Asia Lebanon 89; 3C Protease

<400> SEQUENCE: 1

agt ggt gcc cca ccg acc gac ttg caa aag atg gtc atg agc aac act       48
Ser Gly Ala Pro Pro Thr Asp Leu Gln Lys Met Val Met Ser Asn Thr
1               5                   10                  15

aag cct gtt gag ctc atc ctt gac ggt aag acg gtg gcc atc tgc tgc       96
Lys Pro Val Glu Leu Ile Leu Asp Gly Lys Thr Val Ala Ile Cys Cys
            20                  25                  30

gcc acc gga gtg ttt ggt act gcc tac ctc gtg cct cgt cac ctt ttc      144
Ala Thr Gly Val Phe Gly Thr Ala Tyr Leu Val Pro Arg His Leu Phe
        35                  40                  45

gca gaa aag tac gac agg atc atg ttg gac ggc agg gcc atg aca gac      192
Ala Glu Lys Tyr Asp Arg Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gct gcg ctc atg gtg ctc cac cgt ggc aac cgt gtg      288
Met Leu Ser Asp Ala Ala Leu Met Val Leu His Arg Gly Asn Arg Val
                85                  90                  95

aga gac atc acg aaa cac ttt cgt gat aca gca aga atg aag aaa ggt      336
Arg Asp Ile Thr Lys His Phe Arg Asp Thr Ala Arg Met Lys Lys Gly
            100                 105                 110

acc ccc gtt gtc ggc gtg atc aac aac gcc gac gtt ggg aga ctg att      384
Thr Pro Val Val Gly Val Ile Asn Asn Ala Asp Val Gly Arg Leu Ile
        115                 120                 125

ttc tcc ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

gga gac acc atg ccg ggc cta ttt gcc tac aga gcc gct acc aag gct      480
Gly Asp Thr Met Pro Gly Leu Phe Ala Tyr Arg Ala Ala Thr Lys Ala
145                 150                 155                 160

ggc tac tgt gga gga gcc gtt ctt gcc aag gac gga gct gac aca ttt      528
Gly Tyr Cys Gly Gly Ala Val Leu Ala Lys Asp Gly Ala Asp Thr Phe
                165                 170                 175

atc gtc ggc act cac tcc gca gga ggc aat gga gtc ggg tac tgc tca      576
Ile Val Gly Thr His Ser Ala Gly Gly Asn Gly Val Gly Tyr Cys Ser
            180                 185                 190

tgc gta tct agg tcc atg ctc ttg aag atg aag gca cac att gac ccc      624
Cys Val Ser Arg Ser Met Leu Leu Lys Met Lys Ala His Ile Asp Pro
        195                 200                 205
```

-continued

```
gaa cca cac cac gag                                               639
Glu Pro His His Glu
    210


<210> SEQ ID NO 2
<211> LENGTH: 213
<212> TYPE: PRT
<213> ORGANISM: Foot-and-mouth disease virus

<400> SEQUENCE: 2

Ser Gly Ala Pro Pro Thr Asp Leu Gln Lys Met Val Met Ser Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Arg Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 3
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: O1 Manissa Iso87;  3C Protease

<400> SEQUENCE: 3

agt ggt gcc cca ccg acc gac ttg cag aag atg gtc atg ggc aac act      48
Ser Gly Ala Pro Pro Thr Asp Leu Gln Lys Met Val Met Gly Asn Thr
1               5                   10                  15

aag cct gtt gag ctc atc ctc gac ggg aag acg gta gcc atc tgc tgt      96
Lys Pro Val Glu Leu Ile Leu Asp Gly Lys Thr Val Ala Ile Cys Cys
            20                  25                  30

gct acc gga gtg ttt ggc act gcc tac ctc gta cct cgt cac ctc ttc     144
Ala Thr Gly Val Phe Gly Thr Ala Tyr Leu Val Pro Arg His Leu Phe
        35                  40                  45

gcg gag aag tac gac aag ata atg ttg gac ggt aga gcc atg aca gac     192
```

-continued

```
Ala Glu Lys Tyr Asp Lys Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gct gca ctc atg gtg ctt cac cgt ggg aac cgc gtg      288
Met Leu Ser Asp Ala Ala Leu Met Val Leu His Arg Gly Asn Arg Val
                85                  90                  95

aga gac atc acg aaa cat ttt cgt gac aca gca aga atg aag aaa ggc      336
Arg Asp Ile Thr Lys His Phe Arg Asp Thr Ala Arg Met Lys Lys Gly
            100                 105                 110

acc ccc gtt gtc ggt gtg atc aac aac gcc gac gtt ggg aga ctg att      384
Thr Pro Val Val Gly Val Ile Asn Asn Ala Asp Val Gly Arg Leu Ile
        115                 120                 125

ttc tct gga gag gcc ctt acc tac aaa gac att gta gtg tgc atg gat      432
Phe Ser Gly Glu Ala Leu Thr Tyr Lys Asp Ile Val Val Cys Met Asp
    130                 135                 140

gga gac acc atg ccg ggc ctg ttt gcc tac aga gcc gcc acc aag gct      480
Gly Asp Thr Met Pro Gly Leu Phe Ala Tyr Arg Ala Ala Thr Lys Ala
145                 150                 155                 160

ggt tac tgc ggg gga gcc gtt ctc gcc aag gac gga gcc gac aca ttc      528
Gly Tyr Cys Gly Gly Ala Val Leu Ala Lys Asp Gly Ala Asp Thr Phe
                165                 170                 175

atc gtt ggc act cac tcc gca ggt ggt aac gga gtt gga tac tgc tcg      576
Ile Val Gly Thr His Ser Ala Gly Gly Asn Gly Val Gly Tyr Cys Ser
            180                 185                 190

tgc gtg tcc agg tcc atg ctc ctg aaa atg aag gca cac att gac cct      624
Cys Val Ser Arg Ser Met Leu Leu Lys Met Lys Ala His Ile Asp Pro
        195                 200                 205

gaa cca cac cac gag                                                  639
Glu Pro His His Glu
    210


<210> SEQ ID NO 4
<211> LENGTH: 213
<212> TYPE: PRT
<213> ORGANISM: Foot-and-mouth disease virus

<400> SEQUENCE: 4

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
```

-continued

```
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 5
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: O1 pan Asia; 3C Protease

<400> SEQUENCE: 5

agt ggt gct cca ccg act gac ttg caa aag atg gtc atg ggt aac acc       48
Ser Gly Ala Pro Pro Thr Asp Leu Gln Lys Met Val Met Gly Asn Thr
1               5                   10                  15

aag ccc gtt gag ctc ata ctt gac ggg aag aca gta gcc atc tgc tgt       96
Lys Pro Val Glu Leu Ile Leu Asp Gly Lys Thr Val Ala Ile Cys Cys
            20                  25                  30

gct act gga gtg ttt ggc acc gcc tac ctc gtg cct cgt cat ctt ttc      144
Ala Thr Gly Val Phe Gly Thr Ala Tyr Leu Val Pro Arg His Leu Phe
        35                  40                  45

gca gag aag tat gac aag atc atg ttg gac ggc aga gcc atg aca gac      192
Ala Glu Lys Tyr Asp Lys Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gcc gcg ctc atg gtg ctc cac cgt ggg aat cgc gtg      288
Met Leu Ser Asp Ala Ala Leu Met Val Leu His Arg Gly Asn Arg Val
                85                  90                  95

cgg gac atc acg aaa cac ttc cgt gat gtg gca aga atg aag aaa gga      336
Arg Asp Ile Thr Lys His Phe Arg Asp Val Ala Arg Met Lys Lys Gly
            100                 105                 110

acc ccc gtc gtt ggt gtt atc aac aac gcc gat gtc ggg aga ctg att      384
Thr Pro Val Val Gly Val Ile Asn Asn Ala Asp Val Gly Arg Leu Ile
        115                 120                 125

ttc tct ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

gga gac acc atg cct ggc ctc ttt gcc tac aag gcc gcc acc aag gcc      480
Gly Asp Thr Met Pro Gly Leu Phe Ala Tyr Lys Ala Ala Thr Lys Ala
145                 150                 155                 160

ggc tac tgt gga gga gcc gtt ctc gca aag gac gga gcc gag act ttc      528
Gly Tyr Cys Gly Gly Ala Val Leu Ala Lys Asp Gly Ala Glu Thr Phe
                165                 170                 175

atc gtc ggc aca cac tct gcg ggc ggc aac gga gtt gga tac tgc tcc      576
Ile Val Gly Thr His Ser Ala Gly Gly Asn Gly Val Gly Tyr Cys Ser
            180                 185                 190

tgc gtg tcc agg tcc atg ctg ctc aag atg aag gca cac ata gat cct      624
Cys Val Ser Arg Ser Met Leu Leu Lys Met Lys Ala His Ile Asp Pro
        195                 200                 205

gaa cca cac cat gaa                                                  639
```

```
Glu Pro His His Glu
    210


<210> SEQ ID NO 6
<211> LENGTH: 213
<212> TYPE: PRT
<213> ORGANISM: Foot-and-mouth disease virus

<400> SEQUENCE: 6

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Val Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Glu Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 7
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: A24 Cruzeiro iso71; 3C Protease

<400> SEQUENCE: 7

agt ggt gcc cca ccg acc gac ttg caa aag ttg gtc atg ggc aac acc       48
Ser Gly Ala Pro Pro Thr Asp Leu Gln Lys Leu Val Met Gly Asn Thr
1               5                   10                  15

aag ccc gtt gag ctc atc ctt gac ggg aag acg gta gcc att tgc tgt       96
Lys Pro Val Glu Leu Ile Leu Asp Gly Lys Thr Val Ala Ile Cys Cys
            20                  25                  30

gct act gga gtt ttc ggc act gct tac ctc gtg cct cgt cat ctt ttc      144
Ala Thr Gly Val Phe Gly Thr Ala Tyr Leu Val Pro Arg His Leu Phe
        35                  40                  45

gca gaa aag tac gac aag atc atg ttg gac ggc aga gcc atg aca gat      192
Ala Glu Lys Tyr Asp Lys Ile Met Leu Asp Gly Arg Ala Met Thr Asp
```

```
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gct gcg ctc atg gtg ctc cac cgt ggg aat cgc gtg      288
Met Leu Ser Asp Ala Ala Leu Met Val Leu His Arg Gly Asn Arg Val
                85                  90                  95

aga gac atc acg aaa cac ttt cgt gac aca gca aga atg aag aaa ggc      336
Arg Asp Ile Thr Lys His Phe Arg Asp Thr Ala Arg Met Lys Lys Gly
            100                 105                 110

acc ccc gtc gtt ggt gtg atc aac aac gcc gat gtc ggg aga ctg att      384
Thr Pro Val Val Gly Val Ile Asn Asn Ala Asp Val Gly Arg Leu Ile
        115                 120                 125

ttc tct ggt gaa gcc ctt acc tac aag gac att gta gtg tgc atg gat      432
Phe Ser Gly Glu Ala Leu Thr Tyr Lys Asp Ile Val Val Cys Met Asp
    130                 135                 140

gga gac acc atg cct ggg ctc ttt gcc tac aaa gcc gca acc aag gct      480
Gly Asp Thr Met Pro Gly Leu Phe Ala Tyr Lys Ala Ala Thr Lys Ala
145                 150                 155                 160

ggt tat tgc gga gga gcc gtc ctc gct aag gac ggg gct gac acg ttc      528
Gly Tyr Cys Gly Gly Ala Val Leu Ala Lys Asp Gly Ala Asp Thr Phe
                165                 170                 175

atc gtt ggc acc cac tcc gct gga ggc aat ggc gtt gga tac tgc tct      576
Ile Val Gly Thr His Ser Ala Gly Gly Asn Gly Val Gly Tyr Cys Ser
            180                 185                 190

tgc gtt tcc agg tcc atg ctt ctc aag atg aag gca cac gtt gac ccc      624
Cys Val Ser Arg Ser Met Leu Leu Lys Met Lys Ala His Val Asp Pro
        195                 200                 205

gaa cca cac cac gag                                                  639
Glu Pro His His Glu
    210


<210> SEQ ID NO 8
<211> LENGTH: 213
<212> TYPE: PRT
<213> ORGANISM: Foot-and-mouth disease virus

<400> SEQUENCE: 8

Ser Gly Ala Pro Pro Thr Asp Leu Gln Lys Leu Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Lys Ala Ala Thr Lys Ala
145                 150                 155                 160
```

-continued

Gly Tyr Cys Gly Gly Ala Val Leu Ala Lys Asp Gly Ala Asp Thr Phe
165 170 175

Ile Val Gly Thr His Ser Ala Gly Gly Asn Gly Val Gly Tyr Cys Ser
180 185 190

Cys Val Ser Arg Ser Met Leu Leu Lys Met Lys Ala His Val Asp Pro
195 200 205

Glu Pro His His Glu
210

<210> SEQ ID NO 9
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: A Turkey/2006; 3C Protease

<400> SEQUENCE: 9 agt ggt gcc ccc ccg acc gac ttg caa aag atg gtc atg ggc aac acc 48
Ser Gly Ala Pro Pro Thr Asp Leu Gln Lys Met Val Met Gly Asn Thr
1 5 10 15 aag cct gtt gag ctc atc ctc gac ggg aag acg gta gcc atc tgt tgc 96
Lys Pro Val Glu Leu Ile Leu Asp Gly Lys Thr Val Ala Ile Cys Cys
20 25 30 gct acc gga gtg ttt ggc act gct tac ctt gtg cca cgt cat ctt ttc 144
Ala Thr Gly Val Phe Gly Thr Ala Tyr Leu Val Pro Arg His Leu Phe
35 40 45 gcg gag aag tat gac aag atc atg ctg gac ggc aga gcc atg aca gac 192
Ala Glu Lys Tyr Asp Lys Ile Met Leu Asp Gly Arg Ala Met Thr Asp
50 55 60 agt gac tac aga gtg ttt gag ttt gag att aaa gta aaa ggg cag gac 240
Ser Asp Tyr Arg Val Phe Glu Phe Glu Ile Lys Val Lys Gly Gln Asp
65 70 75 80 atg ctc tca gat gcc gcg ctc atg gtg ctc cac cgt ggg aat cgc gtg 288
Met Leu Ser Asp Ala Ala Leu Met Val Leu His Arg Gly Asn Arg Val
85 90 95 aga gac atc acg aaa cac ttt cgt gat aca gca aga atg aag aag ggc 336
Arg Asp Ile Thr Lys His Phe Arg Asp Thr Ala Arg Met Lys Lys Gly
100 105 110 acc ccc gtt gtc ggt gtt atc aac aac gct gat gtc ggg aga ctg att 384
Thr Pro Val Val Gly Val Ile Asn Asn Ala Asp Val Gly Arg Leu Ile
115 120 125 ttc tct ggt gag gcc ctt acc tac aag gac att gta gtg tgc atg gat 432
Phe Ser Gly Glu Ala Leu Thr Tyr Lys Asp Ile Val Val Cys Met Asp
130 135 140 gga gac acc atg cct ggc ctc ttt gcc tac aga gcc gcc acc aag gct 480
Gly Asp Thr Met Pro Gly Leu Phe Ala Tyr Arg Ala Ala Thr Lys Ala
145 150 155 160 ggc tat tgt gga gga gct gtt ctt gca aag gac gga gcc gag acc ttc 528
Gly Tyr Cys Gly Gly Ala Val Leu Ala Lys Asp Gly Ala Glu Thr Phe
165 170 175 atc gtc ggc act cac tcc gca ggt ggt aat gga gtt gga tac tgt tca 576
Ile Val Gly Thr His Ser Ala Gly Gly Asn Gly Val Gly Tyr Cys Ser
180 185 190 tgc gtt tcc agg tcc atg ctg cta aag atg aag gca cac atc gac cct 624
Cys Val Ser Arg Ser Met Leu Leu Lys Met Lys Ala His Ile Asp Pro
195 200 205 gag cca cac cac gag 639
Glu Pro His His Glu

210

<210> SEQ ID NO 10
<211> LENGTH: 213
<212> TYPE: PRT
<213> ORGANISM: Foot-and-mouth disease virus

<400> SEQUENCE: 10

```
Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Glu Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210
```

<210> SEQ ID NO 11
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: SAT2 Egypt 2010; 3C Protease

<400> SEQUENCE: 11

```
agt gga gcg cca ccc acc gac ttg caa aag atg gtg atg gcc aac acc       48
Ser Gly Ala Pro Pro Thr Asp Leu Gln Lys Met Val Met Ala Asn Thr
1               5                   10                  15

aaa cca gtc gag ctc ata ctc gat ggt aag aca gtg gcg atc tgc tgt       96
Lys Pro Val Glu Leu Ile Leu Asp Gly Lys Thr Val Ala Ile Cys Cys
            20                  25                  30

gcc act gga gtg ttt ggg act gcc tat ctc gtg cct cgt cat ctt ttc      144
Ala Thr Gly Val Phe Gly Thr Ala Tyr Leu Val Pro Arg His Leu Phe
        35                  40                  45

gct gag aag tat gac aag atc atg att gac ggc agg gcc atg aca gac      192
Ala Glu Lys Tyr Asp Lys Ile Met Ile Asp Gly Arg Ala Met Thr Asp
    50                  55                  60
```

-continued

```
cgt gat ttc aga gtg ttt gag ttt gag att aaa gta aaa gga cag gac      240
Arg Asp Phe Arg Val Phe Glu Phe Glu Ile Lys Val Lys Gly Gln Asp
65                  70                  75                  80

atg ctc tcg gac gcc gcc ctc atg gtg ctg cac cgt ggg aac cgc gtg      288
Met Leu Ser Asp Ala Ala Leu Met Val Leu His Arg Gly Asn Arg Val
                85                  90                  95

aga gac atc acg aag cac ttt cgt gat caa gca aga atg aga aaa gga      336
Arg Asp Ile Thr Lys His Phe Arg Asp Gln Ala Arg Met Arg Lys Gly
            100                 105                 110

acc ccc gtg gtt ggc gtg atc aac aac gcc gac gtt ggg aga ctc atc      384
Thr Pro Val Val Gly Val Ile Asn Asn Ala Asp Val Gly Arg Leu Ile
        115                 120                 125

ttc tct gga gag gca ctc acc tac aaa gac att gta gtg tgt atg gat      432
Phe Ser Gly Glu Ala Leu Thr Tyr Lys Asp Ile Val Val Cys Met Asp
    130                 135                 140

ggc gac acc atg cca ggc ctc ttt gcc tat aaa gcc gcc acc aaa gct      480
Gly Asp Thr Met Pro Gly Leu Phe Ala Tyr Lys Ala Ala Thr Lys Ala
145                 150                 155                 160

ggc tac tgt gga gga gcc gtt ctt gcg aaa gac gga gcc gag act ttc      528
Gly Tyr Cys Gly Gly Ala Val Leu Ala Lys Asp Gly Ala Glu Thr Phe
                165                 170                 175

atc gtc ggc act cac tcc gct gga gga aac gga gtt ggt tac tgc tct      576
Ile Val Gly Thr His Ser Ala Gly Gly Asn Gly Val Gly Tyr Cys Ser
            180                 185                 190

tgc gtt tcc aag tcc atg ctc ctg caa atg aag gca cac att gat cct      624
Cys Val Ser Lys Ser Met Leu Leu Gln Met Lys Ala His Ile Asp Pro
        195                 200                 205

gaa cca cac cac gaa                                                  639
Glu Pro His His Glu
    210


<210> SEQ ID NO 12
<211> LENGTH: 213
<212> TYPE: PRT
<213> ORGANISM: Foot-and-mouth disease virus

<400> SEQUENCE: 12

Ser Gly Ala Pro Pro Thr Asp Leu Gln Lys Met Val Met Ala Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Ile Asp Gly Arg Ala Met Thr Asp
    50                  55                  60

Arg Asp Phe Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Gln Ala Arg Met Arg Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Lys Ala Ala Thr Lys Ala
145                 150                 155                 160
```

-continued

```
Gly Tyr Cys Gly Gly Ala Val Leu Ala Lys Asp Gly Ala Glu Thr Phe
                165                 170                 175

Ile Val Gly Thr His Ser Ala Gly Gly Asn Gly Val Gly Tyr Cys Ser
            180                 185                 190

Cys Val Ser Lys Ser Met Leu Leu Gln Met Lys Ala His Ile Asp Pro
        195                 200                 205

Glu Pro His His Glu
    210


<210> SEQ ID NO 13
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: C3 indaial; 3C Protease

<400> SEQUENCE: 13

agc ggt gcc cca ccg acc gac ttg caa aag atg gtc atg ggc aac acc       48
Ser Gly Ala Pro Pro Thr Asp Leu Gln Lys Met Val Met Gly Asn Thr
1               5                   10                  15

aag cct gtt gag ctg att ctc gat ggg aag acg gtg gcc atc tgc tgc       96
Lys Pro Val Glu Leu Ile Leu Asp Gly Lys Thr Val Ala Ile Cys Cys
            20                  25                  30

gcc acc gga gtg ttt ggc act gct tac ctc gtg ccg cgt cat ctt ttc      144
Ala Thr Gly Val Phe Gly Thr Ala Tyr Leu Val Pro Arg His Leu Phe
        35                  40                  45

gca gag aag tat gac aag atc atg ttg gac ggc aga gcc atg aca gac      192
Ala Glu Lys Tyr Asp Lys Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tcg gac gcc gca ctc atg gtg cta cac cgt ggg aat cgc gtg      288
Met Leu Ser Asp Ala Ala Leu Met Val Leu His Arg Gly Asn Arg Val
                85                  90                  95

aga gac atc acg aag cac ttt cgt gac aca gca aga atg aag aaa ggc      336
Arg Asp Ile Thr Lys His Phe Arg Asp Thr Ala Arg Met Lys Lys Gly
            100                 105                 110

acc ccc gtc gta ggc gtg att aac aac gcc gac gtt ggg aga ctg att      384
Thr Pro Val Val Gly Val Ile Asn Asn Ala Asp Val Gly Arg Leu Ile
        115                 120                 125

ttc tct ggt gag gcc ctt acc tac aaa gac att gtg gtg tgc atg gat      432
Phe Ser Gly Glu Ala Leu Thr Tyr Lys Asp Ile Val Val Cys Met Asp
    130                 135                 140

gga gac acc atg cct ggc ctc ttt gcc tac aga gcc gcc acc aag gct      480
Gly Asp Thr Met Pro Gly Leu Phe Ala Tyr Arg Ala Ala Thr Lys Ala
145                 150                 155                 160

ggt tac tgt gga gga gcc gtc ctt gcc aag gat gga gct gac aca ttc      528
Gly Tyr Cys Gly Gly Ala Val Leu Ala Lys Asp Gly Ala Asp Thr Phe
                165                 170                 175

atc gtc ggc act cac tct gct gga ggc aat gga gtt ggt tac tgc tca      576
Ile Val Gly Thr His Ser Ala Gly Gly Asn Gly Val Gly Tyr Cys Ser
            180                 185                 190

tgc gtt tcc aga tcc atg ctt ctc aag atg aag gca cac att gac cct      624
Cys Val Ser Arg Ser Met Leu Leu Lys Met Lys Ala His Ile Asp Pro
        195                 200                 205

gag cca cac cac gag                                                  639
Glu Pro His His Glu
    210
```

```
<210> SEQ ID NO 14
<211> LENGTH: 213
<212> TYPE: PRT
<213> ORGANISM: Foot-and-mouth disease virus

<400> SEQUENCE: 14

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 15
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: SAT3 ZIM/6/91); 3C Protease

<400> SEQUENCE: 15

agc gga tgc cca ccg acc gac ttg caa aag atg gtc atg gca aac gta      48
Ser Gly Cys Pro Pro Thr Asp Leu Gln Lys Met Val Met Ala Asn Val
1               5                   10                  15

aag cct gtt gag ctc atc ctc gac ggg aag acc gtt gcg ctc tgc tgc      96
Lys Pro Val Glu Leu Ile Leu Asp Gly Lys Thr Val Ala Leu Cys Cys
            20                  25                  30

gcg acg gga gtg ttt ggg aca gct tac ctc gtg ccc cgt cat ctt ttc     144
Ala Thr Gly Val Phe Gly Thr Ala Tyr Leu Val Pro Arg His Leu Phe
        35                  40                  45

gca gag aag tat gac aag atc atg ctg gac ggc cgc gcc ctg aca gac     192
Ala Glu Lys Tyr Asp Lys Ile Met Leu Asp Gly Arg Ala Leu Thr Asp
    50                  55                  60
```

-continued

```
agt gac ttt aga gtg ttt gag ttt gag gtg aaa gta aaa gga cag gac      240
Ser Asp Phe Arg Val Phe Glu Phe Glu Val Lys Val Lys Gly Gln Asp
65                  70                  75                  80

atg ctc tct gat gcc gca ctc atg gtt ctc cac tct gga aac cgt gtg      288
Met Leu Ser Asp Ala Ala Leu Met Val Leu His Ser Gly Asn Arg Val
                85                  90                  95

cgc gat ctc acg gga cac ttc cgt gac acc atg aaa ctg tcg aaa ggc      336
Arg Asp Leu Thr Gly His Phe Arg Asp Thr Met Lys Leu Ser Lys Gly
            100                 105                 110

agc ccc gtc gtt ggt gtt gtc aac aac gct gat gtc gga aga ctc atc      384
Ser Pro Val Val Gly Val Val Asn Asn Ala Asp Val Gly Arg Leu Ile
        115                 120                 125

ttc tca gga gac gca ctg acc tac aaa gac ctg gtc gtt tgt atg gac      432
Phe Ser Gly Asp Ala Leu Thr Tyr Lys Asp Leu Val Val Cys Met Asp
    130                 135                 140

ggt gat acc atg cct gga ctc ttc gct tac cgc gca ggg acc aag gtt      480
Gly Asp Thr Met Pro Gly Leu Phe Ala Tyr Arg Ala Gly Thr Lys Val
145                 150                 155                 160

gga tac tgc gga gct gcc gtt ctc gca aag gac ggc gcc aag act gtg      528
Gly Tyr Cys Gly Ala Ala Val Leu Ala Lys Asp Gly Ala Lys Thr Val
                165                 170                 175

atc gtt ggc acc cac tca gcc gga ggc aac gga gtg ggc tac tgc tcc      576
Ile Val Gly Thr His Ser Ala Gly Gly Asn Gly Val Gly Tyr Cys Ser
            180                 185                 190

tgc gtc tca cga tcc atg ctc ctg cag atg aag gcc cac att gat ccg      624
Cys Val Ser Arg Ser Met Leu Leu Gln Met Lys Ala His Ile Asp Pro
        195                 200                 205

gct cct cac acc gag                                                  639
Ala Pro His Thr Glu
    210


<210> SEQ ID NO 16
<211> LENGTH: 213
<212> TYPE: PRT
<213> ORGANISM: Foot-and-mouth disease virus

<400> SEQUENCE: 16

Ser Gly Cys Pro Pro Thr Asp Leu Gln Lys Met Val Met Ala Asn Val
1               5                   10                  15

Lys Pro Val Glu Leu Ile Leu Asp Gly Lys Thr Val Ala Leu Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Leu Thr Asp
    50                  55                  60

Ser Asp Phe Arg Val Phe Glu Phe Glu Val Lys Val Lys Gly Gln Asp
65                  70                  75                  80

Met Leu Ser Asp Ala Ala Leu Met Val Leu His Ser Gly Asn Arg Val
                85                  90                  95

Arg Asp Leu Thr Gly His Phe Arg Asp Thr Met Lys Leu Ser Lys Gly
            100                 105                 110

Ser Pro Val Val Gly Val Val Asn Asn Ala Asp Val Gly Arg Leu Ile
        115                 120                 125

Phe Ser Gly Asp Ala Leu Thr Tyr Lys Asp Leu Val Val Cys Met Asp
    130                 135                 140

Gly Asp Thr Met Pro Gly Leu Phe Ala Tyr Arg Ala Gly Thr Lys Val
145                 150                 155                 160

Gly Tyr Cys Gly Ala Ala Val Leu Ala Lys Asp Gly Ala Lys Thr Val
```

-continued

```
                165                 170                 175

Ile Val Gly Thr His Ser Ala Gly Gly Asn Gly Val Gly Tyr Cys Ser
            180                 185                 190

Cys Val Ser Arg Ser Met Leu Leu Gln Met Lys Ala His Ile Asp Pro
        195                 200                 205

Ala Pro His Thr Glu
    210


<210> SEQ ID NO 17
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: SAT1-20 iso11; 3C Protease

<400> SEQUENCE: 17

agt ggt gcc cca ccg acc gac ttg caa aag atg gtc atg agc aac act       48
Ser Gly Ala Pro Pro Thr Asp Leu Gln Lys Met Val Met Ser Asn Thr
1               5                   10                  15

aag cct gtt gag ctc atc ctt gac ggt aag acg gtg gcc atc tgc tgc       96
Lys Pro Val Glu Leu Ile Leu Asp Gly Lys Thr Val Ala Ile Cys Cys
            20                  25                  30

gcc acc gga gtg ttt ggt act gcc tac ctc gtg cct cgt cac ctt ttc      144
Ala Thr Gly Val Phe Gly Thr Ala Tyr Leu Val Pro Arg His Leu Phe
        35                  40                  45

gca gaa aag tac gac agg atc atg ttg gac ggc agg gcc atg aca gac      192
Ala Glu Lys Tyr Asp Arg Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gct gcg ctc atg gtg ctc cac cgt ggc aac cgt gtg      288
Met Leu Ser Asp Ala Ala Leu Met Val Leu His Arg Gly Asn Arg Val
                85                  90                  95

aga gac atc acg aaa cac ttt cgt gat aca gca aga atg aag aaa ggt      336
Arg Asp Ile Thr Lys His Phe Arg Asp Thr Ala Arg Met Lys Lys Gly
            100                 105                 110

acc ccc gtt gtc ggc gtg atc aac aac gcc gac gtt ggg aga ctg att      384
Thr Pro Val Val Gly Val Ile Asn Asn Ala Asp Val Gly Arg Leu Ile
        115                 120                 125

ttc tcc ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

gga gac acc atg ccg ggc cta ttt gcc tac aga gcc gct acc aag gct      480
Gly Asp Thr Met Pro Gly Leu Phe Ala Tyr Arg Ala Ala Thr Lys Ala
145                 150                 155                 160

ggc tac tgt gga gga gcc gtt ctt gcc aag gac gga gct gac aca ttt      528
Gly Tyr Cys Gly Gly Ala Val Leu Ala Lys Asp Gly Ala Asp Thr Phe
                165                 170                 175

atc gtc ggc act cac tcc gca gga ggc aat gga gtc ggg tac tgc tca      576
Ile Val Gly Thr His Ser Ala Gly Gly Asn Gly Val Gly Tyr Cys Ser
            180                 185                 190

tgc gta tct agg tcc atg ctc ttg aag atg aag gca cac att gac ccc      624
Cys Val Ser Arg Ser Met Leu Leu Lys Met Lys Ala His Ile Asp Pro
        195                 200                 205

gaa cca cac cac gag                                                  639
Glu Pro His His Glu
    210
```

<210> SEQ ID NO 18
<211> LENGTH: 213
<212> TYPE: PRT
<213> ORGANISM: Foot-and-mouth disease virus

<400> SEQUENCE: 18

```
Ser Gly Ala Pro Pro Thr Asp Leu Gln Lys Met Val Met Ser Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Arg Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210
```

<210> SEQ ID NO 19
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: Asia1 Shamir; 3C Protease

<400> SEQUENCE: 19

```
agt ggt gcc cca ccg acc gac ttg caa aag atg gtc atg agc aac act       48
Ser Gly Ala Pro Pro Thr Asp Leu Gln Lys Met Val Met Ser Asn Thr
1               5                   10                  15

aag cct gtt gag ctc atc ctt gac ggt aag acg gtg gcc atc tgc tgc       96
Lys Pro Val Glu Leu Ile Leu Asp Gly Lys Thr Val Ala Ile Cys Cys
            20                  25                  30

gcc acc gga gtg ttt ggt act gcc tac ctc gtg cct cgt cac ctt ttc      144
Ala Thr Gly Val Phe Gly Thr Ala Tyr Leu Val Pro Arg His Leu Phe
        35                  40                  45

gca gaa aag tac gac agg atc atg ttg gac ggc agg gcc atg aca gac      192
Ala Glu Lys Tyr Asp Arg Ile Met Leu Asp Gly Arg Ala Met Thr Asp
    50                  55                  60

agt gac tac aga gtg ttt gag ttt gag att aaa gta aaa gga cag gac      240
```

```
Ser Asp Tyr Arg Val Phe Glu Phe Glu Ile Lys Val Lys Gly Gln Asp
65                  70                  75                  80

atg ctc tca gac gct gcg ctc atg gtg ctc cac cgt ggc aac cgt gtg      288
Met Leu Ser Asp Ala Ala Leu Met Val Leu His Arg Gly Asn Arg Val
                85                  90                  95

aga gac atc acg aaa cac ttt cgt gat aca gca aga atg aag aaa ggt      336
Arg Asp Ile Thr Lys His Phe Arg Asp Thr Ala Arg Met Lys Lys Gly
            100                 105                 110

acc ccc gtt gtc ggc gtg atc aac aac gcc gac gtt ggg aga ttg att      384
Thr Pro Val Val Gly Val Ile Asn Asn Ala Asp Val Gly Arg Leu Ile
        115                 120                 125

ttc tcc ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

gga gac acc atg ccg ggc cta ttt gcc tac aga gcc gct acc aag gct      480
Gly Asp Thr Met Pro Gly Leu Phe Ala Tyr Arg Ala Ala Thr Lys Ala
145                 150                 155                 160

ggc tac tgt gga gga gcc gtt ctt gcc aag gac gga gct gac aca ttt      528
Gly Tyr Cys Gly Gly Ala Val Leu Ala Lys Asp Gly Ala Asp Thr Phe
                165                 170                 175

atc gtc ggc act cac tcc gca gga ggc aat gga gtc ggg tac tgc tca      576
Ile Val Gly Thr His Ser Ala Gly Gly Asn Gly Val Gly Tyr Cys Ser
            180                 185                 190

tgc gta tct agg tcc atg ctc ttg aag atg aag gca cac att gac ccc      624
Cys Val Ser Arg Ser Met Leu Leu Lys Met Lys Ala His Ile Asp Pro
        195                 200                 205

gaa cca cac cac gag                                                  639
Glu Pro His His Glu
    210


<210> SEQ ID NO 20
<211> LENGTH: 213
<212> TYPE: PRT
<213> ORGANISM: Foot-and-mouth disease virus

<400> SEQUENCE: 20

Ser Gly Ala Pro Pro Thr Asp Leu Gln Lys Met Val Met Ser Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Arg Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175
```

```
Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 21
<211> LENGTH: 2232
<212> TYPE: DNA
<213> ORGANISM: Foot-and-mouth disease virus
<220> FEATURE:
<221> NAME/KEY: misc_feature
<223> OTHER INFORMATION: GenBank: DQ009716.1 Foot-and-mouth disease
      virus - type SAT 1 isolate KNP/196/91 P1 polyprotein gene, partial
      cds
<220> FEATURE:
<221> NAME/KEY: CDS
<222> LOCATION: (1)..(2232)

<400> SEQUENCE: 21

gga gcg ggc cag tcg tcc ccc gcc act ggg tcc cag aac cag tct ggc       48
Gly Ala Gly Gln Ser Ser Pro Ala Thr Gly Ser Gln Asn Gln Ser Gly
1               5                   10                  15

aac act ggc agc atc atc aac aac tac tac atg caa cag tac caa aat       96
Asn Thr Gly Ser Ile Ile Asn Asn Tyr Tyr Met Gln Gln Tyr Gln Asn
            20                  25                  30

tcc atg gac acc caa ctc gga gac aac gcc atc tcc ggt ggg tca aat      144
Ser Met Asp Thr Gln Leu Gly Asp Asn Ala Ile Ser Gly Gly Ser Asn
        35                  40                  45

gag ggt tcg acc gac aca acg tcg acc cac acc agc aac acc caa aac      192
Glu Gly Ser Thr Asp Thr Thr Ser Thr His Thr Ser Asn Thr Gln Asn
    50                  55                  60

aac gat tgg ttt tca aaa ttg gct caa tcg gcc ttc tct gga ttg gtt      240
Asn Asp Trp Phe Ser Lys Leu Ala Gln Ser Ala Phe Ser Gly Leu Val
65                  70                  75                  80

ggt gcg ttg ctt gcc gac aag aag act gag gaa acc aca ctc ctc gag      288
Gly Ala Leu Leu Ala Asp Lys Lys Thr Glu Glu Thr Thr Leu Leu Glu
                85                  90                  95

gat cgc atc ctc acg acc agt cac ggc aca acc acc tcg acc aca caa      336
Asp Arg Ile Leu Thr Thr Ser His Gly Thr Thr Thr Ser Thr Thr Gln
            100                 105                 110

agt tca gtg ggc ata acc tac ggt tac gcc gac tcg gac cgt ttc ctc      384
Ser Ser Val Gly Ile Thr Tyr Gly Tyr Ala Asp Ser Asp Arg Phe Leu
        115                 120                 125

ccc ggc cca aac acc aac ggg ctg gag aca cgt gtg gaa caa gca gag      432
Pro Gly Pro Asn Thr Asn Gly Leu Glu Thr Arg Val Glu Gln Ala Glu
    130                 135                 140

agg ttt ttc aaa cac aaa tta ttt gat tgg aca ctt gaa caa cga ttt      480
Arg Phe Phe Lys His Lys Leu Phe Asp Trp Thr Leu Glu Gln Arg Phe
145                 150                 155                 160

gga aca aca cac gtt ttg gaa ctg ccc aca gac cac aaa ggc atc tat      528
Gly Thr Thr His Val Leu Glu Leu Pro Thr Asp His Lys Gly Ile Tyr
                165                 170                 175

gga caa ctt gtt gac tcc cac tca tac att cgc aat ggg tgg gac gtt      576
Gly Gln Leu Val Asp Ser His Ser Tyr Ile Arg Asn Gly Trp Asp Val
            180                 185                 190

gag gtc tcc gcg acc gca acg cag ttc aac ggg ggc tgc ctc ctg gta      624
Glu Val Ser Ala Thr Ala Thr Gln Phe Asn Gly Gly Cys Leu Leu Val
        195                 200                 205

gcg atg gtg ccc gaa ttg tgc aaa ctg tcg gaa aga gag aaa tac caa      672
```

-continued

```
Ala Met Val Pro Glu Leu Cys Lys Leu Ser Glu Arg Glu Lys Tyr Gln
    210                 215                 220

ctc act ctc ttc cct cat caa ttt ctc gac cca agg acc aac acc acg      720
Leu Thr Leu Phe Pro His Gln Phe Leu Asp Pro Arg Thr Asn Thr Thr
225                 230                 235                 240

gca cac atc cag gta ccc tac ctg ggc gtg gat cgc cac gac caa gga      768
Ala His Ile Gln Val Pro Tyr Leu Gly Val Asp Arg His Asp Gln Gly
                245                 250                 255

aca cgc cac aaa gcg tgg acc ctg gtt gtc atg gtg gtg gca ccc tac      816
Thr Arg His Lys Ala Trp Thr Leu Val Val Met Val Val Ala Pro Tyr
            260                 265                 270

aca aac gat cag acg att ggc tcg aac aaa gcc gag gtg tac gtg aac      864
Thr Asn Asp Gln Thr Ile Gly Ser Asn Lys Ala Glu Val Tyr Val Asn
        275                 280                 285

att gct ccc aca aac gtt tac gtc gcc ggt gag aag ccc gca aaa cag      912
Ile Ala Pro Thr Asn Val Tyr Val Ala Gly Glu Lys Pro Ala Lys Gln
    290                 295                 300

ggc att ctc ccc gtg gcc gtc tcc gtt ggc tat ggt ggc ttc caa aat      960
Gly Ile Leu Pro Val Ala Val Ser Val Gly Tyr Gly Gly Phe Gln Asn
305                 310                 315                 320

aca gat ccc aaa aca tcg gac ccc gta tac ggg cac gtg tac aac ccg     1008
Thr Asp Pro Lys Thr Ser Asp Pro Val Tyr Gly His Val Tyr Asn Pro
                325                 330                 335

gct cgc acc ggc cta cct ggg agg ttc aca aac ctc ttg gat gtg gct     1056
Ala Arg Thr Gly Leu Pro Gly Arg Phe Thr Asn Leu Leu Asp Val Ala
            340                 345                 350

gaa gcg tgc cct aca ctg ctt gac ttc aac gga gtt ccg tac gtg acc     1104
Glu Ala Cys Pro Thr Leu Leu Asp Phe Asn Gly Val Pro Tyr Val Thr
        355                 360                 365

acc cag gca aac tct gga tct aaa gtg tta act tgt ttt gat ttg gct     1152
Thr Gln Ala Asn Ser Gly Ser Lys Val Leu Thr Cys Phe Asp Leu Ala
    370                 375                 380

ttt ggt cac aaa aat ttg aaa aat aca ttt atg tct ggt ctt gcc cag     1200
Phe Gly His Lys Asn Leu Lys Asn Thr Phe Met Ser Gly Leu Ala Gln
385                 390                 395                 400

tac tac acc cag tac agt ggc aca ctc aac ctg cac ttc atg tac aca     1248
Tyr Tyr Thr Gln Tyr Ser Gly Thr Leu Asn Leu His Phe Met Tyr Thr
                405                 410                 415

ggc cca acc aac aac aag gct aag tac atg gtg gcc tac atc cca cct     1296
Gly Pro Thr Asn Asn Lys Ala Lys Tyr Met Val Ala Tyr Ile Pro Pro
            420                 425                 430

ggg aca cac cct ctc ccg gaa aca ccg gag atg gag tcc cac tgt cac     1344
Gly Thr His Pro Leu Pro Glu Thr Pro Glu Met Glu Ser His Cys His
        435                 440                 445

cac gcc gag tgg gac aca ggc ctg aac tca acc ttc aca ttc acc gtg     1392
His Ala Glu Trp Asp Thr Gly Leu Asn Ser Thr Phe Thr Phe Thr Val
    450                 455                 460

ccg tac gtg tcg gct gcc gac ttc gcg tac acc tac tct gac gag cct     1440
Pro Tyr Val Ser Ala Ala Asp Phe Ala Tyr Thr Tyr Ser Asp Glu Pro
465                 470                 475                 480

gaa cag gct tcg gtt cag ggt tgg gtg ggc gta tac cag gtg act gac     1488
Glu Gln Ala Ser Val Gln Gly Trp Val Gly Val Tyr Gln Val Thr Asp
                485                 490                 495

aca cac gag aag gac ggt gca gtt gtt gtg tcc gtc agt gct gga ccc     1536
Thr His Glu Lys Asp Gly Ala Val Val Val Ser Val Ser Ala Gly Pro
            500                 505                 510

gac ttc gag ttc agg atg ccc atc agc ccc tcg cgc cag acc aca tcc     1584
Asp Phe Glu Phe Arg Met Pro Ile Ser Pro Ser Arg Gln Thr Thr Ser
        515                 520                 525
```

-continued

```
gct ggc gaa gga gcg gag cct gtc acg act gat gct tcc caa cac gga      1632
Ala Gly Glu Gly Ala Glu Pro Val Thr Thr Asp Ala Ser Gln His Gly
    530                 535                 540

ggc gac aga cgg aca act cgt agg cat cac act gat gtg agc ttc ttg      1680
Gly Asp Arg Arg Thr Thr Arg Arg His His Thr Asp Val Ser Phe Leu
545                 550                 555                 560

ctc gac cgg ttc aca ctg gtt ggt aaa aca cag gac aac aaa ctg aca      1728
Leu Asp Arg Phe Thr Leu Val Gly Lys Thr Gln Asp Asn Lys Leu Thr
                565                 570                 575

cta gac ctg ctc caa acc aag gaa aaa gca ctg gtt ggc gca atc ctg      1776
Leu Asp Leu Leu Gln Thr Lys Glu Lys Ala Leu Val Gly Ala Ile Leu
            580                 585                 590

cgc gca gcc acg tac tac ttc tct gac ttg gag gtt gcg tgt gtg ggt      1824
Arg Ala Ala Thr Tyr Tyr Phe Ser Asp Leu Glu Val Ala Cys Val Gly
        595                 600                 605

gac aac aaa tgg gtc ggc tgg act ccc aac gga gct cca gaa ctt gcg      1872
Asp Asn Lys Trp Val Gly Trp Thr Pro Asn Gly Ala Pro Glu Leu Ala
    610                 615                 620

gaa gtg ggc gac aac cca gtc gtc ttt tcc aaa ggt aga acc acc cgt      1920
Glu Val Gly Asp Asn Pro Val Val Phe Ser Lys Gly Arg Thr Thr Arg
625                 630                 635                 640

ttt gca ctg ccc tac acc gct cca cac agg tgc ttg gcg aca gcc tac      1968
Phe Ala Leu Pro Tyr Thr Ala Pro His Arg Cys Leu Ala Thr Ala Tyr
                645                 650                 655

aac ggt gac tgc aag tac aaa ccc act ggc aca gct cca cgc gaa aac      2016
Asn Gly Asp Cys Lys Tyr Lys Pro Thr Gly Thr Ala Pro Arg Glu Asn
            660                 665                 670

att cgt gga gac ctc gca act ctc gcg gcg agg att gca agt gag aca      2064
Ile Arg Gly Asp Leu Ala Thr Leu Ala Ala Arg Ile Ala Ser Glu Thr
        675                 680                 685

cac att cca acc acc ttc aac tat ggc agg att tac aca gac act gag      2112
His Ile Pro Thr Thr Phe Asn Tyr Gly Arg Ile Tyr Thr Asp Thr Glu
    690                 695                 700

gtc gac gtg tac gtc agg atg aag cgc gcg gag ctc tac tgc ccg cga      2160
Val Asp Val Tyr Val Arg Met Lys Arg Ala Glu Leu Tyr Cys Pro Arg
705                 710                 715                 720

ccc gtt ctc acg cac tac gac cac ggt ggc agg gat cgc tac aga act      2208
Pro Val Leu Thr His Tyr Asp His Gly Gly Arg Asp Arg Tyr Arg Thr
                725                 730                 735

gcg atc acc aaa cct gtc aaa cag                                      2232
Ala Ile Thr Lys Pro Val Lys Gln
            740


<210> SEQ ID NO 22
<211> LENGTH: 744
<212> TYPE: PRT
<213> ORGANISM: Foot-and-mouth disease virus

<400> SEQUENCE: 22

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Ser Asn Thr Gln Asn
    50                  55                  60

Asn Asp Trp Phe Ser Lys Leu Ala Gln Ser Ala Phe Ser Gly Leu Val
65                  70                  75                  80
```

-continued

```
Gly Ala Leu Leu Ala Asp Lys Lys Thr Glu Glu Thr Thr Leu Leu Glu
                85                  90                  95

Asp Arg Ile Leu Thr Thr Ser His Gly Thr Thr Thr Ser Thr Thr Gln
            100                 105                 110

Ser Ser Val Gly Ile Thr Tyr Gly Tyr Ala Asp Ser Asp Arg Phe Leu
        115                 120                 125

Pro Gly Pro Asn Thr Asn Gly Leu Glu Thr Arg Val Glu Gln Ala Glu
    130                 135                 140

Arg Phe Phe Lys His Lys Leu Phe Asp Trp Thr Leu Glu Gln Arg Phe
145                 150                 155                 160

Gly Thr Thr His Val Leu Glu Leu Pro Thr Asp His Lys Gly Ile Tyr
                165                 170                 175

Gly Gln Leu Val Asp Ser His Ser Tyr Ile Arg Asn Gly Trp Asp Val
            180                 185                 190

Glu Val Ser Ala Thr Ala Thr Gln Phe Asn Gly Gly Cys Leu Leu Val
        195                 200                 205

Ala Met Val Pro Glu Leu Cys Lys Leu Ser Glu Arg Glu Lys Tyr Gln
    210                 215                 220

Leu Thr Leu Phe Pro His Gln Phe Leu Asp Pro Arg Thr Asn Thr Thr
225                 230                 235                 240

Ala His Ile Gln Val Pro Tyr Leu Gly Val Asp Arg His Asp Gln Gly
                245                 250                 255

Thr Arg His Lys Ala Trp Thr Leu Val Val Met Val Val Ala Pro Tyr
            260                 265                 270

Thr Asn Asp Gln Thr Ile Gly Ser Asn Lys Ala Glu Val Tyr Val Asn
        275                 280                 285

Ile Ala Pro Thr Asn Val Tyr Val Ala Gly Glu Lys Pro Ala Lys Gln
    290                 295                 300

Gly Ile Leu Pro Val Ala Val Ser Val Gly Tyr Gly Gly Phe Gln Asn
305                 310                 315                 320

Thr Asp Pro Lys Thr Ser Asp Pro Val Tyr Gly His Val Tyr Asn Pro
                325                 330                 335

Ala Arg Thr Gly Leu Pro Gly Arg Phe Thr Asn Leu Leu Asp Val Ala
            340                 345                 350

Glu Ala Cys Pro Thr Leu Leu Asp Phe Asn Gly Val Pro Tyr Val Thr
        355                 360                 365

Thr Gln Ala Asn Ser Gly Ser Lys Val Leu Thr Cys Phe Asp Leu Ala
    370                 375                 380

Phe Gly His Lys Asn Leu Lys Asn Thr Phe Met Ser Gly Leu Ala Gln
385                 390                 395                 400

Tyr Tyr Thr Gln Tyr Ser Gly Thr Leu Asn Leu His Phe Met Tyr Thr
                405                 410                 415

Gly Pro Thr Asn Asn Lys Ala Lys Tyr Met Val Ala Tyr Ile Pro Pro
            420                 425                 430

Gly Thr His Pro Leu Pro Glu Thr Pro Glu Met Glu Ser His Cys His
        435                 440                 445

His Ala Glu Trp Asp Thr Gly Leu Asn Ser Thr Phe Thr Phe Thr Val
    450                 455                 460

Pro Tyr Val Ser Ala Ala Asp Phe Ala Tyr Thr Tyr Ser Asp Glu Pro
465                 470                 475                 480

Glu Gln Ala Ser Val Gln Gly Trp Val Gly Val Tyr Gln Val Thr Asp
                485                 490                 495

Thr His Glu Lys Asp Gly Ala Val Val Val Ser Val Ser Ala Gly Pro
```

```
            500                 505                 510

Asp Phe Glu Phe Arg Met Pro Ile Ser Pro Ser Arg Gln Thr Thr Ser
        515                 520                 525

Ala Gly Glu Gly Ala Glu Pro Val Thr Thr Asp Ala Ser Gln His Gly
    530                 535                 540

Gly Asp Arg Arg Thr Thr Arg Arg His His Thr Asp Val Ser Phe Leu
545                 550                 555                 560

Leu Asp Arg Phe Thr Leu Val Gly Lys Thr Gln Asp Asn Lys Leu Thr
                565                 570                 575

Leu Asp Leu Leu Gln Thr Lys Glu Lys Ala Leu Val Gly Ala Ile Leu
            580                 585                 590

Arg Ala Ala Thr Tyr Tyr Phe Ser Asp Leu Glu Val Ala Cys Val Gly
        595                 600                 605

Asp Asn Lys Trp Val Gly Trp Thr Pro Asn Gly Ala Pro Glu Leu Ala
    610                 615                 620

Glu Val Gly Asp Asn Pro Val Val Phe Ser Lys Gly Arg Thr Thr Arg
625                 630                 635                 640

Phe Ala Leu Pro Tyr Thr Ala Pro His Arg Cys Leu Ala Thr Ala Tyr
                645                 650                 655

Asn Gly Asp Cys Lys Tyr Lys Pro Thr Gly Thr Ala Pro Arg Glu Asn
            660                 665                 670

Ile Arg Gly Asp Leu Ala Thr Leu Ala Ala Arg Ile Ala Ser Glu Thr
        675                 680                 685

His Ile Pro Thr Thr Phe Asn Tyr Gly Arg Ile Tyr Thr Asp Thr Glu
    690                 695                 700

Val Asp Val Tyr Val Arg Met Lys Arg Ala Glu Leu Tyr Cys Pro Arg
705                 710                 715                 720

Pro Val Leu Thr His Tyr Asp His Gly Gly Arg Asp Arg Tyr Arg Thr
                725                 730                 735

Ala Ile Thr Lys Pro Val Lys Gln
            740


<210> SEQ ID NO 23
<211> LENGTH: 2220
<212> TYPE: DNA
<213> ORGANISM: Foot-and-mouth disease virus
<220> FEATURE:
<221> NAME/KEY: misc_feature
<222> LOCATION: (1)..(2220)
<223> OTHER INFORMATION: GenBank: DQ009740.1 Foot-and-mouth disease
      virus - type SAT 3 isolate ZIM/05/91/3 P1 polyprotein gene,
      partial cds
<220> FEATURE:
<221> NAME/KEY: CDS
<222> LOCATION: (1)..(2220)

<400> SEQUENCE: 23

gga gcg ggc cag tct tcc cct gcc aca ggg tcg cag aac caa tct ggc       48
Gly Ala Gly Gln Ser Ser Pro Ala Thr Gly Ser Gln Asn Gln Ser Gly
1               5                   10                  15

aac act ggc agc atc ata aac aac tac tac atg cag cag tac cag aat       96
Asn Thr Gly Ser Ile Ile Asn Asn Tyr Tyr Met Gln Gln Tyr Gln Asn
            20                  25                  30

tca atg gac acc cag ctt ggc gac aac gcc atc tcg ggt ggt tca aat      144
Ser Met Asp Thr Gln Leu Gly Asp Asn Ala Ile Ser Gly Gly Ser Asn
        35                  40                  45

gaa ggc agc acg gac acc acg tcc aca cac acc aac aac acc caa aac      192
Glu Gly Ser Thr Asp Thr Thr Ser Thr His Thr Asn Asn Thr Gln Asn
    50                  55                  60
```

-continued

```
aat gat tgg ttt tca aaa ttg gcc caa tcc gcc att tca gga ctc ttc      240
Asn Asp Trp Phe Ser Lys Leu Ala Gln Ser Ala Ile Ser Gly Leu Phe
65                  70                  75                  80

ggg gct ctg ttg gcg gac aaa aag acc gag gaa aca acc ttg ctc gag      288
Gly Ala Leu Leu Ala Asp Lys Lys Thr Glu Glu Thr Thr Leu Leu Glu
                85                  90                  95

gac cga atc ctc aca aca cgc cac aat act acc aca tcc acc acg cag      336
Asp Arg Ile Leu Thr Thr Arg His Asn Thr Thr Thr Ser Thr Thr Gln
            100                 105                 110

agt tcg gtg gga gtg acg tac ggt tac gcg tcc gct gac cgg ttt ctc      384
Ser Ser Val Gly Val Thr Tyr Gly Tyr Ala Ser Ala Asp Arg Phe Leu
        115                 120                 125

cca gga ccg aac aca agt ggg ctg gaa acg cga gtg gaa cag gcc gag      432
Pro Gly Pro Asn Thr Ser Gly Leu Glu Thr Arg Val Glu Gln Ala Glu
    130                 135                 140

aga ttc ttc aag gag aga ctc ttc act tgg acc gct tcg cag cag tac      480
Arg Phe Phe Lys Glu Arg Leu Phe Thr Trp Thr Ala Ser Gln Gln Tyr
145                 150                 155                 160

gcc cac gtt cac ctg ctt gaa ctt ccc acc gac cac aag ggc atc tac      528
Ala His Val His Leu Leu Glu Leu Pro Thr Asp His Lys Gly Ile Tyr
                165                 170                 175

ggt gcc atg gtg gac aac cac gcg tac ata cgc aac gga tgg gac gtg      576
Gly Ala Met Val Asp Asn His Ala Tyr Ile Arg Asn Gly Trp Asp Val
            180                 185                 190

cag gtc tcc gcg acc agc acg cag ttc aat ggt ggt aca ttg ctc gtg      624
Gln Val Ser Ala Thr Ser Thr Gln Phe Asn Gly Gly Thr Leu Leu Val
        195                 200                 205

gca atg gtc cca gag tta cac gcg ctc gac acg cgt agt gtt tca cag      672
Ala Met Val Pro Glu Leu His Ala Leu Asp Thr Arg Ser Val Ser Gln
    210                 215                 220

ctc acg ctg ttt cca cac caa ttc atc aac cca cgc aca aac acc act      720
Leu Thr Leu Phe Pro His Gln Phe Ile Asn Pro Arg Thr Asn Thr Thr
225                 230                 235                 240

gcc cac att gtg gtt ccc tac att ggg gta aac agg cat gac cag gta      768
Ala His Ile Val Val Pro Tyr Ile Gly Val Asn Arg His Asp Gln Val
                245                 250                 255

aaa atg cac aag gcc tgg aca ttg gtg gtc gcg gtt ctc gca ccg ctc      816
Lys Met His Lys Ala Trp Thr Leu Val Val Ala Val Leu Ala Pro Leu
            260                 265                 270

acc aca tca aac atg gga cag gac aac gtt gag gtg tac gcc aac atc      864
Thr Thr Ser Asn Met Gly Gln Asp Asn Val Glu Val Tyr Ala Asn Ile
        275                 280                 285

gca cca acc aac gtt ttt gtg gct ggc gag aag cct acc aaa caa ggc      912
Ala Pro Thr Asn Val Phe Val Ala Gly Glu Lys Pro Thr Lys Gln Gly
    290                 295                 300

atc ttc ccc gtg gcc tgc aac gac ggc tac ggt ggc ttt cag aac act      960
Ile Phe Pro Val Ala Cys Asn Asp Gly Tyr Gly Gly Phe Gln Asn Thr
305                 310                 315                 320

gat ccc aag acc tct gac ccc ata tac ggg ctg gtg gca aac cca cct     1008
Asp Pro Lys Thr Ser Asp Pro Ile Tyr Gly Leu Val Ala Asn Pro Pro
                325                 330                 335

cgc acc gct ttt ccc ggg agg ttc acc aac ttc ctg gac gtg gcg gag     1056
Arg Thr Ala Phe Pro Gly Arg Phe Thr Asn Phe Leu Asp Val Ala Glu
            340                 345                 350

gca tgc ccg acc ttt ctg gac ttc aac gga aca cct tac gtc aag acc     1104
Ala Cys Pro Thr Phe Leu Asp Phe Asn Gly Thr Pro Tyr Val Lys Thr
        355                 360                 365

aga cac aac agt ggg agc aag ata ctc acc cac ata gat ttg gct ttt     1152
Arg His Asn Ser Gly Ser Lys Ile Leu Thr His Ile Asp Leu Ala Phe
```

```
    370                 375                 380

ggg cac aag agt ttc aag aac act tat ctt gct ggt ctc gcc cag tat      1200
Gly His Lys Ser Phe Lys Asn Thr Tyr Leu Ala Gly Leu Ala Gln Tyr
385                 390                 395                 400

tac gcc caa tac agt gga tct ctc aac ctg cac ttc atg tac acg ggt      1248
Tyr Ala Gln Tyr Ser Gly Ser Leu Asn Leu His Phe Met Tyr Thr Gly
                405                 410                 415

ccc acg caa tca aag gca cgc ttt atg gtt gca tac gta cca ccc ggg      1296
Pro Thr Gln Ser Lys Ala Arg Phe Met Val Ala Tyr Val Pro Pro Gly
            420                 425                 430

acg gag ccc gta cca tca aca ccc gag gaa gcg gcg cac tgc tac cac      1344
Thr Glu Pro Val Pro Ser Thr Pro Glu Glu Ala Ala His Cys Tyr His
        435                 440                 445

tcg gaa tgg gac act gga ctg aac tcc aag ttc acg ttc aca gtg ccg      1392
Ser Glu Trp Asp Thr Gly Leu Asn Ser Lys Phe Thr Phe Thr Val Pro
    450                 455                 460

tac atg tct gca gct gac tat gcc tac acc tac tgc gac gag cct gaa      1440
Tyr Met Ser Ala Ala Asp Tyr Ala Tyr Thr Tyr Cys Asp Glu Pro Glu
465                 470                 475                 480

cag gcc tcc gca caa ggg tgg gta aca ctg tac caa att act gac aca      1488
Gln Ala Ser Ala Gln Gly Trp Val Thr Leu Tyr Gln Ile Thr Asp Thr
                485                 490                 495

cat gac cct gat tcg gct gtc ctc atc tca gtt agc gca ggc gct gac      1536
His Asp Pro Asp Ser Ala Val Leu Ile Ser Val Ser Ala Gly Ala Asp
            500                 505                 510

ttt gag ctc agg ctg ccc atc aac ccc gtt act cag aca acg agc gcg      1584
Phe Glu Leu Arg Leu Pro Ile Asn Pro Val Thr Gln Thr Thr Ser Ala
        515                 520                 525

ggg gaa ggc gca gac gtg gtg acc acg gac gtt acc acc cat gga gga      1632
Gly Glu Gly Ala Asp Val Val Thr Thr Asp Val Thr Thr His Gly Gly
    530                 535                 540

aca gtt gac aca cca aga agg cag cac acc aac gtg gag ttt ctg ctg      1680
Thr Val Asp Thr Pro Arg Arg Gln His Thr Asn Val Glu Phe Leu Leu
545                 550                 555                 560

gac aga ttc aca cac att ggg tcg atc acc gcc tca aag acc att gac      1728
Asp Arg Phe Thr His Ile Gly Ser Ile Thr Ala Ser Lys Thr Ile Asp
                565                 570                 575

ctc ctc gag aca aaa gaa cac acg ctg gtg ggc gca ctc ctg cgt tca      1776
Leu Leu Glu Thr Lys Glu His Thr Leu Val Gly Ala Leu Leu Arg Ser
            580                 585                 590

gct acg tac tac ttt tgt gac ctc gag gtc gcg gtg ctt ggc aac gcg      1824
Ala Thr Tyr Tyr Phe Cys Asp Leu Glu Val Ala Val Leu Gly Asn Ala
        595                 600                 605

aag tgg gtt gga tgg gtg ccg aat ggc tgc cca cac acc gac cgc gtg      1872
Lys Trp Val Gly Trp Val Pro Asn Gly Cys Pro His Thr Asp Arg Val
    610                 615                 620

gaa gac aac cca gtc gtt cac gcc aag ggg aat gtt acc cgc ttt gca      1920
Glu Asp Asn Pro Val Val His Ala Lys Gly Asn Val Thr Arg Phe Ala
625                 630                 635                 640

ctg ccc tac aca gcc ccg cac gga gtg ctt gcc acg acc tac aac ggg      1968
Leu Pro Tyr Thr Ala Pro His Gly Val Leu Ala Thr Thr Tyr Asn Gly
                645                 650                 655

act tgc aag tat tcc aag acg caa agt gtt aaa cca cgc cgt ggc gac      2016
Thr Cys Lys Tyr Ser Lys Thr Gln Ser Val Lys Pro Arg Arg Gly Asp
            660                 665                 670

atg gct gtg ctg gca caa cgc gtt gaa ggt gaa caa caa aga tgc aaa      2064
Met Ala Val Leu Ala Gln Arg Val Glu Gly Glu Gln Gln Arg Cys Lys
        675                 680                 685

ccc acg aca ttc aac ttc ggt cga ttg ttg tgt gat tcg ggt gac gtg      2112
```

```
Pro Thr Thr Phe Asn Phe Gly Arg Leu Leu Cys Asp Ser Gly Asp Val
    690                 695                 700

tac tac cga atg aag cgg gcc gag ctt tac tgc cca cgt ccg ctg atg      2160
Tyr Tyr Arg Met Lys Arg Ala Glu Leu Tyr Cys Pro Arg Pro Leu Met
705                 710                 715                 720

gtc agg tac act cac acc aca gac aga tac aaa gtt gcg ctt gtg tca      2208
Val Arg Tyr Thr His Thr Thr Asp Arg Tyr Lys Val Ala Leu Val Ser
                725                 730                 735

cca gct aag caa                                                      2220
Pro Ala Lys Gln
            740


<210> SEQ ID NO 24
<211> LENGTH: 740
<212> TYPE: PRT
<213> ORGANISM: Foot-and-mouth disease virus

<400> SEQUENCE: 24

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Asn Asn Thr Gln Asn
    50                  55                  60

Asn Asp Trp Phe Ser Lys Leu Ala Gln Ser Ala Ile Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg His Asn Thr Thr Thr Ser Thr Thr Gln
            100                 105                 110

Ser Ser Val Gly Val Thr Tyr Gly Tyr Ala Ser Ala Asp Arg Phe Leu
        115                 120                 125

Pro Gly Pro Asn Thr Ser Gly Leu Glu Thr Arg Val Glu Gln Ala Glu
    130                 135                 140

Arg Phe Phe Lys Glu Arg Leu Phe Thr Trp Thr Ala Ser Gln Gln Tyr
145                 150                 155                 160

Ala His Val His Leu Leu Glu Leu Pro Thr Asp His Lys Gly Ile Tyr
                165                 170                 175

Gly Ala Met Val Asp Asn His Ala Tyr Ile Arg Asn Gly Trp Asp Val
            180                 185                 190

Gln Val Ser Ala Thr Ser Thr Gln Phe Asn Gly Gly Thr Leu Leu Val
        195                 200                 205

Ala Met Val Pro Glu Leu His Ala Leu Asp Thr Arg Ser Val Ser Gln
    210                 215                 220

Leu Thr Leu Phe Pro His Gln Phe Ile Asn Pro Arg Thr Asn Thr Thr
225                 230                 235                 240

Ala His Ile Val Val Pro Tyr Ile Gly Val Asn Arg His Asp Gln Val
                245                 250                 255

Lys Met His Lys Ala Trp Thr Leu Val Val Ala Val Leu Ala Pro Leu
            260                 265                 270

Thr Thr Ser Asn Met Gly Gln Asp Asn Val Glu Val Tyr Ala Asn Ile
        275                 280                 285

Ala Pro Thr Asn Val Phe Val Ala Gly Glu Lys Pro Thr Lys Gln Gly
    290                 295                 300
```

-continued

```
Ile Phe Pro Val Ala Cys Asn Asp Gly Tyr Gly Gly Phe Gln Asn Thr
305                 310                 315                 320

Asp Pro Lys Thr Ser Asp Pro Ile Tyr Gly Leu Val Ala Asn Pro Pro
                325                 330                 335

Arg Thr Ala Phe Pro Gly Arg Phe Thr Asn Phe Leu Asp Val Ala Glu
            340                 345                 350

Ala Cys Pro Thr Phe Leu Asp Phe Asn Gly Thr Pro Tyr Val Lys Thr
        355                 360                 365

Arg His Asn Ser Gly Ser Lys Ile Leu Thr His Ile Asp Leu Ala Phe
    370                 375                 380

Gly His Lys Ser Phe Lys Asn Thr Tyr Leu Ala Gly Leu Ala Gln Tyr
385                 390                 395                 400

Tyr Ala Gln Tyr Ser Gly Ser Leu Asn Leu His Phe Met Tyr Thr Gly
                405                 410                 415

Pro Thr Gln Ser Lys Ala Arg Phe Met Val Ala Tyr Val Pro Pro Gly
            420                 425                 430

Thr Glu Pro Val Pro Ser Thr Pro Glu Glu Ala Ala His Cys Tyr His
        435                 440                 445

Ser Glu Trp Asp Thr Gly Leu Asn Ser Lys Phe Thr Phe Thr Val Pro
    450                 455                 460

Tyr Met Ser Ala Ala Asp Tyr Ala Tyr Thr Tyr Cys Asp Glu Pro Glu
465                 470                 475                 480

Gln Ala Ser Ala Gln Gly Trp Val Thr Leu Tyr Gln Ile Thr Asp Thr
                485                 490                 495

His Asp Pro Asp Ser Ala Val Leu Ile Ser Val Ser Ala Gly Ala Asp
            500                 505                 510

Phe Glu Leu Arg Leu Pro Ile Asn Pro Val Thr Gln Thr Thr Ser Ala
        515                 520                 525

Gly Glu Gly Ala Asp Val Val Thr Thr Asp Val Thr Thr His Gly Gly
    530                 535                 540

Thr Val Asp Thr Pro Arg Arg Gln His Thr Asn Val Glu Phe Leu Leu
545                 550                 555                 560

Asp Arg Phe Thr His Ile Gly Ser Ile Thr Ala Ser Lys Thr Ile Asp
                565                 570                 575

Leu Leu Glu Thr Lys Glu His Thr Leu Val Gly Ala Leu Leu Arg Ser
            580                 585                 590

Ala Thr Tyr Tyr Phe Cys Asp Leu Glu Val Ala Val Leu Gly Asn Ala
        595                 600                 605

Lys Trp Val Gly Trp Val Pro Asn Gly Cys Pro His Thr Asp Arg Val
    610                 615                 620

Glu Asp Asn Pro Val Val His Ala Lys Gly Asn Val Thr Arg Phe Ala
625                 630                 635                 640

Leu Pro Tyr Thr Ala Pro His Gly Val Leu Ala Thr Thr Tyr Asn Gly
                645                 650                 655

Thr Cys Lys Tyr Ser Lys Thr Gln Ser Val Lys Pro Arg Arg Gly Asp
            660                 665                 670

Met Ala Val Leu Ala Gln Arg Val Glu Gly Glu Gln Gln Arg Cys Lys
        675                 680                 685

Pro Thr Thr Phe Asn Phe Gly Arg Leu Leu Cys Asp Ser Gly Asp Val
    690                 695                 700

Tyr Tyr Arg Met Lys Arg Ala Glu Leu Tyr Cys Pro Arg Pro Leu Met
705                 710                 715                 720
```

```
Val Arg Tyr Thr His Thr Thr Asp Arg Tyr Lys Val Ala Leu Val Ser
                725                 730                 735

Pro Ala Lys Gln
            740


<210> SEQ ID NO 25
<211> LENGTH: 711
<212> TYPE: DNA
<213> ORGANISM: Tobacco etch virus
<220> FEATURE:
<221> NAME/KEY: CDS
<222> LOCATION: (1)..(711)
<223> OTHER INFORMATION: TEV S219V protease mutant

<400> SEQUENCE: 25

ggg gaa agt ttg ttt aag ggg ccg cgt gat tac aac ccg atc tca agc       48
Gly Glu Ser Leu Phe Lys Gly Pro Arg Asp Tyr Asn Pro Ile Ser Ser
1               5                   10                  15

acc att tgt cat ttg acg aat gaa tct gat ggg cac aca aca tcg ttg       96
Thr Ile Cys His Leu Thr Asn Glu Ser Asp Gly His Thr Thr Ser Leu
            20                  25                  30

tat ggt att gga ttt ggt ccc ttc atc att aca aac aag cac ttg ttt      144
Tyr Gly Ile Gly Phe Gly Pro Phe Ile Ile Thr Asn Lys His Leu Phe
        35                  40                  45

aga aga aat aat gga aca ctg ttg gtt caa tca cta cat ggt gta ttc      192
Arg Arg Asn Asn Gly Thr Leu Leu Val Gln Ser Leu His Gly Val Phe
    50                  55                  60

aag gtc aag aac acc acg act ttg caa caa cac ctc att gat ggg agg      240
Lys Val Lys Asn Thr Thr Thr Leu Gln Gln His Leu Ile Asp Gly Arg
65                  70                  75                  80

gac atg ata att att cgc atg cca aag gat ttc cca cca ttt cct caa      288
Asp Met Ile Ile Ile Arg Met Pro Lys Asp Phe Pro Pro Phe Pro Gln
                85                  90                  95

aag ctg aaa ttt aga gag cca caa agg gaa gag cgc atc tgt ctt gtg      336
Lys Leu Lys Phe Arg Glu Pro Gln Arg Glu Glu Arg Ile Cys Leu Val
            100                 105                 110

aca acc aac ttc caa act aag agc atg tct agc atg gtg tca gac acc      384
Thr Thr Asn Phe Gln Thr Lys Ser Met Ser Ser Met Val Ser Asp Thr
        115                 120                 125

agt tgc aca ttc cct tca tct gat ggc ata ttc tgg aag cat tgg att      432
Ser Cys Thr Phe Pro Ser Ser Asp Gly Ile Phe Trp Lys His Trp Ile
    130                 135                 140

caa acc aag gat ggg cag tgt ggc agt cca tta gta tca act aga gat      480
Gln Thr Lys Asp Gly Gln Cys Gly Ser Pro Leu Val Ser Thr Arg Asp
145                 150                 155                 160

ggg ttc att gtt ggt att cac tca gca tcg aat ttc acc aac aca aac      528
Gly Phe Ile Val Gly Ile His Ser Ala Ser Asn Phe Thr Asn Thr Asn
                165                 170                 175

aat tat ttc aca agc gtg ccg aag aac ttt atg gaa ttg ttg aca aat      576
Asn Tyr Phe Thr Ser Val Pro Lys Asn Phe Met Glu Leu Leu Thr Asn
            180                 185                 190

cag gag gcg cag cag tgg gtt agt ggt tgg cga tta aat gct gac tca      624
Gln Glu Ala Gln Gln Trp Val Ser Gly Trp Arg Leu Asn Ala Asp Ser
        195                 200                 205

gta ttg tgg ggg ggc cat aaa gtt ttc atg gtg aaa cct gaa gag cct      672
Val Leu Trp Gly Gly His Lys Val Phe Met Val Lys Pro Glu Glu Pro
    210                 215                 220

ttt cag cca gtt aag gaa gcg act caa ctc atg aat taa                  711
Phe Gln Pro Val Lys Glu Ala Thr Gln Leu Met Asn
225                 230                 235
```

<210> SEQ ID NO 26
<211> LENGTH: 236
<212> TYPE: PRT
<213> ORGANISM: Tobacco etch virus

<400> SEQUENCE: 26

```
Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Val Lys Pro Glu Glu Pro
    210                 215                 220

Phe Gln Pro Val Lys Glu Ala Thr Gln Leu Met Asn
225                 230                 235
```

<210> SEQ ID NO 27

<400> SEQUENCE: 27

000

<210> SEQ ID NO 28

<400> SEQUENCE: 28

000

<210> SEQ ID NO 29
<211> LENGTH: 7
<212> TYPE: PRT
<213> ORGANISM: Artificial Sequence
<220> FEATURE:
<223> OTHER INFORMATION: TEV Protease minimal target sequence motif
<220> FEATURE:
<221> NAME/KEY: MISC_FEATURE
<222> LOCATION: (2)..(2)
<223> OTHER INFORMATION: Xaa at position 2 is any amino acid residue
<220> FEATURE:
<221> NAME/KEY: MISC_FEATURE
<222> LOCATION: (3)..(3)
<223> OTHER INFORMATION: Xaa at position 3 is any amino acid residue
<220> FEATURE:
<221> NAME/KEY: MISC_FEATURE
<222> LOCATION: (5)..(5)
<223> OTHER INFORMATION: Xaa at position 5 is any amino acid residue
<220> FEATURE:
<221> NAME/KEY: MISC_FEATURE
<222> LOCATION: (7)..(7)
<223> OTHER INFORMATION: Xaa at position 7 is G or S

<400> SEQUENCE: 29

Glu Xaa Xaa Tyr Xaa Gln Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: TEV protease optimal target site motif

<400> SEQUENCE: 30

Glu Asn Leu Tyr Phe Gln Ser
1               5

<210> SEQ ID NO 31
<211> LENGTH: 7
<212> TYPE: PRT
<213> ORGANISM: Artificial Sequence
<220> FEATURE:
<223> OTHER INFORMATION: pMM VP4 (1A)-VP2(1B) junction TEV cleavage site tested construct

<400> SEQUENCE: 31

Glu Gly Ala Tyr Leu Gln Ser
1               5

<210> SEQ ID NO 32
<211> LENGTH: 7
<212> TYPE: PRT
<213> ORGANISM: Artificial Sequence
<220> FEATURE:
<223> OTHER INFORMATION: pMM VP2 (1B)-VP3(1C) junction TEV cleavage site tested construct

<400> SEQUENCE: 32

Glu Phe Pro Tyr Lys Gln Gly
1               5

<210> SEQ ID NO 33
<211> LENGTH: 7
<212> TYPE: PRT
<213> ORGANISM: Artificial Sequence
<220> FEATURE:
<223> OTHER INFORMATION: pMM VP3(1C)-VP1(1D) junction TEV cleavage site tested construct

<400> SEQUENCE: 33

Glu Asp Ala Tyr Thr Gln Ser
1               5

<210> SEQ ID NO 34
<211> LENGTH: 7
<212> TYPE: PRT
<213> ORGANISM: Artificial Sequence
<220> FEATURE:
<223> OTHER INFORMATION: pOM TEV protease cleavage sites between VP4/ VP2; VP2/VP3; VP3/VP1; VP1/2A (tested constructs). pVOJ TEV protease cleavage sites between VP2/VP3, VP3/VP1, VP1/2A

<400> SEQUENCE: 34

Glu Asn Leu Tyr Phe Gln Ser
1 5

<210> SEQ ID NO 35
<211> LENGTH: 7
<212> TYPE: PRT
<213> ORGANISM: Artificial Sequence
<220> FEATURE:
<223> OTHER INFORMATION: VP4(1A)-VP2(1B) junction consensus sequence serotypes O, A, Asia, SAT1, SAT2, SAT3
<220> FEATURE:
<221> NAME/KEY: MISC_FEATURE
<222> LOCATION: (1)..(1)
<223> OTHER INFORMATION: Xaa at position 1 is F or V

<400> SEQUENCE: 35

Xaa Gly Ala Leu Leu Ala Asp
1 5

<210> SEQ ID NO 36
<211> LENGTH: 7
<212> TYPE: PRT
<213> ORGANISM: Artificial Sequence
<220> FEATURE:
<223> OTHER INFORMATION: VP2(1B)-VP3(1C) junction consensus sequence serotypes O, A, Asia, SAT1, SAT2, SAT3
<220> FEATURE:
<221> NAME/KEY: MISC_FEATURE
<222> LOCATION: (2)..(2)
<223> OTHER INFORMATION: Xaa at position 2 is F, L or K
<220> FEATURE:
<221> NAME/KEY: MISC_FEATURE
<222> LOCATION: (4)..(4)
<223> OTHER INFORMATION: Xaa at position 4 is S, A. G or T
<220> FEATURE:
<221> NAME/KEY: MISC_FEATURE
<222> LOCATION: (6)..(6)
<223> OTHER INFORMATION: Xaa at position 6 is E or Q

<400> SEQUENCE: 36

Glu Xaa Pro Xaa Lys Xaa Gly
1 5

<210> SEQ ID NO 37
<211> LENGTH: 7
<212> TYPE: PRT
<213> ORGANISM: Artificial Sequence
<220> FEATURE:
<223> OTHER INFORMATION: VP3(1C)-VP1(1D) junction consensus sequence serotypes O, A, Asia, SAT1, SAT2, SAT3
<220> FEATURE:
<221> NAME/KEY: MISC_FEATURE
<222> LOCATION: (1)..(1)
<223> OTHER INFORMATION: Xaa at position 1 is V or I
<220> FEATURE:
<221> NAME/KEY: MISC_FEATURE
<222> LOCATION: (2)..(2)
<223> OTHER INFORMATION: Xaa at position 2 is D, S or N
<220> FEATURE:
<221> NAME/KEY: MISC_FEATURE
<222> LOCATION: (3)..(3)
<223> OTHER INFORMATION: Xaa at position 3 is A or P
<220> FEATURE:
<221> NAME/KEY: MISC_FEATURE
<222> LOCATION: (4)..(4)
<223> OTHER INFORMATION: Xaa at position 4 is R, S or V
<220> FEATURE:
<221> NAME/KEY: MISC_FEATURE
<222> LOCATION: (5)..(5)
<223> OTHER INFORMATION: Xaa at position 5 is T, Q, or R

<400> SEQUENCE: 37

Xaa Xaa Xaa Xaa Xaa Gln Thr
1 5

<210> SEQ ID NO 38
<211> LENGTH: 7
<212> TYPE: PRT
<213> ORGANISM: Artificial Sequence
<220> FEATURE:
<223> OTHER INFORMATION: VP1(1D)-2A) junction consensus sequence
serotypes O, A, Asia, SAT1, SAT2, SAT3
<220> FEATURE:
<221> NAME/KEY: MISC_FEATURE
<222> LOCATION: (1)..(1)
<223> OTHER INFORMATION: Xaa at position 1 is V, I or T
<220> FEATURE:
<221> NAME/KEY: MISC_FEATURE
<222> LOCATION: (2)..(2)
<223> OTHER INFORMATION: Xaa at position 2 is A, K or G
<220> FEATURE:
<221> NAME/KEY: MISC_FEATURE
<222> LOCATION: (3)..(3)
<223> OTHER INFORMATION: Xaa at position 3 is P or V
<220> FEATURE:
<221> NAME/KEY: MISC_FEATURE
<222> LOCATION: (4)..(4)
<223> OTHER INFORMATION: Xaa at position 4 is V, A, E, or D
<220> FEATURE:
<221> NAME/KEY: MISC_FEATURE
<222> LOCATION: (5)..(5)
<223> OTHER INFORMATION: Xaa at position 5 is K or R
<220> FEATURE:
<221> NAME/KEY: MISC_FEATURE
<222> LOCATION: (7)..(7)
<223> OTHER INFORMATION: Xaa at position 7 is L, V, T or M

<400> SEQUENCE: 38

Xaa Xaa Xaa Xaa Xaa Gln Xaa
1 5

<210> SEQ ID NO 39
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 39

Glu Asp Ala Tyr Thr Gln Ser
1 5

<210> SEQ ID NO 40
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 40

Glu Phe Leu Tyr Lys Gln Gly
1 5

<210> SEQ ID NO 41
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 41

```
Glu Asp Leu Tyr Phe Gln Ser
1               5


<210> SEQ ID NO 42
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 42

Glu Lys Leu Tyr Lys Gln Gly
1               5


<210> SEQ ID NO 43
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 43

Glu Leu Leu Tyr Lys Gln Gly
1               5


<210> SEQ ID NO 44
<211> LENGTH: 7
<212> TYPE: PRT
<213> ORGANISM: Artificial Sequence
<220> FEATURE:
<223> OTHER INFORMATION: TEV protease recognition sequence

<400> SEQUENCE: 44

Glu Ala Leu Tyr Lys Gln Ser
1               5


<210> SEQ ID NO 45

<400> SEQUENCE: 45

000


<210> SEQ ID NO 46

<400> SEQUENCE: 46

000


<210> SEQ ID NO 47

<400> SEQUENCE: 47

000


<210> SEQ ID NO 48

<400> SEQUENCE: 48

000


<210> SEQ ID NO 49

<400> SEQUENCE: 49

000
```

```
<210> SEQ ID NO 50
<211> LENGTH: 243
<212> TYPE: PRT
<213> ORGANISM: Plum pox virus
<220> FEATURE:
<221> NAME/KEY: MISC_FEATURE
<222> LOCATION: (1)..(243)
<223> OTHER INFORMATION: NIa protein; GenBank: CDO19251.1

<400> SEQUENCE: 50

Ser Lys Ser Leu Phe Arg Gly Leu Arg Asp Tyr Asn Pro Ile Ala Ser
1               5                   10                  15

Ser Ile Cys Gln Leu Asn Asn Ser Ser Gly Ala Arg Gln Ser Glu Met
            20                  25                  30

Phe Gly Leu Gly Phe Gly Gly Leu Ile Val Thr Asn Gln His Leu Phe
        35                  40                  45

Lys Arg Asn Asp Gly Glu Leu Thr Ile Arg Ser His His Gly Glu Phe
    50                  55                  60

Val Val Lys Asp Thr Lys Thr Leu Lys Leu Leu Pro Cys Lys Gly Arg
65                  70                  75                  80

Asp Ile Val Ile Ile Arg Leu Pro Lys Asp Phe Pro Pro Phe Pro Arg
                85                  90                  95

Arg Leu Gln Phe Arg Thr Pro Thr Thr Glu Asp Arg Val Cys Leu Ile
            100                 105                 110

Gly Ser Asn Phe Gln Thr Lys Ser Ile Ser Ser Thr Met Ser Glu Thr
        115                 120                 125

Ser Ala Thr Tyr Pro Val Asp Asn Ser His Phe Trp Lys His Trp Ile
    130                 135                 140

Ser Thr Lys Asp Gly His Cys Gly Leu Pro Ile Val Ser Thr Arg Asp
145                 150                 155                 160

Gly Ser Ile Leu Gly Leu His Ser Leu Ala Asn Ser Thr Asn Thr Gln
                165                 170                 175

Asn Phe Tyr Ala Ala Phe Pro Asp Asn Phe Glu Thr Thr Tyr Leu Ser
            180                 185                 190

Asn Gln Asp Asn Asp Asn Trp Val Lys Gln Trp Arg Tyr Asn Pro Asp
        195                 200                 205

Glu Val Cys Trp Gly Ser Leu Gln Leu Lys Arg Asp Ile Pro Gln Ser
    210                 215                 220

Pro Phe Thr Ile Cys Lys Leu Leu Thr Asp Leu Asp Gly Glu Phe Val
225                 230                 235                 240

Tyr Thr Gln


<210> SEQ ID NO 51
<211> LENGTH: 241
<212> TYPE: PRT
<213> ORGANISM: Tobacco vein mottling virus
<220> FEATURE:
<221> NAME/KEY: MISC_FEATURE
<222> LOCATION: (1)..(241)
<223> OTHER INFORMATION: NIa-pro protein; NCBI Reference Sequence:
      NP_734334.1

<400> SEQUENCE: 51

Ser Lys Ala Leu Leu Lys Gly Val Arg Asp Phe Asn Pro Ile Ser Ala
1               5                   10                  15

Cys Val Trp Leu Leu Glu Asn Ser Ser Asp Gly His Ser Glu Arg Leu
            20                  25                  30

Phe Gly Ile Gly Phe Gly Pro Tyr Ile Ile Ala Asn Gln His Leu Phe
        35                  40                  45
```

```
Arg Arg Asn Asn Gly Glu Leu Thr Ile Lys Thr Met His Gly Glu Phe
    50                  55                  60

Lys Val Lys Asn Ser Thr Gln Leu Gln Met Lys Pro Val Glu Gly Arg
65                  70                  75                  80

Asp Ile Ile Val Ile Lys Met Ala Lys Asp Phe Pro Pro Phe Pro Gln
                85                  90                  95

Lys Leu Lys Phe Arg Gln Pro Thr Ile Lys Asp Arg Val Cys Met Val
            100                 105                 110

Ser Thr Asn Phe Gln Gln Lys Ser Val Ser Ser Leu Val Ser Glu Ser
        115                 120                 125

Ser His Ile Val His Lys Glu Asp Thr Ser Phe Trp Gln His Trp Ile
    130                 135                 140

Thr Thr Lys Asp Gly Gln Cys Gly Ser Pro Leu Val Ser Ile Ile Asp
145                 150                 155                 160

Gly Asn Ile Leu Gly Ile His Ser Leu Thr His Thr Thr Asn Gly Ser
                165                 170                 175

Asn Tyr Phe Val Glu Phe Pro Glu Lys Phe Val Ala Thr Tyr Leu Asp
            180                 185                 190

Ala Ala Asp Gly Trp Cys Lys Asn Trp Lys Phe Asn Ala Asp Lys Ile
        195                 200                 205

Ser Trp Gly Ser Phe Thr Leu Val Glu Asp Ala Pro Glu Asp Asp Phe
    210                 215                 220

Met Ala Lys Lys Thr Val Ala Ala Ile Met Asp Asp Leu Val Arg Thr
225                 230                 235                 240

Gln


<210> SEQ ID NO 52
<211> LENGTH: 244
<212> TYPE: PRT
<213> ORGANISM: Potato virus Y
<220> FEATURE:
<221> NAME/KEY: MISC_FEATURE
<222> LOCATION: (1)..(244)
<223> OTHER INFORMATION: NIa protein; GenBank: AJT60331.2

<400> SEQUENCE: 52

Ala Lys Ser Leu Met Arg Gly Leu Arg Asp Phe Asn Pro Ile Ala Gln
1               5                   10                  15

Thr Val Cys Arg Val Lys Val Ser Val Glu Tyr Gly Thr Ser Glu Met
            20                  25                  30

Tyr Gly Val Gly Phe Gly Ala Tyr Ile Ile Val Asn His His Leu Phe
        35                  40                  45

Lys Ser Phe Asn Gly Ser Met Glu Val Arg Ser Met His Gly Thr Phe
    50                  55                  60

Arg Val Lys Asn Leu His Ser Leu Ser Val Leu Pro Ile Lys Gly Arg
65                  70                  75                  80

Asp Ile Ile Ile Ile Lys Met Pro Lys Asp Phe Pro Val Phe Pro Gln
                85                  90                  95

Lys Leu His Phe Arg Ala Pro Val Gln Asn Glu Arg Ile Cys Leu Val
            100                 105                 110

Gly Thr Asn Phe Gln Glu Lys His Ala Ser Ser Ile Ile Thr Glu Thr
        115                 120                 125

Ser Thr Thr Tyr Asn Val Pro Gly Ser Thr Phe Trp Lys His Trp Ile
    130                 135                 140

Glu Thr Asn Asp Gly His Cys Gly Leu Pro Val Val Ser Thr Ala Asp
```

```
145                 150                 155                 160

Gly Cys Leu Val Gly Ile His Ser Leu Ala Asn Asn Val Gln Thr Thr
                165                 170                 175

Asn Tyr Tyr Ser Ala Phe Asp Glu Asp Phe Glu Ser Lys Tyr Leu Arg
            180                 185                 190

Thr Asn Glu His Asn Glu Trp Thr Lys Ser Trp Val Tyr Asn Pro Asp
        195                 200                 205

Thr Val Leu Trp Gly Pro Leu Lys Leu Lys Glu Ser Thr Pro Lys Gly
    210                 215                 220

Leu Phe Lys Thr Thr Lys Leu Val Gln Asp Leu Ile Asp His Asp Val
225                 230                 235                 240

Val Val Glu Gln


<210> SEQ ID NO 53
<211> LENGTH: 246
<212> TYPE: PRT
<213> ORGANISM: Pea seed-borne mosaic virus
<220> FEATURE:
<221> NAME/KEY: MISC_FEATURE
<222> LOCATION: (1)..(246)
<223> OTHER INFORMATION: NIa-Pro protein; GenBank: ANI76458.1

<400> SEQUENCE: 53

Ala Ala Ser Leu His Phe Gly Leu Arg Asp Tyr Asn Pro Ile Ala Gln
1               5                   10                  15

Ala Val Cys Arg Ile Thr Asn Thr Gly Val Asp Tyr Asp Arg Ser Ile
            20                  25                  30

Phe Gly Ile Gly Phe Gly Gln Phe Leu Ile Thr Asn Ala His Cys Phe
        35                  40                  45

Lys Leu Asn Glu Gly Glu Thr Arg Ile Val Ser Arg His Gly Gln Phe
    50                  55                  60

Thr Ile Glu Lys Thr His Ser Leu Pro Ile His Gln Val Lys Asp Lys
65                  70                  75                  80

Asp Met Val Ile Val Arg Leu Pro Lys Asp Phe Pro Pro Phe Pro Gln
                85                  90                  95

Arg Leu Gln Phe Arg Ala Pro Gln Glu Arg Glu Lys Ile Cys Leu Val
            100                 105                 110

Gly Ser Asn Phe Gln Glu Lys Ser Ile Gln Ser Val Ile Thr Glu Ser
        115                 120                 125

Cys Met Thr Phe Lys His Asn Gly Gly Lys Tyr Trp Lys His Trp Ile
    130                 135                 140

Thr Thr Lys Glu Gly His Cys Gly Leu Pro Val Val Ala Leu Lys Asp
145                 150                 155                 160

Gly His Ile Val Gly Ile His Asn Leu Gly Gly Glu Asn Thr Asn Ile
                165                 170                 175

Asn Tyr Phe Thr Pro Phe Asp Ala Asp Ile Leu Asp Lys Tyr Leu Leu
            180                 185                 190

Asn Ala Glu Ala Leu Gln Trp Thr Lys Gly Trp Lys Tyr Asn Lys Asn
        195                 200                 205

Lys Val Cys Trp Gly Gly Leu Glu Leu Leu Asp Asp Asn Glu Pro Glu
    210                 215                 220

Glu Ser Gly Leu Phe Arg Met Val Lys Leu Leu Lys Ser Leu Glu Glu
225                 230                 235                 240

Asp Gly Val Arg Thr Gln
                245
```

<210> SEQ ID NO 54
<211> LENGTH: 243
<212> TYPE: PRT
<213> ORGANISM: Turnip mosaic virus
<220> FEATURE:
<221> NAME/KEY: MISC_FEATURE
<222> LOCATION: (1)..(243)
<223> OTHER INFORMATION: NIa protein; GenBank: ABN13682.1

<400> SEQUENCE: 54

```
Ser Asn Ser Met Phe Arg Gly Leu Arg Asp Tyr Asn Pro Ile Ser Asn
1               5                   10                  15

Asn Ile Cys His Leu Thr Asn Val Ser Asp Gly Glu Ser Asn Ser Leu
            20                  25                  30

Tyr Gly Val Gly Phe Gly Pro Leu Ile Leu Thr Asn Arg His Leu Phe
        35                  40                  45

Glu Arg Asn Asn Gly Glu Leu Val Ile Lys Ser Arg His Gly Glu Phe
    50                  55                  60

Val Ile Lys Asn Thr Thr Gln Leu Asn Leu Leu Pro Ile Pro Asp Arg
65                  70                  75                  80

Asp Leu Leu Leu Ile Arg Leu Pro Lys Asp Val Pro Pro Phe Pro Gln
                85                  90                  95

Lys Leu Gly Phe Arg Gln Pro Glu Lys Gly Glu Arg Ile Cys Met Val
            100                 105                 110

Gly Ser Asn Phe Gln Thr Lys Ser Ile Thr Ser Ile Val Ser Glu Thr
        115                 120                 125

Ser Thr Ile Met Pro Val Glu Asn Ser Gln Phe Trp Lys His Trp Ile
    130                 135                 140

Ser Thr Lys Asp Gly Gln Cys Gly Ser Pro Met Val Ser Thr Lys Asp
145                 150                 155                 160

Gly Lys Ile Leu Gly Leu His Ser Leu Ala Asn Phe Gln Asn Ser Ile
                165                 170                 175

Asn Tyr Phe Ala Ala Phe Pro Asp Asp Phe Ala Glu Lys Tyr Leu His
            180                 185                 190

Thr Ile Glu Ala His Glu Trp Val Lys His Trp Lys Tyr Asn Thr Ser
        195                 200                 205

Ala Ile Ser Trp Gly Ser Leu Asn Ile Gln Ala Ala Gln Pro Ser Gly
    210                 215                 220

Leu Phe Lys Val Ser Lys Leu Ile Ser Asp Leu Asp Ser Thr Ala Val
225                 230                 235                 240

Tyr Ala Gln
```

<210> SEQ ID NO 55
<211> LENGTH: 243
<212> TYPE: PRT
<213> ORGANISM: Clover yellow vein virus
<220> FEATURE:
<221> NAME/KEY: MISC_FEATURE
<222> LOCATION: (1)..(243)
<223> OTHER INFORMATION: NIa-pro protein; NCBI Reference Sequence: NP_734170.1

<400> SEQUENCE: 55

```
Ser Leu Asn Arg Ile Ser Gly Leu Arg Asp Tyr Asn Pro Ile Ser Gln
1               5                   10                  15

Asn Val Cys Leu Leu Thr Asn Glu Ser Glu Gly His Arg Glu Lys Met
            20                  25                  30

Phe Gly Ile Gly Tyr Gly Ser Val Ile Ile Thr Asn Gln His Leu Phe
```

```
        35                  40                  45

Arg Arg Asn Asn Gly Glu Leu Ser Ile Gln Ser Lys His Gly Tyr Phe
    50                  55                  60

Arg Cys Arg Asn Thr Thr Ser Leu Lys Met Leu Pro Leu Glu Gly His
65                  70                  75                  80

Asp Ile Leu Leu Ile Gln Leu Pro Arg Asp Phe Pro Val Phe Pro Gln
                85                  90                  95

Lys Ile Arg Phe Arg Glu Pro Arg Val Asp Asp Lys Ile Val Leu Val
            100                 105                 110

Ser Thr Asn Phe Gln Glu Lys Ser Ser Ser Ser Thr Val Ser Glu Ser
        115                 120                 125

Ser Asn Ile Ser Arg Val Gln Ser Ala Asn Phe Tyr Lys His Trp Ile
    130                 135                 140

Ser Thr Val Ala Gly His Cys Gly Asn Pro Met Val Ser Thr Lys Asp
145                 150                 155                 160

Gly Phe Ile Val Gly Ile His Ser Leu Ala Ser Leu Thr Gly Asp Val
                165                 170                 175

Asn Ile Phe Thr Ser Phe Pro Pro Gln Phe Glu Asn Lys Tyr Leu Gln
            180                 185                 190

Lys Leu Ser Glu His Thr Trp Cys Ser Gly Trp Lys Leu Asn Leu Gly
        195                 200                 205

Lys Ile Ser Trp Gly Gly Ile Asn Ile Val Glu Asp Ala Pro Glu Glu
    210                 215                 220

Pro Phe Ile Thr Ser Lys Met Ala Ser Leu Leu Ser Asp Leu Asn Cys
225                 230                 235                 240

Ser Phe Gln


<210> SEQ ID NO 56
<211> LENGTH: 243
<212> TYPE: PRT
<213> ORGANISM: Pepper vein banding virus
<220> FEATURE:
<221> NAME/KEY: MISC_FEATURE
<222> LOCATION: (1)..(243)
<223> OTHER INFORMATION: Pepper vein banding virus NIa protein; NCBI
      Reference Sequence: NP_982342.1; synonym: nuclear inclusion
      protein A [Chilli veinal mottle virus]

<400> SEQUENCE: 56

Ala Arg Ser Leu Asn Arg Gly Leu Arg Asp His Asn Gln Val Ser Lys
1               5                   10                  15

Leu Ile Cys Lys Leu Glu Asn Asp Ser Asp Asp Cys Val Thr Ser Ile
            20                  25                  30

His Gly Val Gly Phe Gly Ser Ile Ile Ile Thr Asn Arg His Leu Leu
        35                  40                  45

Lys Arg Asn Asn Gly Thr Leu Arg Val Lys Thr Ala His Gly Asp Phe
    50                  55                  60

Lys Val Ala Asn Thr Lys Glu Met Lys Val Phe Pro Val Glu Lys His
65                  70                  75                  80

Asp Ile Leu Leu Ile Arg Leu Pro Lys Asp Phe Pro Pro Phe Pro Val
                85                  90                  95

Lys Ser Lys Phe Arg Glu Pro Lys Val Asn Asp Ser Ile Cys Leu Val
            100                 105                 110

Gly Thr Asn Phe Gln Glu Lys Phe Leu Ser Ser Leu Ile Ser Ala Asp
        115                 120                 125

Ser Thr Thr Ser Pro Val Ser Gly Ser Lys Phe Trp Arg His Trp Ile
```

```
    130                 135                 140

Asp Thr Lys Asp Gly His Cys Gly Leu Pro Leu Val Ala Arg Asp Asp
145                 150                 155                 160

Gly Ala Ile Val Gly Phe His Ser Leu Thr Ser Ile Asn Thr Glu Gln
                165                 170                 175

Asn Tyr Phe Ala Ala Val Pro Glu Ala Phe Met Glu Leu Ile Ala Gln
            180                 185                 190

Val Glu Thr Leu Glu Trp Arg Lys Ser Trp Val Tyr Asn Pro Asn Glu
        195                 200                 205

Ile Gly Trp Gly Ser Leu Lys Leu Lys Ser Asp Gln Pro Thr Gly Met
    210                 215                 220

Phe Lys Ile Glu Lys Leu Ile Glu Asp Ile Gln Ser Ala Phe Val Arg
225                 230                 235                 240

Glu Gln Ala


<210> SEQ ID NO 57
<211> LENGTH: 242
<212> TYPE: PRT
<213> ORGANISM: Habenaria mosaic virus
<220> FEATURE:
<221> NAME/KEY: MISC_FEATURE
<222> LOCATION: (1)..(242)
<223> OTHER INFORMATION: NIa protein

<400> SEQUENCE: 57

Ser Lys Ser Leu Asn Arg Gly Leu Arg Asp Tyr Thr Pro Ile Ser Lys
1               5                   10                  15

Ser Ile Cys Leu Leu Gln Asn Thr Ser Asp Gly Cys Ser Thr Thr Ile
            20                  25                  30

His Gly Val Gly Tyr Gly Ser Leu Ile Val Ser Asn Ala His Leu Leu
        35                  40                  45

Lys Arg Asn Asn Gly Thr Leu Thr Ile Lys Ser Met His Gly Glu Phe
    50                  55                  60

Lys Ile Gln Asn Thr Thr Ala Ile Arg Ile Ala Pro Val Pro Asn Cys
65                  70                  75                  80

Asp Leu Ile Val Leu Arg Leu Pro Lys Asp Phe Pro Pro Phe Ser Thr
                85                  90                  95

Lys Leu Lys Phe Arg Val Pro Glu Ser Asn Glu Gln Val Cys Met Val
            100                 105                 110

Gly Thr Asn Phe Gln Glu Lys Trp Met Ser Ser Thr Val Ser Ser Thr
        115                 120                 125

Ser Tyr Ile Gln His Ile Pro Gly Thr Gln Phe Val Lys His Trp Ile
    130                 135                 140

Asp Thr Lys Asp Gly His Cys Gly Leu Pro Met Val Ala Ser Lys Asp
145                 150                 155                 160

Gly Ala Ile Leu Gly Leu His Ser Leu Thr Asn Thr Lys Gln Glu Tyr
                165                 170                 175

Asn Cys Phe Ala Ser Ala Thr Ser Val Leu Met Glu Ile Leu Asp Ala
            180                 185                 190

Pro Glu His Ala Asp Trp Arg Lys Gly Trp Met Tyr Asn Pro Asn Asp
        195                 200                 205

Ile Ser Trp Gly Phe Met Arg Leu Lys Glu Ser Thr Pro Ser Gly Leu
    210                 215                 220

Phe Lys Pro Ala Lys Ser Ile Arg Asp Leu Glu Leu Asp Ile Val Asn
225                 230                 235                 240
```

Glu Gln

<210> SEQ ID NO 58
<211> LENGTH: 239
<212> TYPE: PRT
<213> ORGANISM: Moroccan Watermelon Mosaic Virus
<220> FEATURE:
<221> NAME/KEY: MISC_FEATURE
<222> LOCATION: (1)..(239)
<223> OTHER INFORMATION: NIa protein

<400> SEQUENCE: 58

```
Gly Lys Ser Leu Tyr Gln Gly Met Lys Asn Tyr Asn Gly Ile Ser Ser
1               5                   10                  15

Val Val Cys His Leu Thr Asn Thr Ser Gly Val Gly Ser Ser Leu Tyr
            20                  25                  30

Gly Ile Gly Tyr Asn Ser Tyr Ile Leu Thr Asn Arg His Leu Phe Arg
        35                  40                  45

Gln Asn Asn Gly Ser Leu Val Val Gln Ser Ser His Gly Arg Phe Val
    50                  55                  60

Val Lys Asn Thr Leu Thr Leu Lys Val Ala Pro Val Gly Lys Thr Asp
65                  70                  75                  80

Ile Val Ile Ile Arg Met Pro Lys Asp Phe Pro Pro Phe His Ser Arg
                85                  90                  95

Leu Arg Phe Arg Glu Pro His Lys Ala Asp Arg Val Cys Leu Val Gly
            100                 105                 110

Ala Asp Phe Gln Asp Lys Tyr Ile Ala Ser Lys Val Ser Glu Ala Ser
        115                 120                 125

Gln Ile Val Asp Asp Phe Gly Gly Thr Phe Gly Arg His Trp Ile Ser
    130                 135                 140

Thr Asn Asp Gly Asp Cys Gly Leu Pro Leu Val Ser Val Gln Asp Gly
145                 150                 155                 160

Phe Ile Ile Gly Leu His Ser Leu Ser Ser Thr Ala Asn Ile Ala Asn
                165                 170                 175

Tyr Phe Ala Met Ile Pro Glu Asn Phe Glu Glu Thr Tyr Ile Lys Lys
            180                 185                 190

Leu Asp Thr Leu Lys Trp Asp Ser His Trp Arg Tyr Asn Ser Asn Glu
        195                 200                 205

Ile Ser Trp Gly Ser Leu Thr Ile His Glu Ser Lys Pro Glu Glu Pro
    210                 215                 220

Phe Arg Ile Val Lys Glu Ile His Gly Leu Gln Val Tyr Glu Gln
225                 230                 235
```

<210> SEQ ID NO 59
<211> LENGTH: 239
<212> TYPE: PRT
<213> ORGANISM: Zucchini Shoestring Virus
<220> FEATURE:
<221> NAME/KEY: MISC_FEATURE
<222> LOCATION: (1)..(239)
<223> OTHER INFORMATION: NIa protein

<400> SEQUENCE: 59

```
Gly Lys Ser Leu Cys Asn Ser Met Arg Asp Tyr Asn Asn Val Ser Ser
1               5                   10                  15

Val Ile Cys Ala Leu Gln Asn Thr Ser Gly Gly Gly Thr Ser Leu Tyr
            20                  25                  30

Gly Val Gly Phe Asn Ser Phe Ile Ile Thr Asn Arg His Leu Phe Arg
        35                  40                  45
```

Glu Asn Asn Gly Ser Leu Glu Val Gln Ser Cys His Gly Lys Phe His
    50                  55                  60

Val Arg Asn Thr Thr Thr Leu Lys Val Ala Pro Val Gly Lys Thr Asp
65                  70                  75                  80

Leu Ile Ile Ile Arg Met Pro Lys Asp Phe Pro Pro Phe Pro Ser Lys
                85                  90                  95

Leu Arg Phe Arg Ala Pro Asn Ala Gly Asp Lys Val Cys Leu Val Gly
            100                 105                 110

Ala Asn Phe Gln Glu Lys Tyr Leu Ser Ser Arg Val Ser Glu Ser Ser
        115                 120                 125

His Ile Ser Asp Ser Phe Gly Gly Ser Phe Gly Arg His Trp Ile Ser
    130                 135                 140

Thr Asn Asp Gly Asp Cys Gly Leu Pro Leu Val Ser Val Lys Asp Gly
145                 150                 155                 160

Phe Ile Leu Gly Leu His Ser Leu Ser Ser Ala Lys Asn Ile Ala Asn
                165                 170                 175

Tyr Phe Ala Ile Ile Pro Ala Asp Phe Glu Glu Ala Tyr Ile Arg Lys
            180                 185                 190

Leu Glu Ser Leu Ser Trp Ser Ser His Trp Arg Tyr Asn Thr Asn Glu
        195                 200                 205

Ile Cys Trp Gly Pro Leu Lys Ile His Asp Ser Lys Pro Glu Phe Pro
    210                 215                 220

Phe Gln Val Ser Lys Glu Leu Asn Pro Leu Gln Val Tyr Glu Gln
225                 230                 235

<210> SEQ ID NO 60
<211> LENGTH: 243
<212> TYPE: PRT
<213> ORGANISM: Daphne Virus Y
<220> FEATURE:
<221> NAME/KEY: MISC_FEATURE
<222> LOCATION: (1)..(243)
<223> OTHER INFORMATION: NIa protein

<400> SEQUENCE: 60

Gly Lys Thr Thr Leu Thr Gly Leu Arg Asp Tyr Asn Asn Ile Ser Ala
1               5                   10                  15

Cys Val Cys Leu Val Glu Asn His Ser Asp Gly Ile Glu Thr Lys Met
            20                  25                  30

His Ala Leu Gly Phe Gly Ser Tyr Leu Val Leu Asn Gly His Phe Phe
        35                  40                  45

Arg Lys Asn Asn Gly Tyr Met Ile Ile Lys Ser His His Gly Glu Phe
    50                  55                  60

Arg Val Lys Asn Met Lys Gln Leu Lys Ile Phe Gly Val Asp Arg Lys
65                  70                  75                  80

Asp Met Ala Leu Leu Gln Leu Pro Lys Asp Phe Pro Pro Phe Pro Arg
                85                  90                  95

Lys Leu Arg Phe Arg Ala Pro Glu Lys Gly Glu Ser Ile Val Leu Val
            100                 105                 110

Gly Asn Asn Phe Gln Asp Lys Tyr Ile Ser Ser Met Val Ser Glu Ser
        115                 120                 125

Cys Lys Thr Phe Pro Arg Asp Ala Gly Gly Phe Trp Lys His Trp Ile
    130                 135                 140

Ser Thr Lys Glu Gly Ser Cys Gly Gln Pro Leu Val Ser Val Arg Asp
145                 150                 155                 160

Gly Phe Ile Val Gly Ile His Ser Leu Cys Ser Glu Val Ser Glu Val
165 170 175

Asn Tyr His Thr Ser Val Ala Asp Asp Phe Glu Ala Arg Ile Leu Ala
180 185 190

Lys Thr Asp Ser Leu Glu Trp Glu Lys Asn Trp Phe Tyr Asn Pro Asn
195 200 205

Ser Val Cys Trp Gly Gly Ile Ser Ile Pro Asp Asn Lys Pro Asp Asp
210 215 220

Ile Phe Arg Ala Asp Lys Val Ala Glu Thr Leu Met Ser Glu Ile Val
225 230 235 240

Ser Glu Gln

<210> SEQ ID NO 61
<211> LENGTH: 243
<212> TYPE: PRT
<213> ORGANISM: Cantharanthus Mosaic Virus

<400> SEQUENCE: 61

Gly Ala Ser Met Val Pro Gly Val Lys Asp Tyr Asn Pro Ile Ser Asn
1 5 10 15

Ala Val Cys Lys Leu Ile Asn Glu Ser Asp Gly His Lys Arg Thr Leu
20 25 30

Tyr Gly Val Gly Tyr Gly His Phe Ile Ile Thr Asn Arg His Leu Phe
35 40 45

Glu His Asn Asn Gly Lys Val Ile Val Lys Ser Lys His Gly Glu Phe
50 55 60

Leu Ile Pro Asn Ser Thr Ser Leu Met Leu Leu Pro Val Pro Asp Arg
65 70 75 80

Asp Ile Leu Val Ile Lys Leu Pro Lys Asp Phe Pro Pro Phe Pro Gln
85 90 95

Arg Ile His Phe Ser Ala Pro Glu Glu Gly Met Thr Val Thr Met Val
100 105 110

Gly Ala Leu Phe Gln Glu Arg Ser Gln Thr Pro Leu Ile Ser Pro Thr
115 120 125

Cys Ala Thr Phe Arg Lys Asp Glu Ser His Phe Trp Lys His Trp Ile
130 135 140

Ser Thr Lys Asp Gly Gln Cys Gly Thr Pro Phe Val Glu Val Lys Thr
145 150 155 160

Asn Ala Ile Val Gly Leu His Ser Leu Gly Ser Cys Asn Ser Lys Thr
165 170 175

Asn Tyr Phe Val Gly Phe Pro His Asn Phe Val Asp Glu Phe Ile Thr
180 185 190

Lys Glu Asn Thr Glu Ala Trp Arg Lys Cys Trp Arg Tyr Asn Pro Asp
195 200 205

Gln Ile Asn Trp Gly Ser Met Asn Val Lys Arg Asn Ile Pro Thr Gly
210 215 220

Leu Phe Lys Val Ser Lys Leu Pro Tyr Asp Leu Asn Leu Glu Glu Val
225 230 235 240

Ile Glu Gln

<210> SEQ ID NO 62
<211> LENGTH: 243
<212> TYPE: PRT
<213> ORGANISM: Lupine Mosaic Virus
<220> FEATURE:
<221> NAME/KEY: MISC_FEATURE
<222> LOCATION: (1)..(243)
<223> OTHER INFORMATION: NIa protein

<400> SEQUENCE: 62

Ser Asn Ala Leu Tyr Arg Gly Pro Arg Asp Tyr Asn Pro Ile Ala Ser
1 5 10 15

Val Ile Cys Glu Leu Ala Tyr Thr Ser Ala Leu Gly Thr Arg Val Thr
20 25 30

Tyr Gly Val Gly Tyr Gly Pro Tyr Leu Ile Thr Asn Gln His Leu Phe
35 40 45

Gly Asp Asn Asn Gly Glu Leu Gln Val Arg Ser Arg His Gly Thr Phe
50 55 60

Asn Ile Lys Asn Thr Thr Gln Ile Lys Met Lys Pro Leu Lys Lys Thr
65 70 75 80

Asp Ile Leu Leu Ile Arg Met Pro Lys Asp Phe Pro Pro Phe Pro Gln
85 90 95

Lys Leu Gln Phe Arg Ser Pro Ile Thr Ala Glu Arg Ile Cys Met Val
100 105 110

Gly Ser Leu Phe Gln Glu Lys Ser Ile Thr Ser Thr Val Ser Glu Ser
115 120 125

Ser Ser Thr Tyr Pro Lys Asp Asp Ser Thr Phe Trp Ser His Trp Ile
130 135 140

Thr Thr Lys Val Gly His Cys Gly Leu Pro Leu Val Ser Thr Lys Asp
145 150 155 160

Gly Tyr Ile Leu Gly Leu His Ser Leu Gly Asn Phe Thr Gln Thr Lys
165 170 175

Asn Phe Tyr Ala Ala Phe Pro Ser Asp Phe Val Glu Asn Phe Leu Ala
180 185 190

Thr Ala Glu Asn Ser Glu Trp Val Lys Asn Trp Gln Tyr Asn Pro Asp
195 200 205

Asn Val Cys Trp Gly Ser Leu Gln Leu His Ala Ser Gly Pro Gln Glu
210 215 220

Pro Phe Lys Thr Ala Lys Leu Tyr Glu Asp Leu Asn His Asp Asp Val
225 230 235 240

Tyr Ser Gln

<210> SEQ ID NO 63
<211> LENGTH: 242
<212> TYPE: PRT
<213> ORGANISM: Leek Yellow Stripe Virus
<220> FEATURE:
<221> NAME/KEY: MISC_FEATURE
<222> LOCATION: (1)..(242)
<223> OTHER INFORMATION: NIa protease

<400> SEQUENCE: 63

Gly Lys Ser Leu Leu Ser Gly Leu Arg Asp Tyr Asn Pro Ile Ala Ala
1 5 10 15

Cys Val Cys Lys Ile Thr Asn Glu Ser Asp Gly Ile Val Thr His Ile
20 25 30

Phe Gly Ile Gly Tyr Gly Pro Tyr Ile Ile Thr Asn Gln His Leu Phe
35 40 45

His Arg Asn Asn Gly Ile Leu Arg Ile Asn Thr His Ala Gly Glu Tyr
50 55 60

Leu Val Asn Asn Ala Cys Thr Leu Lys Met His Pro Ile Pro Glu Arg
65 70 75 80

-continued

```
Asp Ile Ile Ile Ile Arg Leu Pro Lys Asp Phe Thr Pro Phe Pro Gln
                85                  90                  95

Arg Leu Arg Phe Arg Thr Thr Arg Val Gly Glu His Val Cys Leu Val
            100                 105                 110

Ser Ser Asn Phe Gln Thr Lys Ser Ile Ser Ser Val Val Ser Ala Thr
        115                 120                 125

Ser Ala Thr Ala Gly Thr Ala Asn Lys Asn Phe Phe Lys His Trp Ile
    130                 135                 140

Ser Thr Lys His Gly Gln Cys Gly Asn Pro Leu Val Ser Val Thr Asp
145                 150                 155                 160

Gly Ser Ile Val Gly Ile His Ser Met Ala Ser Thr Val Ser Ser Met
                165                 170                 175

Asn Met Tyr Ala Gly Phe Pro Glu Asn Phe Val Glu Asp Tyr Leu Ser
            180                 185                 190

Asn Asp Met Leu Glu Trp Thr Lys Gly Trp Lys Leu Asn Ala Asp Arg
        195                 200                 205

Ser Cys Trp Asp Gly Ile Thr Leu Val Asn Ser Lys Ala Glu Gly Leu
    210                 215                 220

Phe Lys Met Ala Lys Asp Ile Phe Thr Leu Asp Asp Gly Asn Trp Glu
225                 230                 235                 240

Phe Gln


<210> SEQ ID NO 64
<211> LENGTH: 243
<212> TYPE: PRT
<213> ORGANISM: Zucchini Yellow Mosaic Virus
<220> FEATURE:
<221> NAME/KEY: MISC_FEATURE
<222> LOCATION: (1)..(243)
<223> OTHER INFORMATION: NIa protein

<400> SEQUENCE: 64

Ser Lys Ser Ile Tyr Lys Gly Val Arg Asp Tyr Asn Gly Ile Ser Thr
1               5                   10                  15

Ile Val Cys Gln Leu Thr Asn Asp Ser Asp Gly Leu Lys Glu Thr Met
            20                  25                  30

Tyr Gly Ile Gly Tyr Gly Pro Ile Ile Ile Thr Asn Gly His Leu Phe
        35                  40                  45

Arg Lys Asn Asn Gly Thr Leu Leu Val Arg Ser Trp His Gly Glu Phe
    50                  55                  60

Thr Val Lys Asn Thr Thr Thr Leu Lys Val His Phe Ile Glu Gly Lys
65                  70                  75                  80

Asp Val Val Leu Val Arg Met Pro Lys Asp Phe Pro Pro Phe Lys Ser
                85                  90                  95

Asn Ala Ser Phe Arg Ala Pro Lys Arg Glu Glu Arg Ala Cys Leu Val
            100                 105                 110

Gly Thr Asn Phe Gln Glu Lys Ser Leu Arg Ser Thr Val Ser Glu Ser
        115                 120                 125

Ser Met Thr Val Pro Glu Gly Thr Gly Ser Tyr Trp Ile His Trp Ile
    130                 135                 140

Ser Thr Asn Glu Gly Asp Cys Gly Leu Pro Met Val Ser Thr Thr Asp
145                 150                 155                 160

Gly Lys Ile Ile Gly Val His Gly Leu Ala Ser Thr Val Ser Ser Lys
                165                 170                 175

Asn Tyr Phe Val Pro Phe Thr Asp Asp Phe Ile Ala Thr His Leu Ser
            180                 185                 190
```

```
Lys Leu Asp Asp Leu Thr Trp Thr Gln His Trp Leu Trp Gln Pro Ser
        195                 200                 205

Lys Ile Ala Trp Gly Thr Leu Asn Leu Val Asp Glu Gln Pro Gly Pro
    210                 215                 220

Glu Phe Arg Ile Ser Asn Leu Val Lys Asp Leu Phe Thr Ser Gly Val
225                 230                 235                 240

Glu Thr Gln


<210> SEQ ID NO 65
<211> LENGTH: 244
<212> TYPE: PRT
<213> ORGANISM: Sunflower chlorotic mottle virus
<220> FEATURE:
<221> NAME/KEY: MISC_FEATURE
<222> LOCATION: (1)..(244)
<223> OTHER INFORMATION: NIa protein; NCBI Reference Sequence:
      YP_003582552.1

<400> SEQUENCE: 65

Ser Lys Ser Leu Met Lys Gly Leu Arg Asp Tyr Asn Pro Ile Ala Gln
1               5                   10                  15

Thr Ile Cys Lys Leu Lys Val Thr Ser Glu Phe Gly Thr Ser Glu Met
            20                  25                  30

Tyr Gly Ile Gly Phe Gly Ala Tyr Ile Ile Ser Asn His His Leu Phe
        35                  40                  45

Lys Ser Phe Asn Gly Thr Leu Glu Val Arg Ser His His Gly Thr Phe
    50                  55                  60

Lys Val Asn Asn Met Met Ala Leu Gln Val Lys Pro Ile Ala Gly Arg
65                  70                  75                  80

Asp Ile Ile Ile Ile Lys Met Pro Lys Asp Phe Pro Val Phe Pro Gln
                85                  90                  95

Lys Leu His Phe Arg Ser Pro Lys Asn Asn Glu Arg Met Cys Ile Val
            100                 105                 110

Gly Thr Asn Phe Gln Glu Lys Ser Ala Ser Ser Thr Ile Thr Glu Thr
        115                 120                 125

Ser Ala Thr Tyr Met Val Pro Arg Ser Ser Phe Trp Lys His Trp Ile
    130                 135                 140

Ala Thr Asp Asp Gly His Cys Gly Leu Pro Val Val Ser Thr Ile Asp
145                 150                 155                 160

Gly Lys Ile Ile Gly Ile His Ser Leu Ala Asn Asn Ala Asn Ser Glu
                165                 170                 175

Asn Tyr Tyr Ala Ala Phe Asp Asp Asp Phe Glu Glu Lys Phe Leu Arg
            180                 185                 190

Thr Ser Glu His Thr Asp Trp Val Lys Asn Trp Arg Tyr Asn Pro Asp
        195                 200                 205

Thr Val Val Trp Gly Pro Leu Lys Leu Thr Glu Ser Thr Pro Lys Gly
    210                 215                 220

Leu Phe Lys Pro Thr Lys Ile Leu Glu Asp Leu Phe Glu Tyr Asn Ser
225                 230                 235                 240

Val Arg Glu Gln


<210> SEQ ID NO 66
<211> LENGTH: 243
<212> TYPE: PRT
<213> ORGANISM: Lettuce mosaic virus
<220> FEATURE:
<221> NAME/KEY: MISC_FEATURE
```

<222> LOCATION: (1)..(243)
<223> OTHER INFORMATION: NIa protein; GenBank: AIA66377.1

<400> SEQUENCE: 66

Ser Lys Thr Leu Phe Arg Gly Leu Arg Asp Tyr Asn Pro Ile Ala Ala
1 5 10 15

Ala Ile Cys Leu Leu Thr Asn Glu Ser Asp Gly Met Lys Glu Thr Met
20 25 30

Tyr Gly Ile Gly Phe Gly Asn Thr Ile Ile Thr Asn Gln His Leu Phe
35 40 45

Arg Arg Asn Asn Gly Val Leu Arg Val Gln Ser Arg His Gly Glu Tyr
50 55 60

Val Leu Pro Asn Thr Thr Gln Leu Lys Val Leu Pro Cys Glu Gly Arg
65 70 75 80

Asp Ile Met Val Ile Ile Leu Thr Pro Asp Phe Pro Pro Phe Pro Gln
85 90 95

Lys Leu Lys Phe Arg Pro Pro Ile Lys Gly Glu Lys Val Cys Leu Val
100 105 110

Gly Ser Leu Phe Gln Asp Lys Ser Ile Thr Ser Thr Val Ser Glu Thr
115 120 125

Ser Val Thr Thr Pro Val Asp Asn Ser Phe Leu Trp Lys His Trp Ile
130 135 140

Thr Thr Lys Asp Gly His Cys Gly Leu Pro Leu Val Ser Pro Asn Asp
145 150 155 160

Gly Tyr Ile Val Gly Ile His Ser Ala Thr Ser Ser Arg Gln Thr Gln
165 170 175

Asn Tyr His Ala Ala Met Pro Glu Asp Phe His Gln Thr His Leu Ile
180 185 190

Asp Pro Val Ser Lys Ser Trp Val Lys His Trp Lys Tyr Asn Pro Asp
195 200 205

Asn Met Val Trp Gly Gly Ile Asn Leu Ile Asn Ser Thr Pro Lys Glu
210 215 220

Pro Phe Lys Ile Ser Lys Leu Val Thr Asp Leu Tyr Gly Asp Ala Val
225 230 235 240

Gln Phe Gln

<210> SEQ ID NO 67
<211> LENGTH: 244
<212> TYPE: PRT
<213> ORGANISM: Bidens mottle virus
<220> FEATURE:
<221> NAME/KEY: MISC_FEATURE
<222> LOCATION: (1)..(244)
<223> OTHER INFORMATION: NIa protein; NCBI Reference Sequence:
YP_006423954.1

<400> SEQUENCE: 67

Ser Lys Ser Leu Leu Arg Gly Leu Arg Asp Phe Asn Pro Val Ala Thr
1 5 10 15

Val Val Cys Lys Leu Ile Ala Lys Thr Asp Met Gly Ile Lys Ser Met
20 25 30

His Gly Ile Gly Phe Gly Ser Tyr Leu Ile Ala Asn His His Leu Phe
35 40 45

Lys Thr Phe Asn Gly Ala Leu Glu Val His Thr His Met Gly Ile Phe
50 55 60

Lys Ala Pro Asn Met Thr Ser Leu Gln Val Phe Pro Leu Gln Gly Arg
65 70 75 80

```
Asp Leu Ile Ile Val Lys Met Pro Lys Asp Phe Pro Ala Phe Pro Gln
                85                  90                  95

Lys Leu His Phe Arg Gly Pro Arg Ala Asn Glu Arg Val Cys Met Val
            100                 105                 110

Gly Ser Asn Phe Gln Asn Lys Ser Ile Ser Ser Thr Val Ser Glu Thr
        115                 120                 125

Ser Pro Thr His Pro Ile Gln Arg Ser Thr Phe Trp Lys His Trp Ile
    130                 135                 140

Asp Thr Asn Asp Gly Gln Cys Gly Leu Pro Ile Ala Ser Thr His Asp
145                 150                 155                 160

Gly Ser Ile Leu Gly Leu His Ser Leu Ala Asn Asn Asn Thr Ser Glu
                165                 170                 175

Asn Tyr Phe Val Ala Phe Asp Asp Glu Phe Glu Glu Lys His Leu Arg
            180                 185                 190

Thr Ser Glu His Thr Glu Trp Val Lys Asn Trp Lys Tyr Asn Pro Asp
        195                 200                 205

Lys Val Leu Trp Gly Ser Leu Gln Leu Lys Glu Asp Lys Pro Asn Gly
    210                 215                 220

Leu Phe Lys Thr Thr Lys Leu Val Ser Asp Leu His Glu Ser Thr Ser
225                 230                 235                 240

Val Arg Glu Gln


<210> SEQ ID NO 68

<400> SEQUENCE: 68

000


<210> SEQ ID NO 69

<400> SEQUENCE: 69

000


<210> SEQ ID NO 70
<211> LENGTH: 7
<212> TYPE: PRT
<213> ORGANISM: Plum pox virus
<220> FEATURE:
<221> NAME/KEY: MISC_FEATURE
<222> LOCATION: (1)..(7)
<223> OTHER INFORMATION: Plum pox virus NIa protease recognition
      sequence

<400> SEQUENCE: 70

Asn Val Val Val His Gln Ala
1               5


<210> SEQ ID NO 71
<211> LENGTH: 7
<212> TYPE: PRT
<213> ORGANISM: Tobacco vein mottling virus
<220> FEATURE:
<221> NAME/KEY: MISC_FEATURE
<222> LOCATION: (1)..(7)
<223> OTHER INFORMATION: Tobacco vein mottling virus NIa protease
      recognition sequence

<400> SEQUENCE: 71

Glu Thr Val Arg Phe Gln Ser
1               5
```

<210> SEQ ID NO 72
<211> LENGTH: 7
<212> TYPE: PRT
<213> ORGANISM: Potato virus Y
<220> FEATURE:
<221> NAME/KEY: MISC_FEATURE
<222> LOCATION: (1)..(7)
<223> OTHER INFORMATION: Potato virus Y NIa protease recognition
      sequence

<400> SEQUENCE: 72

Tyr Glu Val His His Gln Ala
1               5

<210> SEQ ID NO 73
<211> LENGTH: 6
<212> TYPE: PRT
<213> ORGANISM: Turnip mosaic virus
<220> FEATURE:
<221> NAME/KEY: MISC_FEATURE
<222> LOCATION: (1)..(6)
<223> OTHER INFORMATION: Turnip Mosaic virus NIa protease recognition
      sequence derivative

<400> SEQUENCE: 73

Ile Val Arg His Gln Ser
1               5

<210> SEQ ID NO 74
<211> LENGTH: 7
<212> TYPE: PRT
<213> ORGANISM: Pea seed-borne mosaic virus
<220> FEATURE:
<221> NAME/KEY: MISC_FEATURE
<222> LOCATION: (1)..(7)
<223> OTHER INFORMATION: Pea seed-borne NIa protease recognition
      sequence

<400> SEQUENCE: 74

Ile Lys Val Arg Leu Gln Ala
1               5

<210> SEQ ID NO 75
<211> LENGTH: 6
<212> TYPE: PRT
<213> ORGANISM: Turnip mosaic virus
<220> FEATURE:
<221> NAME/KEY: MISC_FEATURE
<222> LOCATION: (1)..(1)
<223> OTHER INFORMATION: X at position 1 is E, A, L or I
<220> FEATURE:
<221> NAME/KEY: MISC_FEATURE
<222> LOCATION: (1)..(6)
<223> OTHER INFORMATION: Turnip mosaic virus recognition sequence

<400> SEQUENCE: 75

Xaa Val Arg His Gln Ser
1               5

<210> SEQ ID NO 76
<211> LENGTH: 7
<212> TYPE: PRT
<213> ORGANISM: Clover yellow mosaic virus
<220> FEATURE:
<221> NAME/KEY: MISC_FEATURE
<222> LOCATION: (1)..(6)
<223> OTHER INFORMATION: Clover yellow vein virus NIa protease
      recognition sequence

<400> SEQUENCE: 76

Met Leu Phe Val Phe Gln Ser
1               5

<210> SEQ ID NO 77
<211> LENGTH: 8
<212> TYPE: PRT
<213> ORGANISM: Pepper vein banding virus
<220> FEATURE:
<221> NAME/KEY: MISC_FEATURE
<222> LOCATION: (1)..(8)
<223> OTHER INFORMATION: Pepper vein banding virus NIa protease
      recogntion sequence

<400> SEQUENCE: 77

Gly Gly Gln Val Ala His Gln Ala
1               5

<210> SEQ ID NO 78
<211> LENGTH: 7
<212> TYPE: PRT
<213> ORGANISM: chilli veinal mottle virus
<220> FEATURE:
<221> NAME/KEY: MISC_FEATURE
<222> LOCATION: (1)..(7)
<223> OTHER INFORMATION: Chilli veinal mottle virus NIa protease
      recognition sequence

<400> SEQUENCE: 78

Gly Gln Val Ala His Gln Ala
1               5

<210> SEQ ID NO 79
<211> LENGTH: 6
<212> TYPE: PRT
<213> ORGANISM: Sunflower chlorotic mottle virus
<220> FEATURE:
<221> NAME/KEY: MISC_FEATURE
<222> LOCATION: (1)..(6)
<223> OTHER INFORMATION: Sunflower chlortic mosaic virus NIa protease
      recognition sequence
<220> FEATURE:
<221> NAME/KEY: MISC_FEATURE
<222> LOCATION: (1)..(6)
<223> OTHER INFORMATION: Sunflower chlortic mottle virus NIa protease
      recognition sequence

<400> SEQUENCE: 79

Glu Val Arg His Gln Ser
1               5

<210> SEQ ID NO 80
<211> LENGTH: 6
<212> TYPE: PRT
<213> ORGANISM: lettuce mosaic virus
<220> FEATURE:
<221> NAME/KEY: MISC_FEATURE
<222> LOCATION: (1)..(6)
<223> OTHER INFORMATION: Lettuce mosaic virus NIa protease recognition
      sequence

<400> SEQUENCE: 80

Ala Val Arg His Gln Ser
1               5

<210> SEQ ID NO 81
<211> LENGTH: 6
<212> TYPE: PRT
<213> ORGANISM: Bidens mottle virus
<220> FEATURE:

<221> NAME/KEY: MISC_FEATURE
<222> LOCATION: (1)..(6)
<223> OTHER INFORMATION: Bidens mottle virus NIa protease recognition
sequence

<400> SEQUENCE: 81

Leu Val Arg His Gln Ser
1 5

<210> SEQ ID NO 82
<211> LENGTH: 7
<212> TYPE: PRT
<213> ORGANISM: tobacco etch virus
<220> FEATURE:
<221> NAME/KEY: MISC_FEATURE
<222> LOCATION: (1)..(7)
<223> OTHER INFORMATION: Tobacco etch virus NIa protease recognition
sequence

<400> SEQUENCE: 82

Glu Asn Leu Tyr Phe Gln Ser
1 5

<210> SEQ ID NO 83
<211> LENGTH: 7
<212> TYPE: PRT
<213> ORGANISM: Tobacco etch virus
<220> FEATURE:
<221> NAME/KEY: MISC_FEATURE
<222> LOCATION: (1)..(7)
<223> OTHER INFORMATION: Tobacco etch virus NIa protease recognition
sequence

<400> SEQUENCE: 83

Glu Asn Leu Tyr Phe Gln Gly
1 5

<210> SEQ ID NO 84

<400> SEQUENCE: 84

000

<210> SEQ ID NO 85
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: O1 Manissa 3C protease

<400> SEQUENCE: 85 agt ggt gcc ccc ccg acc gac ttg caa aag atg gtc atg ggc aac acc 48
Ser Gly Ala Pro Pro Thr Asp Leu Gln Lys Met Val Met Gly Asn Thr
1 5 10 15 aag ccc gtc gaa ctc atc ctc gac ggg aag aca gta gcc atc tgt tgt 96
Lys Pro Val Glu Leu Ile Leu Asp Gly Lys Thr Val Ala Ile Cys Cys
20 25 30 gct act gga gtg ttt ggc act gcc tac ctc gtg cct cgt cac ctt ttc 144
Ala Thr Gly Val Phe Gly Thr Ala Tyr Leu Val Pro Arg His Leu Phe
35 40 45 gca gaa aag tac gac aag atc atg ctg gac ggc aga gcc atg aca gac 192
Ala Glu Lys Tyr Asp Lys Ile Met Leu Asp Gly Arg Ala Met Thr Asp
50 55 60 agt gac tac aga gtg ttt gag ttt gag att aaa gta aaa ggg cag gac 240
Ser Asp Tyr Arg Val Phe Glu Phe Glu Ile Lys Val Lys Gly Gln Asp

```
65                  70                  75                  80

atg ctc tca gac gcc gca ctc atg gtg ctc cac cgc ggg aac cgc gtg      288
Met Leu Ser Asp Ala Ala Leu Met Val Leu His Arg Gly Asn Arg Val
                85                  90                  95

aga gac atc acg aaa cac ttt cgt gac aca gca aaa atg aag aaa ggc      336
Arg Asp Ile Thr Lys His Phe Arg Asp Thr Ala Lys Met Lys Lys Gly
            100                 105                 110

acc ccc gtc gtt ggt gtg atc aac aat gcc gac gtt ggg aga ttg att      384
Thr Pro Val Val Gly Val Ile Asn Asn Ala Asp Val Gly Arg Leu Ile
        115                 120                 125

ttc tct ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

ggc gac acc atg cct ggc ctc ttt gcc tac aga gca gcc acc aag gct      480
Gly Asp Thr Met Pro Gly Leu Phe Ala Tyr Arg Ala Ala Thr Lys Ala
145                 150                 155                 160

ggt tac tgc gga gga gcc gtt ctt gct aag gac gga gct gac aca ttc      528
Gly Tyr Cys Gly Gly Ala Val Leu Ala Lys Asp Gly Ala Asp Thr Phe
                165                 170                 175

atc gtt ggc act cac tct gcg ggt ggc aat gga gtt gga tat tgc tca      576
Ile Val Gly Thr His Ser Ala Gly Gly Asn Gly Val Gly Tyr Cys Ser
            180                 185                 190

tgc gtt tcc agg tcc atg ctt ttg aaa atg aag gca cac att gac ccc      624
Cys Val Ser Arg Ser Met Leu Leu Lys Met Lys Ala His Ile Asp Pro
        195                 200                 205

gaa cca cac cac gag                                                  639
Glu Pro His His Glu
    210


<210> SEQ ID NO 86
<211> LENGTH: 213
<212> TYPE: PRT
<213> ORGANISM: Foot-and-mouth disease virus

<400> SEQUENCE: 86

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Lys Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175
```

```
Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 87
<211> LENGTH: 639
<212> TYPE: DNA
<213> ORGANISM: Foot-and-mouth disease virus
<220> FEATURE:
<221> NAME/KEY: CDS
<222> LOCATION: (1)..(639)
<223> OTHER INFORMATION: FMDV Asia Lebanon 89 3C Protease

<400> SEQUENCE: 87

agt ggt gcc cca ccg acc gac ttg caa aag atg gtc atg agc aac act       48
Ser Gly Ala Pro Pro Thr Asp Leu Gln Lys Met Val Met Ser Asn Thr
1               5                   10                  15

aag cct gtt gag ctc atc ctt gac ggt aag acg gtg gcc atc tgc tgc       96
Lys Pro Val Glu Leu Ile Leu Asp Gly Lys Thr Val Ala Ile Cys Cys
            20                  25                  30

gcc acc gga gtg ttt ggt act gcc tac ctc gtg cct cgt cac ctt ttc      144
Ala Thr Gly Val Phe Gly Thr Ala Tyr Leu Val Pro Arg His Leu Phe
        35                  40                  45

gca gaa aag tac gac agg atc atg ttg gac ggc agg gcc atg aca gac      192
Ala Glu Lys Tyr Asp Arg Ile Met Leu Asp Gly Arg Ala Met Thr Asp
    50                  55                  60

agt gac tac aga gtg ttt gag ttt gag att aaa gta aaa gga cag gac      240
Ser Asp Tyr Arg Val Phe Glu Phe Glu Ile Lys Val Lys Gly Gln Asp
65                  70                  75                  80

atg ctc tca gac gct gcg ctc atg gtg ctc cac cgt ggc aac cgt gtg      288
Met Leu Ser Asp Ala Ala Leu Met Val Leu His Arg Gly Asn Arg Val
                85                  90                  95

aga gac atc acg aaa cac ttt cgt gat aca gca aga atg aag aaa ggt      336
Arg Asp Ile Thr Lys His Phe Arg Asp Thr Ala Arg Met Lys Lys Gly
            100                 105                 110

acc ccc gtt gtc ggc gtg atc aac aac gcc gac gtt ggg aga ctg att      384
Thr Pro Val Val Gly Val Ile Asn Asn Ala Asp Val Gly Arg Leu Ile
        115                 120                 125

ttc tcc ggt gag gcc ctc acc tac aag gac att gta gtg tgc atg gat      432
Phe Ser Gly Glu Ala Leu Thr Tyr Lys Asp Ile Val Val Cys Met Asp
    130                 135                 140

gga gac acc atg ccg ggc cta ttt gcc tac aga gcc gct acc aag gct      480
Gly Asp Thr Met Pro Gly Leu Phe Ala Tyr Arg Ala Ala Thr Lys Ala
145                 150                 155                 160

ggc tac tgt gga gga gcc gtt ctt gcc aag gac gga gct gac aca ttt      528
Gly Tyr Cys Gly Gly Ala Val Leu Ala Lys Asp Gly Ala Asp Thr Phe
                165                 170                 175

atc gtc ggc act cac tcc gca gga ggc aat gga gtc ggg tac tgc tca      576
Ile Val Gly Thr His Ser Ala Gly Gly Asn Gly Val Gly Tyr Cys Ser
            180                 185                 190

tgc gta tct agg tcc atg ctc ttg aag atg aag gca cac att gac ccc      624
Cys Val Ser Arg Ser Met Leu Leu Lys Met Lys Ala His Ile Asp Pro
        195                 200                 205

gaa cca cac cac gag                                                  639
Glu Pro His His Glu
    210


<210> SEQ ID NO 88
```

```
<211> LENGTH: 213
<212> TYPE: PRT
<213> ORGANISM: Foot-and-mouth disease virus

<400> SEQUENCE: 88

Ser Gly Ala Pro Pro Thr Asp Leu Gln Lys Met Val Met Ser Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Arg Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
    130                 135                 140

Gly Asp Thr Met Pro Gly Leu Phe Ala Tyr Arg Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu
    210


<210> SEQ ID NO 89
<211> LENGTH: 564
<212> TYPE: DNA
<213> ORGANISM: Foot-and-mouth disease virus
<220> FEATURE:
<221> NAME/KEY: CDS
<222> LOCATION: (1)..(564)
<223> OTHER INFORMATION: SAT1 3C(wt) Accession Number: AY593838.1

<400> SEQUENCE: 89

agc gga tgt cca ccg acc gac ctg cag agg atg gtc atg gca aac gtg       48
Ser Gly Cys Pro Pro Thr Asp Leu Gln Arg Met Val Met Ala Asn Val
1               5                   10                  15

aaa ccc gtt gag ctc atc ctc gat ggg aag acc gtt gcg ctc tgc tgc       96
Lys Pro Val Glu Leu Ile Leu Asp Gly Lys Thr Val Ala Leu Cys Cys
            20                  25                  30

gct acg gga gtg ttc ggg acg gct tat ctc gtg cct cgt cat ctt ttc      144
Ala Thr Gly Val Phe Gly Thr Ala Tyr Leu Val Pro Arg His Leu Phe
        35                  40                  45

gca gag aag tac gac aag atc atg ctg gac ggc cgt gcc ctg aca gac      192
Ala Glu Lys Tyr Asp Lys Ile Met Leu Asp Gly Arg Ala Leu Thr Asp
    50                  55                  60

agt gac ttc aga gtg ttt gag ttt gag gtg aaa gta aaa gga cag gac      240
Ser Asp Phe Arg Val Phe Glu Phe Glu Val Lys Val Lys Gly Gln Asp
65                  70                  75                  80
```

```
atg ctc tca gat gcc gcg ctc atg gtt ctc cac tcc gga aac cgt gtg      288
Met Leu Ser Asp Ala Ala Leu Met Val Leu His Ser Gly Asn Arg Val
                85                  90                  95

cgc gat ctc acg gga cac ttc cgt gac aca atg aaa ctg tcg aaa ggc      336
Arg Asp Leu Thr Gly His Phe Arg Asp Thr Met Lys Leu Ser Lys Gly
            100                 105                 110

agt ccc gtc gtt ggt gtg gtc aac aac gcc gac gtc gga aga ctc atc      384
Ser Pro Val Val Gly Val Val Asn Asn Ala Asp Val Gly Arg Leu Ile
        115                 120                 125

ttc tca gga gac gca ctg acc tac aaa gac ctg gtc gtt tgt atg gac      432
Phe Ser Gly Asp Ala Leu Thr Tyr Lys Asp Leu Val Val Cys Met Asp
    130                 135                 140

ggt gac acc atg ccc gga ctc ttc gca tac cgc gcg ggg acc aag gtt      480
Gly Asp Thr Met Pro Gly Leu Phe Ala Tyr Arg Ala Gly Thr Lys Val
145                 150                 155                 160

ggt tat tgt gga gca gcc gtt ctt gca aaa gac ggc gcc aag act gtg      528
Gly Tyr Cys Gly Ala Ala Val Leu Ala Lys Asp Gly Ala Lys Thr Val
                165                 170                 175

atc gtc ggc acc cac tca gcc ggt ggc aac gga gta                      564
Ile Val Gly Thr His Ser Ala Gly Gly Asn Gly Val
            180                 185


<210> SEQ ID NO 90
<211> LENGTH: 188
<212> TYPE: PRT
<213> ORGANISM: Foot-and-mouth disease virus

<400> SEQUENCE: 90

Ser Gly Cys Pro Pro Thr Asp Leu Gln Arg Met Val Met Ala Asn Val
1               5                   10                  15

Lys Pro Val Glu Leu Ile Leu Asp Gly Lys Thr Val Ala Leu Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Leu Thr Asp
    50                  55                  60

Ser Asp Phe Arg Val Phe Glu Phe Glu Val Lys Val Lys Gly Gln Asp
65                  70                  75                  80

Met Leu Ser Asp Ala Ala Leu Met Val Leu His Ser Gly Asn Arg Val
                85                  90                  95

Arg Asp Leu Thr Gly His Phe Arg Asp Thr Met Lys Leu Ser Lys Gly
            100                 105                 110

Ser Pro Val Val Gly Val Val Asn Asn Ala Asp Val Gly Arg Leu Ile
        115                 120                 125

Phe Ser Gly Asp Ala Leu Thr Tyr Lys Asp Leu Val Val Cys Met Asp
    130                 135                 140

Gly Asp Thr Met Pro Gly Leu Phe Ala Tyr Arg Ala Gly Thr Lys Val
145                 150                 155                 160

Gly Tyr Cys Gly Ala Ala Val Leu Ala Lys Asp Gly Ala Lys Thr Val
                165                 170                 175

Ile Val Gly Thr His Ser Ala Gly Gly Asn Gly Val
            180                 185


<210> SEQ ID NO 91
<211> LENGTH: 639
<212> TYPE: DNA
<213> ORGANISM: Foot-and-mouth disease virus
<220> FEATURE:
```

```
<221> NAME/KEY: CDS
<222> LOCATION: (1)..(639)
<223> OTHER INFORMATION: SAT2 Egypt 3/2012 3C; Accession Number:
      KC440884.1

<400> SEQUENCE: 91

agt gga gcg cca ccc acc gac ttg caa aag atg gtg atg gcc aac acc       48
Ser Gly Ala Pro Pro Thr Asp Leu Gln Lys Met Val Met Ala Asn Thr
1               5                   10                  15

aaa cca gtc gag ctc ata ctc gat ggt aag aca gtg gcg atc tgc tgt       96
Lys Pro Val Glu Leu Ile Leu Asp Gly Lys Thr Val Ala Ile Cys Cys
            20                  25                  30

gcc act gga gtg ttt ggg act gcc tat ctc gtg cct cgt cat ctt ttc      144
Ala Thr Gly Val Phe Gly Thr Ala Tyr Leu Val Pro Arg His Leu Phe
        35                  40                  45

gct gag aag tat gac aag atc atg att gac ggc agg gcc atg aca gac      192
Ala Glu Lys Tyr Asp Lys Ile Met Ile Asp Gly Arg Ala Met Thr Asp
    50                  55                  60

cgt gat ttc aga gtg ttt gag ttt gag att aaa gta aaa gga cag gac      240
Arg Asp Phe Arg Val Phe Glu Phe Glu Ile Lys Val Lys Gly Gln Asp
65                  70                  75                  80

atg ctc tcg gac gcc gcc ctc atg gtg ctg cac cgt ggg aac cgc gtg      288
Met Leu Ser Asp Ala Ala Leu Met Val Leu His Arg Gly Asn Arg Val
                85                  90                  95

aga gac atc acg aag cac ttt cgt gat caa gca aga atg aga aaa gga      336
Arg Asp Ile Thr Lys His Phe Arg Asp Gln Ala Arg Met Arg Lys Gly
            100                 105                 110

acc ccc gtg gtt ggc gtg atc aac aac gcc gac gtt ggg aga ctc atc      384
Thr Pro Val Val Gly Val Ile Asn Asn Ala Asp Val Gly Arg Leu Ile
        115                 120                 125

ttc tct gga gag gca ctc acc tac aaa gac att gta gtg tgt atg gat      432
Phe Ser Gly Glu Ala Leu Thr Tyr Lys Asp Ile Val Val Cys Met Asp
    130                 135                 140

ggc gac acc atg cca ggc ctc ttt gcc tat aaa gcc gcc acc aaa gct      480
Gly Asp Thr Met Pro Gly Leu Phe Ala Tyr Lys Ala Ala Thr Lys Ala
145                 150                 155                 160

ggc tac tgt gga gga gcc gtt ctt gcg aaa gac gga gcc gag act ttc      528
Gly Tyr Cys Gly Gly Ala Val Leu Ala Lys Asp Gly Ala Glu Thr Phe
                165                 170                 175

atc gtc ggc act cac tcc gct gga gga aac gga gtt ggt tac tgc tct      576
Ile Val Gly Thr His Ser Ala Gly Gly Asn Gly Val Gly Tyr Cys Ser
            180                 185                 190

tgc gtt tcc aag tcc atg ctc ctg caa atg aag gca cac att gat cct      624
Cys Val Ser Lys Ser Met Leu Leu Gln Met Lys Ala His Ile Asp Pro
        195                 200                 205

gaa cca cac cac gaa                                                  639
Glu Pro His His Glu
    210


<210> SEQ ID NO 92
<211> LENGTH: 213
<212> TYPE: PRT
<213> ORGANISM: Foot-and-mouth disease virus

<400> SEQUENCE: 92

Ser Gly Ala Pro Pro Thr Asp Leu Gln Lys Met Val Met Ala Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45
```

Ala Glu Lys Tyr Asp Lys Ile Met Ile Asp Gly Arg Ala Met Thr Asp
50 55 60

Arg Asp Phe Arg Val Phe Glu Phe Glu Ile Lys Val Lys Gly Gln Asp
65 70 75 80

Met Leu Ser Asp Ala Ala Leu Met Val Leu His Arg Gly Asn Arg Val
85 90 95

Arg Asp Ile Thr Lys His Phe Arg Asp Gln Ala Arg Met Arg Lys Gly
100 105 110

Thr Pro Val Val Gly Val Ile Asn Asn Ala Asp Val Gly Arg Leu Ile
115 120 125

Phe Ser Gly Glu Ala Leu Thr Tyr Lys Asp Ile Val Val Cys Met Asp
130 135 140

Gly Asp Thr Met Pro Gly Leu Phe Ala Tyr Lys Ala Ala Thr Lys Ala
145 150 155 160

Gly Tyr Cys Gly Gly Ala Val Leu Ala Lys Asp Gly Ala Glu Thr Phe
165 170 175

Ile Val Gly Thr His Ser Ala Gly Gly Asn Gly Val Gly Tyr Cys Ser
180 185 190

Cys Val Ser Lys Ser Met Leu Leu Gln Met Lys Ala His Ile Asp Pro
195 200 205

Glu Pro His His Glu
210

<210> SEQ ID NO 93
<211> LENGTH: 3012
<212> TYPE: DNA
<213> ORGANISM: Artificial Sequence
<220> FEATURE:
<223> OTHER INFORMATION: pMM construct containing modified P1 with minimum TEV recognition sequence at VP4/VP2, VP2/VP3 and VP3/VP4 junction sites.
<220> FEATURE:
<221> NAME/KEY: CDS
<222> LOCATION: (1)..(3012)

<400> SEQUENCE: 93 atg gga gcc ggg caa tcc agc ccg gca acc ggg tca cag aac caa tca 48
Met Gly Ala Gly Gln Ser Ser Pro Ala Thr Gly Ser Gln Asn Gln Ser
1 5 10 15 ggc aac act ggg agc atc atc aac aat tac tac atg cag cag tac caa 96
Gly Asn Thr Gly Ser Ile Ile Asn Asn Tyr Tyr Met Gln Gln Tyr Gln
20 25 30 aac tct atg gac aca caa ctt ggt gac aac gct aca agc gga ggc tca 144
Asn Ser Met Asp Thr Gln Leu Gly Asp Asn Ala Thr Ser Gly Gly Ser
35 40 45 aac gag ggg tcc acg gac aca acc tcc acc cac aca acc aac act cag 192
Asn Glu Gly Ser Thr Asp Thr Thr Ser Thr His Thr Thr Asn Thr Gln
50 55 60 aac aac gac tgg ttc tcg aag ctg gcc agt tcc gct ttc agc ggt ctt 240
Asn Asn Asp Trp Phe Ser Lys Leu Ala Ser Ser Ala Phe Ser Gly Leu
65 70 75 80 gaa ggc gct tat ctc caa tcc aag aaa acc gag gag acc act ctt ctt 288
Glu Gly Ala Tyr Leu Gln Ser Lys Lys Thr Glu Glu Thr Thr Leu Leu
85 90 95 gag gac cgc atc ctc act act cgt aac gga cac acc acc tcg aca acc 336
Glu Asp Arg Ile Leu Thr Thr Arg Asn Gly His Thr Thr Ser Thr Thr
100 105 110 cag tcg agc gta gga gtc aca tac ggg tat gca acg gct gag gat ttc 384
Gln Ser Ser Val Gly Val Thr Tyr Gly Tyr Ala Thr Ala Glu Asp Phe -continued

```
        115                 120                 125

gtg agc ggg cca aac acc tct ggt ctt gag acc agg gtt gcc cag gca      432
Val Ser Gly Pro Asn Thr Ser Gly Leu Glu Thr Arg Val Ala Gln Ala
    130                 135                 140

gag cgg ttc ttt aaa acc cac ctg ttc gac tgg gtc aca agt gac ccg      480
Glu Arg Phe Phe Lys Thr His Leu Phe Asp Trp Val Thr Ser Asp Pro
145                 150                 155                 160

ttc gga cgg tgc cac ctg cta gaa ctt cca act gac cac aaa ggt gtc      528
Phe Gly Arg Cys His Leu Leu Glu Leu Pro Thr Asp His Lys Gly Val
                165                 170                 175

tat ggc agc ctg acc gac tcg tat gct tat atg agg aac ggc tgg gat      576
Tyr Gly Ser Leu Thr Asp Ser Tyr Ala Tyr Met Arg Asn Gly Trp Asp
            180                 185                 190

gtt gaa gtc act gct gtg gga aat cag ttc aat gga gga tgc ctg ttg      624
Val Glu Val Thr Ala Val Gly Asn Gln Phe Asn Gly Gly Cys Leu Leu
        195                 200                 205

gtg gct atg gtg cca gaa ctt tgc tcc ata cag aag agg gag ctg tac      672
Val Ala Met Val Pro Glu Leu Cys Ser Ile Gln Lys Arg Glu Leu Tyr
    210                 215                 220

cag ctc acg ctc ttt cct cac cag ttc atc aac cct cgg acg aac atg      720
Gln Leu Thr Leu Phe Pro His Gln Phe Ile Asn Pro Arg Thr Asn Met
225                 230                 235                 240

aca gca cac atc act gtg ccc ttt gtt ggc gtc aac cgt tat gac cag      768
Thr Ala His Ile Thr Val Pro Phe Val Gly Val Asn Arg Tyr Asp Gln
                245                 250                 255

tac aag gta cac aaa cct tgg acc ctc gtg gtt atg gtt gta gcc ccc      816
Tyr Lys Val His Lys Pro Trp Thr Leu Val Val Met Val Val Ala Pro
            260                 265                 270

ctg acc gtc aac agt gaa ggt gcc ccg caa atc aag gtg tat gcc aac      864
Leu Thr Val Asn Ser Glu Gly Ala Pro Gln Ile Lys Val Tyr Ala Asn
        275                 280                 285

atc gca cct acc aac gta cac gtc gcg ggt gag ttc cct tat aaa cag      912
Ile Ala Pro Thr Asn Val His Val Ala Gly Glu Phe Pro Tyr Lys Gln
    290                 295                 300

ggg atc ttc cct gtg gct tgc agc gat ggt tat ggc ggt ctg gtg aca      960
Gly Ile Phe Pro Val Ala Cys Ser Asp Gly Tyr Gly Gly Leu Val Thr
305                 310                 315                 320

act gac ccg aaa acg gct gac ccc gct tac ggg aaa gtg ttt aac ccc     1008
Thr Asp Pro Lys Thr Ala Asp Pro Ala Tyr Gly Lys Val Phe Asn Pro
                325                 330                 335

ccc cgc aac atg ttg ccg ggg cgg ttc acc aat ttt ctt gac gtg gct     1056
Pro Arg Asn Met Leu Pro Gly Arg Phe Thr Asn Phe Leu Asp Val Ala
            340                 345                 350

gag gcg tgc ccc acg ttt ctc cac ttc gag ggt gac gtg cca tac gtg     1104
Glu Ala Cys Pro Thr Phe Leu His Phe Glu Gly Asp Val Pro Tyr Val
        355                 360                 365

acc acg aag acg gat tca gac agg gtg ctc gct cag ttc gac ttg tct     1152
Thr Thr Lys Thr Asp Ser Asp Arg Val Leu Ala Gln Phe Asp Leu Ser
    370                 375                 380

ttg gca gca aag cac atg tcc aac acc ttc ctt gca ggt ctc gcc cag     1200
Leu Ala Ala Lys His Met Ser Asn Thr Phe Leu Ala Gly Leu Ala Gln
385                 390                 395                 400

tac tac aca cag tac agc ggc acc atc aac ctg cac ttc atg ttc aca     1248
Tyr Tyr Thr Gln Tyr Ser Gly Thr Ile Asn Leu His Phe Met Phe Thr
                405                 410                 415

ggg cct act gac gcg aag gcg cgt tac atg att gcg tat gct cct cct     1296
Gly Pro Thr Asp Ala Lys Ala Arg Tyr Met Ile Ala Tyr Ala Pro Pro
            420                 425                 430

ggc atg gaa cca cct aaa acg cca gag gcg gct gcc cac tgc atc cat     1344
```

-continued

```
Gly Met Glu Pro Pro Lys Thr Pro Glu Ala Ala Ala His Cys Ile His
        435                 440                 445

gct gaa tgg gac aca ggg ttg aac tca aaa ttc aca ttt tca atc cct      1392
Ala Glu Trp Asp Thr Gly Leu Asn Ser Lys Phe Thr Phe Ser Ile Pro
    450                 455                 460

tac ctt tcg gcg gct gat tac gct tac aca gcg tct gac act gct gag      1440
Tyr Leu Ser Ala Ala Asp Tyr Ala Tyr Thr Ala Ser Asp Thr Ala Glu
465                 470                 475                 480

acc aca aat gta cag gga tgg gtt tgc ctg ttt caa ata aca cac ggg      1488
Thr Thr Asn Val Gln Gly Trp Val Cys Leu Phe Gln Ile Thr His Gly
                485                 490                 495

aaa gct gac ggc gac gca ctg gtc gtt ttg gcc agc gcc gga aag gac      1536
Lys Ala Asp Gly Asp Ala Leu Val Val Leu Ala Ser Ala Gly Lys Asp
            500                 505                 510

ttt gag ctg cgc ctg ccg gaa gat gct tac aca cag tcc acc tca gcg      1584
Phe Glu Leu Arg Leu Pro Glu Asp Ala Tyr Thr Gln Ser Thr Ser Ala
        515                 520                 525

ggc gag tca gca gac ccc gtg acc gcc acc gtt gag aat tac ggt ggc      1632
Gly Glu Ser Ala Asp Pro Val Thr Ala Thr Val Glu Asn Tyr Gly Gly
    530                 535                 540

gag aca cag gtc cag agg cgc caa cac acg gac gtg tca ttt ata tta      1680
Glu Thr Gln Val Gln Arg Arg Gln His Thr Asp Val Ser Phe Ile Leu
545                 550                 555                 560

gac aga ttt gtg aaa gtg aca cca aaa gac caa att aat gta ttg gac      1728
Asp Arg Phe Val Lys Val Thr Pro Lys Asp Gln Ile Asn Val Leu Asp
                565                 570                 575

ctg atg caa acc cct gct cac act ttg gtg gga gca ctc ctt cgt act      1776
Leu Met Gln Thr Pro Ala His Thr Leu Val Gly Ala Leu Leu Arg Thr
            580                 585                 590

gcc act tac tat ttc gct gac tta gag gtg gca gtg aag cac gag gga      1824
Ala Thr Tyr Tyr Phe Ala Asp Leu Glu Val Ala Val Lys His Glu Gly
        595                 600                 605

aac ctc acc tgg gtg ccg aac ggg gcg cct gaa gcg gcg ttg gac aac      1872
Asn Leu Thr Trp Val Pro Asn Gly Ala Pro Glu Ala Ala Leu Asp Asn
    610                 615                 620

acc acc aac cca aca gct tac cac aag gca cca ctc acc cga ctt gca      1920
Thr Thr Asn Pro Thr Ala Tyr His Lys Ala Pro Leu Thr Arg Leu Ala
625                 630                 635                 640

ctg cct tac acg gcg cca cac cgc gtg ttg gct act gtt tac aac ggg      1968
Leu Pro Tyr Thr Ala Pro His Arg Val Leu Ala Thr Val Tyr Asn Gly
                645                 650                 655

aac agc aag tat ggt gac ggc acg gtg gcc aat gtg aga ggt gat ctg      2016
Asn Ser Lys Tyr Gly Asp Gly Thr Val Ala Asn Val Arg Gly Asp Leu
            660                 665                 670

caa gtg ttg gcc cag aag gcg gcg aga gcg ctg cct acc tcc ttc aac      2064
Gln Val Leu Ala Gln Lys Ala Ala Arg Ala Leu Pro Thr Ser Phe Asn
        675                 680                 685

tac ggt gcc att aaa gct act cgg gtg act gaa ctg ctt tac cgc atg      2112
Tyr Gly Ala Ile Lys Ala Thr Arg Val Thr Glu Leu Leu Tyr Arg Met
    690                 695                 700

aag agg gct gag aca tac tgt ccc cgg cct ctt ttg gcc att cac ccg      2160
Lys Arg Ala Glu Thr Tyr Cys Pro Arg Pro Leu Leu Ala Ile His Pro
705                 710                 715                 720

gac cag gct aga cac aag cag aag att gtg gaa ccg tat aaa cag agt      2208
Asp Gln Ala Arg His Lys Gln Lys Ile Val Glu Pro Tyr Lys Gln Ser
                725                 730                 735

cta aat ttt gac ctg ctc aaa ttg gcg gga gat gtg gag tcc aac cct      2256
Leu Asn Phe Asp Leu Leu Lys Leu Ala Gly Asp Val Glu Ser Asn Pro
            740                 745                 750
```

```
ggg ccc gcg gcc gcc atg gac tat aaa gac gac gac gac aaa ccc ggg      2304
Gly Pro Ala Ala Ala Met Asp Tyr Lys Asp Asp Asp Asp Lys Pro Gly
        755                 760                 765

gaa agt ttg ttt aag ggg ccg cgt gat tac aac ccg atc tca agc acc      2352
Glu Ser Leu Phe Lys Gly Pro Arg Asp Tyr Asn Pro Ile Ser Ser Thr
    770                 775                 780

att tgt cat ttg acg aat gaa tct gat ggg cac aca aca tcg ttg tat      2400
Ile Cys His Leu Thr Asn Glu Ser Asp Gly His Thr Thr Ser Leu Tyr
785                 790                 795                 800

ggt att gga ttt ggt ccc ttc atc att aca aac aag cac ttg ttt aga      2448
Gly Ile Gly Phe Gly Pro Phe Ile Ile Thr Asn Lys His Leu Phe Arg
                805                 810                 815

aga aat aat gga aca ctg ttg gtt caa tca cta cat ggt gta ttc aag      2496
Arg Asn Asn Gly Thr Leu Leu Val Gln Ser Leu His Gly Val Phe Lys
            820                 825                 830

gtc aag aac acc acg act ttg caa caa cac ctc att gat ggg agg gac      2544
Val Lys Asn Thr Thr Thr Leu Gln Gln His Leu Ile Asp Gly Arg Asp
        835                 840                 845

atg ata att att cgc atg cca aag gat ttc cca cca ttt cct caa aag      2592
Met Ile Ile Ile Arg Met Pro Lys Asp Phe Pro Pro Phe Pro Gln Lys
    850                 855                 860

ctg aaa ttt aga gag cca caa agg gaa gag cgc atc tgt ctt gtg aca      2640
Leu Lys Phe Arg Glu Pro Gln Arg Glu Glu Arg Ile Cys Leu Val Thr
865                 870                 875                 880

acc aac ttc caa act aag agc atg tct agc atg gtg tca gac acc agt      2688
Thr Asn Phe Gln Thr Lys Ser Met Ser Ser Met Val Ser Asp Thr Ser
                885                 890                 895

tgc aca ttc cct tca tct gat ggc ata ttc tgg aag cat tgg att caa      2736
Cys Thr Phe Pro Ser Ser Asp Gly Ile Phe Trp Lys His Trp Ile Gln
            900                 905                 910

acc aag gat ggg cag tgt ggc agt cca tta gta tca act aga gat ggg      2784
Thr Lys Asp Gly Gln Cys Gly Ser Pro Leu Val Ser Thr Arg Asp Gly
        915                 920                 925

ttc att gtt ggt att cac tca gca tcg aat ttc acc aac aca aac aat      2832
Phe Ile Val Gly Ile His Ser Ala Ser Asn Phe Thr Asn Thr Asn Asn
    930                 935                 940

tat ttc aca agc gtg ccg aag aac ttt atg gaa ttg ttg aca aat cag      2880
Tyr Phe Thr Ser Val Pro Lys Asn Phe Met Glu Leu Leu Thr Asn Gln
945                 950                 955                 960

gag gcg cag cag tgg gtt agt ggt tgg cga tta aat gct gac tca gta      2928
Glu Ala Gln Gln Trp Val Ser Gly Trp Arg Leu Asn Ala Asp Ser Val
                965                 970                 975

ttg tgg ggg ggc cat aaa gtt ttc atg gtg aaa cct gaa gag cct ttt      2976
Leu Trp Gly Gly His Lys Val Phe Met Val Lys Pro Glu Glu Pro Phe
            980                 985                 990

cag cca gtt aag gaa gcg act caa  ctc atg aat taa                     3012
Gln Pro Val Lys Glu Ala Thr Gln  Leu Met Asn
        995                 1000


<210> SEQ ID NO 94
<211> LENGTH: 1003
<212> TYPE: PRT
<213> ORGANISM: Artificial Sequence
<220> FEATURE:
<223> OTHER INFORMATION: Synthetic Construct

<400> SEQUENCE: 94

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30
```

```
Asn Ser Met Asp Thr Gln Leu Gly Asp Asn Ala Thr Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Glu Gly Ala Tyr Leu Gln Ser Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Ala Gln Ala
    130                 135                 140

Glu Arg Phe Phe Lys Thr His Leu Phe Asp Trp Val Thr Ser Asp Pro
145                 150                 155                 160

Phe Gly Arg Cys His Leu Leu Glu Leu Pro Thr Asp His Lys Gly Val
                165                 170                 175

Tyr Gly Ser Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Leu Cys Ser Ile Gln Lys Arg Glu Leu Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Phe Val Gly Val Asn Arg Tyr Asp Gln
                245                 250                 255

Tyr Lys Val His Lys Pro Trp Thr Leu Val Val Met Val Val Ala Pro
            260                 265                 270

Leu Thr Val Asn Ser Glu Gly Ala Pro Gln Ile Lys Val Tyr Ala Asn
        275                 280                 285

Ile Ala Pro Thr Asn Val His Val Ala Gly Glu Phe Pro Tyr Lys Gln
    290                 295                 300

Gly Ile Phe Pro Val Ala Cys Ser Asp Gly Tyr Gly Gly Leu Val Thr
305                 310                 315                 320

Thr Asp Pro Lys Thr Ala Asp Pro Ala Tyr Gly Lys Val Phe Asn Pro
                325                 330                 335

Pro Arg Asn Met Leu Pro Gly Arg Phe Thr Asn Phe Leu Asp Val Ala
            340                 345                 350

Glu Ala Cys Pro Thr Phe Leu His Phe Glu Gly Asp Val Pro Tyr Val
        355                 360                 365

Thr Thr Lys Thr Asp Ser Asp Arg Val Leu Ala Gln Phe Asp Leu Ser
    370                 375                 380

Leu Ala Ala Lys His Met Ser Asn Thr Phe Leu Ala Gly Leu Ala Gln
385                 390                 395                 400

Tyr Tyr Thr Gln Tyr Ser Gly Thr Ile Asn Leu His Phe Met Phe Thr
                405                 410                 415

Gly Pro Thr Asp Ala Lys Ala Arg Tyr Met Ile Ala Tyr Ala Pro Pro
            420                 425                 430

Gly Met Glu Pro Pro Lys Thr Pro Glu Ala Ala Ala His Cys Ile His
        435                 440                 445
```

```
Ala Glu Trp Asp Thr Gly Leu Asn Ser Lys Phe Thr Phe Ser Ile Pro
    450                 455                 460

Tyr Leu Ser Ala Ala Asp Tyr Ala Tyr Thr Ala Ser Asp Thr Ala Glu
465                 470                 475                 480

Thr Thr Asn Val Gln Gly Trp Val Cys Leu Phe Gln Ile Thr His Gly
                485                 490                 495

Lys Ala Asp Gly Asp Ala Leu Val Val Leu Ala Ser Ala Gly Lys Asp
            500                 505                 510

Phe Glu Leu Arg Leu Pro Glu Asp Ala Tyr Thr Gln Ser Thr Ser Ala
        515                 520                 525

Gly Glu Ser Ala Asp Pro Val Thr Ala Thr Val Glu Asn Tyr Gly Gly
    530                 535                 540

Glu Thr Gln Val Gln Arg Arg Gln His Thr Asp Val Ser Phe Ile Leu
545                 550                 555                 560

Asp Arg Phe Val Lys Val Thr Pro Lys Asp Gln Ile Asn Val Leu Asp
                565                 570                 575

Leu Met Gln Thr Pro Ala His Thr Leu Val Gly Ala Leu Leu Arg Thr
            580                 585                 590

Ala Thr Tyr Tyr Phe Ala Asp Leu Glu Val Ala Val Lys His Glu Gly
        595                 600                 605

Asn Leu Thr Trp Val Pro Asn Gly Ala Pro Glu Ala Ala Leu Asp Asn
    610                 615                 620

Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Asn Ser Lys Tyr Gly Asp Gly Thr Val Ala Asn Val Arg Gly Asp Leu
            660                 665                 670

Gln Val Leu Ala Gln Lys Ala Ala Arg Ala Leu Pro Thr Ser Phe Asn
        675                 680                 685

Tyr Gly Ala Ile Lys Ala Thr Arg Val Thr Glu Leu Leu Tyr Arg Met
    690                 695                 700

Lys Arg Ala Glu Thr Tyr Cys Pro Arg Pro Leu Leu Ala Ile His Pro
705                 710                 715                 720

Asp Gln Ala Arg His Lys Gln Lys Ile Val Glu Pro Tyr Lys Gln Ser
                725                 730                 735

Leu Asn Phe Asp Leu Leu Lys Leu Ala Gly Asp Val Glu Ser Asn Pro
            740                 745                 750

Gly Pro Ala Ala Ala Met Asp Tyr Lys Asp Asp Asp Asp Lys Pro Gly
        755                 760                 765

Glu Ser Leu Phe Lys Gly Pro Arg Asp Tyr Asn Pro Ile Ser Ser Thr
    770                 775                 780

Ile Cys His Leu Thr Asn Glu Ser Asp Gly His Thr Thr Ser Leu Tyr
785                 790                 795                 800

Gly Ile Gly Phe Gly Pro Phe Ile Ile Thr Asn Lys His Leu Phe Arg
                805                 810                 815

Arg Asn Asn Gly Thr Leu Leu Val Gln Ser Leu His Gly Val Phe Lys
            820                 825                 830

Val Lys Asn Thr Thr Thr Leu Gln Gln His Leu Ile Asp Gly Arg Asp
        835                 840                 845

Met Ile Ile Ile Arg Met Pro Lys Asp Phe Pro Pro Phe Pro Gln Lys
    850                 855                 860

Leu Lys Phe Arg Glu Pro Gln Arg Glu Glu Arg Ile Cys Leu Val Thr
```

```
865                 870                 875                 880

Thr Asn Phe Gln Thr Lys Ser Met Ser Ser Met Val Ser Asp Thr Ser
                885                 890                 895

Cys Thr Phe Pro Ser Ser Asp Gly Ile Phe Trp Lys His Trp Ile Gln
            900                 905                 910

Thr Lys Asp Gly Gln Cys Gly Ser Pro Leu Val Ser Thr Arg Asp Gly
        915                 920                 925

Phe Ile Val Gly Ile His Ser Ala Ser Asn Phe Thr Asn Thr Asn Asn
    930                 935                 940

Tyr Phe Thr Ser Val Pro Lys Asn Phe Met Glu Leu Leu Thr Asn Gln
945                 950                 955                 960

Glu Ala Gln Gln Trp Val Ser Gly Trp Arg Leu Asn Ala Asp Ser Val
                965                 970                 975

Leu Trp Gly Gly His Lys Val Phe Met Val Lys Pro Glu Glu Pro Phe
            980                 985                 990

Gln Pro Val Lys Glu Ala Thr Gln  Leu Met Asn
        995                 1000


<210> SEQ ID NO 95
<211> LENGTH: 3000
<212> TYPE: DNA
<213> ORGANISM: Artificial Sequence
<220> FEATURE:
<223> OTHER INFORMATION: Nucleotide sequence for pOM construct
      containing a P1 modified with the optimum TEV recognition sequence
      present at VP4/VP2, VP2/VP3, VP3/VP4, and VP1/2A junction sites.
<220> FEATURE:
<221> NAME/KEY: CDS
<222> LOCATION: (1)..(3000)

<400> SEQUENCE: 95

atg gga gcc ggg caa tcc agc ccg gca acc ggg tca cag aac caa tca       48
Met Gly Ala Gly Gln Ser Ser Pro Ala Thr Gly Ser Gln Asn Gln Ser
1               5                   10                  15

ggc aac act ggg agc atc atc aac aat tac tac atg cag cag tac caa       96
Gly Asn Thr Gly Ser Ile Ile Asn Asn Tyr Tyr Met Gln Gln Tyr Gln
            20                  25                  30

aac tct atg gac aca caa ctt ggt gac aac gct aca agc gga ggc tca      144
Asn Ser Met Asp Thr Gln Leu Gly Asp Asn Ala Thr Ser Gly Gly Ser
        35                  40                  45

aac gag ggg tcc acg gac aca acc tcc acc cac aca acc aac act cag      192
Asn Glu Gly Ser Thr Asp Thr Thr Ser Thr His Thr Thr Asn Thr Gln
    50                  55                  60

aac aac gac tgg ttc tcg aag ctg gcc agt tcc gct ttc agc ggt ctt      240
Asn Asn Asp Trp Phe Ser Lys Leu Ala Ser Ser Ala Phe Ser Gly Leu
65                  70                  75                  80

gaa aac ctt tat ttc caa tcc aag aaa acc gag gag acc act ctt cta      288
Glu Asn Leu Tyr Phe Gln Ser Lys Lys Thr Glu Glu Thr Thr Leu Leu
                85                  90                  95

gag gac cgc atc ctc act act cgt aac gga cac acc acc tcg aca acc      336
Glu Asp Arg Ile Leu Thr Thr Arg Asn Gly His Thr Thr Ser Thr Thr
            100                 105                 110

cag tcg agc gta gga gtc aca tac ggg tat gca acg gct gag gat ttc      384
Gln Ser Ser Val Gly Val Thr Tyr Gly Tyr Ala Thr Ala Glu Asp Phe
        115                 120                 125

gtg agc ggg cca aac acc tct ggt ctt gag acc agg gtt gcc cag gca      432
Val Ser Gly Pro Asn Thr Ser Gly Leu Glu Thr Arg Val Ala Gln Ala
    130                 135                 140

gag cgg ttc ttt aaa acc cac ctg ttc gac tgg gtc aca agt gac ccg      480
Glu Arg Phe Phe Lys Thr His Leu Phe Asp Trp Val Thr Ser Asp Pro
```

```
145                 150                 155                 160

ttc gga cgg tgc cac ctg cta gaa ctt cca act gac cac aaa ggt gtc      528
Phe Gly Arg Cys His Leu Leu Glu Leu Pro Thr Asp His Lys Gly Val
                165                 170                 175

tat ggc agc ctg acc gac tcg tat gct tat atg agg aac ggc tgg gat      576
Tyr Gly Ser Leu Thr Asp Ser Tyr Ala Tyr Met Arg Asn Gly Trp Asp
            180                 185                 190

gtt gaa gtc act gct gtg gga aat cag ttc aat gga gga tgc ctg ttg      624
Val Glu Val Thr Ala Val Gly Asn Gln Phe Asn Gly Gly Cys Leu Leu
        195                 200                 205

gtg gct atg gtg cca gaa ctt tgc tcc ata cag aag agg gag ctg tac      672
Val Ala Met Val Pro Glu Leu Cys Ser Ile Gln Lys Arg Glu Leu Tyr
    210                 215                 220

cag ctc acg ctc ttt cct cac cag ttc atc aac cct cgg acg aac atg      720
Gln Leu Thr Leu Phe Pro His Gln Phe Ile Asn Pro Arg Thr Asn Met
225                 230                 235                 240

aca gca cac atc act gtg ccc ttt gtt ggc gtc aac cgt tat gac cag      768
Thr Ala His Ile Thr Val Pro Phe Val Gly Val Asn Arg Tyr Asp Gln
                245                 250                 255

tac aag gta cac aaa cct tgg acc ctc gtg gtt atg gtt gta gcc ccc      816
Tyr Lys Val His Lys Pro Trp Thr Leu Val Val Met Val Val Ala Pro
            260                 265                 270

ctg acc gtc aac agt gaa ggt gcc ccg caa atc aag gtg tat gcc aac      864
Leu Thr Val Asn Ser Glu Gly Ala Pro Gln Ile Lys Val Tyr Ala Asn
        275                 280                 285

atc gca cct acc aac gta cac gtc gcg ggt gag aac ctt tat ttt cag      912
Ile Ala Pro Thr Asn Val His Val Ala Gly Glu Asn Leu Tyr Phe Gln
    290                 295                 300

tcg atc ttc cct gtg gct tgc agc gat ggt tat ggc ggt ctg gtg acc      960
Ser Ile Phe Pro Val Ala Cys Ser Asp Gly Tyr Gly Gly Leu Val Thr
305                 310                 315                 320

act gac ccg aaa acg gct gac ccc gct tac ggg aaa gtg ttt aac ccc     1008
Thr Asp Pro Lys Thr Ala Asp Pro Ala Tyr Gly Lys Val Phe Asn Pro
                325                 330                 335

ccc cgc aac atg ttg ccg ggg cgg ttc acc aat ttt ctt gac gtg gct     1056
Pro Arg Asn Met Leu Pro Gly Arg Phe Thr Asn Phe Leu Asp Val Ala
            340                 345                 350

gag gcg tgc ccc acg ttt ctc cac ttc gag ggt gac gtg cca tac gtg     1104
Glu Ala Cys Pro Thr Phe Leu His Phe Glu Gly Asp Val Pro Tyr Val
        355                 360                 365

acc acg aag acg gat tca gac agg gtg ctc gct cag ttc gac ttg tct     1152
Thr Thr Lys Thr Asp Ser Asp Arg Val Leu Ala Gln Phe Asp Leu Ser
    370                 375                 380

ttg gca gca aag cac atg tcc aac acc ttc ctt gca ggt ctc gcc cag     1200
Leu Ala Ala Lys His Met Ser Asn Thr Phe Leu Ala Gly Leu Ala Gln
385                 390                 395                 400

tac tac aca cag tac agc ggc acc atc aac ctg cac ttc atg ttc aca     1248
Tyr Tyr Thr Gln Tyr Ser Gly Thr Ile Asn Leu His Phe Met Phe Thr
                405                 410                 415

ggg cct act gac gcg aag gcg cgt tac atg att gcg tat gct cct cct     1296
Gly Pro Thr Asp Ala Lys Ala Arg Tyr Met Ile Ala Tyr Ala Pro Pro
            420                 425                 430

ggc atg gaa cca cct aaa acg cca gag gcg gct gcc cac tgc atc cat     1344
Gly Met Glu Pro Pro Lys Thr Pro Glu Ala Ala Ala His Cys Ile His
        435                 440                 445

gct gaa tgg gac aca ggg ttg aac tca aaa ttc aca ttt tca atc cct     1392
Ala Glu Trp Asp Thr Gly Leu Asn Ser Lys Phe Thr Phe Ser Ile Pro
    450                 455                 460

tac ctt tcg gcg gct gat tac gct tac aca gcg tct gac act gct gag     1440
```

```
Tyr Leu Ser Ala Ala Asp Tyr Ala Tyr Thr Ala Ser Asp Thr Ala Glu
465                 470                 475                 480

acc aca aat gta cag gga tgg gtt tgc ctg ttt caa ata aca cac ggg      1488
Thr Thr Asn Val Gln Gly Trp Val Cys Leu Phe Gln Ile Thr His Gly
                485                 490                 495

aaa gct gac ggc gac gca ctg gtc gtt ttg gcc agc gcc gga aag gac      1536
Lys Ala Asp Gly Asp Ala Leu Val Val Leu Ala Ser Ala Gly Lys Asp
            500                 505                 510

ttt gag ctt cgg ctg ccg gaa aat ctt tac ttt cag tcc acc tca gcg      1584
Phe Glu Leu Arg Leu Pro Glu Asn Leu Tyr Phe Gln Ser Thr Ser Ala
        515                 520                 525

ggc gag tca gca gac ccc gtg acc gcc acc gtt gag aat tac ggt ggc      1632
Gly Glu Ser Ala Asp Pro Val Thr Ala Thr Val Glu Asn Tyr Gly Gly
    530                 535                 540

gag aca cag gtc cag agg cgc caa cac acg gac gtg tca ttt ata tta      1680
Glu Thr Gln Val Gln Arg Arg Gln His Thr Asp Val Ser Phe Ile Leu
545                 550                 555                 560

gac aga ttt gtg aaa gtg aca cca aaa gac caa att aat gta ttg gac      1728
Asp Arg Phe Val Lys Val Thr Pro Lys Asp Gln Ile Asn Val Leu Asp
                565                 570                 575

ctg atg caa acc cct gct cac act ttg gtg gga gca ctc ctt cgt act      1776
Leu Met Gln Thr Pro Ala His Thr Leu Val Gly Ala Leu Leu Arg Thr
            580                 585                 590

gcc act tac tat ttc gct gac tta gag gtg gca gtg aag cac gag gga      1824
Ala Thr Tyr Tyr Phe Ala Asp Leu Glu Val Ala Val Lys His Glu Gly
        595                 600                 605

aac ctc acc tgg gtg ccg aac ggg gcg cct gaa gcg gcg ttg gac aac      1872
Asn Leu Thr Trp Val Pro Asn Gly Ala Pro Glu Ala Ala Leu Asp Asn
    610                 615                 620

acc acc aac cca aca gct tac cac aag gca cca ctc acc cga ctt gca      1920
Thr Thr Asn Pro Thr Ala Tyr His Lys Ala Pro Leu Thr Arg Leu Ala
625                 630                 635                 640

ctg cct tac acg gcg cca cac cgc gtg ttg gct act gtt tac aac ggg      1968
Leu Pro Tyr Thr Ala Pro His Arg Val Leu Ala Thr Val Tyr Asn Gly
                645                 650                 655

aac agc aag tat ggt gac ggc acg gtg gcc aat gtg aga ggt gat ctg      2016
Asn Ser Lys Tyr Gly Asp Gly Thr Val Ala Asn Val Arg Gly Asp Leu
            660                 665                 670

caa gtg ttg gcc cag aag gcg gcg aga gcg ctg cct acc tcc ttc aac      2064
Gln Val Leu Ala Gln Lys Ala Ala Arg Ala Leu Pro Thr Ser Phe Asn
        675                 680                 685

tac ggt gcc att aaa gct act cgg gtg act gaa ctg ctt tac cgc atg      2112
Tyr Gly Ala Ile Lys Ala Thr Arg Val Thr Glu Leu Leu Tyr Arg Met
    690                 695                 700

aag agg gct gag aca tac tgt ccc cgg cct ctt ttg gcc att cac ccg      2160
Lys Arg Ala Glu Thr Tyr Cys Pro Arg Pro Leu Leu Ala Ile His Pro
705                 710                 715                 720

gac cag gct aga cac aag cag aag att gtg gaa aat ttg tat ttt caa      2208
Asp Gln Ala Arg His Lys Gln Lys Ile Val Glu Asn Leu Tyr Phe Gln
                725                 730                 735

tct aat ttt gac ctg ctc aaa ttg gcg gga gat gtg gag tcc aac cct      2256
Ser Asn Phe Asp Leu Leu Lys Leu Ala Gly Asp Val Glu Ser Asn Pro
            740                 745                 750

ggg ccc gac tat aaa gac gac gac gac aaa ccc ggg gaa agt ttg ttt      2304
Gly Pro Asp Tyr Lys Asp Asp Asp Asp Lys Pro Gly Glu Ser Leu Phe
        755                 760                 765

aag ggg ccg cgt gat tac aac ccg atc tca agc acc att tgt cat ttg      2352
Lys Gly Pro Arg Asp Tyr Asn Pro Ile Ser Ser Thr Ile Cys His Leu
    770                 775                 780
```

-continued

```
acg aat gaa tct gat ggg cac aca aca tcg ttg tat ggt att gga ttt     2400
Thr Asn Glu Ser Asp Gly His Thr Thr Ser Leu Tyr Gly Ile Gly Phe
785                 790                 795                 800

ggt ccc ttc atc att aca aac aag cac ttg ttt aga aga aat aat gga     2448
Gly Pro Phe Ile Ile Thr Asn Lys His Leu Phe Arg Arg Asn Asn Gly
                805                 810                 815

aca ctg ttg gtt caa tca cta cat ggt gta ttc aag gtc aag aac acc     2496
Thr Leu Leu Val Gln Ser Leu His Gly Val Phe Lys Val Lys Asn Thr
            820                 825                 830

acg act ttg caa caa cac ctc att gat ggg agg gac atg ata att att     2544
Thr Thr Leu Gln Gln His Leu Ile Asp Gly Arg Asp Met Ile Ile Ile
        835                 840                 845

cgc atg cca aag gat ttc cca cca ttt cct caa aag ctg aaa ttt aga     2592
Arg Met Pro Lys Asp Phe Pro Pro Phe Pro Gln Lys Leu Lys Phe Arg
    850                 855                 860

gag cca caa agg gaa gag cgc atc tgt ctt gtg aca acc aac ttc caa     2640
Glu Pro Gln Arg Glu Glu Arg Ile Cys Leu Val Thr Thr Asn Phe Gln
865                 870                 875                 880

act aag agc atg tct agc atg gtg tca gac acc agt tgc aca ttc cct     2688
Thr Lys Ser Met Ser Ser Met Val Ser Asp Thr Ser Cys Thr Phe Pro
                885                 890                 895

tca tct gat ggc ata ttc tgg aag cat tgg att caa acc aag gat ggg     2736
Ser Ser Asp Gly Ile Phe Trp Lys His Trp Ile Gln Thr Lys Asp Gly
            900                 905                 910

cag tgt ggc agt cca tta gta tca act aga gat ggg ttc att gtt ggt     2784
Gln Cys Gly Ser Pro Leu Val Ser Thr Arg Asp Gly Phe Ile Val Gly
        915                 920                 925

att cac tca gca tcg aat ttc acc aac aca aac aat tat ttc aca agc     2832
Ile His Ser Ala Ser Asn Phe Thr Asn Thr Asn Asn Tyr Phe Thr Ser
    930                 935                 940

gtg ccg aag aac ttt atg gaa ttg ttg aca aat cag gag gcg cag cag     2880
Val Pro Lys Asn Phe Met Glu Leu Leu Thr Asn Gln Glu Ala Gln Gln
945                 950                 955                 960

tgg gtt agt ggt tgg cga tta aat gct gac tca gta ttg tgg ggg ggc     2928
Trp Val Ser Gly Trp Arg Leu Asn Ala Asp Ser Val Leu Trp Gly Gly
                965                 970                 975

cat aaa gtt ttc atg gtg aaa cct gaa gag cct ttt cag cca gtt aag     2976
His Lys Val Phe Met Val Lys Pro Glu Glu Pro Phe Gln Pro Val Lys
            980                 985                 990

gaa gcg act caa ctc atg aat taa                                     3000
Glu Ala Thr Gln Leu Met Asn
        995
```

<210> SEQ ID NO 96
<211> LENGTH: 999
<212> TYPE: PRT
<213> ORGANISM: Artificial Sequence
<220> FEATURE:
<223> OTHER INFORMATION: Synthetic Construct

<400> SEQUENCE: 96

```
Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Thr Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
```

-continued

```
65                  70                  75                  80

Glu Asn Leu Tyr Phe Gln Ser Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Ala Gln Ala
    130                 135                 140

Glu Arg Phe Phe Lys Thr His Leu Phe Asp Trp Val Thr Ser Asp Pro
145                 150                 155                 160

Phe Gly Arg Cys His Leu Leu Glu Leu Pro Thr Asp His Lys Gly Val
                165                 170                 175

Tyr Gly Ser Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Leu Cys Ser Ile Gln Lys Arg Glu Leu Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Phe Val Gly Val Asn Arg Tyr Asp Gln
                245                 250                 255

Tyr Lys Val His Lys Pro Trp Thr Leu Val Val Met Val Val Ala Pro
            260                 265                 270

Leu Thr Val Asn Ser Glu Gly Ala Pro Gln Ile Lys Val Tyr Ala Asn
        275                 280                 285

Ile Ala Pro Thr Asn Val His Val Ala Gly Glu Asn Leu Tyr Phe Gln
    290                 295                 300

Ser Ile Phe Pro Val Ala Cys Ser Asp Gly Tyr Gly Gly Leu Val Thr
305                 310                 315                 320

Thr Asp Pro Lys Thr Ala Asp Pro Ala Tyr Gly Lys Val Phe Asn Pro
                325                 330                 335

Pro Arg Asn Met Leu Pro Gly Arg Phe Thr Asn Phe Leu Asp Val Ala
            340                 345                 350

Glu Ala Cys Pro Thr Phe Leu His Phe Glu Gly Asp Val Pro Tyr Val
        355                 360                 365

Thr Thr Lys Thr Asp Ser Asp Arg Val Leu Ala Gln Phe Asp Leu Ser
    370                 375                 380

Leu Ala Ala Lys His Met Ser Asn Thr Phe Leu Ala Gly Leu Ala Gln
385                 390                 395                 400

Tyr Tyr Thr Gln Tyr Ser Gly Thr Ile Asn Leu His Phe Met Phe Thr
                405                 410                 415

Gly Pro Thr Asp Ala Lys Ala Arg Tyr Met Ile Ala Tyr Ala Pro Pro
            420                 425                 430

Gly Met Glu Pro Pro Lys Thr Pro Glu Ala Ala Ala His Cys Ile His
        435                 440                 445

Ala Glu Trp Asp Thr Gly Leu Asn Ser Lys Phe Thr Phe Ser Ile Pro
    450                 455                 460

Tyr Leu Ser Ala Ala Asp Tyr Ala Tyr Thr Ala Ser Asp Thr Ala Glu
465                 470                 475                 480

Thr Thr Asn Val Gln Gly Trp Val Cys Leu Phe Gln Ile Thr His Gly
                485                 490                 495
```

-continued

```
Lys Ala Asp Gly Asp Ala Leu Val Val Leu Ala Ser Ala Gly Lys Asp
            500                 505                 510

Phe Glu Leu Arg Leu Pro Glu Asn Leu Tyr Phe Gln Ser Thr Ser Ala
        515                 520                 525

Gly Glu Ser Ala Asp Pro Val Thr Ala Thr Val Glu Asn Tyr Gly Gly
    530                 535                 540

Glu Thr Gln Val Gln Arg Arg Gln His Thr Asp Val Ser Phe Ile Leu
545                 550                 555                 560

Asp Arg Phe Val Lys Val Thr Pro Lys Asp Gln Ile Asn Val Leu Asp
                565                 570                 575

Leu Met Gln Thr Pro Ala His Thr Leu Val Gly Ala Leu Leu Arg Thr
            580                 585                 590

Ala Thr Tyr Tyr Phe Ala Asp Leu Glu Val Ala Val Lys His Glu Gly
        595                 600                 605

Asn Leu Thr Trp Val Pro Asn Gly Ala Pro Glu Ala Ala Leu Asp Asn
    610                 615                 620

Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Asn Ser Lys Tyr Gly Asp Gly Thr Val Ala Asn Val Arg Gly Asp Leu
            660                 665                 670

Gln Val Leu Ala Gln Lys Ala Ala Arg Ala Leu Pro Thr Ser Phe Asn
        675                 680                 685

Tyr Gly Ala Ile Lys Ala Thr Arg Val Thr Glu Leu Leu Tyr Arg Met
    690                 695                 700

Lys Arg Ala Glu Thr Tyr Cys Pro Arg Pro Leu Leu Ala Ile His Pro
705                 710                 715                 720

Asp Gln Ala Arg His Lys Gln Lys Ile Val Glu Asn Leu Tyr Phe Gln
                725                 730                 735

Ser Asn Phe Asp Leu Leu Lys Leu Ala Gly Asp Val Glu Ser Asn Pro
            740                 745                 750

Gly Pro Asp Tyr Lys Asp Asp Asp Asp Lys Pro Gly Glu Ser Leu Phe
        755                 760                 765

Lys Gly Pro Arg Asp Tyr Asn Pro Ile Ser Ser Thr Ile Cys His Leu
    770                 775                 780

Thr Asn Glu Ser Asp Gly His Thr Thr Ser Leu Tyr Gly Ile Gly Phe
785                 790                 795                 800

Gly Pro Phe Ile Ile Thr Asn Lys His Leu Phe Arg Arg Asn Asn Gly
                805                 810                 815

Thr Leu Leu Val Gln Ser Leu His Gly Val Phe Lys Val Lys Asn Thr
            820                 825                 830

Thr Thr Leu Gln Gln His Leu Ile Asp Gly Arg Asp Met Ile Ile Ile
        835                 840                 845

Arg Met Pro Lys Asp Phe Pro Pro Phe Pro Gln Lys Leu Lys Phe Arg
    850                 855                 860

Glu Pro Gln Arg Glu Glu Arg Ile Cys Leu Val Thr Thr Asn Phe Gln
865                 870                 875                 880

Thr Lys Ser Met Ser Ser Met Val Ser Asp Thr Ser Cys Thr Phe Pro
                885                 890                 895

Ser Ser Asp Gly Ile Phe Trp Lys His Trp Ile Gln Thr Lys Asp Gly
            900                 905                 910
```

```
Gln Cys Gly Ser Pro Leu Val Ser Thr Arg Asp Gly Phe Ile Val Gly
        915                 920                 925

Ile His Ser Ala Ser Asn Phe Thr Asn Thr Asn Asn Tyr Phe Thr Ser
    930                 935                 940

Val Pro Lys Asn Phe Met Glu Leu Leu Thr Asn Gln Glu Ala Gln Gln
945                 950                 955                 960

Trp Val Ser Gly Trp Arg Leu Asn Ala Asp Ser Val Leu Trp Gly Gly
                965                 970                 975

His Lys Val Phe Met Val Lys Pro Glu Glu Pro Phe Gln Pro Val Lys
            980                 985                 990

Glu Ala Thr Gln Leu Met Asn
        995


<210> SEQ ID NO 97
<211> LENGTH: 3000
<212> TYPE: DNA
<213> ORGANISM: Artificial Sequence
<220> FEATURE:
<223> OTHER INFORMATION: Nucleotide sequence for pV0J construct
      containing a P1 modified with the optimum TEV recognition sequence
      present at VP2/VP3, VP3/VP4, and VP1/2A junction sites.
<220> FEATURE:
<221> NAME/KEY: CDS
<222> LOCATION: (1)..(3000)

<400> SEQUENCE: 97

atg gga gcc ggg caa tcc agc ccg gca acc ggg tca cag aac caa tca       48
Met Gly Ala Gly Gln Ser Ser Pro Ala Thr Gly Ser Gln Asn Gln Ser
1               5                   10                  15

ggc aac act ggg agc atc atc aac aat tac tac atg cag cag tac caa       96
Gly Asn Thr Gly Ser Ile Ile Asn Asn Tyr Tyr Met Gln Gln Tyr Gln
            20                  25                  30

aac tct atg gac aca caa ctt ggt gac aac gct aca agc gga ggc tca      144
Asn Ser Met Asp Thr Gln Leu Gly Asp Asn Ala Thr Ser Gly Gly Ser
        35                  40                  45

aac gag ggg tcc acg gac aca acc tcc acc cac aca acc aac act cag      192
Asn Glu Gly Ser Thr Asp Thr Thr Ser Thr His Thr Thr Asn Thr Gln
    50                  55                  60

aac aac gac tgg ttc tcg aag ctg gcc agt tcc gct ttc agc ggt ctt      240
Asn Asn Asp Trp Phe Ser Lys Leu Ala Ser Ser Ala Phe Ser Gly Leu
65                  70                  75                  80

ttc ggc gct ctt ctc gcc gac aag aaa acc gag gag acc act ctt cta      288
Phe Gly Ala Leu Leu Ala Asp Lys Lys Thr Glu Glu Thr Thr Leu Leu
                85                  90                  95

gag gac cgc atc ctc act act cgt aac gga cac acc acc tcg aca acc      336
Glu Asp Arg Ile Leu Thr Thr Arg Asn Gly His Thr Thr Ser Thr Thr
            100                 105                 110

cag tcg agc gta gga gtc aca tac ggg tat gca acg gct gag gat ttc      384
Gln Ser Ser Val Gly Val Thr Tyr Gly Tyr Ala Thr Ala Glu Asp Phe
        115                 120                 125

gtg agc ggg cca aac acc tct ggt ctt gag acc agg gtt gcc cag gca      432
Val Ser Gly Pro Asn Thr Ser Gly Leu Glu Thr Arg Val Ala Gln Ala
    130                 135                 140

gag cgg ttc ttt aaa acc cac ctg ttc gac tgg gtc aca agt gac ccg      480
Glu Arg Phe Phe Lys Thr His Leu Phe Asp Trp Val Thr Ser Asp Pro
145                 150                 155                 160

ttc gga cgg tgc cac ctg cta gaa ctt cca act gac cac aaa ggt gtc      528
Phe Gly Arg Cys His Leu Leu Glu Leu Pro Thr Asp His Lys Gly Val
                165                 170                 175

tat ggc agc ctg acc gac tcg tat gct tat atg agg aac ggc tgg gat      576
Tyr Gly Ser Leu Thr Asp Ser Tyr Ala Tyr Met Arg Asn Gly Trp Asp
```

-continued

```
        180                 185                 190

gtt gaa gtc act gct gtg gga aat cag ttc aat gga gga tgc ctg ttg      624
Val Glu Val Thr Ala Val Gly Asn Gln Phe Asn Gly Gly Cys Leu Leu
        195                 200                 205

gtg gct atg gtg cca gaa ctt tgc tcc ata cag aag agg gag ctg tac      672
Val Ala Met Val Pro Glu Leu Cys Ser Ile Gln Lys Arg Glu Leu Tyr
    210                 215                 220

cag ctc acg ctc ttt cct cac cag ttc atc aac cct cgg acg aac atg      720
Gln Leu Thr Leu Phe Pro His Gln Phe Ile Asn Pro Arg Thr Asn Met
225                 230                 235                 240

aca gca cac atc act gtg ccc ttt gtt ggc gtc aac cgt tat gac cag      768
Thr Ala His Ile Thr Val Pro Phe Val Gly Val Asn Arg Tyr Asp Gln
                245                 250                 255

tac aag gta cac aaa cct tgg acc ctc gtg gtt atg gtt gta gcc ccc      816
Tyr Lys Val His Lys Pro Trp Thr Leu Val Val Met Val Val Ala Pro
            260                 265                 270

ctg acc gtc aac agt gaa ggt gcc ccg caa atc aag gtg tat gcc aac      864
Leu Thr Val Asn Ser Glu Gly Ala Pro Gln Ile Lys Val Tyr Ala Asn
        275                 280                 285

atc gca cct acc aac gta cac gtc gcg ggt gag aac ctt tat ttt cag      912
Ile Ala Pro Thr Asn Val His Val Ala Gly Glu Asn Leu Tyr Phe Gln
    290                 295                 300

tcg atc ttc cct gtg gct tgc agc gat ggt tat ggc ggt ctg gtg acc      960
Ser Ile Phe Pro Val Ala Cys Ser Asp Gly Tyr Gly Gly Leu Val Thr
305                 310                 315                 320

act gac ccg aaa acg gct gac ccc gct tac ggg aaa gtg ttt aac ccc     1008
Thr Asp Pro Lys Thr Ala Asp Pro Ala Tyr Gly Lys Val Phe Asn Pro
                325                 330                 335

ccc cgc aac atg ttg ccg ggg cgg ttc acc aat ttt ctt gac gtg gct     1056
Pro Arg Asn Met Leu Pro Gly Arg Phe Thr Asn Phe Leu Asp Val Ala
            340                 345                 350

gag gcg tgc ccc acg ttt ctc cac ttc gag ggt gac gtg cca tac gtg     1104
Glu Ala Cys Pro Thr Phe Leu His Phe Glu Gly Asp Val Pro Tyr Val
        355                 360                 365

acc acg aag acg gat tca gac agg gtg ctc gct cag ttc gac ttg tct     1152
Thr Thr Lys Thr Asp Ser Asp Arg Val Leu Ala Gln Phe Asp Leu Ser
    370                 375                 380

ttg gca gca aag cac atg tcc aac acc ttc ctt gca ggt ctc gcc cag     1200
Leu Ala Ala Lys His Met Ser Asn Thr Phe Leu Ala Gly Leu Ala Gln
385                 390                 395                 400

tac tac aca cag tac agc ggc acc atc aac ctg cac ttc atg ttc aca     1248
Tyr Tyr Thr Gln Tyr Ser Gly Thr Ile Asn Leu His Phe Met Phe Thr
                405                 410                 415

ggg cct act gac gcg aag gcg cgt tac atg att gcg tat gct cct cct     1296
Gly Pro Thr Asp Ala Lys Ala Arg Tyr Met Ile Ala Tyr Ala Pro Pro
            420                 425                 430

ggc atg gaa cca cct aaa acg cca gag gcg gct gcc cac tgc atc cat     1344
Gly Met Glu Pro Pro Lys Thr Pro Glu Ala Ala Ala His Cys Ile His
        435                 440                 445

gct gaa tgg gac aca ggg ttg aac tca aaa ttc aca ttt tca atc cct     1392
Ala Glu Trp Asp Thr Gly Leu Asn Ser Lys Phe Thr Phe Ser Ile Pro
    450                 455                 460

tac ctt tcg gcg gct gat tac gct tac aca gcg tct gac act gct gag     1440
Tyr Leu Ser Ala Ala Asp Tyr Ala Tyr Thr Ala Ser Asp Thr Ala Glu
465                 470                 475                 480

acc aca aat gta cag gga tgg gtt tgc ctg ttt caa ata aca cac ggg     1488
Thr Thr Asn Val Gln Gly Trp Val Cys Leu Phe Gln Ile Thr His Gly
                485                 490                 495

aaa gct gac ggc gac gca ctg gtc gtt ttg gcc agc gcc gga aag gac     1536
```

-continued

```
Lys Ala Asp Gly Asp Ala Leu Val Val Leu Ala Ser Ala Gly Lys Asp
            500                 505                 510

ttt gag ctt cgg ctg ccg gaa aat ctt tac ttt cag tcc acc tca gcg     1584
Phe Glu Leu Arg Leu Pro Glu Asn Leu Tyr Phe Gln Ser Thr Ser Ala
        515                 520                 525

ggc gag tca gca gac ccc gtg acc gcc acc gtt gag aat tac ggt ggc     1632
Gly Glu Ser Ala Asp Pro Val Thr Ala Thr Val Glu Asn Tyr Gly Gly
    530                 535                 540

gag aca cag gtc cag agg cgc caa cac acg gac gtg tca ttt ata tta     1680
Glu Thr Gln Val Gln Arg Arg Gln His Thr Asp Val Ser Phe Ile Leu
545                 550                 555                 560

gac aga ttt gtg aaa gtg aca cca aaa gac caa att aat gta ttg gac     1728
Asp Arg Phe Val Lys Val Thr Pro Lys Asp Gln Ile Asn Val Leu Asp
                565                 570                 575

ctg atg caa acc cct gct cac act ttg gtg gga gca ctc ctt cgt act     1776
Leu Met Gln Thr Pro Ala His Thr Leu Val Gly Ala Leu Leu Arg Thr
            580                 585                 590

gcc act tac tat ttc gct gac tta gag gtg gca gtg aag cac gag gga     1824
Ala Thr Tyr Tyr Phe Ala Asp Leu Glu Val Ala Val Lys His Glu Gly
        595                 600                 605

aac ctc acc tgg gtg ccg aac ggg gcg cct gaa gcg gcg ttg gac aac     1872
Asn Leu Thr Trp Val Pro Asn Gly Ala Pro Glu Ala Ala Leu Asp Asn
    610                 615                 620

acc acc aac cca aca gct tac cac aag gca cca ctc acc cga ctt gca     1920
Thr Thr Asn Pro Thr Ala Tyr His Lys Ala Pro Leu Thr Arg Leu Ala
625                 630                 635                 640

ctg cct tac acg gcg cca cac cgc gtg ttg gct act gtt tac aac ggg     1968
Leu Pro Tyr Thr Ala Pro His Arg Val Leu Ala Thr Val Tyr Asn Gly
                645                 650                 655

aac agc aag tat ggt gac ggc acg gtg gcc aat gtg aga ggt gat ctg     2016
Asn Ser Lys Tyr Gly Asp Gly Thr Val Ala Asn Val Arg Gly Asp Leu
            660                 665                 670

caa gtg ttg gcc cag aag gcg gcg aga gcg ctg cct acc tcc ttc aac     2064
Gln Val Leu Ala Gln Lys Ala Ala Arg Ala Leu Pro Thr Ser Phe Asn
        675                 680                 685

tac ggt gcc att aaa gct act cgg gtg act gaa ctg ctt tac cgc atg     2112
Tyr Gly Ala Ile Lys Ala Thr Arg Val Thr Glu Leu Leu Tyr Arg Met
    690                 695                 700

aag agg gct gag aca tac tgt ccc cgg cct ctt ttg gcc att cac ccg     2160
Lys Arg Ala Glu Thr Tyr Cys Pro Arg Pro Leu Leu Ala Ile His Pro
705                 710                 715                 720

gac cag gct aga cac aag cag aag att gtg gaa aat ttg tat ttt caa     2208
Asp Gln Ala Arg His Lys Gln Lys Ile Val Glu Asn Leu Tyr Phe Gln
                725                 730                 735

tct aat ttt gac ctg ctc aaa ttg gcg gga gat gtg gag tcc aac cct     2256
Ser Asn Phe Asp Leu Leu Lys Leu Ala Gly Asp Val Glu Ser Asn Pro
            740                 745                 750

ggg ccc gac tat aaa gac gac gac gac aaa ccc ggg gaa agt ttg ttt     2304
Gly Pro Asp Tyr Lys Asp Asp Asp Asp Lys Pro Gly Glu Ser Leu Phe
        755                 760                 765

aag ggg ccg cgt gat tac aac ccg atc tca agc acc att tgt cat ttg     2352
Lys Gly Pro Arg Asp Tyr Asn Pro Ile Ser Ser Thr Ile Cys His Leu
    770                 775                 780

acg aat gaa tct gat ggg cac aca aca tcg ttg tat ggt att gga ttt     2400
Thr Asn Glu Ser Asp Gly His Thr Thr Ser Leu Tyr Gly Ile Gly Phe
785                 790                 795                 800

ggt ccc ttc atc att aca aac aag cac ttg ttt aga aga aat aat gga     2448
Gly Pro Phe Ile Ile Thr Asn Lys His Leu Phe Arg Arg Asn Asn Gly
                805                 810                 815
```

```
aca ctg ttg gtt caa tca cta cat ggt gta ttc aag gtc aag aac acc     2496
Thr Leu Leu Val Gln Ser Leu His Gly Val Phe Lys Val Lys Asn Thr
            820                 825                 830

acg act ttg caa caa cac ctc att gat ggg agg gac atg ata att att     2544
Thr Thr Leu Gln Gln His Leu Ile Asp Gly Arg Asp Met Ile Ile Ile
        835                 840                 845

cgc atg cca aag gat ttc cca cca ttt cct caa aag ctg aaa ttt aga     2592
Arg Met Pro Lys Asp Phe Pro Pro Phe Pro Gln Lys Leu Lys Phe Arg
    850                 855                 860

gag cca caa agg gaa gag cgc atc tgt ctt gtg aca acc aac ttc caa     2640
Glu Pro Gln Arg Glu Glu Arg Ile Cys Leu Val Thr Thr Asn Phe Gln
865                 870                 875                 880

act aag agc atg tct agc atg gtg tca gac acc agt tgc aca ttc cct     2688
Thr Lys Ser Met Ser Ser Met Val Ser Asp Thr Ser Cys Thr Phe Pro
                885                 890                 895

tca tct gat ggc ata ttc tgg aag cat tgg att caa acc aag gat ggg     2736
Ser Ser Asp Gly Ile Phe Trp Lys His Trp Ile Gln Thr Lys Asp Gly
            900                 905                 910

cag tgt ggc agt cca tta gta tca act aga gat ggg ttc att gtt ggt     2784
Gln Cys Gly Ser Pro Leu Val Ser Thr Arg Asp Gly Phe Ile Val Gly
        915                 920                 925

att cac tca gca tcg aat ttc acc aac aca aac aat tat ttc aca agc     2832
Ile His Ser Ala Ser Asn Phe Thr Asn Thr Asn Asn Tyr Phe Thr Ser
    930                 935                 940

gtg ccg aag aac ttt atg gaa ttg ttg aca aat cag gag gcg cag cag     2880
Val Pro Lys Asn Phe Met Glu Leu Leu Thr Asn Gln Glu Ala Gln Gln
945                 950                 955                 960

tgg gtt agt ggt tgg cga tta aat gct gac tca gta ttg tgg ggg ggc     2928
Trp Val Ser Gly Trp Arg Leu Asn Ala Asp Ser Val Leu Trp Gly Gly
                965                 970                 975

cat aaa gtt ttc atg gtg aaa cct gaa gag cct ttt cag cca gtt aag     2976
His Lys Val Phe Met Val Lys Pro Glu Glu Pro Phe Gln Pro Val Lys
            980                 985                 990

gaa gcg act caa ctc atg aat taa                                     3000
Glu Ala Thr Gln Leu Met Asn
        995
```

```
<210> SEQ ID NO 98
<211> LENGTH: 999
<212> TYPE: PRT
<213> ORGANISM: Artificial Sequence
<220> FEATURE:
<223> OTHER INFORMATION: Synthetic Construct

<400> SEQUENCE: 98

Met Gly Ala Gly Gln Ser Ser Pro Ala Thr Gly Ser Gln Asn Gln Ser
1               5                   10                  15

Gly Asn Thr Gly Ser Ile Ile Asn Asn Tyr Tyr Met Gln Gln Tyr Gln
            20                  25                  30

Asn Ser Met Asp Thr Gln Leu Gly Asp Asn Ala Thr Ser Gly Gly Ser
        35                  40                  45

Asn Glu Gly Ser Thr Asp Thr Thr Ser Thr His Thr Thr Asn Thr Gln
    50                  55                  60

Asn Asn Asp Trp Phe Ser Lys Leu Ala Ser Ser Ala Phe Ser Gly Leu
65                  70                  75                  80

Phe Gly Ala Leu Leu Ala Asp Lys Lys Thr Glu Glu Thr Thr Leu Leu
                85                  90                  95

Glu Asp Arg Ile Leu Thr Thr Arg Asn Gly His Thr Thr Ser Thr Thr
            100                 105                 110
```

-continued

```
Gln Ser Ser Val Gly Val Thr Tyr Gly Tyr Ala Thr Ala Glu Asp Phe
        115                 120                 125

Val Ser Gly Pro Asn Thr Ser Gly Leu Glu Thr Arg Val Ala Gln Ala
    130                 135                 140

Glu Arg Phe Phe Lys Thr His Leu Phe Asp Trp Val Thr Ser Asp Pro
145                 150                 155                 160

Phe Gly Arg Cys His Leu Leu Glu Leu Pro Thr Asp His Lys Gly Val
                165                 170                 175

Tyr Gly Ser Leu Thr Asp Ser Tyr Ala Tyr Met Arg Asn Gly Trp Asp
            180                 185                 190

Val Glu Val Thr Ala Val Gly Asn Gln Phe Asn Gly Gly Cys Leu Leu
        195                 200                 205

Val Ala Met Val Pro Glu Leu Cys Ser Ile Gln Lys Arg Glu Leu Tyr
    210                 215                 220

Gln Leu Thr Leu Phe Pro His Gln Phe Ile Asn Pro Arg Thr Asn Met
225                 230                 235                 240

Thr Ala His Ile Thr Val Pro Phe Val Gly Val Asn Arg Tyr Asp Gln
                245                 250                 255

Tyr Lys Val His Lys Pro Trp Thr Leu Val Val Met Val Val Ala Pro
            260                 265                 270

Leu Thr Val Asn Ser Glu Gly Ala Pro Gln Ile Lys Val Tyr Ala Asn
        275                 280                 285

Ile Ala Pro Thr Asn Val His Val Ala Gly Glu Asn Leu Tyr Phe Gln
    290                 295                 300

Ser Ile Phe Pro Val Ala Cys Ser Asp Gly Tyr Gly Gly Leu Val Thr
305                 310                 315                 320

Thr Asp Pro Lys Thr Ala Asp Pro Ala Tyr Gly Lys Val Phe Asn Pro
                325                 330                 335

Pro Arg Asn Met Leu Pro Gly Arg Phe Thr Asn Phe Leu Asp Val Ala
            340                 345                 350

Glu Ala Cys Pro Thr Phe Leu His Phe Glu Gly Asp Val Pro Tyr Val
        355                 360                 365

Thr Thr Lys Thr Asp Ser Asp Arg Val Leu Ala Gln Phe Asp Leu Ser
    370                 375                 380

Leu Ala Ala Lys His Met Ser Asn Thr Phe Leu Ala Gly Leu Ala Gln
385                 390                 395                 400

Tyr Tyr Thr Gln Tyr Ser Gly Thr Ile Asn Leu His Phe Met Phe Thr
                405                 410                 415

Gly Pro Thr Asp Ala Lys Ala Arg Tyr Met Ile Ala Tyr Ala Pro Pro
            420                 425                 430

Gly Met Glu Pro Pro Lys Thr Pro Glu Ala Ala Ala His Cys Ile His
        435                 440                 445

Ala Glu Trp Asp Thr Gly Leu Asn Ser Lys Phe Thr Phe Ser Ile Pro
    450                 455                 460

Tyr Leu Ser Ala Ala Asp Tyr Ala Tyr Thr Ala Ser Asp Thr Ala Glu
465                 470                 475                 480

Thr Thr Asn Val Gln Gly Trp Val Cys Leu Phe Gln Ile Thr His Gly
                485                 490                 495

Lys Ala Asp Gly Asp Ala Leu Val Val Leu Ala Ser Ala Gly Lys Asp
            500                 505                 510

Phe Glu Leu Arg Leu Pro Glu Asn Leu Tyr Phe Gln Ser Thr Ser Ala
        515                 520                 525

Gly Glu Ser Ala Asp Pro Val Thr Ala Thr Val Glu Asn Tyr Gly Gly
```

-continued

```
    530                 535                 540

Glu Thr Gln Val Gln Arg Arg Gln His Thr Asp Val Ser Phe Ile Leu
545                 550                 555                 560

Asp Arg Phe Val Lys Val Thr Pro Lys Asp Gln Ile Asn Val Leu Asp
                565                 570                 575

Leu Met Gln Thr Pro Ala His Thr Leu Val Gly Ala Leu Leu Arg Thr
            580                 585                 590

Ala Thr Tyr Tyr Phe Ala Asp Leu Glu Val Ala Val Lys His Glu Gly
        595                 600                 605

Asn Leu Thr Trp Val Pro Asn Gly Ala Pro Glu Ala Ala Leu Asp Asn
    610                 615                 620

Thr Thr Asn Pro Thr Ala Tyr His Lys Ala Pro Leu Thr Arg Leu Ala
625                 630                 635                 640

Leu Pro Tyr Thr Ala Pro His Arg Val Leu Ala Thr Val Tyr Asn Gly
                645                 650                 655

Asn Ser Lys Tyr Gly Asp Gly Thr Val Ala Asn Val Arg Gly Asp Leu
            660                 665                 670

Gln Val Leu Ala Gln Lys Ala Ala Arg Ala Leu Pro Thr Ser Phe Asn
        675                 680                 685

Tyr Gly Ala Ile Lys Ala Thr Arg Val Thr Glu Leu Leu Tyr Arg Met
    690                 695                 700

Lys Arg Ala Glu Thr Tyr Cys Pro Arg Pro Leu Leu Ala Ile His Pro
705                 710                 715                 720

Asp Gln Ala Arg His Lys Gln Lys Ile Val Glu Asn Leu Tyr Phe Gln
                725                 730                 735

Ser Asn Phe Asp Leu Leu Lys Leu Ala Gly Asp Val Glu Ser Asn Pro
            740                 745                 750

Gly Pro Asp Tyr Lys Asp Asp Asp Asp Lys Pro Gly Glu Ser Leu Phe
        755                 760                 765

Lys Gly Pro Arg Asp Tyr Asn Pro Ile Ser Ser Thr Ile Cys His Leu
    770                 775                 780

Thr Asn Glu Ser Asp Gly His Thr Thr Ser Leu Tyr Gly Ile Gly Phe
785                 790                 795                 800

Gly Pro Phe Ile Ile Thr Asn Lys His Leu Phe Arg Arg Asn Asn Gly
                805                 810                 815

Thr Leu Leu Val Gln Ser Leu His Gly Val Phe Lys Val Lys Asn Thr
            820                 825                 830

Thr Thr Leu Gln Gln His Leu Ile Asp Gly Arg Asp Met Ile Ile Ile
        835                 840                 845

Arg Met Pro Lys Asp Phe Pro Pro Phe Pro Gln Lys Leu Lys Phe Arg
    850                 855                 860

Glu Pro Gln Arg Glu Glu Arg Ile Cys Leu Val Thr Thr Asn Phe Gln
865                 870                 875                 880

Thr Lys Ser Met Ser Ser Met Val Ser Asp Thr Ser Cys Thr Phe Pro
                885                 890                 895

Ser Ser Asp Gly Ile Phe Trp Lys His Trp Ile Gln Thr Lys Asp Gly
            900                 905                 910

Gln Cys Gly Ser Pro Leu Val Ser Thr Arg Asp Gly Phe Ile Val Gly
        915                 920                 925

Ile His Ser Ala Ser Asn Phe Thr Asn Thr Asn Asn Tyr Phe Thr Ser
    930                 935                 940

Val Pro Lys Asn Phe Met Glu Leu Leu Thr Asn Gln Glu Ala Gln Gln
945                 950                 955                 960
```

```
Trp Val Ser Gly Trp Arg Leu Asn Ala Asp Ser Val Leu Trp Gly Gly
                965                 970                 975

His Lys Val Phe Met Val Lys Pro Glu Glu Pro Phe Gln Pro Val Lys
            980                 985                 990

Glu Ala Thr Gln Leu Met Asn
        995


<210> SEQ ID NO 99

<400> SEQUENCE: 99

000


<210> SEQ ID NO 100
<211> LENGTH: 23
<212> TYPE: DNA
<213> ORGANISM: Artificial Sequence
<220> FEATURE:
<223> OTHER INFORMATION: Primer mpTarget-F

<400> SEQUENCE: 100

gacatccact ttgcctttct ctc                                              23


<210> SEQ ID NO 101
<211> LENGTH: 17
<212> TYPE: DNA
<213> ORGANISM: Artificial Sequence
<220> FEATURE:
<223> OTHER INFORMATION: Primer O1VPO-2j-R

<400> SEQUENCE: 101

tcctctagaa gagtggt                                                     17


<210> SEQ ID NO 102

<400> SEQUENCE: 102

000


<210> SEQ ID NO 103

<400> SEQUENCE: 103

000


<210> SEQ ID NO 104
<211> LENGTH: 8
<212> TYPE: PRT
<213> ORGANISM: Artificial Sequence
<220> FEATURE:
<223> OTHER INFORMATION: Epitope tag

<400> SEQUENCE: 104

Asp Tyr Lys Asp Asp Asp Asp Lys
1               5


<210> SEQ ID NO 105
<211> LENGTH: 24
<212> TYPE: DNA
<213> ORGANISM: Artificial Sequence
<220> FEATURE:
<223> OTHER INFORMATION: FLAG tag
<220> FEATURE:
<221> NAME/KEY: CDS
<222> LOCATION: (1)..(24)
```

<400> SEQUENCE: 105 gac tat aag gac gac gac gac aag 24
Asp Tyr Lys Asp Asp Asp Asp Lys
1 5

<210> SEQ ID NO 106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 106

Asp Tyr Lys Asp Asp Asp Asp Lys
1 5

<210> SEQ ID NO 107
<211> LENGTH: 18
<212> TYPE: DNA
<213> ORGANISM: Artificial Sequence
<220> FEATURE:
<223> OTHER INFORMATION: His-6 tag
<220> FEATURE:
<221> NAME/KEY: CDS
<222> LOCATION: (1)..(18)

<400> SEQUENCE: 107 cat cat cac cat cac cac 18
His His His His His His
1 5

<210> SEQ ID NO 108
<211> LENGTH: 6
<212> TYPE: PRT
<213> ORGANISM: Artificial Sequence
<220> FEATURE:
<223> OTHER INFORMATION: Synthetic Construct

<400> SEQUENCE: 108

His His His His His His
1 5

<210> SEQ ID NO 109
<211> LENGTH: 93
<212> TYPE: DNA
<213> ORGANISM: Artificial Sequence
<220> FEATURE:
<223> OTHER INFORMATION: Sequence of Delta-1D2A construct
<220> FEATURE:
<221> NAME/KEY: CDS
<222> LOCATION: (1)..(93)

<400> SEQUENCE: 109 agc cac aag caa aag atc att gca cca gca aag cag ctt ctg aat ttt 48
Ser His Lys Gln Lys Ile Ile Ala Pro Ala Lys Gln Leu Leu Asn Phe
1 5 10 15 gac ctg ctc aag ttg gcc gga gac gtt gag tcc aac cct gga ccc 93
Asp Leu Leu Lys Leu Ala Gly Asp Val Glu Ser Asn Pro Gly Pro
20 25 30

<210> SEQ ID NO 110
<211> LENGTH: 31
<212> TYPE: PRT
<213> ORGANISM: Artificial Sequence
<220> FEATURE:
<223> OTHER INFORMATION: Synthetic Construct

<400> SEQUENCE: 110

```
Ser His Lys Gln Lys Ile Ile Ala Pro Ala Lys Gln Leu Leu Asn Phe
1               5                   10                  15

Asp Leu Leu Lys Leu Ala Gly Asp Val Glu Ser Asn Pro Gly Pro
            20                  25                  30


<210> SEQ ID NO 111
<211> LENGTH: 90
<212> TYPE: DNA
<213> ORGANISM: Artificial Sequence
<220> FEATURE:
<223> OTHER INFORMATION: Delta 1D2A interrupter sequence
<220> FEATURE:
<221> NAME/KEY: CDS
<222> LOCATION: (34)..(90)
<223> OTHER INFORMATION: Nucleotides 34-90 code for the 2A sequence.

<400> SEQUENCE: 111

cayaagcaaa agatcattgc accagcaaag cag ctt ctg aat ttt gac ctg ctc      54
                                     Leu Leu Asn Phe Asp Leu Leu
                                     1               5

aag ttg gcc gga gac gtt gag tcc aac cct gga ccc                       90
Lys Leu Ala Gly Asp Val Glu Ser Asn Pro Gly Pro
        10                  15


<210> SEQ ID NO 112
<211> LENGTH: 19
<212> TYPE: PRT
<213> ORGANISM: Artificial Sequence
<220> FEATURE:
<223> OTHER INFORMATION: Synthetic Construct

<400> SEQUENCE: 112

Leu Leu Asn Phe Asp Leu Leu Lys Leu Ala Gly Asp Val Glu Ser Asn
1               5                   10                  15

Pro Gly Pro


<210> SEQ ID NO 113
<211> LENGTH: 8
<212> TYPE: PRT
<213> ORGANISM: Artificial Sequence
<220> FEATURE:
<223> OTHER INFORMATION: 2A-like motif
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid

<400> SEQUENCE: 113

Asp Xaa Glu Xaa Asn Pro Gly Pro
1               5


<210> SEQ ID NO 114
<211> LENGTH: 30
<212> TYPE: PRT
<213> ORGANISM: Artificial Sequence
<220> FEATURE:
<223> OTHER INFORMATION: 2A-like protein motif
<220> FEATURE:
<221> NAME/KEY: MISC_FEATURE
<222> LOCATION: (1)..(1)
<223> OTHER INFORMATION: Xaa 1 is H, R, Y or D (Xaa at position 1)
<220> FEATURE:
<221> NAME/KEY: MISC_FEATURE
<222> LOCATION: (2)..(2)
```

<223> OTHER INFORMATION: Xaa 2 is K or R
<220> FEATURE:
<221> NAME/KEY: MISC_FEATURE
<222> LOCATION: (3)..(3)
<223> OTHER INFORMATION: Xaa 3 is Q, T. F or V.
<220> FEATURE:
<221> NAME/KEY: MISC_FEATURE
<222> LOCATION: (4)..(4)
<223> OTHER INFORMATION: Xaa 4 is E, K, P, A or D
<220> FEATURE:
<221> NAME/KEY: MISC_FEATURE
<222> LOCATION: (5)..(5)
<223> OTHER INFORMATION: Xaa 5 is I, P, L or A
<220> FEATURE:
<221> NAME/KEY: MISC_FEATURE
<222> LOCATION: (6)..(6)
<223> OTHER INFORMATION: Xaa 6 is I, T or V
<220> FEATURE:
<221> NAME/KEY: MISC_FEATURE
<222> LOCATION: (7)..(7)
<223> OTHER INFORMATION: Xaa 7 is A, K, G or S
<220> FEATURE:
<221> NAME/KEY: MISC_FEATURE
<222> LOCATION: (8)..(8)
<223> OTHER INFORMATION: Xaa 8 is P or V
<220> FEATURE:
<221> NAME/KEY: MISC_FEATURE
<222> LOCATION: (9)..(9)
<223> OTHER INFORMATION: Xaa 9 is E, A or V
<220> FEATURE:
<221> NAME/KEY: MISC_FEATURE
<222> LOCATION: (10)..(10)
<223> OTHER INFORMATION: Xaa 10 is K or R
<220> FEATURE:
<221> NAME/KEY: MISC_FEATURE
<222> LOCATION: (12)..(12)
<223> OTHER INFORMATION: Xaa 12 is V, L, M or T
<220> FEATURE:
<221> NAME/KEY: MISC_FEATURE
<222> LOCATION: (13)..(13)
<223> OTHER INFORMATION: Xaa 13 is L or C
<220> FEATURE:
<221> NAME/KEY: MISC_FEATURE
<222> LOCATION: (14)..(14)
<223> OTHER INFORMATION: Xaa 14 is N or S

<400> SEQUENCE: 114

```
Xaa Xaa Xaa Xaa Xaa Xaa Xaa Xaa Xaa Xaa Gln Xaa Xaa Xaa Phe Asp
1               5                   10                  15

Leu Leu Lys Leu Ala Gly Asp Val Glu Ser Asn Pro Gly Pro
            20                  25                  30
```

<210> SEQ ID NO 115
<211> LENGTH: 17
<212> TYPE: PRT
<213> ORGANISM: Artificial Sequence
<220> FEATURE:
<223> OTHER INFORMATION: 2A-like protein motif
<220> FEATURE:
<221> NAME/KEY: MISC_FEATURE
<222> LOCATION: (1)..(1)
<223> OTHER INFORMATION: Xaa at position 1 is A, V, I, L, M, or T
<220> FEATURE:
<221> NAME/KEY: MISC_FEATURE
<222> LOCATION: (2)..(2)
<223> OTHER INFORMATION: Xaa at position 2 is T, S, L or C
<220> FEATURE:
<221> NAME/KEY: MISC_FEATURE
<222> LOCATION: (3)..(3)
<223> OTHER INFORMATION: Xaa at position 3 is N or S
<220> FEATURE:
<221> NAME/KEY: MISC_FEATURE
<222> LOCATION: (4)..(4)
<223> OTHER INFORMATION: Xaa at position 4 is F or K
<220> FEATURE:
<221> NAME/KEY: MISC_FEATURE
<222> LOCATION: (5)..(5)
<223> OTHER INFORMATION: Xaa at position 5 is D, S or E
<220> FEATURE:
<221> NAME/KEY: MISC_FEATURE
<222> LOCATION: (8)..(8)
<223> OTHER INFORMATION: Xaa at position 8 is K, Q or L
<220> FEATURE:
<221> NAME/KEY: MISC_FEATURE
<222> LOCATION: (9)..(9)
<223> OTHER INFORMATION: Xaa at position 9 is Q, R or L
<220> FEATURE:
<221> NAME/KEY: MISC_FEATURE
<222> LOCATION: (13)..(13)
<223> OTHER INFORMATION: Xaa at position 13 is V or I
<220> FEATURE:
<221> NAME/KEY: MISC_FEATURE
<222> LOCATION: (15)..(15)
<223> OTHER INFORMATION: Xaa at position 15 is T, C or S

<400> SEQUENCE: 115

```
Xaa Xaa Xaa Xaa Xaa Leu Leu Xaa Xaa Ala Gly Glu Xaa Asn Pro Gly
1               5                   10                  15

Pro
```

<210> SEQ ID NO 116
<211> LENGTH: 10
<212> TYPE: PRT
<213> ORGANISM: Artificial Sequence
<220> FEATURE:
<223> OTHER INFORMATION: 2A-like protein motif
<220> FEATURE:
<221> NAME/KEY: MISC_FEATURE
<222> LOCATION: (4)..(4)
<223> OTHER INFORMATION: Xaa at position 4 is V or I
<220> FEATURE:
<221> NAME/KEY: MISC_FEATURE
<222> LOCATION: (6)..(6)
<223> OTHER INFORMATION: Xaa at position 6 is T, C or S

<400> SEQUENCE: 116

```
Ala Gly Asp Xaa Glu Xaa Asn Pro Gly Pro
1               5                   10
```

<210> SEQ ID NO 117
<211> LENGTH: 14
<212> TYPE: PRT
<213> ORGANISM: Artificial Sequence
<220> FEATURE:
<223> OTHER INFORMATION: 2a-like protein motif
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid

<400> SEQUENCE: 117

```
Leu Leu Xaa Xaa Ala Gly Asp Xaa Glu Xaa Asn Pro Gly Pro
1               5                   10
```

<210> SEQ ID NO 118
<211> LENGTH: 558
<212> TYPE: DNA
<213> ORGANISM: Gaussia princeps
<220> FEATURE:
<221> NAME/KEY: CDS

```
<222> LOCATION: (1)..(558)
<220> FEATURE:
<221> NAME/KEY: misc_feature
<222> LOCATION: (1)..(558)
<223> OTHER INFORMATION: GLuc

<400> SEQUENCE: 118

atg gga gtc aaa gtt ctg ttt gcc ctg atc tgc atc gct gtg gcc gag       48
Met Gly Val Lys Val Leu Phe Ala Leu Ile Cys Ile Ala Val Ala Glu
1               5                   10                  15

gcc aag ccc acc gag aac aac gaa gac ttc aac atc gtg gcc gtg gcc       96
Ala Lys Pro Thr Glu Asn Asn Glu Asp Phe Asn Ile Val Ala Val Ala
            20                  25                  30

agc aac ttc gcg acc acg gat ctc gat gct gac cgc ggg aag ttg ccc      144
Ser Asn Phe Ala Thr Thr Asp Leu Asp Ala Asp Arg Gly Lys Leu Pro
        35                  40                  45

ggc aag aag ctg ccg ctg gag gtg ctc aaa gag atg gaa gcc aat gcc      192
Gly Lys Lys Leu Pro Leu Glu Val Leu Lys Glu Met Glu Ala Asn Ala
    50                  55                  60

cgg aaa gct ggc tgc acc agg ggc tgt ctg atc tgc ctg tcc cac atc      240
Arg Lys Ala Gly Cys Thr Arg Gly Cys Leu Ile Cys Leu Ser His Ile
65                  70                  75                  80

aag tgc acg ccc aag atg aag aag ttc atc cca gga cgc tgc cac acc      288
Lys Cys Thr Pro Lys Met Lys Lys Phe Ile Pro Gly Arg Cys His Thr
                85                  90                  95

tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
            100                 105                 110

gtc gac att cct gag att cct ggg ttc aag gac ttg gag ccc atg gag      384
Val Asp Ile Pro Glu Ile Pro Gly Phe Lys Asp Leu Glu Pro Met Glu
        115                 120                 125

cag ttc atc gca cag gtc gat ctg tgt gtg gac tgc aca act ggc tgc      432
Gln Phe Ile Ala Gln Val Asp Leu Cys Val Asp Cys Thr Thr Gly Cys
    130                 135                 140

ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160

ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175

gac aag atc aag ggg gcc ggt ggt gac taa                              558
Asp Lys Ile Lys Gly Ala Gly Gly Asp
            180                 185


<210> SEQ ID NO 119
<211> LENGTH: 185
<212> TYPE: PRT
<213> ORGANISM: Gaussia princeps

<400> SEQUENCE: 119

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80
```

-continued

```
Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185


<210> SEQ ID NO 120
<211> LENGTH: 558
<212> TYPE: DNA
<213> ORGANISM: Gaussia princeps
<220> FEATURE:
<221> NAME/KEY: CDS
<222> LOCATION: (1)..(558)
<220> FEATURE:
<221> NAME/KEY: misc_feature
<222> LOCATION: (1)..(558)
<223> OTHER INFORMATION: SGLUC

<400> SEQUENCE: 120

atg gga gtc aaa gtt ctg ttt gcc ctg atc tgc atc gct gtg gcc gag       48
Met Gly Val Lys Val Leu Phe Ala Leu Ile Cys Ile Ala Val Ala Glu
1               5                   10                  15

gcc aag ccc acc gag aac aac gaa gac ttc aac atc gtg gcc gtg gcc       96
Ala Lys Pro Thr Glu Asn Asn Glu Asp Phe Asn Ile Val Ala Val Ala
            20                  25                  30

agc aac ttt gcg acc acg gat ctc gat gct gac cga ggg aag ttg ccc      144
Ser Asn Phe Ala Thr Thr Asp Leu Asp Ala Asp Arg Gly Lys Leu Pro
        35                  40                  45

ggc aag aag ctg ccg ctg gag gtg ctc aaa gag atg gaa gcc aat gcc      192
Gly Lys Lys Leu Pro Leu Glu Val Leu Lys Glu Met Glu Ala Asn Ala
    50                  55                  60

cgg aaa gct ggc tgc acc agg ggc tgt ctg atc tgc ctg tcc cac atc      240
Arg Lys Ala Gly Cys Thr Arg Gly Cys Leu Ile Cys Leu Ser His Ile
65                  70                  75                  80

aag tgc acg ccc aag atg aag aag tgg ctc cca gga cgc tgc cac acc      288
Lys Cys Thr Pro Lys Met Lys Lys Trp Leu Pro Gly Arg Cys His Thr
                85                  90                  95

tac gaa ggc gac aaa gag tcc gca cag ggc ggc ata ggc gag gcg atc      336
Tyr Glu Gly Asp Lys Glu Ser Ala Gln Gly Gly Ile Gly Glu Ala Ile
            100                 105                 110

gtc gat att cct gag att cct ggg ttc aag gac ttg gag cca atg gag      384
Val Asp Ile Pro Glu Ile Pro Gly Phe Lys Asp Leu Glu Pro Met Glu
        115                 120                 125

cag ttc atc gca cag gtc gat ctg tgt gtg gac tgc aca act ggc tgc      432
Gln Phe Ile Ala Gln Val Asp Leu Cys Val Asp Cys Thr Thr Gly Cys
    130                 135                 140

ctc aaa ggg ctt gcc aac gtg cag tgt tct gac ctg ctc aag aag tgg      480
Leu Lys Gly Leu Ala Asn Val Gln Cys Ser Asp Leu Leu Lys Lys Trp
145                 150                 155                 160

ctg ccg caa cgc tgt gcg acc ttt gcc agc aag atc cag ggc cag gtg      528
Leu Pro Gln Arg Cys Ala Thr Phe Ala Ser Lys Ile Gln Gly Gln Val
                165                 170                 175
```

```
gac aag atc aag ggg gcc ggt ggt gac taa                             558
Asp Lys Ile Lys Gly Ala Gly Gly Asp
            180                 185


<210> SEQ ID NO 121
<211> LENGTH: 185
<212> TYPE: PRT
<213> ORGANISM: Gaussia princeps

<400> SEQUENCE: 121

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Trp Leu Pro Gly Arg Cys His Thr
                85                  90                  95

Tyr Glu Gly Asp Lys Glu Ser Ala Gln Gly Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185


<210> SEQ ID NO 122
<211> LENGTH: 8903
<212> TYPE: DNA
<213> ORGANISM: Artificial Sequence
<220> FEATURE:
<223> OTHER INFORMATION: pSNAP vector and insert

<400> SEQUENCE: 122

aactacgtca ggtggcactt ttcggggaaa tgtgcgcgga acccctattt gtttattttt     60

ctaaatacat tcaaatatgt atccgctcat gagacaataa ccctgataaa tgcttcaata    120

atattgaaaa aggaagagta tgagtattca acatttccgt gtcgccctta ttcccttttt    180

tgcggcattt tgccttcctg tttttgctca cccagaaacg ctggtgaaag taaaagatgc    240

tgaagatcag ttgggtgcac gagtgggtta catcgaactg gatctcaaca gcggtaagat    300

ccttgagagt tttcgccccg aagaacgttt cccaatgatg agcactttta aagttctgct    360

atgtggcgcg gtattatccc gtgttgacgc cgggcaagag caactcggtc gccgcataca    420

ctattctcag aatgacttgg ttgagtactc accagtcaca gaaaagcatc ttacggatgg    480

catgacagta agagaattat gcagtgctgc cataaccatg agtgataaca ctgcggccaa    540

cttacttctg acaacgatcg gaggaccgaa ggagctaacc gcttttttgc acaacatggg    600
```

-continued

```
ggatcatgta actcgccttg atcgttggga accggagctg aatgaagcca taccaaacga    660
cgagcgtgac accacgatgc ctgtagcaat ggcaacaacg ttgcgcaaac tattaactgg    720
cgaactactt actctagctt cccggcaaca attaatagac tggatggagg cggataaagt    780
tgcaggacca cttctgcgct cggcccttcc ggctggctgg tttattgctg ataaatctgg    840
agccggtgag cgtgggtctc gcggtatcat tgcagcactg gggccagatg gtaagccctc    900
ccgtatcgta gttatctaca cgacggggag tcaggcaact atggatgaac gaaatagaca    960
gatcgctgag ataggtgcct cactgattaa gcattggtaa ctgtcagacc aagtttactc   1020
atatatactt tagattgatt taccccggtt gataatcaga aaagccccaa aaacaggaag   1080
attgtataag caaatattta aattgtaaac gttaatattt tgttaaaatt cgcgttaaat   1140
ttttgttaaa tcagctcatt ttttaaccaa taggccgaaa tcggcaaaat cccttataaa   1200
tcaaaagaat agcccgagat agggttgagt gttgttccag tttggaacaa gagtccacta   1260
ttaaagaacg tggactccaa cgtcaaaggg cgaaaaaccg tctatcaggg cgatggccca   1320
ctacgtgaac catcacccaa atcaagtttt ttggggtcga ggtgccgtaa agcactaaat   1380
cggaacccta aagggagccc ccgatttaga gcttgacggg gaaagccggc gaacgtggcg   1440
agaaaggaag ggaagaaagc gaaaggagcg ggcgctaggg cgctggcaag tgtagcggtc   1500
acgctgcgcg taaccaccac acccgccgcg cttaatgcgc cgctacaggg cgcgtaaaag   1560
gatctaggtg aagatccttt ttgataatct catgaccaaa atcccttaac gtgagttttc   1620
gttccactga gcgtcagacc ccgtagaaaa gatcaaagga tcttcttgag atcctttttt   1680
tctgcgcgta atctgctgct tgcaaacaaa aaaaccaccg ctaccagcgg tggtttgttt   1740
gccggatcaa gagctaccaa ctctttttcc gaaggtaact ggcttcagca gagcgcagat   1800
accaaatact gtccttctag tgtagccgta gttaggccac cacttcaaga actctgtagc   1860
accgcctaca tacctcgctc tgctaatcct gttaccagtg gctgctgcca gtggcgataa   1920
gtcgtgtctt accgggttgg actcaagacg atagttaccg gataaggcgc agcggtcggg   1980
ctgaacgggg ggttcgtgca cacagcccag cttggagcga acgacctaca ccgaactgag   2040
atacctacag cgtgagctat gagaaagcgc cacgcttccc gaagggagaa aggcggacag   2100
gtatccggta agcggcaggg tcggaacagg agagcgcacg agggagcttc caggggggaaa   2160
cgcctggtat ctttatagtc ctgtcgggtt tcgccacctc tgacttgagc gtcgattttt   2220
gtgatgctcg tcaggggggc ggagcctatg gaaaaacgcc agcaacgcgg cctttttacg   2280
gttcctggcc ttttgctggc cttttgctca catgttcttt cctgcgttat cccctgattc   2340
tgtggataac cgtattaccg cctttgagtg agctgatacc gctcgccgca gccgaacgac   2400
cgagcgcagc gagtcagtga gcgaggaagc tatggtgcac tctcagtaca atctgctctg   2460
atgccgcata gttaagccag tatacactcc gctatcgcta cgtgactggg tcatggctgc   2520
gccccgacac ccgccaacac ccgctgacgc gccctgacgg gcttgtctgc tcccggcatc   2580
cgcttacaga caagctgtga ccgtctccgg gagctgcatg tgtcagaggt tttcaccgtc   2640
atcaccgaaa cgcgcgaggc agctgcggta aagctcatca gcgtggtcgt gcagcgattc   2700
acagatgtct gcctgttcat ccgcgtccag ctcgttgagt ttctccagaa gcgttaatgt   2760
ctggcttctg ataaagcggg ccatgttaag ggcggttttt tcctgtttgg tcactgatgc   2820
ctccgtgtaa gggggatttc tgttcatggg ggtaatgata ccgatgaaac gagagaggat   2880
gctcacgata cgggttactg atgatgaaca tgcccggtta ctggaacgtt gtgagggtaa   2940
acaactggcg gtatggatgc ggcgggacca gagaaaaatc actcagggtc aatgccagcc   3000
```

```
gaacgccagc aagacgtagc ccagcgcgtc ggccgccatg ccggcgataa tggcctgctt   3060
ctcgccgaaa cgtttggtgg cgggaccagt gacgaaggct tgagcgaggg cgtgcaagat   3120
tccgaatacc gcaagcgaca ggccgatcat cgtcgcgctc cagcgaaagc ggtcctcgcc   3180
gaaaatgacc cagagcgctg ccggcacctg tcctacgagt tgcatgataa agaagacagt   3240
cataagtgcg gcgacgatag tcatgccccg cgcccaccgg aaggagctga ctgggttgaa   3300
ggctctcaag ggcatcggtc gagatcccgg tgcctaatga gtgagctaac ttacattaat   3360
tgcgttgcgc tcactgcccg ctttccagtc gggaaacctg tcgtgccagc tgcattaatg   3420
aatcggccaa cgcgcgggga gaggcggttt gcgtattggg cgccagggtg gtttttcttt   3480
tcaccagtga gacgggcaac agctgattgc ccttcaccgc ctggccctga gagagttgca   3540
gcaagcggtc cacgctggtt tgccccagca ggcgaaaatc ctgtttgatg gtggttaacg   3600
gcgggatata acatgagctg tcttcggtat cgtcgtatcc cactaccgag atgtccgcac   3660
caacgcgcag cccggactcg gtaatggcgc gcattgcgcc cagcgccatc tgatcgttgg   3720
caaccagcat cgcagtggga acgatgccct cattcagcat ttgcatggtt tgttgaaaac   3780
cggacatggc actccagtcg ccttcccgtt ccgctatcgg ctgaatttga ttgcgagtga   3840
gatatttatg ccagccagcc agacgcagac gcgccgagac agaacttaat gggcccgcta   3900
acagcgcgat ttgctggtga cccaatgcga ccagatgctc cacgcccagt cgcgtaccgt   3960
cttcatggga gaaaataata ctgttgatgg gtgtctggtc agagacatca agaaataacg   4020
ccggaacatt agtgcaggca gcttccacag caatggcatc ctggtcatcc agcggatagt   4080
taatgatcag cccactgacg cgttgcgcga gaagattgtg caccgccgct ttacaggctt   4140
cgacgccgct tcgttctacc atcgacacca ccacgctggc acccagttga tcggcgcgag   4200
atttaatcgc cgcgacaatt tgcgacggcg cgtgcagggc cagactggag gtggcaacgc   4260
caatcagcaa cgactgtttg cccgccagtt gttgtgccac gcggttggga atgtaattca   4320
gctccgccat cgccgcttcc actttttccc gcgttttcgc agaaacgtgg ctggcctggt   4380
tcaccacgcg ggaaacggtc tgataagaga caccggcata ctctgcgaca tcgtataacg   4440
ttactggttt cacattcacc accctgaatt gactctcttc cgggcgctat catgccatac   4500
cgcgaaaggt tttgcgccat tcgatggtgt ccgggatctc gacgctctcc cttatgcgac   4560
tcctgcatta ggaagcagcc cagtagtagg ttgaggccgt tgagcaccgc cgccgcaagg   4620
aatggtgcat gccggcatgc cgccctttcg tcttcaagaa ttaattccca attccccagg   4680
catcaaataa aacgaaaggc tcagtcgaaa gactgggcct ttcgttttat ctgttgtttg   4740
tcggtgaacg ctctcctgag taggacaaat ccgccgggag cggatttgaa cgttgcgaag   4800
caacggcccg gagggtggcg ggcaggacgc ccgccataaa ctgccaggaa ttaattcccc   4860
aggcatcaaa taaaacgaaa ggctcagtcg aaagactggg cctttcgttt tatctgttgt   4920
ttgtcggtga acgctctcct gagtaggaca aatccgccgg gagcggattt gaacgttgcg   4980
aagcaacggc ccggagggtg gcgggcagga cgcccgccat aaactgccag gaattaattc   5040
cccaggcatc aaataaaacg aaaggctcag tcgaaagact gggcctttcg ttttatctgt   5100
tgtttgtcgg tgaacgctct cctgagtagg acaaatccgc cgggagcgga tttgaacgtt   5160
gcgaagcaac ggcccggagg gtggcgggca ggacgcccgc cataaactgc caggaattaa   5220
ttccccaggc atcaaataaa acgaaaggct cagtcgaaag actgggcctt tcgttttatc   5280
tgttgtttgt cggtgaacgc tctcctgagt aggacaaatc cgccgggagc ggatttgaac   5340
```

-continued

```
gttgcgaagc aacggcccgg agggtggcgg gcaggacgcc cgccataaac tgccaggaat   5400
taattcccca ggcatcaaat aaaacgaaag gctcagtcga aagactgggc ctttcgtttt   5460
atctgttgtt tgtcggtgaa cgctctcctg agtaggacaa atccgccggg agcggatttg   5520
aacgttgcga agcaacggcc cggagggtgg cgggcaggac gcccgccata aactgccagg   5580
aattggggat cggaattaat tcccggttta aaccggggat ctcgatcccg cgaaattaat   5640
acgactcact ataggggaat tgtgagcgga taacaattcc cctctagaaa taattttgtt   5700
taactttaag aaggagatat acatatggga tccgccgcca ccatgggagc cgggcaatcc   5760
agcccggcaa ccgggtcaca gaaccaatca ggcaacactg ggagcatcat caacaattac   5820
tacatgcagc agtaccaaaa ctctatggac acacaacttg gtgacaacgc tacaagcgga   5880
ggctcaaacg aggggtccac ggacacaacc tccacccaca caaccaacac tcagaacaac   5940
gactggttct cgaagctggc cagttccgct ttcagcggtc ttgaaaacct ttatttccaa   6000
tccaagaaaa ccgaggagac cactcttcta gaggaccgca tcctcactac tcgtaacgga   6060
cacaccacct cgacaaccca gtcgagcgta ggagtcacat acgggtatgc aacggctgag   6120
gatttcgtga gcgggccaaa cacctctggt cttgagacca gggttgccca ggcagagcgg   6180
ttctttaaaa cccacctgtt cgactgggtc acaagtgacc cgttcggacg gtgccacctg   6240
ctagaacttc caactgacca caaaggtgtc tatggcagcc tgaccgactc gtatgcttat   6300
atgaggaacg gctgggatgt tgaagtcact gctgtgggaa atcagttcaa tggaggatgc   6360
ctgttggtgg ctatggtgcc agaactttgc tccatacaga agagggagct gtaccagctc   6420
acgctctttc ctcaccagtt catcaaccct cggacgaaca tgacagcaca catcactgtg   6480
ccctttgttg gcgtcaaccg ttatgaccag tacaaggtac acaaaccttg gaccctcgtg   6540
gttatggttg tagccccccct gaccgtcaac agtgaaggtg ccccgcaaat caaggtgtat   6600
gccaacatcg cacctaccaa cgtacacgtc gcgggtgaga acctttattt tcagtcgatc   6660
ttccctgtgg cttgcagcga tggttatggc ggtctggtga ccactgaccc gaaaacggct   6720
gaccccgctt acgggaaagt gtttaacccc ccccgcaaca tgttgccggg gcggttcacc   6780
aattttcttg acgtggctga ggcgtgcccc acgtttctcc acttcgaggg tgacgtgcca   6840
tacgtgacca cgaagacgga ttcagacagg gtgctcgctc agttcgactt gtctttggca   6900
gcaaagcaca tgtccaacac cttccttgca ggtctcgccc agtactacac acagtacagc   6960
ggcaccatca acctgcactt catgttcaca gggcctactg acgcgaaggc gcgttacatg   7020
attgcgtatg ctcctcctgg catggaacca cctaaaacgc cagaggcggc tgcccactgc   7080
atccatgctg aatgggacac agggttgaac tcaaaattca cattttcaat cccttacctt   7140
tcggcggctg attacgctta cacagcgtct gacactgctg agaccacaaa tgtacaggga   7200
tgggtttgcc tgtttcaaat aacacacggg aaagctgacg gcgacgcact ggtcgttttg   7260
gccagcgccg gaaaggactt tgagcttcgg ctgccggaaa atctttactt tcagtccacc   7320
tcagcgggcg agtcagcaga ccccgtgacc gccaccgttg agaattacgg tggcgagaca   7380
caggtccaga ggcgccaaca cacggacgtg tcatttatat tagacagatt tgtgaaagtg   7440
acaccaaaag accaaattaa tgtattggac ctgatgcaaa cccctgctca cactttggtg   7500
ggagcactcc ttcgtactgc cacttactat ttcgctgact tagaggtggc agtgaagcac   7560
gagggaaacc tcacctgggt gccgaacggg gcgcctgaag cggcgttgga caacaccacc   7620
aacccaacag cttaccacaa ggcaccactc acccgacttg cactgcctta cacggcgcca   7680
caccgcgtgt tggctactgt ttacaacggg aacagcaagt atggtgacgg cacggtggcc   7740
```

```
aatgtgagag gtgatctgca agtgttggcc cagaaggcgg cgagagcgct gcctacctcc   7800

ttcaactacg gtgccattaa agctactcgg gtgactgaac tgctttaccg catgaagagg   7860

gctgagacat actgtccccg gcctcttttg gccattcacc cggaccaggc tagacacaag   7920

cagaagattg tggaaaattt gtattttcaa tctaattttg acctgctcaa attggcggga   7980

gatgtggagt ccaaccctgg gcccgactat aaagacgacg acgacaaacc cggggaaagt   8040

ttgtttaagg ggccgcgtga ttacaacccg atctcaagca ccatttgtca tttgacgaat   8100

gaatctgatg ggcacacaac atcgttgtat ggtattggat ttggtccctt catcattaca   8160

aacaagcact tgtttagaag aaataatgga acactgttgg ttcaatcact acatggtgta   8220

ttcaaggtca agaacaccac gactttgcaa caacacctca ttgatgggag ggacatgata   8280

attattcgca tgccaaagga tttcccacca tttcctcaaa agctgaaatt tagagagcca   8340

caaagggaag agcgcatctg tcttgtgaca accaacttcc aaactaagag catgtctagc   8400

atggtgtcag acaccagttg cacattccct tcatctgatg gcatattctg gaagcattgg   8460

attcaaacca aggatgggca gtgtggcagt ccattagtat caactagaga tgggttcatt   8520

gttggtattc actcagcatc gaatttcacc aacacaaaca attatttcac aagcgtgccg   8580

aagaacttta tggaattgtt gacaaatcag gaggcgcagc agtgggttag tggttggcga   8640

ttaaatgctg actcagtatt gtgggggggc cataaagttt tcatggtgaa acctgaagag   8700

ccttttcagc cagttaagga agcgactcaa ctcatgaatt aagaattctt aattaagcgg   8760

ccgcattgat ccggctgcta acaaagcccg aaaggaagct gagttggctg ctgccaccgc   8820

tgagcaataa ctagcataac cccttggggc ctctaaacgg gtcttgaggg gtttttttgct   8880

gaaaggagga actatatccg gat                                           8903
```

<210> SEQ ID NO 123
<211> LENGTH: 2259
<212> TYPE: DNA
<213> ORGANISM: foot and mouth disease virus
<220> FEATURE:
<221> NAME/KEY: CDS
<222> LOCATION: (1)..(2259)
<223> OTHER INFORMATION: O1 Manisa Iso87; P1; Accession: AY593823

<400> SEQUENCE: 123

```
gga gcc ggg caa tcc agc ccg gca acc ggg tca cag aac caa tca ggc       48
Gly Ala Gly Gln Ser Ser Pro Ala Thr Gly Ser Gln Asn Gln Ser Gly
1               5                   10                  15

aac act ggg agc atc atc aac aat tac tac atg cag cag tac caa aac       96
Asn Thr Gly Ser Ile Ile Asn Asn Tyr Tyr Met Gln Gln Tyr Gln Asn
            20                  25                  30

tcc atg gac aca caa ctt ggt gac aac gct aca agc gga ggc tca aac      144
Ser Met Asp Thr Gln Leu Gly Asp Asn Ala Thr Ser Gly Gly Ser Asn
        35                  40                  45

gag ggg tcc acg gac aca acc tcc acc cac aca acc aac act cag aac      192
Glu Gly Ser Thr Asp Thr Thr Ser Thr His Thr Thr Asn Thr Gln Asn
    50                  55                  60

aac gac tgg ttc tcg aag ctg gcc agt tcc gct ttc agc ggt ctt ttc      240
Asn Asp Trp Phe Ser Lys Leu Ala Ser Ser Ala Phe Ser Gly Leu Phe
65                  70                  75                  80

ggc gct ctt ctc gcc gac aag aaa acc gag gag acc act ctt ctc gag      288
Gly Ala Leu Leu Ala Asp Lys Lys Thr Glu Glu Thr Thr Leu Leu Glu
                85                  90                  95

gac cgc atc ctc act act cgt aac gga cac acc acc tcg aca acc cag      336
Asp Arg Ile Leu Thr Thr Arg Asn Gly His Thr Thr Ser Thr Thr Gln
```

-continued

```
            100                 105                 110

tcg agc gtt gga gtc acg tac ggg tat gca aca gct gag gat ttc gtg      384
Ser Ser Val Gly Val Thr Tyr Gly Tyr Ala Thr Ala Glu Asp Phe Val
        115                 120                 125

agc ggg cca aac acc tct ggt ctc gag acc agg gtt gcc cag gca gag      432
Ser Gly Pro Asn Thr Ser Gly Leu Glu Thr Arg Val Ala Gln Ala Glu
    130                 135                 140

cgg ttc ttt aaa acc cac ctg ttc gac tgg gtc acc agt gac ccg ttc      480
Arg Phe Phe Lys Thr His Leu Phe Asp Trp Val Thr Ser Asp Pro Phe
145                 150                 155                 160

gga cgg tgc cac ctg ctg gaa ctt cca act gac cac aaa ggt gtc tac      528
Gly Arg Cys His Leu Leu Glu Leu Pro Thr Asp His Lys Gly Val Tyr
                165                 170                 175

ggc agc ctg acc gac tcg tat gct tat atg agg aac ggc tgg gat gtt      576
Gly Ser Leu Thr Asp Ser Tyr Ala Tyr Met Arg Asn Gly Trp Asp Val
            180                 185                 190

gaa gtc act gca gtg gga aac cag ttc aat gga gga tgc ctg ttg gtg      624
Glu Val Thr Ala Val Gly Asn Gln Phe Asn Gly Gly Cys Leu Leu Val
        195                 200                 205

gcc atg gtg cca gaa ctt tgc tcc ata cag aag agg gag ctg tac cag      672
Ala Met Val Pro Glu Leu Cys Ser Ile Gln Lys Arg Glu Leu Tyr Gln
    210                 215                 220

ctc acg ctc ttt cct cac cag ttc atc aac cct cgg acg aac atg aca      720
Leu Thr Leu Phe Pro His Gln Phe Ile Asn Pro Arg Thr Asn Met Thr
225                 230                 235                 240

gca cac atc act gtg ccc ttt gtt ggc gtc aac cgt tat gac cag tac      768
Ala His Ile Thr Val Pro Phe Val Gly Val Asn Arg Tyr Asp Gln Tyr
                245                 250                 255

aag gta cac aaa cct tgg acc ctc gtg gtt atg gtt gta gcc ccc ctg      816
Lys Val His Lys Pro Trp Thr Leu Val Val Met Val Val Ala Pro Leu
            260                 265                 270

acc gtc aac agt gaa ggt gcc ccg caa atc aag gtg tat gcc aac atc      864
Thr Val Asn Ser Glu Gly Ala Pro Gln Ile Lys Val Tyr Ala Asn Ile
        275                 280                 285

gca cct acc aac gta cac gtc gcg ggt gag ttc cct tcc aaa gag ggg      912
Ala Pro Thr Asn Val His Val Ala Gly Glu Phe Pro Ser Lys Glu Gly
    290                 295                 300

atc ttc cct gtg gct tgc agc gat ggt tat ggc ggt ctg gtg acc act      960
Ile Phe Pro Val Ala Cys Ser Asp Gly Tyr Gly Gly Leu Val Thr Thr
305                 310                 315                 320

gac ccg aaa acg gct gac ccc gct tac ggg aaa gtg ttt aac ccc ccc     1008
Asp Pro Lys Thr Ala Asp Pro Ala Tyr Gly Lys Val Phe Asn Pro Pro
                325                 330                 335

cgc aac atg ttg ccg ggg cgg ttc acc aat ttt ctt gac gtg gct gag     1056
Arg Asn Met Leu Pro Gly Arg Phe Thr Asn Phe Leu Asp Val Ala Glu
            340                 345                 350

gcg tgc ccc acg ttt ctc cac ttc gag ggt gac gtg cca tac gtg acc     1104
Ala Cys Pro Thr Phe Leu His Phe Glu Gly Asp Val Pro Tyr Val Thr
        355                 360                 365

acg aag acg gat tca gac agg gtg ctc gct cag ttc gac ttg tct ttg     1152
Thr Lys Thr Asp Ser Asp Arg Val Leu Ala Gln Phe Asp Leu Ser Leu
    370                 375                 380

gca gca aag cac atg tcg aac acc ttc ctt gca ggt ctc gcc cag tac     1200
Ala Ala Lys His Met Ser Asn Thr Phe Leu Ala Gly Leu Ala Gln Tyr
385                 390                 395                 400

tac aca cag tac agc ggc acc atc aac ctg cac ttc atg ttc aca ggg     1248
Tyr Thr Gln Tyr Ser Gly Thr Ile Asn Leu His Phe Met Phe Thr Gly
                405                 410                 415

cct act gac gcg aag gcg cgt tac atg att gcg tat gct cct cct ggc     1296
```

-continued

```
Pro Thr Asp Ala Lys Ala Arg Tyr Met Ile Ala Tyr Ala Pro Pro Gly
            420                 425                 430

atg gaa cca cct aaa acg cca gag gcg gct gcc cac tgc att cat gct      1344
Met Glu Pro Pro Lys Thr Pro Glu Ala Ala Ala His Cys Ile His Ala
        435                 440                 445

gaa tgg gac aca ggg ttg aac tca aaa ttc aca ttt tca atc cct tac      1392
Glu Trp Asp Thr Gly Leu Asn Ser Lys Phe Thr Phe Ser Ile Pro Tyr
    450                 455                 460

ctt tcg gcg gct gat tac gct tac aca gcg tct gac act gct gag acc      1440
Leu Ser Ala Ala Asp Tyr Ala Tyr Thr Ala Ser Asp Thr Ala Glu Thr
465                 470                 475                 480

aca aat gta cag gga tgg gtt tgc ctg ttt caa ata aca cac ggg aaa      1488
Thr Asn Val Gln Gly Trp Val Cys Leu Phe Gln Ile Thr His Gly Lys
                485                 490                 495

gct gac ggc gac gca ctg gtc gtt ttg gct agc gcc gga aag gac ttt      1536
Ala Asp Gly Asp Ala Leu Val Val Leu Ala Ser Ala Gly Lys Asp Phe
            500                 505                 510

gag ctg cgc ctg ccg gtg gat gct cgc aca cag act acc tcc gcg ggc      1584
Glu Leu Arg Leu Pro Val Asp Ala Arg Thr Gln Thr Thr Ser Ala Gly
        515                 520                 525

gag tca gct gac ccc gtg acc gcc acc gtt gag aat tac ggt ggc gag      1632
Glu Ser Ala Asp Pro Val Thr Ala Thr Val Glu Asn Tyr Gly Gly Glu
    530                 535                 540

aca cag gtc cag agg cgc caa cac acg gac gtc tca ttt ata tta gac      1680
Thr Gln Val Gln Arg Arg Gln His Thr Asp Val Ser Phe Ile Leu Asp
545                 550                 555                 560

aga ttt gtg aaa gtg aca cca aaa gac caa att aat gta ttg gac ctg      1728
Arg Phe Val Lys Val Thr Pro Lys Asp Gln Ile Asn Val Leu Asp Leu
                565                 570                 575

atg caa acc cct gct cac act ttg gtg gga gca ctc ctt cgt act gcc      1776
Met Gln Thr Pro Ala His Thr Leu Val Gly Ala Leu Leu Arg Thr Ala
            580                 585                 590

act tac tat ttc gct gac tta gag gtg gca gtg aag cac gag gga aac      1824
Thr Tyr Tyr Phe Ala Asp Leu Glu Val Ala Val Lys His Glu Gly Asn
        595                 600                 605

ctc acc tgg gtc ccg aac ggg gcg cct gaa gcg gcg ttg gac aac acc      1872
Leu Thr Trp Val Pro Asn Gly Ala Pro Glu Ala Ala Leu Asp Asn Thr
    610                 615                 620

acc aac cca aca gct tac cac aag gca cca ctc acc cga ctt gca ctg      1920
Thr Asn Pro Thr Ala Tyr His Lys Ala Pro Leu Thr Arg Leu Ala Leu
625                 630                 635                 640

cct tac acg gcg cca cac cgc gtg ttg gct act gtt tac aac ggg aac      1968
Pro Tyr Thr Ala Pro His Arg Val Leu Ala Thr Val Tyr Asn Gly Asn
                645                 650                 655

agc aag tat ggt gac ggc acg gtg gcc aat gtg aga ggt gac ctg caa      2016
Ser Lys Tyr Gly Asp Gly Thr Val Ala Asn Val Arg Gly Asp Leu Gln
            660                 665                 670

gtg ttg gcc cag aag gcg gcg aga gcg ctg cct acc tcc ttc aac tac      2064
Val Leu Ala Gln Lys Ala Ala Arg Ala Leu Pro Thr Ser Phe Asn Tyr
        675                 680                 685

ggt gcc att aaa gct act cgg gtg act gaa ctg ctt tac cgc atg aag      2112
Gly Ala Ile Lys Ala Thr Arg Val Thr Glu Leu Leu Tyr Arg Met Lys
    690                 695                 700

agg gct gag aca tac tgt ccc cgg cct ctt ttg gcc att cac ccg gac      2160
Arg Ala Glu Thr Tyr Cys Pro Arg Pro Leu Leu Ala Ile His Pro Asp
705                 710                 715                 720

cag gct aga cac aag cag aag att gtg gca ccg gtg aaa cag ctt cta      2208
Gln Ala Arg His Lys Gln Lys Ile Val Ala Pro Val Lys Gln Leu Leu
                725                 730                 735
```

```
aat ttt gac ctg ctc aaa ttg gcg gga gat gtg gag tcc aac cct ggg     2256
Asn Phe Asp Leu Leu Lys Leu Ala Gly Asp Val Glu Ser Asn Pro Gly
            740                 745                 750

ccc                                                                 2259
Pro


<210> SEQ ID NO 124
<211> LENGTH: 753
<212> TYPE: PRT
<213> ORGANISM: foot and mouth disease virus

<400> SEQUENCE: 124

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Thr Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Ala Gln Ala Glu
    130                 135                 140

Arg Phe Phe Lys Thr His Leu Phe Asp Trp Val Thr Ser Asp Pro Phe
145                 150                 155                 160

Gly Arg Cys His Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Gln Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu
            260                 265                 270

Thr Val Asn Ser Glu Gly Ala Pro Gln Ile Lys Val Tyr Ala Asn Ile
        275                 280                 285

Ala Pro Thr Asn Val His Val Ala Gly Glu Phe Pro Ser Lys Glu Gly
    290                 295                 300

Ile Phe Pro Val Ala Cys Ser Asp Gly Tyr Gly Gly Leu Val Thr Thr
305                 310                 315                 320

Asp Pro Lys Thr Ala Asp Pro Ala Tyr Gly Lys Val Phe Asn Pro Pro
                325                 330                 335

Arg Asn Met Leu Pro Gly Arg Phe Thr Asn Phe Leu Asp Val Ala Glu
```

340 345 350

Ala Cys Pro Thr Phe Leu His Phe Glu Gly Asp Val Pro Tyr Val Thr
355 360 365

Thr Lys Thr Asp Ser Asp Arg Val Leu Ala Gln Phe Asp Leu Ser Leu
370 375 380

Ala Ala Lys His Met Ser Asn Thr Phe Leu Ala Gly Leu Ala Gln Tyr
385 390 395 400

Tyr Thr Gln Tyr Ser Gly Thr Ile Asn Leu His Phe Met Phe Thr Gly
405 410 415

Pro Thr Asp Ala Lys Ala Arg Tyr Met Ile Ala Tyr Ala Pro Pro Gly
420 425 430

Met Glu Pro Pro Lys Thr Pro Glu Ala Ala Ala His Cys Ile His Ala
435 440 445

Glu Trp Asp Thr Gly Leu Asn Ser Lys Phe Thr Phe Ser Ile Pro Tyr
450 455 460

Leu Ser Ala Ala Asp Tyr Ala Tyr Thr Ala Ser Asp Thr Ala Glu Thr
465 470 475 480

Thr Asn Val Gln Gly Trp Val Cys Leu Phe Gln Ile Thr His Gly Lys
485 490 495

Ala Asp Gly Asp Ala Leu Val Val Leu Ala Ser Ala Gly Lys Asp Phe
500 505 510

Glu Leu Arg Leu Pro Val Asp Ala Arg Thr Gln Thr Thr Ser Ala Gly
515 520 525

Glu Ser Ala Asp Pro Val Thr Ala Thr Val Glu Asn Tyr Gly Gly Glu
530 535 540

Thr Gln Val Gln Arg Arg Gln His Thr Asp Val Ser Phe Ile Leu Asp
545 550 555 560

Arg Phe Val Lys Val Thr Pro Lys Asp Gln Ile Asn Val Leu Asp Leu
565 570 575

Met Gln Thr Pro Ala His Thr Leu Val Gly Ala Leu Leu Arg Thr Ala
580 585 590

Thr Tyr Tyr Phe Ala Asp Leu Glu Val Ala Val Lys His Glu Gly Asn
595 600 605

Leu Thr Trp Val Pro Asn Gly Ala Pro Glu Ala Ala Leu Asp Asn Thr
610 615 620

Thr Asn Pro Thr Ala Tyr His Lys Ala Pro Leu Thr Arg Leu Ala Leu
625 630 635 640

Pro Tyr Thr Ala Pro His Arg Val Leu Ala Thr Val Tyr Asn Gly Asn
645 650 655

Ser Lys Tyr Gly Asp Gly Thr Val Ala Asn Val Arg Gly Asp Leu Gln
660 665 670

Val Leu Ala Gln Lys Ala Ala Arg Ala Leu Pro Thr Ser Phe Asn Tyr
675 680 685

Gly Ala Ile Lys Ala Thr Arg Val Thr Glu Leu Leu Tyr Arg Met Lys
690 695 700

Arg Ala Glu Thr Tyr Cys Pro Arg Pro Leu Leu Ala Ile His Pro Asp
705 710 715 720

Gln Ala Arg His Lys Gln Lys Ile Val Ala Pro Val Lys Gln Leu Leu
725 730 735

Asn Phe Asp Leu Leu Lys Leu Ala Gly Asp Val Glu Ser Asn Pro Gly
740 745 750

Pro

<210> SEQ ID NO 125
<211> LENGTH: 2259
<212> TYPE: DNA
<213> ORGANISM: foot and mouth disease virus
<220> FEATURE:
<221> NAME/KEY: CDS
<222> LOCATION: (1)..(2259)
<223> OTHER INFORMATION: O1 pan Asia; P1

<400> SEQUENCE: 125

```
ggt gct ggg caa tcc agc ccg gcg act ggg tca cag aac cag tca ggc       48
Gly Ala Gly Gln Ser Ser Pro Ala Thr Gly Ser Gln Asn Gln Ser Gly
1               5                   10                  15

aac act gga agc atc atc aac aac tac tac atg cag cag tac cag aac       96
Asn Thr Gly Ser Ile Ile Asn Asn Tyr Tyr Met Gln Gln Tyr Gln Asn
            20                  25                  30

tcc atg gac aca caa ctt ggt gac aac gct atc agc gga ggc tct aac      144
Ser Met Asp Thr Gln Leu Gly Asp Asn Ala Ile Ser Gly Gly Ser Asn
        35                  40                  45

gaa ggg tct aca gac acc acc tcc acc cac aca acc aac act cag aac      192
Glu Gly Ser Thr Asp Thr Thr Ser Thr His Thr Thr Asn Thr Gln Asn
    50                  55                  60

aac gac tgg ttt tca aaa cta gcc agt tcc gct ttc agc ggt ctt ttc      240
Asn Asp Trp Phe Ser Lys Leu Ala Ser Ser Ala Phe Ser Gly Leu Phe
65                  70                  75                  80

ggc gct ctt ctc gcc gac aag aaa acc gag gag act act ctt ctc gag      288
Gly Ala Leu Leu Ala Asp Lys Lys Thr Glu Glu Thr Thr Leu Leu Glu
                85                  90                  95

gac cgc atc ctc act acc cgt aac gga cac aca acc tcg aca acc cag      336
Asp Arg Ile Leu Thr Thr Arg Asn Gly His Thr Thr Ser Thr Thr Gln
            100                 105                 110

tcg agc gtt gga gtc act tac ggg tac gca aca gcc gag gat ttt gtg      384
Ser Ser Val Gly Val Thr Tyr Gly Tyr Ala Thr Ala Glu Asp Phe Val
        115                 120                 125

agc ggg cca aac aca tct ggc ctt gag acc agg gtt gtg caa gca gag      432
Ser Gly Pro Asn Thr Ser Gly Leu Glu Thr Arg Val Val Gln Ala Glu
    130                 135                 140

cgg ttc ttc aaa acc cac ttg ttc gat tgg gtc act agt gac tcg ttc      480
Arg Phe Phe Lys Thr His Leu Phe Asp Trp Val Thr Ser Asp Ser Phe
145                 150                 155                 160

gga cga tgc cac ctg ctg gaa ctt cca act gac cac aaa ggt gtc tac      528
Gly Arg Cys His Leu Leu Glu Leu Pro Thr Asp His Lys Gly Val Tyr
                165                 170                 175

ggc agc ctg act gat tct tat gcg tac atg aga aac ggt tgg gat gtc      576
Gly Ser Leu Thr Asp Ser Tyr Ala Tyr Met Arg Asn Gly Trp Asp Val
            180                 185                 190

gag gtc act gcg gtg gga aac cag ttc aac gga gga tgc ctg ttg gtg      624
Glu Val Thr Ala Val Gly Asn Gln Phe Asn Gly Gly Cys Leu Leu Val
        195                 200                 205

gcc atg gtg cca gaa ctc tgc tct atc agc aaa aga gag ctg tac cag      672
Ala Met Val Pro Glu Leu Cys Ser Ile Ser Lys Arg Glu Leu Tyr Gln
    210                 215                 220

ctc acg ctc ttt ccc cac cag ttc atc aac ccc cgg acg aac atg acg      720
Leu Thr Leu Phe Pro His Gln Phe Ile Asn Pro Arg Thr Asn Met Thr
225                 230                 235                 240

gca cac atc acc gtg ccc ttt gtc ggc gtc aac cgc tac gac cag tac      768
Ala His Ile Thr Val Pro Phe Val Gly Val Asn Arg Tyr Asp Gln Tyr
                245                 250                 255

aag gta cac aaa cct tgg acc ctc gtg gtc atg gtc gtg gcc ccg ctg      816
Lys Val His Lys Pro Trp Thr Leu Val Val Met Val Val Ala Pro Leu
            260                 265                 270
```

-continued

```
act gtc aac act gaa ggt gct cca cag atc aag gtt tat gcc aac atc      864
Thr Val Asn Thr Glu Gly Ala Pro Gln Ile Lys Val Tyr Ala Asn Ile
        275                 280                 285

gcc cct acc aac gtg cac gtc gcg ggt gag ttc ccc tcc aag gaa ggg      912
Ala Pro Thr Asn Val His Val Ala Gly Glu Phe Pro Ser Lys Glu Gly
    290                 295                 300

atc ttc ccc gtg gcc tgc agt gac ggt tac ggc ggt ctt gtg acc act      960
Ile Phe Pro Val Ala Cys Ser Asp Gly Tyr Gly Gly Leu Val Thr Thr
305                 310                 315                 320

gac cca aag acg gct gac ccc gtt tac ggg aaa gtt ttc aat ccc cct     1008
Asp Pro Lys Thr Ala Asp Pro Val Tyr Gly Lys Val Phe Asn Pro Pro
                325                 330                 335

cgc agc atg ttg cca ggg cga ttc acc aac ttc ctt gat gtg gct gag     1056
Arg Ser Met Leu Pro Gly Arg Phe Thr Asn Phe Leu Asp Val Ala Glu
            340                 345                 350

gcg tgc cct acg ttt ctg cat ttt gag ggt gac gta cca tac gtg acc     1104
Ala Cys Pro Thr Phe Leu His Phe Glu Gly Asp Val Pro Tyr Val Thr
        355                 360                 365

aca aag acg gat tcg gac agg gtt ctc gct cag ttt gac ttg tct ttg     1152
Thr Lys Thr Asp Ser Asp Arg Val Leu Ala Gln Phe Asp Leu Ser Leu
    370                 375                 380

gca gcg aag cac atg tca aac acc ttt ctt gca ggt ctc gcc cag tac     1200
Ala Ala Lys His Met Ser Asn Thr Phe Leu Ala Gly Leu Ala Gln Tyr
385                 390                 395                 400

tac gca cag tac agt ggc act att aac ctg cac ttc atg ttc aca ggg     1248
Tyr Ala Gln Tyr Ser Gly Thr Ile Asn Leu His Phe Met Phe Thr Gly
                405                 410                 415

ccc act gac gcg aaa gcg cgt tac atg att gca tat gcc ccc ccc ggc     1296
Pro Thr Asp Ala Lys Ala Arg Tyr Met Ile Ala Tyr Ala Pro Pro Gly
            420                 425                 430

atg gag ccg cct aaa aca cct gag gca gcc gct cac tgc att cac gcg     1344
Met Glu Pro Pro Lys Thr Pro Glu Ala Ala Ala His Cys Ile His Ala
        435                 440                 445

gag tgg gat act gga ttg aat tca aaa ttc aca ttc tca atc cct tac     1392
Glu Trp Asp Thr Gly Leu Asn Ser Lys Phe Thr Phe Ser Ile Pro Tyr
    450                 455                 460

ctc tcg gcg gct gac tac gcg tac acc gcg tct gac acc gcc gag acc     1440
Leu Ser Ala Ala Asp Tyr Ala Tyr Thr Ala Ser Asp Thr Ala Glu Thr
465                 470                 475                 480

aca aat gta cag gga tgg gtt tgc ctg ttt caa atc acg cac ggg aag     1488
Thr Asn Val Gln Gly Trp Val Cys Leu Phe Gln Ile Thr His Gly Lys
                485                 490                 495

gcc gat ggt gac gca ctt gtt gtc ctg gct agc gcc ggt aag gac ttc     1536
Ala Asp Gly Asp Ala Leu Val Val Leu Ala Ser Ala Gly Lys Asp Phe
            500                 505                 510

gag ctg cgg ttg cca gtt gat gcc cgc acg cag acc acc tcc aca ggt     1584
Glu Leu Arg Leu Pro Val Asp Ala Arg Thr Gln Thr Thr Ser Thr Gly
        515                 520                 525

gag tca gct gac ccc gtg act gcc act gtt gag aac tac ggt ggc gaa     1632
Glu Ser Ala Asp Pro Val Thr Ala Thr Val Glu Asn Tyr Gly Gly Glu
    530                 535                 540

aca cag gtc cag aga cgc cag cac acg gac gtc tcg ttt ata ttg gac     1680
Thr Gln Val Gln Arg Arg Gln His Thr Asp Val Ser Phe Ile Leu Asp
545                 550                 555                 560

aga ttt gtg aaa gtg aca cca aaa gac caa atc aat gtg ttg gac ctg     1728
Arg Phe Val Lys Val Thr Pro Lys Asp Gln Ile Asn Val Leu Asp Leu
                565                 570                 575

atg caa acc ccc gcc cac act ttg gta ggt gca ctc ctc cgc acc gcc     1776
Met Gln Thr Pro Ala His Thr Leu Val Gly Ala Leu Leu Arg Thr Ala
```

```
            580                 585                 590

acc tac tac ttc gca gat tta gag gtg gca gta aaa cac gag ggg aac      1824
Thr Tyr Tyr Phe Ala Asp Leu Glu Val Ala Val Lys His Glu Gly Asn
        595                 600                 605

ctt acc tgg gtc ccg aat ggg gcg ccc gag aca gcg ttg gat aac acc      1872
Leu Thr Trp Val Pro Asn Gly Ala Pro Glu Thr Ala Leu Asp Asn Thr
    610                 615                 620

act aat cca acg gct tac cac aag gca ccg ctc act cgt ctt gca ctg      1920
Thr Asn Pro Thr Ala Tyr His Lys Ala Pro Leu Thr Arg Leu Ala Leu
625                 630                 635                 640

cct tac acg gca ccg cac cgt gtc ttg gct acc gtt tac aac ggg aac      1968
Pro Tyr Thr Ala Pro His Arg Val Leu Ala Thr Val Tyr Asn Gly Asn
                645                 650                 655

tgc aag tac gac gag agc agc aca acc aac gtg aga ggt gac ctg caa      2016
Cys Lys Tyr Asp Glu Ser Ser Thr Thr Asn Val Arg Gly Asp Leu Gln
            660                 665                 670

gtg ttg gcc caa aag gcg gcg agg acg ctg ccc acc tcc ttc aac tac      2064
Val Leu Ala Gln Lys Ala Ala Arg Thr Leu Pro Thr Ser Phe Asn Tyr
        675                 680                 685

ggt gcc atc aaa gct acc cgg gtg aac gag ttg ctt tac cgc atg aag      2112
Gly Ala Ile Lys Ala Thr Arg Val Asn Glu Leu Leu Tyr Arg Met Lys
    690                 695                 700

agg gct gaa aca tac tgc ccc cgg cct ctt ttg gcc att cat ccg aat      2160
Arg Ala Glu Thr Tyr Cys Pro Arg Pro Leu Leu Ala Ile His Pro Asn
705                 710                 715                 720

gaa gca aga cac aag caa aag ata gtg gca cct gcg aag caa ctc ctg      2208
Glu Ala Arg His Lys Gln Lys Ile Val Ala Pro Ala Lys Gln Leu Leu
                725                 730                 735

aac ttc gac ctg ctc aag ttg gcg gga gac gtt gag tcc aac cct ggg      2256
Asn Phe Asp Leu Leu Lys Leu Ala Gly Asp Val Glu Ser Asn Pro Gly
            740                 745                 750

ccc                                                                  2259
Pro


<210> SEQ ID NO 126
<211> LENGTH: 753
<212> TYPE: PRT
<213> ORGANISM: foot and mouth disease virus

<400> SEQUENCE: 126

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Val Gln Ala Glu
    130                 135                 140
```

-continued

```
Arg Phe Phe Lys Thr His Leu Phe Asp Trp Val Thr Ser Asp Ser Phe
145                 150                 155                 160

Gly Arg Cys His Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Ser Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu
            260                 265                 270

Thr Val Asn Thr Glu Gly Ala Pro Gln Ile Lys Val Tyr Ala Asn Ile
        275                 280                 285

Ala Pro Thr Asn Val His Val Ala Gly Glu Phe Pro Ser Lys Glu Gly
    290                 295                 300

Ile Phe Pro Val Ala Cys Ser Asp Gly Tyr Gly Gly Leu Val Thr Thr
305                 310                 315                 320

Asp Pro Lys Thr Ala Asp Pro Val Tyr Gly Lys Val Phe Asn Pro Pro
                325                 330                 335

Arg Ser Met Leu Pro Gly Arg Phe Thr Asn Phe Leu Asp Val Ala Glu
            340                 345                 350

Ala Cys Pro Thr Phe Leu His Phe Glu Gly Asp Val Pro Tyr Val Thr
        355                 360                 365

Thr Lys Thr Asp Ser Asp Arg Val Leu Ala Gln Phe Asp Leu Ser Leu
    370                 375                 380

Ala Ala Lys His Met Ser Asn Thr Phe Leu Ala Gly Leu Ala Gln Tyr
385                 390                 395                 400

Tyr Ala Gln Tyr Ser Gly Thr Ile Asn Leu His Phe Met Phe Thr Gly
                405                 410                 415

Pro Thr Asp Ala Lys Ala Arg Tyr Met Ile Ala Tyr Ala Pro Pro Gly
            420                 425                 430

Met Glu Pro Pro Lys Thr Pro Glu Ala Ala Ala His Cys Ile His Ala
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Thr Ala Glu Thr
465                 470                 475                 480

Thr Asn Val Gln Gly Trp Val Cys Leu Phe Gln Ile Thr His Gly Lys
                485                 490                 495

Ala Asp Gly Asp Ala Leu Val Val Leu Ala Ser Ala Gly Lys Asp Phe
            500                 505                 510

Glu Leu Arg Leu Pro Val Asp Ala Arg Thr Gln Thr Thr Ser Thr Gly
        515                 520                 525

Glu Ser Ala Asp Pro Val Thr Ala Thr Val Glu Asn Tyr Gly Gly Glu
    530                 535                 540

Thr Gln Val Gln Arg Arg Gln His Thr Asp Val Ser Phe Ile Leu Asp
545                 550                 555                 560
```

```
Arg Phe Val Lys Val Thr Pro Lys Asp Gln Ile Asn Val Leu Asp Leu
            565                 570                 575

Met Gln Thr Pro Ala His Thr Leu Val Gly Ala Leu Leu Arg Thr Ala
            580                 585                 590

Thr Tyr Tyr Phe Ala Asp Leu Glu Val Ala Val Lys His Glu Gly Asn
        595                 600                 605

Leu Thr Trp Val Pro Asn Gly Ala Pro Glu Thr Ala Leu Asp Asn Thr
    610                 615                 620

Thr Asn Pro Thr Ala Tyr His Lys Ala Pro Leu Thr Arg Leu Ala Leu
625                 630                 635                 640

Pro Tyr Thr Ala Pro His Arg Val Leu Ala Thr Val Tyr Asn Gly Asn
            645                 650                 655

Cys Lys Tyr Asp Glu Ser Ser Thr Thr Asn Val Arg Gly Asp Leu Gln
            660                 665                 670

Val Leu Ala Gln Lys Ala Ala Arg Thr Leu Pro Thr Ser Phe Asn Tyr
        675                 680                 685

Gly Ala Ile Lys Ala Thr Arg Val Asn Glu Leu Leu Tyr Arg Met Lys
    690                 695                 700

Arg Ala Glu Thr Tyr Cys Pro Arg Pro Leu Leu Ala Ile His Pro Asn
705                 710                 715                 720

Glu Ala Arg His Lys Gln Lys Ile Val Ala Pro Ala Lys Gln Leu Leu
            725                 730                 735

Asn Phe Asp Leu Leu Lys Leu Ala Gly Asp Val Glu Ser Asn Pro Gly
            740                 745                 750

Pro


<210> SEQ ID NO 127
<211> LENGTH: 2262
<212> TYPE: DNA
<213> ORGANISM: foot and mouth disease virus
<220> FEATURE:
<221> NAME/KEY: CDS
<222> LOCATION: (1)..(2262)
<223> OTHER INFORMATION: A24 Cruzeiro iso71; P1; Accession: AY593768

<400> SEQUENCE: 127

ggg gcc ggg caa tcc agt ccg gcg acc ggc tcg cag aac caa tct ggc       48
Gly Ala Gly Gln Ser Ser Pro Ala Thr Gly Ser Gln Asn Gln Ser Gly
1               5                   10                  15

aac act ggc agc ata att aac aac tac tac atg cag caa tac cag aac       96
Asn Thr Gly Ser Ile Ile Asn Asn Tyr Tyr Met Gln Gln Tyr Gln Asn
            20                  25                  30

tcc atg gac aca cag ttg gga gac aat gcc atc agt gga ggc tcc aac      144
Ser Met Asp Thr Gln Leu Gly Asp Asn Ala Ile Ser Gly Gly Ser Asn
        35                  40                  45

gag ggc tcc acg gac aca act tca aca cac aca acc aac act caa aac      192
Glu Gly Ser Thr Asp Thr Thr Ser Thr His Thr Thr Asn Thr Gln Asn
    50                  55                  60

aat gac tgg ttc tcg aag ctc gcc agt tca gct ttt acc ggt ctg ttc      240
Asn Asp Trp Phe Ser Lys Leu Ala Ser Ser Ala Phe Thr Gly Leu Phe
65                  70                  75                  80

ggt gca ctg ctc gcc gac aag aag aca gag gaa acg aca ctt ctt gag      288
Gly Ala Leu Leu Ala Asp Lys Lys Thr Glu Glu Thr Thr Leu Leu Glu
                85                  90                  95

gac cgc atc ctc acc acc cgc aac ggg cac acc acc tcg acg acc caa      336
Asp Arg Ile Leu Thr Thr Arg Asn Gly His Thr Thr Ser Thr Thr Gln
            100                 105                 110

tcg agt gtg ggt gtc aca cac ggg tac tcc aca gag gag gac cac gtt      384
```

```
Ser Ser Val Gly Val Thr His Gly Tyr Ser Thr Glu Glu Asp His Val
        115                 120                 125

gct ggg ccc aac aca tcg ggc ctg gag acg cga gtg gtg cag gca gag      432
Ala Gly Pro Asn Thr Ser Gly Leu Glu Thr Arg Val Val Gln Ala Glu
    130                 135                 140

aga ttc tac aaa aag tac ttg ttt gac tgg aca acg gac aag gca ttt      480
Arg Phe Tyr Lys Lys Tyr Leu Phe Asp Trp Thr Thr Asp Lys Ala Phe
145                 150                 155                 160

gga cac ctg gaa aag ctg gag ctc ccg tcc gac cac cac ggt gtc ttt      528
Gly His Leu Glu Lys Leu Glu Leu Pro Ser Asp His His Gly Val Phe
                165                 170                 175

gga cac ttg gtg gac tcg tac gcc tat atg aga aat ggc tgg gat gtt      576
Gly His Leu Val Asp Ser Tyr Ala Tyr Met Arg Asn Gly Trp Asp Val
            180                 185                 190

gag gtg tcc gct gtt ggc aac cag ttc aac ggc ggg tgc ctc ctg gtg      624
Glu Val Ser Ala Val Gly Asn Gln Phe Asn Gly Gly Cys Leu Leu Val
        195                 200                 205

gcc atg gta cct gaa tgg aag gaa ttt gac aca cgg gag aaa tac caa      672
Ala Met Val Pro Glu Trp Lys Glu Phe Asp Thr Arg Glu Lys Tyr Gln
    210                 215                 220

ctc acc ctt ttc ccg cac cag ttt att agc ccc aga act aac atg act      720
Leu Thr Leu Phe Pro His Gln Phe Ile Ser Pro Arg Thr Asn Met Thr
225                 230                 235                 240

gcc cac atc acg gtc ccc tac ctt ggt gtg aac agg tat gat cag tac      768
Ala His Ile Thr Val Pro Tyr Leu Gly Val Asn Arg Tyr Asp Gln Tyr
                245                 250                 255

aag aag cat aag ccc tgg aca ttg gtt gtc atg gtc gtg tcg cca ctt      816
Lys Lys His Lys Pro Trp Thr Leu Val Val Met Val Val Ser Pro Leu
            260                 265                 270

acg gtc aac aac act agt gcg gca caa atc aag gtc tac gcc aac ata      864
Thr Val Asn Asn Thr Ser Ala Ala Gln Ile Lys Val Tyr Ala Asn Ile
        275                 280                 285

gct ccg acc tat gtt cac gtg gcc ggt gaa ctc ccc tcg aaa gag ggg      912
Ala Pro Thr Tyr Val His Val Ala Gly Glu Leu Pro Ser Lys Glu Gly
    290                 295                 300

att ttc ccg gtt gca tgt gcg gac ggt tac gga gga ttg gtg acg aca      960
Ile Phe Pro Val Ala Cys Ala Asp Gly Tyr Gly Gly Leu Val Thr Thr
305                 310                 315                 320

gac ccg aag aca gct gac cct gct tat ggc aag gtg tac aac ccg cct     1008
Asp Pro Lys Thr Ala Asp Pro Ala Tyr Gly Lys Val Tyr Asn Pro Pro
                325                 330                 335

agg act aac tac cct ggg cgc ttc acc aac ctg ttg gac gtg gcc gaa     1056
Arg Thr Asn Tyr Pro Gly Arg Phe Thr Asn Leu Leu Asp Val Ala Glu
            340                 345                 350

gcg tgt ccc act ttc ctc tgc ttt gac gac ggg aaa ccg tac gtc acc     1104
Ala Cys Pro Thr Phe Leu Cys Phe Asp Asp Gly Lys Pro Tyr Val Thr
        355                 360                 365

acg cgg acg gat gac acc cga ctt ttg gcc aag ttt gac ctt tcc ctt     1152
Thr Arg Thr Asp Asp Thr Arg Leu Leu Ala Lys Phe Asp Leu Ser Leu
    370                 375                 380

gcc gca aaa cat atg tcc aac aca tac ctg tca ggg att gct cag tac     1200
Ala Ala Lys His Met Ser Asn Thr Tyr Leu Ser Gly Ile Ala Gln Tyr
385                 390                 395                 400

tac aca cag tac tct ggc acc atc aat ttg cat ttc atg ttc aca ggt     1248
Tyr Thr Gln Tyr Ser Gly Thr Ile Asn Leu His Phe Met Phe Thr Gly
                405                 410                 415

tcc act gat tca aag gcc cga tac atg gtg gcc tac atc cca cct ggg     1296
Ser Thr Asp Ser Lys Ala Arg Tyr Met Val Ala Tyr Ile Pro Pro Gly
            420                 425                 430
```

-continued

```
gtg gag aca cca ccg gac aca cct gaa agg gct gcc cac tgc att cac      1344
Val Glu Thr Pro Pro Asp Thr Pro Glu Arg Ala Ala His Cys Ile His
        435                 440                 445

gct gaa tgg gac act gga cta aac tcc aaa ttc act ttc tca atc ccg      1392
Ala Glu Trp Asp Thr Gly Leu Asn Ser Lys Phe Thr Phe Ser Ile Pro
    450                 455                 460

tac gta tcc gcc gcg gat tac gcg tac aca gcg tct gac acg gca gaa      1440
Tyr Val Ser Ala Ala Asp Tyr Ala Tyr Thr Ala Ser Asp Thr Ala Glu
465                 470                 475                 480

aca atc aac gta cag gga tgg gtc tgc atc tac caa att aca cac ggg      1488
Thr Ile Asn Val Gln Gly Trp Val Cys Ile Tyr Gln Ile Thr His Gly
                485                 490                 495

aag gct gaa aat gac acc ttg gtc gtg tcg gtt agc gcc ggc aaa gac      1536
Lys Ala Glu Asn Asp Thr Leu Val Val Ser Val Ser Ala Gly Lys Asp
            500                 505                 510

ttt gag ttg cgc ctc ccg att gac ccc cgc cag cag acc acc gct acc      1584
Phe Glu Leu Arg Leu Pro Ile Asp Pro Arg Gln Gln Thr Thr Ala Thr
        515                 520                 525

ggg gaa tca gca gac ccg gtc acc acc acc gtg gag aac tac ggc ggt      1632
Gly Glu Ser Ala Asp Pro Val Thr Thr Thr Val Glu Asn Tyr Gly Gly
    530                 535                 540

gag aca caa atc cag aga cgt cac cac acg gac att ggt ttc atc atg      1680
Glu Thr Gln Ile Gln Arg Arg His His Thr Asp Ile Gly Phe Ile Met
545                 550                 555                 560

gac aga ttt gtg aag atc caa agc ttg agc cca aca cat gtc att gac      1728
Asp Arg Phe Val Lys Ile Gln Ser Leu Ser Pro Thr His Val Ile Asp
                565                 570                 575

ctc atg cag act cac caa cac ggt ctg gtg ggt gcc ttg ctg cgt gca      1776
Leu Met Gln Thr His Gln His Gly Leu Val Gly Ala Leu Leu Arg Ala
            580                 585                 590

gcc acg tac tac ttt tct gac ctg gaa att gtt gta cgg cac gaa ggc      1824
Ala Thr Tyr Tyr Phe Ser Asp Leu Glu Ile Val Val Arg His Glu Gly
        595                 600                 605

aat ctg acc tgg gtg ccc aac ggc gcc cct gaa tca gcc ctg ttg aac      1872
Asn Leu Thr Trp Val Pro Asn Gly Ala Pro Glu Ser Ala Leu Leu Asn
    610                 615                 620

acc agc aac ccc act gcc tac aac aag gca cca ttc acg aga ctc gct      1920
Thr Ser Asn Pro Thr Ala Tyr Asn Lys Ala Pro Phe Thr Arg Leu Ala
625                 630                 635                 640

ctc ccc tac act gcg ccg cac cgt gtg ctg gca aca gtg tac aac ggg      1968
Leu Pro Tyr Thr Ala Pro His Arg Val Leu Ala Thr Val Tyr Asn Gly
                645                 650                 655

acg agt aag tat gct gtg ggt ggt tca ggc aga aga ggc gac atg ggg      2016
Thr Ser Lys Tyr Ala Val Gly Gly Ser Gly Arg Arg Gly Asp Met Gly
            660                 665                 670

tct ctc gcg gcg cga gtc gtg aaa cag ctt cct gct tca ttt aac tac      2064
Ser Leu Ala Ala Arg Val Val Lys Gln Leu Pro Ala Ser Phe Asn Tyr
        675                 680                 685

ggt gca atc aag gcc gac gcc atc cac gaa ctt ctc gtg cgc atg aaa      2112
Gly Ala Ile Lys Ala Asp Ala Ile His Glu Leu Leu Val Arg Met Lys
    690                 695                 700

cgg gcc gag ctc tac tgc ccc aga ccg ctg ttg gca ata gag gtg tct      2160
Arg Ala Glu Leu Tyr Cys Pro Arg Pro Leu Leu Ala Ile Glu Val Ser
705                 710                 715                 720

tcg caa gac agg cac aag caa aag atc att gca cca gca aag cag ctt      2208
Ser Gln Asp Arg His Lys Gln Lys Ile Ile Ala Pro Ala Lys Gln Leu
                725                 730                 735

ctg aat ttt gac ctg ctc aag ttg gcc gga gac gtt gag tcc aac cct      2256
Leu Asn Phe Asp Leu Leu Lys Leu Ala Gly Asp Val Glu Ser Asn Pro
            740                 745                 750
```

-continued ggg ccc 2262
Gly Pro

<210> SEQ ID NO 128
<211> LENGTH: 754
<212> TYPE: PRT
<213> ORGANISM: foot and mouth disease virus

<400> SEQUENCE: 128

Gly Ala Gly Gln Ser Ser Pro Ala Thr Gly Ser Gln Asn Gln Ser Gly
1 5 10 15

Asn Thr Gly Ser Ile Ile Asn Asn Tyr Tyr Met Gln Gln Tyr Gln Asn
20 25 30

Ser Met Asp Thr Gln Leu Gly Asp Asn Ala Ile Ser Gly Gly Ser Asn
35 40 45

Glu Gly Ser Thr Asp Thr Thr Ser Thr His Thr Thr Asn Thr Gln Asn
50 55 60

Asn Asp Trp Phe Ser Lys Leu Ala Ser Ser Ala Phe Thr Gly Leu Phe
65 70 75 80

Gly Ala Leu Leu Ala Asp Lys Lys Thr Glu Glu Thr Thr Leu Leu Glu
85 90 95

Asp Arg Ile Leu Thr Thr Arg Asn Gly His Thr Thr Ser Thr Thr Gln
100 105 110

Ser Ser Val Gly Val Thr His Gly Tyr Ser Thr Glu Glu Asp His Val
115 120 125

Ala Gly Pro Asn Thr Ser Gly Leu Glu Thr Arg Val Val Gln Ala Glu
130 135 140

Arg Phe Tyr Lys Lys Tyr Leu Phe Asp Trp Thr Thr Asp Lys Ala Phe
145 150 155 160

Gly His Leu Glu Lys Leu Glu Leu Pro Ser Asp His His Gly Val Phe
165 170 175

Gly His Leu Val Asp Ser Tyr Ala Tyr Met Arg Asn Gly Trp Asp Val
180 185 190

Glu Val Ser Ala Val Gly Asn Gln Phe Asn Gly Gly Cys Leu Leu Val
195 200 205

Ala Met Val Pro Glu Trp Lys Glu Phe Asp Thr Arg Glu Lys Tyr Gln
210 215 220

Leu Thr Leu Phe Pro His Gln Phe Ile Ser Pro Arg Thr Asn Met Thr
225 230 235 240

Ala His Ile Thr Val Pro Tyr Leu Gly Val Asn Arg Tyr Asp Gln Tyr
245 250 255

Lys Lys His Lys Pro Trp Thr Leu Val Val Met Val Val Ser Pro Leu
260 265 270

Thr Val Asn Asn Thr Ser Ala Ala Gln Ile Lys Val Tyr Ala Asn Ile
275 280 285

Ala Pro Thr Tyr Val His Val Ala Gly Glu Leu Pro Ser Lys Glu Gly
290 295 300

Ile Phe Pro Val Ala Cys Ala Asp Gly Tyr Gly Gly Leu Val Thr Thr
305 310 315 320

Asp Pro Lys Thr Ala Asp Pro Ala Tyr Gly Lys Val Tyr Asn Pro Pro
325 330 335

Arg Thr Asn Tyr Pro Gly Arg Phe Thr Asn Leu Leu Asp Val Ala Glu
340 345 350

Ala Cys Pro Thr Phe Leu Cys Phe Asp Asp Gly Lys Pro Tyr Val Thr 355 360 365

Thr Arg Thr Asp Asp Thr Arg Leu Leu Ala Lys Phe Asp Leu Ser Leu
370 375 380

Ala Ala Lys His Met Ser Asn Thr Tyr Leu Ser Gly Ile Ala Gln Tyr
385 390 395 400

Tyr Thr Gln Tyr Ser Gly Thr Ile Asn Leu His Phe Met Phe Thr Gly
405 410 415

Ser Thr Asp Ser Lys Ala Arg Tyr Met Val Ala Tyr Ile Pro Pro Gly
420 425 430

Val Glu Thr Pro Pro Asp Thr Pro Glu Arg Ala Ala His Cys Ile His
435 440 445

Ala Glu Trp Asp Thr Gly Leu Asn Ser Lys Phe Thr Phe Ser Ile Pro
450 455 460

Tyr Val Ser Ala Ala Asp Tyr Ala Tyr Thr Ala Ser Asp Thr Ala Glu
465 470 475 480

Thr Ile Asn Val Gln Gly Trp Val Cys Ile Tyr Gln Ile Thr His Gly
485 490 495

Lys Ala Glu Asn Asp Thr Leu Val Val Ser Val Ser Ala Gly Lys Asp
500 505 510

Phe Glu Leu Arg Leu Pro Ile Asp Pro Arg Gln Gln Thr Thr Ala Thr
515 520 525

Gly Glu Ser Ala Asp Pro Val Thr Thr Thr Val Glu Asn Tyr Gly Gly
530 535 540

Glu Thr Gln Ile Gln Arg Arg His His Thr Asp Ile Gly Phe Ile Met
545 550 555 560

Asp Arg Phe Val Lys Ile Gln Ser Leu Ser Pro Thr His Val Ile Asp
565 570 575

Leu Met Gln Thr His Gln His Gly Leu Val Gly Ala Leu Leu Arg Ala
580 585 590

Ala Thr Tyr Tyr Phe Ser Asp Leu Glu Ile Val Val Arg His Glu Gly
595 600 605

Asn Leu Thr Trp Val Pro Asn Gly Ala Pro Glu Ser Ala Leu Leu Asn
610 615 620

Thr Ser Asn Pro Thr Ala Tyr Asn Lys Ala Pro Phe Thr Arg Leu Ala
625 630 635 640

Leu Pro Tyr Thr Ala Pro His Arg Val Leu Ala Thr Val Tyr Asn Gly
645 650 655

Thr Ser Lys Tyr Ala Val Gly Gly Ser Gly Arg Arg Gly Asp Met Gly
660 665 670

Ser Leu Ala Ala Arg Val Val Lys Gln Leu Pro Ala Ser Phe Asn Tyr
675 680 685

Gly Ala Ile Lys Ala Asp Ala Ile His Glu Leu Leu Val Arg Met Lys
690 695 700

Arg Ala Glu Leu Tyr Cys Pro Arg Pro Leu Leu Ala Ile Glu Val Ser
705 710 715 720

Ser Gln Asp Arg His Lys Gln Lys Ile Ile Ala Pro Ala Lys Gln Leu
725 730 735

Leu Asn Phe Asp Leu Leu Lys Leu Ala Gly Asp Val Glu Ser Asn Pro
740 745 750

Gly Pro

<210> SEQ ID NO 129
<211> LENGTH: 2262

```
<212> TYPE: DNA
<213> ORGANISM: foot and mouth disease virus
<220> FEATURE:
<221> NAME/KEY: CDS
<222> LOCATION: (1)..(2262)
<223> OTHER INFORMATION: A Turkey/2006; P1; Accession: JF749841

<400> SEQUENCE: 129

gga gcc ggg caa tcc agt ccg gca acc ggg tca caa aac caa tca ggc       48
Gly Ala Gly Gln Ser Ser Pro Ala Thr Gly Ser Gln Asn Gln Ser Gly
1               5                   10                  15

aac act ggt agt atc atc aac aac tac tac atg cag cag tac cag aac       96
Asn Thr Gly Ser Ile Ile Asn Asn Tyr Tyr Met Gln Gln Tyr Gln Asn
            20                  25                  30

tcc atg gat aca caa ctt ggc gac aac gcc att agc ggt ggt tcc aac      144
Ser Met Asp Thr Gln Leu Gly Asp Asn Ala Ile Ser Gly Gly Ser Asn
        35                  40                  45

gag ggc tcc act gac act acc tcc aca cac aca acc aac aca cag aac      192
Glu Gly Ser Thr Asp Thr Thr Ser Thr His Thr Thr Asn Thr Gln Asn
    50                  55                  60

aat gac tgg ttt tca aag ctg gcc agt tct gcc ttc agc ggt ctc ttc      240
Asn Asp Trp Phe Ser Lys Leu Ala Ser Ser Ala Phe Ser Gly Leu Phe
65                  70                  75                  80

ggc gct ctt ctc gct gac aaa aag aca gag gag act acc ctc ctg gag      288
Gly Ala Leu Leu Ala Asp Lys Lys Thr Glu Glu Thr Thr Leu Leu Glu
                85                  90                  95

gac cgc atc ctt acc acc cgc aac gga cac acc acc tcg aca acc cag      336
Asp Arg Ile Leu Thr Thr Arg Asn Gly His Thr Thr Ser Thr Thr Gln
            100                 105                 110

tcg agt gtg ggt gtc acc tac ggg tac tcc act ggt gaa gac cac gtc      384
Ser Ser Val Gly Val Thr Tyr Gly Tyr Ser Thr Gly Glu Asp His Val
        115                 120                 125

tct gga cct aac aca tct ggc ctg gag acg cga gtg gta cag gca gag      432
Ser Gly Pro Asn Thr Ser Gly Leu Glu Thr Arg Val Val Gln Ala Glu
    130                 135                 140

aga ttc ttc aag aaa cac ttg ttt gat tgg aca act gat aaa gct ttt      480
Arg Phe Phe Lys Lys His Leu Phe Asp Trp Thr Thr Asp Lys Ala Phe
145                 150                 155                 160

gga cac ctg gaa aaa ctg gaa ctc ccc acc gaa cac aag ggt gtc tac      528
Gly His Leu Glu Lys Leu Glu Leu Pro Thr Glu His Lys Gly Val Tyr
                165                 170                 175

ggg cac ttg gtg gac tct ttc gca tac atg aga aat ggc tgg gac gtg      576
Gly His Leu Val Asp Ser Phe Ala Tyr Met Arg Asn Gly Trp Asp Val
            180                 185                 190

gag gtg acc gcc gtt ggc aac cag ttc aac ggt ggg tgt ctc ctg gtg      624
Glu Val Thr Ala Val Gly Asn Gln Phe Asn Gly Gly Cys Leu Leu Val
        195                 200                 205

gcc atg gta cct gag tgg aaa gag ttt acc cct cgt gag aaa tac cag      672
Ala Met Val Pro Glu Trp Lys Glu Phe Thr Pro Arg Glu Lys Tyr Gln
    210                 215                 220

ctc acc ctg ttt cca cac caa ttt atc aac ccc aga acc aac atg aca      720
Leu Thr Leu Phe Pro His Gln Phe Ile Asn Pro Arg Thr Asn Met Thr
225                 230                 235                 240

gcc cac atc acg gtc ccg tac ctt ggt gtc aat agg tat gac cag tac      768
Ala His Ile Thr Val Pro Tyr Leu Gly Val Asn Arg Tyr Asp Gln Tyr
                245                 250                 255

aaa cag cac aaa ccc tgg aca ctg gtc gtg atg gtg gtt tcg cca ctg      816
Lys Gln His Lys Pro Trp Thr Leu Val Val Met Val Val Ser Pro Leu
            260                 265                 270

acc acc agc agc att ggg gcc tca cag att aag gtc tac gcc aac att      864
Thr Thr Ser Ser Ile Gly Ala Ser Gln Ile Lys Val Tyr Ala Asn Ile
```

```
        275                 280                 285

gcc cca acc ttc gtt cac gtg gcc ggc gag ctc cca tcg aaa gaa ggg      912
Ala Pro Thr Phe Val His Val Ala Gly Glu Leu Pro Ser Lys Glu Gly
    290                 295                 300

atc gtg ccg gtt gct tgt aca gac ggg tac ggt ggc ctg gtg aca aca      960
Ile Val Pro Val Ala Cys Thr Asp Gly Tyr Gly Gly Leu Val Thr Thr
305                 310                 315                 320

gac ccg aaa aca gct gac cct gtt tat ggt atg gtg tac aac ccg ccc     1008
Asp Pro Lys Thr Ala Asp Pro Val Tyr Gly Met Val Tyr Asn Pro Pro
                325                 330                 335

aga acc aac tac cct ggg cgc ttt aca aac ttg ttg gac gtg gcc gag     1056
Arg Thr Asn Tyr Pro Gly Arg Phe Thr Asn Leu Leu Asp Val Ala Glu
            340                 345                 350

gct tgc ccg acc ttc ctc tgt ttt gac gac ggg aaa ccg tac gtt gtg     1104
Ala Cys Pro Thr Phe Leu Cys Phe Asp Asp Gly Lys Pro Tyr Val Val
        355                 360                 365

aca agg acg gac gac caa cgc ctc ctg gcc aag ttt gac gtt tct ctt     1152
Thr Arg Thr Asp Asp Gln Arg Leu Leu Ala Lys Phe Asp Val Ser Leu
    370                 375                 380

gct gca aag cac atg tca aac acc tac ctc tca ggg ata gca cag tac     1200
Ala Ala Lys His Met Ser Asn Thr Tyr Leu Ser Gly Ile Ala Gln Tyr
385                 390                 395                 400

tac acg cag tac tct ggc act atc aat ctg cat ttc atg ttc act ggc     1248
Tyr Thr Gln Tyr Ser Gly Thr Ile Asn Leu His Phe Met Phe Thr Gly
                405                 410                 415

tct act gaa tca aag gcc cgg tac atg gtg gcg tac att cca cct ggc     1296
Ser Thr Glu Ser Lys Ala Arg Tyr Met Val Ala Tyr Ile Pro Pro Gly
            420                 425                 430

atg gac aac cca ccg gac aca cct gag aag gct gca cac tgc atc cac     1344
Met Asp Asn Pro Pro Asp Thr Pro Glu Lys Ala Ala His Cys Ile His
        435                 440                 445

gcc gag tgg gac acc ggg ctg aac tcc aaa ttt act ttt tct atc ccg     1392
Ala Glu Trp Asp Thr Gly Leu Asn Ser Lys Phe Thr Phe Ser Ile Pro
    450                 455                 460

tac gtg tct gct gca gac tac gca tac act gcg tct gac gtg gca gaa     1440
Tyr Val Ser Ala Ala Asp Tyr Ala Tyr Thr Ala Ser Asp Val Ala Glu
465                 470                 475                 480

aca aca aac gta cag ggg tgg gtc tgc ata tac caa atc act cac ggg     1488
Thr Thr Asn Val Gln Gly Trp Val Cys Ile Tyr Gln Ile Thr His Gly
                485                 490                 495

aag gct gaa cag gac act ctg gtc gtg tcg gtc agc gcc ggc aag gac     1536
Lys Ala Glu Gln Asp Thr Leu Val Val Ser Val Ser Ala Gly Lys Asp
            500                 505                 510

ttt gaa ctg cgc ctc cca att gac ccc cgc acg caa acc acc act gcc     1584
Phe Glu Leu Arg Leu Pro Ile Asp Pro Arg Thr Gln Thr Thr Thr Ala
        515                 520                 525

ggg gag tca gca gac cct gtc acc acc acc gtt gag aac tac ggt ggt     1632
Gly Glu Ser Ala Asp Pro Val Thr Thr Thr Val Glu Asn Tyr Gly Gly
    530                 535                 540

gag aca cag gct cag cga cgt cag cac act gac gtc ggc ttc atc atg     1680
Glu Thr Gln Ala Gln Arg Arg Gln His Thr Asp Val Gly Phe Ile Met
545                 550                 555                 560

gac agg ttt gcg aaa atc agc ccc gtg agc ccc acg cac gtc att gac     1728
Asp Arg Phe Ala Lys Ile Ser Pro Val Ser Pro Thr His Val Ile Asp
                565                 570                 575

ctc atg caa aca cac caa cac gcg ttg gtg ggt gcc ctt ttg cgt gca     1776
Leu Met Gln Thr His Gln His Ala Leu Val Gly Ala Leu Leu Arg Ala
            580                 585                 590

gcc acg tac tac ttc tcc gat ctg gag att gtg gtg cgt cat gat ggc     1824
```

```
Ala Thr Tyr Tyr Phe Ser Asp Leu Glu Ile Val Val Arg His Asp Gly
        595                 600                 605

aac ttg acg tgg gtg ccc aat gga gca cct gta gaa gcc ttg gcc aac      1872
Asn Leu Thr Trp Val Pro Asn Gly Ala Pro Val Glu Ala Leu Ala Asn
    610                 615                 620

aca agc aac ccc acc gcc tac cac aag cag cca ttt acg aga ctt gcg      1920
Thr Ser Asn Pro Thr Ala Tyr His Lys Gln Pro Phe Thr Arg Leu Ala
625                 630                 635                 640

ctc cct tac acc gcg ccg cac cga gtg ttg gca aca gtg tat aac gga      1968
Leu Pro Tyr Thr Ala Pro His Arg Val Leu Ala Thr Val Tyr Asn Gly
                645                 650                 655

gta agc aag tac tct aca act ggt aat ggc aga agg ggt gac ctg ggg      2016
Val Ser Lys Tyr Ser Thr Thr Gly Asn Gly Arg Arg Gly Asp Leu Gly
            660                 665                 670

cct ctt gcg gcg cgg gtc gcc gca cag ctc ccc agc tct ttc aat ttt      2064
Pro Leu Ala Ala Arg Val Ala Ala Gln Leu Pro Ser Ser Phe Asn Phe
        675                 680                 685

ggt gca att cgg gcc acg acc gtc cac gag ctt ctc gtg cgc atg aaa      2112
Gly Ala Ile Arg Ala Thr Thr Val His Glu Leu Leu Val Arg Met Lys
    690                 695                 700

cgt gcc gag ctc tac tgt ccc agg cct ctg ctg gca gtg gaa gtg ttg      2160
Arg Ala Glu Leu Tyr Cys Pro Arg Pro Leu Leu Ala Val Glu Val Leu
705                 710                 715                 720

tcg cag gac aga cac aag caa aag atc att gca cct gca aag caa ctc      2208
Ser Gln Asp Arg His Lys Gln Lys Ile Ile Ala Pro Ala Lys Gln Leu
                725                 730                 735

ctg aac ttc gac ctg ctc aag ttg gcg gga gac gtt gag tcc aac cct      2256
Leu Asn Phe Asp Leu Leu Lys Leu Ala Gly Asp Val Glu Ser Asn Pro
            740                 745                 750

ggg ccc                                                              2262
Gly Pro


<210> SEQ ID NO 130
<211> LENGTH: 754
<212> TYPE: PRT
<213> ORGANISM: foot and mouth disease virus

<400> SEQUENCE: 130

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ser Thr Gly Glu Asp His Val
        115                 120                 125

Ser Gly Pro Asn Thr Ser Gly Leu Glu Thr Arg Val Val Gln Ala Glu
    130                 135                 140

Arg Phe Phe Lys Lys His Leu Phe Asp Trp Thr Thr Asp Lys Ala Phe
145                 150                 155                 160
```

```
Gly His Leu Glu Lys Leu Glu Leu Pro Thr Glu His Lys Gly Val Tyr
                165                 170                 175

Gly His Leu Val Asp Ser Phe Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Trp Lys Glu Phe Thr Pro Arg Glu Lys Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Gln His Lys Pro Trp Thr Leu Val Val Met Val Val Ser Pro Leu
            260                 265                 270

Thr Thr Ser Ser Ile Gly Ala Ser Gln Ile Lys Val Tyr Ala Asn Ile
        275                 280                 285

Ala Pro Thr Phe Val His Val Ala Gly Glu Leu Pro Ser Lys Glu Gly
    290                 295                 300

Ile Val Pro Val Ala Cys Thr Asp Gly Tyr Gly Gly Leu Val Thr Thr
305                 310                 315                 320

Asp Pro Lys Thr Ala Asp Pro Val Tyr Gly Met Val Tyr Asn Pro Pro
                325                 330                 335

Arg Thr Asn Tyr Pro Gly Arg Phe Thr Asn Leu Leu Asp Val Ala Glu
            340                 345                 350

Ala Cys Pro Thr Phe Leu Cys Phe Asp Asp Gly Lys Pro Tyr Val Val
        355                 360                 365

Thr Arg Thr Asp Asp Gln Arg Leu Leu Ala Lys Phe Asp Val Ser Leu
    370                 375                 380

Ala Ala Lys His Met Ser Asn Thr Tyr Leu Ser Gly Ile Ala Gln Tyr
385                 390                 395                 400

Tyr Thr Gln Tyr Ser Gly Thr Ile Asn Leu His Phe Met Phe Thr Gly
                405                 410                 415

Ser Thr Glu Ser Lys Ala Arg Tyr Met Val Ala Tyr Ile Pro Pro Gly
            420                 425                 430

Met Asp Asn Pro Pro Asp Thr Pro Glu Lys Ala Ala His Cys Ile His
        435                 440                 445

Ala Glu Trp Asp Thr Gly Leu Asn Ser Lys Phe Thr Phe Ser Ile Pro
    450                 455                 460

Tyr Val Ser Ala Ala Asp Tyr Ala Tyr Thr Ala Ser Asp Val Ala Glu
465                 470                 475                 480

Thr Thr Asn Val Gln Gly Trp Val Cys Ile Tyr Gln Ile Thr His Gly
                485                 490                 495

Lys Ala Glu Gln Asp Thr Leu Val Val Ser Val Ser Ala Gly Lys Asp
            500                 505                 510

Phe Glu Leu Arg Leu Pro Ile Asp Pro Arg Thr Gln Thr Thr Thr Ala
        515                 520                 525

Gly Glu Ser Ala Asp Pro Val Thr Thr Thr Val Glu Asn Tyr Gly Gly
    530                 535                 540

Glu Thr Gln Ala Gln Arg Arg Gln His Thr Asp Val Gly Phe Ile Met
545                 550                 555                 560

Asp Arg Phe Ala Lys Ile Ser Pro Val Ser Pro Thr His Val Ile Asp
                565                 570                 575
```

```
Leu Met Gln Thr His Gln His Ala Leu Val Gly Ala Leu Leu Arg Ala
            580                 585                 590

Ala Thr Tyr Tyr Phe Ser Asp Leu Glu Ile Val Val Arg His Asp Gly
        595                 600                 605

Asn Leu Thr Trp Val Pro Asn Gly Ala Pro Val Glu Ala Leu Ala Asn
    610                 615                 620

Thr Ser Asn Pro Thr Ala Tyr His Lys Gln Pro Phe Thr Arg Leu Ala
625                 630                 635                 640

Leu Pro Tyr Thr Ala Pro His Arg Val Leu Ala Thr Val Tyr Asn Gly
                645                 650                 655

Val Ser Lys Tyr Ser Thr Thr Gly Asn Gly Arg Arg Gly Asp Leu Gly
            660                 665                 670

Pro Leu Ala Ala Arg Val Ala Ala Gln Leu Pro Ser Ser Phe Asn Phe
        675                 680                 685

Gly Ala Ile Arg Ala Thr Thr Val His Glu Leu Leu Val Arg Met Lys
    690                 695                 700

Arg Ala Glu Leu Tyr Cys Pro Arg Pro Leu Leu Ala Val Glu Val Leu
705                 710                 715                 720

Ser Gln Asp Arg His Lys Gln Lys Ile Ile Ala Pro Ala Lys Gln Leu
                725                 730                 735

Leu Asn Phe Asp Leu Leu Lys Leu Ala Gly Asp Val Glu Ser Asn Pro
            740                 745                 750

Gly Pro


<210> SEQ ID NO 131
<211> LENGTH: 2277
<212> TYPE: DNA
<213> ORGANISM: foot and mouth disease virus
<220> FEATURE:
<221> NAME/KEY: CDS
<222> LOCATION: (1)..(2277)
<223> OTHER INFORMATION: SAT2 Egypt 2010; P1; Accession: KC440884

<400> SEQUENCE: 131

ggg gcc ggg caa tcc agc ccg gct act gga tcc caa aat caa tca ggc       48
Gly Ala Gly Gln Ser Ser Pro Ala Thr Gly Ser Gln Asn Gln Ser Gly
1               5                   10                  15

aat act ggt agc att att aac aac tac tac atg caa cag tac cag aac       96
Asn Thr Gly Ser Ile Ile Asn Asn Tyr Tyr Met Gln Gln Tyr Gln Asn
            20                  25                  30

tca atg gac aca cag ctt ggt gac aac gcc att agc ggt ggt tcc aac      144
Ser Met Asp Thr Gln Leu Gly Asp Asn Ala Ile Ser Gly Gly Ser Asn
        35                  40                  45

gag ggg tcg acg gac acc acg tcg aca cac aca aac aac aca cag aac      192
Glu Gly Ser Thr Asp Thr Thr Ser Thr His Thr Asn Asn Thr Gln Asn
    50                  55                  60

aat gac tgg ttt tcc aaa ttg gct caa tca gcc att tca ggg ctt ttc      240
Asn Asp Trp Phe Ser Lys Leu Ala Gln Ser Ala Ile Ser Gly Leu Phe
65                  70                  75                  80

gga gct ctg ctt gca gac aag aaa aca gag gag acc aca ctg ctg gag      288
Gly Ala Leu Leu Ala Asp Lys Lys Thr Glu Glu Thr Thr Leu Leu Glu
                85                  90                  95

gac aga atc ctg acc acg cgt cac ggg acc acg acc tcc acc acg caa      336
Asp Arg Ile Leu Thr Thr Arg His Gly Thr Thr Thr Ser Thr Thr Gln
            100                 105                 110

agt tct gtg gga gtg aca ttt ggt tat gct gat gct gat tcg ttt cgc      384
Ser Ser Val Gly Val Thr Phe Gly Tyr Ala Asp Ala Asp Ser Phe Arg
        115                 120                 125
```

-continued

```
cca gga ccc aac acc tct ggg ctt gag acg cgc gtg caa cag gca gaa      432
Pro Gly Pro Asn Thr Ser Gly Leu Glu Thr Arg Val Gln Gln Ala Glu
    130                 135                 140

cgc ttc ttc aag gag aag ctt ttt gac tgg acc agt gac aaa cct ttc      480
Arg Phe Phe Lys Glu Lys Leu Phe Asp Trp Thr Ser Asp Lys Pro Phe
145                 150                 155                 160

ggt acg ctg tac gtg ttg gag ttg ccc aaa gac cac aag ggc atc tac      528
Gly Thr Leu Tyr Val Leu Glu Leu Pro Lys Asp His Lys Gly Ile Tyr
                165                 170                 175

ggt aaa ctt acc gac tcc tac acg tac atg cgt aac ggt tgg gac gtt      576
Gly Lys Leu Thr Asp Ser Tyr Thr Tyr Met Arg Asn Gly Trp Asp Val
            180                 185                 190

cag gtc agc gcg acc agc aca cag ttt aac ggc gga tca ctg ctc gtg      624
Gln Val Ser Ala Thr Ser Thr Gln Phe Asn Gly Gly Ser Leu Leu Val
        195                 200                 205

gca atg gtc cca gag ttg tgc agt cta aaa gcc aga gaa gaa ttt caa      672
Ala Met Val Pro Glu Leu Cys Ser Leu Lys Ala Arg Glu Glu Phe Gln
    210                 215                 220

ctc act ctc tac cca cac cag ttc att aac ccg cgc acc aac aca acc      720
Leu Thr Leu Tyr Pro His Gln Phe Ile Asn Pro Arg Thr Asn Thr Thr
225                 230                 235                 240

gca cac ata cag gtt cct tac ctg ggt gta aac aga cac gac cag ggt      768
Ala His Ile Gln Val Pro Tyr Leu Gly Val Asn Arg His Asp Gln Gly
                245                 250                 255

aag cgc cac cag gcg tgg tct ctg gtt gtg atg gtg ctc acg cct ctt      816
Lys Arg His Gln Ala Trp Ser Leu Val Val Met Val Leu Thr Pro Leu
            260                 265                 270

acc acc gag gcg cag atg aac agc ggc acc gtc gag gtg tac gcc aac      864
Thr Thr Glu Ala Gln Met Asn Ser Gly Thr Val Glu Val Tyr Ala Asn
        275                 280                 285

atc gca cca aca aat gtg gtt gtg gcg ggt gaa ctg ccg ggt aag cag      912
Ile Ala Pro Thr Asn Val Val Val Ala Gly Glu Leu Pro Gly Lys Gln
    290                 295                 300

ggc atc att ccg gtc gct gcc gct gac ggg tat ggt ggt ttc cag aac      960
Gly Ile Ile Pro Val Ala Ala Ala Asp Gly Tyr Gly Gly Phe Gln Asn
305                 310                 315                 320

acc gac ccg aaa acg gct gac ccc att tac ggg cat gtg tac aac ccg     1008
Thr Asp Pro Lys Thr Ala Asp Pro Ile Tyr Gly His Val Tyr Asn Pro
                325                 330                 335

tcc aga aac gac tgc cac ggg cga tac tcc aat ctt atg gat gtc gcc     1056
Ser Arg Asn Asp Cys His Gly Arg Tyr Ser Asn Leu Met Asp Val Ala
            340                 345                 350

gag gcg tgt cca aca ctc ctc aac ttt gat ggc aag ccc tac gtc gtg     1104
Glu Ala Cys Pro Thr Leu Leu Asn Phe Asp Gly Lys Pro Tyr Val Val
        355                 360                 365

acc aag aac aac ggt gac aag gtg atg gca cgc ttc gac gtc gcc ttt     1152
Thr Lys Asn Asn Gly Asp Lys Val Met Ala Arg Phe Asp Val Ala Phe
    370                 375                 380

aca cac aag gtg cat ggg aac acg ttt ctg gcg ggc ttg gcc gac tac     1200
Thr His Lys Val His Gly Asn Thr Phe Leu Ala Gly Leu Ala Asp Tyr
385                 390                 395                 400

tac aca cag tat tca ggc agc cta aac tac cac ttc atg tac act gga     1248
Tyr Thr Gln Tyr Ser Gly Ser Leu Asn Tyr His Phe Met Tyr Thr Gly
                405                 410                 415

ccc aca cat cac aag gca aag ttc atg gtg gca tac gtg ccc cct ggt     1296
Pro Thr His His Lys Ala Lys Phe Met Val Ala Tyr Val Pro Pro Gly
            420                 425                 430

gtt gca gtt gac cag ctg cct agc aca ccg gag gat gct gcg cac tgc     1344
Val Ala Val Asp Gln Leu Pro Ser Thr Pro Glu Asp Ala Ala His Cys
        435                 440                 445
```

-continued

```
tac cat gcg gaa tgg gac acc ggg ttg aat tct tct ttc tcg ttc gca      1392
Tyr His Ala Glu Trp Asp Thr Gly Leu Asn Ser Ser Phe Ser Phe Ala
    450                 455                 460

gtg cct tac atc tcc gct gcg gac ttt tct tac aca cac aca gac aca      1440
Val Pro Tyr Ile Ser Ala Ala Asp Phe Ser Tyr Thr His Thr Asp Thr
465                 470                 475                 480

ccg gcc atg gcc acc acc aat ggc tgg gtg gtt gta ctg cag gtc acc      1488
Pro Ala Met Ala Thr Thr Asn Gly Trp Val Val Val Leu Gln Val Thr
                485                 490                 495

gac acg cac tct gcg gaa gct gcc gtt gta gtg tca gtc agc gcg gga      1536
Asp Thr His Ser Ala Glu Ala Ala Val Val Val Ser Val Ser Ala Gly
            500                 505                 510

cca gat ttg gaa ttc cga ttc cct atc gac cct gtg cga cag act acc      1584
Pro Asp Leu Glu Phe Arg Phe Pro Ile Asp Pro Val Arg Gln Thr Thr
        515                 520                 525

tcg gcg gga gaa ggc gca gat gtt gtc acc acg gac cca tcg aca cac      1632
Ser Ala Gly Glu Gly Ala Asp Val Val Thr Thr Asp Pro Ser Thr His
    530                 535                 540

ggt ggg aat gtt caa gag ggt cga cgc aaa cac acc gac gtt gcg ttc      1680
Gly Gly Asn Val Gln Glu Gly Arg Arg Lys His Thr Asp Val Ala Phe
545                 550                 555                 560

ctt ctt gat cgc agt aca cac gtt cac aca aat aag aca tct ttt gtt      1728
Leu Leu Asp Arg Ser Thr His Val His Thr Asn Lys Thr Ser Phe Val
                565                 570                 575

gtg gac ctc atg gac aca agg gag aag gcg ctc gta ggc gca atc ctg      1776
Val Asp Leu Met Asp Thr Arg Glu Lys Ala Leu Val Gly Ala Ile Leu
            580                 585                 590

cga gca tcc acc tac tac ttt tgt gac ctt gaa att gca tgt gtg ggc      1824
Arg Ala Ser Thr Tyr Tyr Phe Cys Asp Leu Glu Ile Ala Cys Val Gly
        595                 600                 605

gac cac aca agg gtc ttc tgg cag ccc aac ggg gca ccg cgg act acc      1872
Asp His Thr Arg Val Phe Trp Gln Pro Asn Gly Ala Pro Arg Thr Thr
    610                 615                 620

cag ctc ggc gac aac cct atg gtt ttt gcc aag ggc ggc gta acc cgc      1920
Gln Leu Gly Asp Asn Pro Met Val Phe Ala Lys Gly Gly Val Thr Arg
625                 630                 635                 640

ttt gcc atc ccg ttt acg gct cca cac agg ctg ctg tct act gtt tac      1968
Phe Ala Ile Pro Phe Thr Ala Pro His Arg Leu Leu Ser Thr Val Tyr
                645                 650                 655

aac ggc gag tgt gtc tac acc aag gcc gcc gct gcc att cgt ggt gat      2016
Asn Gly Glu Cys Val Tyr Thr Lys Ala Ala Ala Ala Ile Arg Gly Asp
            660                 665                 670

cgt gcg gca ctt gcg gca aag tac gct gac acc aac cac act ttg ccg      2064
Arg Ala Ala Leu Ala Ala Lys Tyr Ala Asp Thr Asn His Thr Leu Pro
        675                 680                 685

cca acc ttc aac ttc ggg tac gtg acc gtt gac aaa cca gtc gac gtt      2112
Pro Thr Phe Asn Phe Gly Tyr Val Thr Val Asp Lys Pro Val Asp Val
    690                 695                 700

tac tac cgg atg aag agg gct gag ctg tac tgc cca cgc cca ctg ctg      2160
Tyr Tyr Arg Met Lys Arg Ala Glu Leu Tyr Cys Pro Arg Pro Leu Leu
705                 710                 715                 720

cca gcc tac aaa cac aca gac aga gac aga ttc gac gcg ccc atc ggc      2208
Pro Ala Tyr Lys His Thr Asp Arg Asp Arg Phe Asp Ala Pro Ile Gly
                725                 730                 735

gtc gaa aga cag acc ctg aat ttt gac ctg ctg aaa ctg gca gga gac      2256
Val Glu Arg Gln Thr Leu Asn Phe Asp Leu Leu Lys Leu Ala Gly Asp
            740                 745                 750

gtt gag tcc aac cct ggg ccc                                          2277
Val Glu Ser Asn Pro Gly Pro
```

755

<210> SEQ ID NO 132
<211> LENGTH: 759
<212> TYPE: PRT
<213> ORGANISM: foot and mouth disease virus

<400> SEQUENCE: 132

Gly Ala Gly Gln Ser Ser Pro Ala Thr Gly Ser Gln Asn Gln Ser Gly
1 5 10 15

Asn Thr Gly Ser Ile Ile Asn Asn Tyr Tyr Met Gln Gln Tyr Gln Asn
20 25 30

Ser Met Asp Thr Gln Leu Gly Asp Asn Ala Ile Ser Gly Gly Ser Asn
35 40 45

Glu Gly Ser Thr Asp Thr Thr Ser Thr His Thr Asn Asn Thr Gln Asn
50 55 60

Asn Asp Trp Phe Ser Lys Leu Ala Gln Ser Ala Ile Ser Gly Leu Phe
65 70 75 80

Gly Ala Leu Leu Ala Asp Lys Lys Thr Glu Glu Thr Thr Leu Leu Glu
85 90 95

Asp Arg Ile Leu Thr Thr Arg His Gly Thr Thr Thr Ser Thr Thr Gln
100 105 110

Ser Ser Val Gly Val Thr Phe Gly Tyr Ala Asp Ala Asp Ser Phe Arg
115 120 125

Pro Gly Pro Asn Thr Ser Gly Leu Glu Thr Arg Val Gln Gln Ala Glu
130 135 140

Arg Phe Phe Lys Glu Lys Leu Phe Asp Trp Thr Ser Asp Lys Pro Phe
145 150 155 160

Gly Thr Leu Tyr Val Leu Glu Leu Pro Lys Asp His Lys Gly Ile Tyr
165 170 175

Gly Lys Leu Thr Asp Ser Tyr Thr Tyr Met Arg Asn Gly Trp Asp Val
180 185 190

Gln Val Ser Ala Thr Ser Thr Gln Phe Asn Gly Gly Ser Leu Leu Val
195 200 205

Ala Met Val Pro Glu Leu Cys Ser Leu Lys Ala Arg Glu Glu Phe Gln
210 215 220

Leu Thr Leu Tyr Pro His Gln Phe Ile Asn Pro Arg Thr Asn Thr Thr
225 230 235 240

Ala His Ile Gln Val Pro Tyr Leu Gly Val Asn Arg His Asp Gln Gly
245 250 255

Lys Arg His Gln Ala Trp Ser Leu Val Val Met Val Leu Thr Pro Leu
260 265 270

Thr Thr Glu Ala Gln Met Asn Ser Gly Thr Val Glu Val Tyr Ala Asn
275 280 285

Ile Ala Pro Thr Asn Val Val Val Ala Gly Glu Leu Pro Gly Lys Gln
290 295 300

Gly Ile Ile Pro Val Ala Ala Ala Asp Gly Tyr Gly Gly Phe Gln Asn
305 310 315 320

Thr Asp Pro Lys Thr Ala Asp Pro Ile Tyr Gly His Val Tyr Asn Pro
325 330 335

Ser Arg Asn Asp Cys His Gly Arg Tyr Ser Asn Leu Met Asp Val Ala
340 345 350

Glu Ala Cys Pro Thr Leu Leu Asn Phe Asp Gly Lys Pro Tyr Val Val
355 360 365

```
Thr Lys Asn Asn Gly Asp Lys Val Met Ala Arg Phe Asp Val Ala Phe
    370                 375                 380

Thr His Lys Val His Gly Asn Thr Phe Leu Ala Gly Leu Ala Asp Tyr
385                 390                 395                 400

Tyr Thr Gln Tyr Ser Gly Ser Leu Asn Tyr His Phe Met Tyr Thr Gly
                405                 410                 415

Pro Thr His His Lys Ala Lys Phe Met Val Ala Tyr Val Pro Pro Gly
            420                 425                 430

Val Ala Val Asp Gln Leu Pro Ser Thr Pro Glu Asp Ala Ala His Cys
        435                 440                 445

Tyr His Ala Glu Trp Asp Thr Gly Leu Asn Ser Ser Phe Ser Phe Ala
    450                 455                 460

Val Pro Tyr Ile Ser Ala Ala Asp Phe Ser Tyr Thr His Thr Asp Thr
465                 470                 475                 480

Pro Ala Met Ala Thr Thr Asn Gly Trp Val Val Val Leu Gln Val Thr
                485                 490                 495

Asp Thr His Ser Ala Glu Ala Ala Val Val Val Ser Val Ser Ala Gly
            500                 505                 510

Pro Asp Leu Glu Phe Arg Phe Pro Ile Asp Pro Val Arg Gln Thr Thr
        515                 520                 525

Ser Ala Gly Glu Gly Ala Asp Val Val Thr Thr Asp Pro Ser Thr His
    530                 535                 540

Gly Gly Asn Val Gln Glu Gly Arg Arg Lys His Thr Asp Val Ala Phe
545                 550                 555                 560

Leu Leu Asp Arg Ser Thr His Val His Thr Asn Lys Thr Ser Phe Val
                565                 570                 575

Val Asp Leu Met Asp Thr Arg Glu Lys Ala Leu Val Gly Ala Ile Leu
            580                 585                 590

Arg Ala Ser Thr Tyr Tyr Phe Cys Asp Leu Glu Ile Ala Cys Val Gly
        595                 600                 605

Asp His Thr Arg Val Phe Trp Gln Pro Asn Gly Ala Pro Arg Thr Thr
    610                 615                 620

Gln Leu Gly Asp Asn Pro Met Val Phe Ala Lys Gly Gly Val Thr Arg
625                 630                 635                 640

Phe Ala Ile Pro Phe Thr Ala Pro His Arg Leu Leu Ser Thr Val Tyr
                645                 650                 655

Asn Gly Glu Cys Val Tyr Thr Lys Ala Ala Ala Ala Ile Arg Gly Asp
            660                 665                 670

Arg Ala Ala Leu Ala Ala Lys Tyr Ala Asp Thr Asn His Thr Leu Pro
        675                 680                 685

Pro Thr Phe Asn Phe Gly Tyr Val Thr Val Asp Lys Pro Val Asp Val
    690                 695                 700

Tyr Tyr Arg Met Lys Arg Ala Glu Leu Tyr Cys Pro Arg Pro Leu Leu
705                 710                 715                 720

Pro Ala Tyr Lys His Thr Asp Arg Asp Arg Phe Asp Ala Pro Ile Gly
                725                 730                 735

Val Glu Arg Gln Thr Leu Asn Phe Asp Leu Leu Lys Leu Ala Gly Asp
            740                 745                 750

Val Glu Ser Asn Pro Gly Pro
        755
```

<210> SEQ ID NO 133
<211> LENGTH: 2247
<212> TYPE: DNA

```
<213> ORGANISM: foot and mouth disease virus
<220> FEATURE:
<221> NAME/KEY: CDS
<222> LOCATION: (1)..(2247)
<223> OTHER INFORMATION: C3 indaial, P1; Accession: AY593806

<400> SEQUENCE: 133

gga gcc gga caa tcc agc ccg gcg act ggc tcg cag aac caa tct ggc       48
Gly Ala Gly Gln Ser Ser Pro Ala Thr Gly Ser Gln Asn Gln Ser Gly
1               5                   10                  15

aac act ggt agc ata atc aac aac tac tac atg caa cag tac caa aat       96
Asn Thr Gly Ser Ile Ile Asn Asn Tyr Tyr Met Gln Gln Tyr Gln Asn
            20                  25                  30

tcc atg gac aca cag ctg ggt gac aat gct att agt ggt ggc tcc aac      144
Ser Met Asp Thr Gln Leu Gly Asp Asn Ala Ile Ser Gly Gly Ser Asn
        35                  40                  45

gag ggc tcc aca gat aca act tcc acc cac aca acc aac act caa aac      192
Glu Gly Ser Thr Asp Thr Thr Ser Thr His Thr Thr Asn Thr Gln Asn
    50                  55                  60

aac gac tgg ttt tcc aaa ctc gcc agt tct gcc ttt agc ggt ctt ttc      240
Asn Asp Trp Phe Ser Lys Leu Ala Ser Ser Ala Phe Ser Gly Leu Phe
65                  70                  75                  80

ggt gct ctt ctt gcc gac aag aag acc gag gaa acc aca cta ctt gaa      288
Gly Ala Leu Leu Ala Asp Lys Lys Thr Glu Glu Thr Thr Leu Leu Glu
                85                  90                  95

gac cgc atc ctc acc acc cgc aac ggc cac acg acg tcg aca act cag      336
Asp Arg Ile Leu Thr Thr Arg Asn Gly His Thr Thr Ser Thr Thr Gln
            100                 105                 110

tcg agc gtt ggg gtc aca tac ggg tac gca aca act gag gat agc acg      384
Ser Ser Val Gly Val Thr Tyr Gly Tyr Ala Thr Thr Glu Asp Ser Thr
        115                 120                 125

tca ggg ccc aac aca tcc ggc ctt gag aca cgt gtt cac cag gca gaa      432
Ser Gly Pro Asn Thr Ser Gly Leu Glu Thr Arg Val His Gln Ala Glu
    130                 135                 140

cgg ttt ttc aag atg aca ctc ttt gaa tgg gtt ccc tcc cag agt ttt      480
Arg Phe Phe Lys Met Thr Leu Phe Glu Trp Val Pro Ser Gln Ser Phe
145                 150                 155                 160

gga cac atg cac aag gtc gtt ctg ccc tca gaa ccg aaa ggt gtc tat      528
Gly His Met His Lys Val Val Leu Pro Ser Glu Pro Lys Gly Val Tyr
                165                 170                 175

ggg ggt ctc gtc aag tca tac gcg tac atg cgc aat ggc tgg gac gtt      576
Gly Gly Leu Val Lys Ser Tyr Ala Tyr Met Arg Asn Gly Trp Asp Val
            180                 185                 190

gag gtg act gct gtt gga aac cag ttc aac ggc ggt tgt ctc ctg gtg      624
Glu Val Thr Ala Val Gly Asn Gln Phe Asn Gly Gly Cys Leu Leu Val
        195                 200                 205

gcg ctc gtt cct gaa atg ggt gac atc agt gac aga gag aag tac caa      672
Ala Leu Val Pro Glu Met Gly Asp Ile Ser Asp Arg Glu Lys Tyr Gln
    210                 215                 220

ctg act ctc tac ccc cac caa ttc atc aac cca cgc act aac atg acg      720
Leu Thr Leu Tyr Pro His Gln Phe Ile Asn Pro Arg Thr Asn Met Thr
225                 230                 235                 240

gca cac atc acc gtg cct tac gtg ggt gtc aac aga tac gac caa tac      768
Ala His Ile Thr Val Pro Tyr Val Gly Val Asn Arg Tyr Asp Gln Tyr
                245                 250                 255

aac caa cac aag ccc tgg act ctt gtc gtc atg gtc gtt gct cca ctt      816
Asn Gln His Lys Pro Trp Thr Leu Val Val Met Val Val Ala Pro Leu
            260                 265                 270

act gtg aac aca tca ggt gcc cag cag atc aag gtg tat gcc aac ata      864
Thr Val Asn Thr Ser Gly Ala Gln Gln Ile Lys Val Tyr Ala Asn Ile
        275                 280                 285
```

```
gcc cca acc aac gtt cac gtt gct ggt gaa ctt ccc tcc aag gag ggg      912
Ala Pro Thr Asn Val His Val Ala Gly Glu Leu Pro Ser Lys Glu Gly
    290                 295                 300

atc ttc ccc gtt gcg tgt gcc gac ggc tat ggc aac atg gtg aca act      960
Ile Phe Pro Val Ala Cys Ala Asp Gly Tyr Gly Asn Met Val Thr Thr
305                 310                 315                 320

gac ccg aag aca gct gac cct gcc tac ggg aaa gtc tac aat cca ccc     1008
Asp Pro Lys Thr Ala Asp Pro Ala Tyr Gly Lys Val Tyr Asn Pro Pro
                325                 330                 335

agg acc gcc ctg ccg ggc cgg ttc aca aac tac ctg gat gtt gct gag     1056
Arg Thr Ala Leu Pro Gly Arg Phe Thr Asn Tyr Leu Asp Val Ala Glu
            340                 345                 350

gct tgc ccc act ctc ctg acg ttc gag aac gtg cct tac gtt tca aca     1104
Ala Cys Pro Thr Leu Leu Thr Phe Glu Asn Val Pro Tyr Val Ser Thr
        355                 360                 365

cgg act gat gga caa agg ctg ttg gcc aag ttc gac gtg tca ttg gca     1152
Arg Thr Asp Gly Gln Arg Leu Leu Ala Lys Phe Asp Val Ser Leu Ala
    370                 375                 380

gcg aaa cac atg tca aac act tac ttg gct ggc ttg gcc cag tac tac     1200
Ala Lys His Met Ser Asn Thr Tyr Leu Ala Gly Leu Ala Gln Tyr Tyr
385                 390                 395                 400

aca cag tac gct ggg aca atc aac ctg cac ttc atg ttc act ggg cca     1248
Thr Gln Tyr Ala Gly Thr Ile Asn Leu His Phe Met Phe Thr Gly Pro
                405                 410                 415

acc gac gcg aaa gct cgg tac atg gtg gca tac gtg ccc cct ggc atg     1296
Thr Asp Ala Lys Ala Arg Tyr Met Val Ala Tyr Val Pro Pro Gly Met
            420                 425                 430

gaa gca cca gac aac cca gag gag gct gcc cac tgc ata cac gca gag     1344
Glu Ala Pro Asp Asn Pro Glu Glu Ala Ala His Cys Ile His Ala Glu
        435                 440                 445

tgg gac act ggt ttg aac tct aag ttc aca ttt tca atc ccg tac atc     1392
Trp Asp Thr Gly Leu Asn Ser Lys Phe Thr Phe Ser Ile Pro Tyr Ile
    450                 455                 460

tcg gcc gct gac tac gca tac acc gcg tcc agc gag gct gaa aca aca     1440
Ser Ala Ala Asp Tyr Ala Tyr Thr Ala Ser Ser Glu Ala Glu Thr Thr
465                 470                 475                 480

agc gta cag gga tgg gtt tgt gtg tac cag atc act cac ggc aag gca     1488
Ser Val Gln Gly Trp Val Cys Val Tyr Gln Ile Thr His Gly Lys Ala
                485                 490                 495

gac gct gac gcg ctc gtc gtc tcc gct tcg gcg ggg aaa gac ttt gag     1536
Asp Ala Asp Ala Leu Val Val Ser Ala Ser Ala Gly Lys Asp Phe Glu
            500                 505                 510

ctc cgg cta cct gtg gac gct aga cag caa act acg acc act ggc gaa     1584
Leu Arg Leu Pro Val Asp Ala Arg Gln Gln Thr Thr Thr Thr Gly Glu
        515                 520                 525

tct gcc gac ccc gtc acc act acc gtt gag aac tac gga gga gaa aca     1632
Ser Ala Asp Pro Val Thr Thr Thr Val Glu Asn Tyr Gly Gly Glu Thr
    530                 535                 540

caa act caa cgt cgc cac cac act gac gtt gcc ttc gtt ctt gac cgg     1680
Gln Thr Gln Arg Arg His His Thr Asp Val Ala Phe Val Leu Asp Arg
545                 550                 555                 560

ttt gtg aag gtc cag gtg tcg ggc aac caa cac aca ctg gac gtt atg     1728
Phe Val Lys Val Gln Val Ser Gly Asn Gln His Thr Leu Asp Val Met
                565                 570                 575

cag gta cac aag gac agt att gtg ggt gca ctc cta cgc gca gcc aca     1776
Gln Val His Lys Asp Ser Ile Val Gly Ala Leu Leu Arg Ala Ala Thr
            580                 585                 590

tac tac ttc tct gac ttg gaa ata gca gtg act cac act ggg aag ctc     1824
Tyr Tyr Phe Ser Asp Leu Glu Ile Ala Val Thr His Thr Gly Lys Leu
```

```
        595                 600                 605

aca tgg gtg ccc aac ggc gcc cca gtt tct gca ctt gac aac aca acc      1872
Thr Trp Val Pro Asn Gly Ala Pro Val Ser Ala Leu Asp Asn Thr Thr
    610                 615                 620

aac ccc act gcc tac cac aag ggg ccg ctg act cgg ctg gct ctc cca      1920
Asn Pro Thr Ala Tyr His Lys Gly Pro Leu Thr Arg Leu Ala Leu Pro
625                 630                 635                 640

tac acc gca cca cac cgc gtg ctg gcc acg gcg tac acc ggt aca acg      1968
Tyr Thr Ala Pro His Arg Val Leu Ala Thr Ala Tyr Thr Gly Thr Thr
                645                 650                 655

gcc tac act acc ggt gta cgc agg gga gac cta gcc cac ttg gcg gcg      2016
Ala Tyr Thr Thr Gly Val Arg Arg Gly Asp Leu Ala His Leu Ala Ala
            660                 665                 670

gcg cac gct cgg cac ctg ccg acg tcg ttc aac ttt ggt gca gtt aaa      2064
Ala His Ala Arg His Leu Pro Thr Ser Phe Asn Phe Gly Ala Val Lys
        675                 680                 685

gca gag aca atc aca gag ctg ctt gtg cgc atg aag cgt gct gaa ctc      2112
Ala Glu Thr Ile Thr Glu Leu Leu Val Arg Met Lys Arg Ala Glu Leu
    690                 695                 700

tac tgc ccc aga ccg gtc ctt ccg gtc caa cca gcg ggc gat agg cac      2160
Tyr Cys Pro Arg Pro Val Leu Pro Val Gln Pro Ala Gly Asp Arg His
705                 710                 715                 720

aaa caa ccg ctc att gcg cca gcg aaa cag ctg ctg aac ttc gac ctt      2208
Lys Gln Pro Leu Ile Ala Pro Ala Lys Gln Leu Leu Asn Phe Asp Leu
                725                 730                 735

ctc aag ttg gcg gga gac gtc gag tcc aac cct ggg ccc                  2247
Leu Lys Leu Ala Gly Asp Val Glu Ser Asn Pro Gly Pro
            740                 745


<210> SEQ ID NO 134
<211> LENGTH: 749
<212> TYPE: PRT
<213> ORGANISM: foot and mouth disease virus

<400> SEQUENCE: 134

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Thr Glu Asp Ser Thr
        115                 120                 125

Ser Gly Pro Asn Thr Ser Gly Leu Glu Thr Arg Val His Gln Ala Glu
    130                 135                 140

Arg Phe Phe Lys Met Thr Leu Phe Glu Trp Val Pro Ser Gln Ser Phe
145                 150                 155                 160

Gly His Met His Lys Val Val Leu Pro Ser Glu Pro Lys Gly Val Tyr
                165                 170                 175
```

-continued

Gly Gly Leu Val Lys Ser Tyr Ala Tyr Met Arg Asn Gly Trp Asp Val
180 185 190

Glu Val Thr Ala Val Gly Asn Gln Phe Asn Gly Gly Cys Leu Leu Val
195 200 205

Ala Leu Val Pro Glu Met Gly Asp Ile Ser Asp Arg Glu Lys Tyr Gln
210 215 220

Leu Thr Leu Tyr Pro His Gln Phe Ile Asn Pro Arg Thr Asn Met Thr
225 230 235 240

Ala His Ile Thr Val Pro Tyr Val Gly Val Asn Arg Tyr Asp Gln Tyr
245 250 255

Asn Gln His Lys Pro Trp Thr Leu Val Val Met Val Val Ala Pro Leu
260 265 270

Thr Val Asn Thr Ser Gly Ala Gln Gln Ile Lys Val Tyr Ala Asn Ile
275 280 285

Ala Pro Thr Asn Val His Val Ala Gly Glu Leu Pro Ser Lys Glu Gly
290 295 300

Ile Phe Pro Val Ala Cys Ala Asp Gly Tyr Gly Asn Met Val Thr Thr
305 310 315 320

Asp Pro Lys Thr Ala Asp Pro Ala Tyr Gly Lys Val Tyr Asn Pro Pro
325 330 335

Arg Thr Ala Leu Pro Gly Arg Phe Thr Asn Tyr Leu Asp Val Ala Glu
340 345 350

Ala Cys Pro Thr Leu Leu Thr Phe Glu Asn Val Pro Tyr Val Ser Thr
355 360 365

Arg Thr Asp Gly Gln Arg Leu Leu Ala Lys Phe Asp Val Ser Leu Ala
370 375 380

Ala Lys His Met Ser Asn Thr Tyr Leu Ala Gly Leu Ala Gln Tyr Tyr
385 390 395 400

Thr Gln Tyr Ala Gly Thr Ile Asn Leu His Phe Met Phe Thr Gly Pro
405 410 415

Thr Asp Ala Lys Ala Arg Tyr Met Val Ala Tyr Val Pro Pro Gly Met
420 425 430

Glu Ala Pro Asp Asn Pro Glu Glu Ala Ala His Cys Ile His Ala Glu
435 440 445

Trp Asp Thr Gly Leu Asn Ser Lys Phe Thr Phe Ser Ile Pro Tyr Ile
450 455 460

Ser Ala Ala Asp Tyr Ala Tyr Thr Ala Ser Ser Glu Ala Glu Thr Thr
465 470 475 480

Ser Val Gln Gly Trp Val Cys Val Tyr Gln Ile Thr His Gly Lys Ala
485 490 495

Asp Ala Asp Ala Leu Val Val Ser Ala Ser Ala Gly Lys Asp Phe Glu
500 505 510

Leu Arg Leu Pro Val Asp Ala Arg Gln Gln Thr Thr Thr Thr Gly Glu
515 520 525

Ser Ala Asp Pro Val Thr Thr Thr Val Glu Asn Tyr Gly Gly Glu Thr
530 535 540

Gln Thr Gln Arg Arg His His Thr Asp Val Ala Phe Val Leu Asp Arg
545 550 555 560

Phe Val Lys Val Gln Val Ser Gly Asn Gln His Thr Leu Asp Val Met
565 570 575

Gln Val His Lys Asp Ser Ile Val Gly Ala Leu Leu Arg Ala Ala Thr
580 585 590

Tyr Tyr Phe Ser Asp Leu Glu Ile Ala Val Thr His Thr Gly Lys Leu

```
        595                 600                 605

Thr Trp Val Pro Asn Gly Ala Pro Val Ser Ala Leu Asp Asn Thr Thr
    610                 615                 620

Asn Pro Thr Ala Tyr His Lys Gly Pro Leu Thr Arg Leu Ala Leu Pro
625                 630                 635                 640

Tyr Thr Ala Pro His Arg Val Leu Ala Thr Ala Tyr Thr Gly Thr Thr
                645                 650                 655

Ala Tyr Thr Thr Gly Val Arg Arg Gly Asp Leu Ala His Leu Ala Ala
            660                 665                 670

Ala His Ala Arg His Leu Pro Thr Ser Phe Asn Phe Gly Ala Val Lys
        675                 680                 685

Ala Glu Thr Ile Thr Glu Leu Leu Val Arg Met Lys Arg Ala Glu Leu
    690                 695                 700

Tyr Cys Pro Arg Pro Val Leu Pro Val Gln Pro Ala Gly Asp Arg His
705                 710                 715                 720

Lys Gln Pro Leu Ile Ala Pro Ala Lys Gln Leu Leu Asn Phe Asp Leu
                725                 730                 735

Leu Lys Leu Ala Gly Asp Val Glu Ser Asn Pro Gly Pro
            740                 745


<210> SEQ ID NO 135
<211> LENGTH: 2250
<212> TYPE: DNA
<213> ORGANISM: foot and mouth disease virus
<220> FEATURE:
<221> NAME/KEY: CDS
<222> LOCATION: (1)..(2250)
<223> OTHER INFORMATION: Asia1 Shamir; P1

<400> SEQUENCE: 135

gga gcc ggt caa tcc agt ccg gca acc ggg tca cag aac caa tct ggc       48
Gly Ala Gly Gln Ser Ser Pro Ala Thr Gly Ser Gln Asn Gln Ser Gly
1               5                   10                  15

aac act gga agc atc att aac aac tac tac atg caa cag tac cag aat       96
Asn Thr Gly Ser Ile Ile Asn Asn Tyr Tyr Met Gln Gln Tyr Gln Asn
            20                  25                  30

tcc atg gac aca cag ctt ggt gac aac gct att agc gga ggt tcc aac      144
Ser Met Asp Thr Gln Leu Gly Asp Asn Ala Ile Ser Gly Gly Ser Asn
        35                  40                  45

gaa ggt tcc acg gat acc act tcc aca cac aca aac aac acc caa aac      192
Glu Gly Ser Thr Asp Thr Thr Ser Thr His Thr Asn Asn Thr Gln Asn
    50                  55                  60

aac gac tgg ttc tcg cgc ctg gct agc tct gca ttc agt ggt ctc ttt      240
Asn Asp Trp Phe Ser Arg Leu Ala Ser Ser Ala Phe Ser Gly Leu Phe
65                  70                  75                  80

ggt gca ctt ttg gct gac aag aag aca gaa gag aca act ctg ctt gaa      288
Gly Ala Leu Leu Ala Asp Lys Lys Thr Glu Glu Thr Thr Leu Leu Glu
                85                  90                  95

gac cgc att ctc acc acc agg aac ggc cac aca aca tcg acg aca cag      336
Asp Arg Ile Leu Thr Thr Arg Asn Gly His Thr Thr Ser Thr Thr Gln
            100                 105                 110

tcg agc gtt ggc gta aca tac ggt tac gct gtg gcc gag gac gcg gtg      384
Ser Ser Val Gly Val Thr Tyr Gly Tyr Ala Val Ala Glu Asp Ala Val
        115                 120                 125

tct gga ccc aat acc tcg ggt cta gag act cgt gtt caa cag gca gaa      432
Ser Gly Pro Asn Thr Ser Gly Leu Glu Thr Arg Val Gln Gln Ala Glu
    130                 135                 140

cgg ttt ttc aag aaa cac ctg ttt gac tgg aca ccg aac ttg gca ttt      480
Arg Phe Phe Lys Lys His Leu Phe Asp Trp Thr Pro Asn Leu Ala Phe
```

-continued

```
145                 150                 155                 160

gga cac tgt tac tac ctg gaa ctt ccc act gaa cac aaa ggc gtg tac      528
Gly His Cys Tyr Tyr Leu Glu Leu Pro Thr Glu His Lys Gly Val Tyr
                165                 170                 175

ggc agt ctc atg ggc tcg tac gcc tac atg aga aat gga tgg gac ata      576
Gly Ser Leu Met Gly Ser Tyr Ala Tyr Met Arg Asn Gly Trp Asp Ile
            180                 185                 190

gag gtg act gct gtt gga aac caa ttc aac ggt ggt tgt ctc ctt gtc      624
Glu Val Thr Ala Val Gly Asn Gln Phe Asn Gly Gly Cys Leu Leu Val
        195                 200                 205

gcg ctc gtg cca gag ctg aag gaa ctc gac acg cga cag aag tac cag      672
Ala Leu Val Pro Glu Leu Lys Glu Leu Asp Thr Arg Gln Lys Tyr Gln
    210                 215                 220

ctg acc ctc ttt ccc cac cag ttc atc aac cca cgc acc aac atg acg      720
Leu Thr Leu Phe Pro His Gln Phe Ile Asn Pro Arg Thr Asn Met Thr
225                 230                 235                 240

gcc cac atc aac gtg ccg tac gtg ggt atc aac agg tac gac cag tac      768
Ala His Ile Asn Val Pro Tyr Val Gly Ile Asn Arg Tyr Asp Gln Tyr
                245                 250                 255

gcc ctc cac aag ccg tgg acg ctt gtt gtg atg gtg gta gcc cca ctc      816
Ala Leu His Lys Pro Trp Thr Leu Val Val Met Val Val Ala Pro Leu
            260                 265                 270

acc gtc aaa act ggt ggt tct gaa cag atc aag gtt tac atg aat gca      864
Thr Val Lys Thr Gly Gly Ser Glu Gln Ile Lys Val Tyr Met Asn Ala
        275                 280                 285

gcg cca acc tac gtg cat gtg gcg gga gag ctg ccc tcg aaa gag gga      912
Ala Pro Thr Tyr Val His Val Ala Gly Glu Leu Pro Ser Lys Glu Gly
    290                 295                 300

ata gtt ccc gtc gcg tgt gcg gac ggt tac ggc aac atg gtg acc acg      960
Ile Val Pro Val Ala Cys Ala Asp Gly Tyr Gly Asn Met Val Thr Thr
305                 310                 315                 320

gac ccg aag acg gcc gat cca gtt tac ggg aaa gtg ttc aac ccc ccc     1008
Asp Pro Lys Thr Ala Asp Pro Val Tyr Gly Lys Val Phe Asn Pro Pro
                325                 330                 335

agg aca aac ctc cct ggg cgc ttc acg aac ttc ctt gat gtt gcg gag     1056
Arg Thr Asn Leu Pro Gly Arg Phe Thr Asn Phe Leu Asp Val Ala Glu
            340                 345                 350

gca tgt cca act ttc ctc cgc ttt gga gaa gta cca ttt gtg aag acg     1104
Ala Cys Pro Thr Phe Leu Arg Phe Gly Glu Val Pro Phe Val Lys Thr
        355                 360                 365

gtg aac tct ggt gac cgc ttg ctg gcc aag ttc gac gtg tcc ctc gct     1152
Val Asn Ser Gly Asp Arg Leu Leu Ala Lys Phe Asp Val Ser Leu Ala
    370                 375                 380

gca ggg cac atg tcc aac acc tac ttg gct ggc ctg gcg cag tac tac     1200
Ala Gly His Met Ser Asn Thr Tyr Leu Ala Gly Leu Ala Gln Tyr Tyr
385                 390                 395                 400

aca cag tac agc ggc acc atg aac gtc cac ttc atg ttc acc ggg ccc     1248
Thr Gln Tyr Ser Gly Thr Met Asn Val His Phe Met Phe Thr Gly Pro
                405                 410                 415

acg gat gct aaa gcc cga tac atg gtg gct tat gtc ccc cct ggc atg     1296
Thr Asp Ala Lys Ala Arg Tyr Met Val Ala Tyr Val Pro Pro Gly Met
            420                 425                 430

aca ccg ccc acg gac cct gag cac gcc gca cac tgc att cac tct gag     1344
Thr Pro Pro Thr Asp Pro Glu His Ala Ala His Cys Ile His Ser Glu
        435                 440                 445

tgg gat act ggt ctt aac tct aag ttt acc ttt tcc ata cct tac ctc     1392
Trp Asp Thr Gly Leu Asn Ser Lys Phe Thr Phe Ser Ile Pro Tyr Leu
    450                 455                 460

tct gct gct gac tat gcc tac act gct tct gac gtg gcg gag acc acg     1440
```

-continued

```
Ser Ala Ala Asp Tyr Ala Tyr Thr Ala Ser Asp Val Ala Glu Thr Thr
465                 470                 475                 480

agt gtg cag gga tgg gtg tgt atc tat cag atc acc cac ggc aag gct      1488
Ser Val Gln Gly Trp Val Cys Ile Tyr Gln Ile Thr His Gly Lys Ala
                485                 490                 495

gag gga gac gca ctg gtc gtt tct gtc agc gcc ggc aaa gac ttt gag      1536
Glu Gly Asp Ala Leu Val Val Ser Val Ser Ala Gly Lys Asp Phe Glu
            500                 505                 510

ttt cgc ttg cct gtt gac gca cgc cag caa acc acc acc act ggc gaa      1584
Phe Arg Leu Pro Val Asp Ala Arg Gln Gln Thr Thr Thr Thr Gly Glu
        515                 520                 525

tca gca gat cca gtc aca acc acg gtt gag aac tat gga gga gag act      1632
Ser Ala Asp Pro Val Thr Thr Thr Val Glu Asn Tyr Gly Gly Glu Thr
    530                 535                 540

cag aca gcc aga cgg ctt cac act gac gtc gcc ttc att ctt gac agg      1680
Gln Thr Ala Arg Arg Leu His Thr Asp Val Ala Phe Ile Leu Asp Arg
545                 550                 555                 560

ttt gtg aaa ctc act gct ccc aag aac atc caa acc ctc gat ctc atg      1728
Phe Val Lys Leu Thr Ala Pro Lys Asn Ile Gln Thr Leu Asp Leu Met
                565                 570                 575

cag atc ccc tca cac acg ctg gtt gga gca cta ctt cgt tct gcg acg      1776
Gln Ile Pro Ser His Thr Leu Val Gly Ala Leu Leu Arg Ser Ala Thr
            580                 585                 590

tac tac ttc tca gac ctg gag gtc gcg ctt gtc cac aca ggc ccg gtc      1824
Tyr Tyr Phe Ser Asp Leu Glu Val Ala Leu Val His Thr Gly Pro Val
        595                 600                 605

acc tgg gtg ccc aac ggc gcg ccc aag gat gct cta aac aac cag acc      1872
Thr Trp Val Pro Asn Gly Ala Pro Lys Asp Ala Leu Asn Asn Gln Thr
    610                 615                 620

aac cca act gcc tat cag aag caa ccc atc acc cgc ctg gca ctc ccc      1920
Asn Pro Thr Ala Tyr Gln Lys Gln Pro Ile Thr Arg Leu Ala Leu Pro
625                 630                 635                 640

tac acc gcc ccc cat cgt gtg ctg gca aca gtg tac aac ggg aag acg      1968
Tyr Thr Ala Pro His Arg Val Leu Ala Thr Val Tyr Asn Gly Lys Thr
                645                 650                 655

gcg tac ggg gaa acg acc tca agg cgc ggc gac atg gcg gcc ctc gca      2016
Ala Tyr Gly Glu Thr Thr Ser Arg Arg Gly Asp Met Ala Ala Leu Ala
            660                 665                 670

caa agg ttg agc gct cgg ctg ccc acc tcc ttc aac tac ggc gcc gtg      2064
Gln Arg Leu Ser Ala Arg Leu Pro Thr Ser Phe Asn Tyr Gly Ala Val
        675                 680                 685

aag gcc gac acc atc act gag ctt ttg atc cgc atg aag cgc gcg gag      2112
Lys Ala Asp Thr Ile Thr Glu Leu Leu Ile Arg Met Lys Arg Ala Glu
    690                 695                 700

aca tat tgc cct agg cct tta cta gcc ctt gac acc act cag gac cgc      2160
Thr Tyr Cys Pro Arg Pro Leu Leu Ala Leu Asp Thr Thr Gln Asp Arg
705                 710                 715                 720

cgc aaa cag gag atc att gca cct gag aag cag gtt ttg aac ttt gac      2208
Arg Lys Gln Glu Ile Ile Ala Pro Glu Lys Gln Val Leu Asn Phe Asp
                725                 730                 735

cta ctc aag ttg gca gga gac gtt gag tcc aac cct ggg ccc              2250
Leu Leu Lys Leu Ala Gly Asp Val Glu Ser Asn Pro Gly Pro
            740                 745                 750
```

<210> SEQ ID NO 136
<211> LENGTH: 750
<212> TYPE: PRT
<213> ORGANISM: foot and mouth disease virus

<400> SEQUENCE: 136

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Asn Asn Thr Gln Asn
    50                  55                  60

Asn Asp Trp Phe Ser Arg Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Val Ala Glu Asp Ala Val
        115                 120                 125

Ser Gly Pro Asn Thr Ser Gly Leu Glu Thr Arg Val Gln Gln Ala Glu
    130                 135                 140

Arg Phe Phe Lys Lys His Leu Phe Asp Trp Thr Pro Asn Leu Ala Phe
145                 150                 155                 160

Gly His Cys Tyr Tyr Leu Glu Leu Pro Thr Glu His Lys Gly Val Tyr
                165                 170                 175

Gly Ser Leu Met Gly Ser Tyr Ala Tyr Met Arg Asn Gly Trp Asp Ile
            180                 185                 190

Glu Val Thr Ala Val Gly Asn Gln Phe Asn Gly Gly Cys Leu Leu Val
        195                 200                 205

Ala Leu Val Pro Glu Leu Lys Glu Leu Asp Thr Arg Gln Lys Tyr Gln
    210                 215                 220

Leu Thr Leu Phe Pro His Gln Phe Ile Asn Pro Arg Thr Asn Met Thr
225                 230                 235                 240

Ala His Ile Asn Val Pro Tyr Val Gly Ile Asn Arg Tyr Asp Gln Tyr
                245                 250                 255

Ala Leu His Lys Pro Trp Thr Leu Val Val Met Val Val Ala Pro Leu
            260                 265                 270

Thr Val Lys Thr Gly Gly Ser Glu Gln Ile Lys Val Tyr Met Asn Ala
        275                 280                 285

Ala Pro Thr Tyr Val His Val Ala Gly Glu Leu Pro Ser Lys Glu Gly
    290                 295                 300

Ile Val Pro Val Ala Cys Ala Asp Gly Tyr Gly Asn Met Val Thr Thr
305                 310                 315                 320

Asp Pro Lys Thr Ala Asp Pro Val Tyr Gly Lys Val Phe Asn Pro Pro
                325                 330                 335

Arg Thr Asn Leu Pro Gly Arg Phe Thr Asn Phe Leu Asp Val Ala Glu
            340                 345                 350

Ala Cys Pro Thr Phe Leu Arg Phe Gly Glu Val Pro Phe Val Lys Thr
        355                 360                 365

Val Asn Ser Gly Asp Arg Leu Leu Ala Lys Phe Asp Val Ser Leu Ala
    370                 375                 380

Ala Gly His Met Ser Asn Thr Tyr Leu Ala Gly Leu Ala Gln Tyr Tyr
385                 390                 395                 400

Thr Gln Tyr Ser Gly Thr Met Asn Val His Phe Met Phe Thr Gly Pro
                405                 410                 415

Thr Asp Ala Lys Ala Arg Tyr Met Val Ala Tyr Val Pro Pro Gly Met
```

-continued

```
            420                 425                 430

Thr Pro Pro Thr Asp Pro Glu His Ala Ala His Cys Ile His Ser Glu
        435                 440                 445

Trp Asp Thr Gly Leu Asn Ser Lys Phe Thr Phe Ser Ile Pro Tyr Leu
    450                 455                 460

Ser Ala Ala Asp Tyr Ala Tyr Thr Ala Ser Asp Val Ala Glu Thr Thr
465                 470                 475                 480

Ser Val Gln Gly Trp Val Cys Ile Tyr Gln Ile Thr His Gly Lys Ala
                485                 490                 495

Glu Gly Asp Ala Leu Val Val Ser Val Ser Ala Gly Lys Asp Phe Glu
            500                 505                 510

Phe Arg Leu Pro Val Asp Ala Arg Gln Gln Thr Thr Thr Thr Gly Glu
        515                 520                 525

Ser Ala Asp Pro Val Thr Thr Thr Val Glu Asn Tyr Gly Gly Glu Thr
    530                 535                 540

Gln Thr Ala Arg Arg Leu His Thr Asp Val Ala Phe Ile Leu Asp Arg
545                 550                 555                 560

Phe Val Lys Leu Thr Ala Pro Lys Asn Ile Gln Thr Leu Asp Leu Met
                565                 570                 575

Gln Ile Pro Ser His Thr Leu Val Gly Ala Leu Leu Arg Ser Ala Thr
            580                 585                 590

Tyr Tyr Phe Ser Asp Leu Glu Val Ala Leu Val His Thr Gly Pro Val
        595                 600                 605

Thr Trp Val Pro Asn Gly Ala Pro Lys Asp Ala Leu Asn Asn Gln Thr
    610                 615                 620

Asn Pro Thr Ala Tyr Gln Lys Gln Pro Ile Thr Arg Leu Ala Leu Pro
625                 630                 635                 640

Tyr Thr Ala Pro His Arg Val Leu Ala Thr Val Tyr Asn Gly Lys Thr
                645                 650                 655

Ala Tyr Gly Glu Thr Thr Ser Arg Arg Gly Asp Met Ala Ala Leu Ala
            660                 665                 670

Gln Arg Leu Ser Ala Arg Leu Pro Thr Ser Phe Asn Tyr Gly Ala Val
        675                 680                 685

Lys Ala Asp Thr Ile Thr Glu Leu Leu Ile Arg Met Lys Arg Ala Glu
    690                 695                 700

Thr Tyr Cys Pro Arg Pro Leu Leu Ala Leu Asp Thr Thr Gln Asp Arg
705                 710                 715                 720

Arg Lys Gln Glu Ile Ile Ala Pro Glu Lys Gln Val Leu Asn Phe Asp
                725                 730                 735

Leu Leu Lys Leu Ala Gly Asp Val Glu Ser Asn Pro Gly Pro
            740                 745                 750
```

PROCESSING ENGINEERED FMDV P1 POLYPEPTIDE USING AN ALTERNATIVE TEV PROTEASE

CROSS REFERENCE TO RELATED APPLICATIONS

This application is a Continuation of U.S. patent application Ser. No. 15/407,982, filed Jan. 17, 2017, the contents of which are herein incorporated by reference in its entirety.

GOVERNMENT RIGHTS

This invention was made with government support under HSHQPM-12-X-00013 and HSHQDC-14-F-00035 awarded by the U.S. Department of Homeland Security. The United States Government has certain rights in this invention.

SEQUENCE LISTING

The instant application contains a Sequence Listing which has been submitted in ASCII format via EFS-Web and is hereby incorporated by reference in its entirety. The ASCII copy is named DHS-092_Sequence_Listing.txt, was created on Jan. 9, 2017, and is 378 KB in size.

BACKGROUND OF THE INVENTION

Field of the Invention

The present disclosure generally relates to a protein engineering and expression platform that uses a protease to process a precursor polypeptide into individual subunit proteins and which minimizes protease-associated damage to the host cells used to recombinantly-express the precursor protein. One example of this platform comprises an engineered foot-and-mouth disease virus ("FMDV") P1 precursor polypeptide, which has been engineered to contain Tobacco Etch Virus NIa protease ("TEV protease") sites at the junctions defining separate viral structural proteins in the unprocessed precursor polypeptide, and a Tobacco Etch Virus NIa protease that recognizes the sites engineered into the FMDV P1 precursor polypeptide. FMDV P1 precursor polypeptide is conventionally processed by the FMDV 3C protease which is toxic to many host cells. The invention obviates the need for use of a toxic FMDV 3C protease for production of processed FMDV structural proteins from the P1 precursor and thus provides a more efficient and productive platform for the recombinant production of FMDV capsid proteins for use in vaccines and/or diagnostic tools for foot-and-mouth disease (FMD).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

FMDV, a prototypic Aphthovirus within the Picornaviridae family, is the causative agent of a highly infectious and sometimes fatal disease, FMD, that affects cloven-hoofed animals such as cattle, pigs, sheep, goats, deer and other animals with divided hooves. There are seven major antigenically distinct FMDV serotypes (A, O, C, Asia 1 and South African Territories or SAT 1, 2 and 3) with multiple subtypes or topotypes existing within each serotype. Infection with any one serotype does not confer protective immunity against another. Serotype O is the most common serotype worldwide.

After an animal is infected with FMDV, the first signs of illness usually appear within 2 to 14 days. These usually include high fever for 2-3 days followed by blisters inside the mouth and on the feet that may rupture and cause lameness.

FMD outbreaks cause significant agro-economic losses and have severe implications for animal farming throughout much of the world. For example, the estimated costs attributable to the 2001 outbreak of FMD in the U.K. were £ 8 billion, including the costs of slaughtering and sanitarily disposing of 6 million livestock. The virus causing the disease is highly contagious and can be spread by direct contact, through aerosols to uninfected livestock by infected livestock, or by domestic or wild animals. FMDV may be also transmitted by contact with contaminated farming equipment, vehicles, clothing, or feed. Consequently, the containment of FMDV demands considerable effort and expenses including those required for vaccination, vigilance and strict monitoring of livestock, or culling and disposal of infected livestock, as well as for accommodating transport and trade restrictions, quarantines and other administrative and legal issues.

The current most commonly used FMD vaccines utilize whole virus that has been killed, inactivated, and/or attenuated. A whole virus vaccine includes dozens of FMDV antigens to provide a broad spectrum of immunity against different FMDV strains and variants, including those arising due to antigenic drift or antigenic shift. However, this vaccine platform is fraught with many limitations and shortcomings. Animals immunized with the whole virus are difficult to distinguish from infected animals. Once exposed to the whole virus antigens one's ability to immunologically differentiate between infected and vaccinated animals is limited. The efficacy of the current vaccine formulations is also limited by immunogenic instability and short vaccine shelf life that results in a loss of potency upon transporation or storage that results in subsequent induction of insufficient immunity or immunity of a short duration. Furthermore, the set-up and running costs of producing the current FMDV vaccine in potent form and securing and maintaining its production facilities are very high. For example, the mode of producing current FMDV vaccine raises safety concerns due to the possibility of virus escape from vaccine production facilities. Recombinant production of FMDV antigens, which could avoid the problems inherent to use of whole virus-based vaccines, is impeded by the promiscuous proteolytic activity of the FMDV 3C protease which is required for the processing of FMDV antigens from the FMDV P1 precursor polypeptide, but which also cleaves proteins in host cells used to express recombinant FMDV antigens. Native FMDV 3C protease is toxic to host cells and significantly reduces their ability to express immunogenic FMDV antigens in significant amounts.

NIa proteases, such as TEV protease, were known but had never been tested or applied in a platform for the production of FMDV antigens or immunogens. It was unknown whether such proteases would ameliorate or exacerbate the problems associated with the use of FMDV 3C protease or other picornavirus proteases. Similarly, the effects of omission of expression of a FMDV 3C protease on the recombinant production and subsequent assembly of FMDV structural proteins into FMDV capsids had never been investigated.

There is a continuing need and interest in the development of new second or third generation vaccines that safely generate strong, stable, and broad protective immune responses against FMDV. With these objectives in mind, the inventors developed modifications to FMDV P1 precursor polypeptide to permit it to be cleaved and processed by a potyvirus NIa protease, such as TEV protease, thus producing immunogenic viral antigens, while reducing or eliminating the cytotoxic effects produced by the FMDV 3C protease conventionally used to recombinantly produce FMDV antigens and immunogens.

BRIEF SUMMARY OF THE INVENTION

The inventors have designed, engineered and tested a TEV protease-based platform that efficiently expresses and processes FMDV P1 precursor polypeptide into individual virus structural proteins without the need for the FMDV 3C protease. This system is free of the cytotoxic effects exerted on host cells by the FMDV 3C protease and produces high yields of virus structural proteins. This platform may be used with other precursor polypeptides of interest that have been engineered to incorporate TEV or other NIa protease cleavage sites and may be configured to use either TEV protease or other NIa proteases. It can be combined with 2A and 2A-like translation interruption sequences or used in combination with a modified FMDV 3C protease that has been engineered to reduce or eliminate the toxicity of this protease on host cells. Additional non-limiting aspects and embodiments of the disclosure are described in the following enumerated paragraphs.

1. A polynucleotide that encodes at least one engineered polypeptide of interest that comprises at least one protease cleavage site that is absent from a corresponding not engineered polypeptide of interest; wherein said at least one protease cleavage site is cleaved by the catalytic domain of a potyvirus nuclear inclusion protein a, hereinafter called potyvirus NIa protease.

2. The polynucleotide of enumerated paragraph 1, further comprising at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the engineered polypeptide of interest.

3. The polynucleotide of enumerated paragraph 1, further comprising at least one cytomegalovirus early promoter operatively linked to, or embedded within, the polynucleotide sequence encoding the engineered polypeptide of interest.

4. The polynucleotide of enumerated paragraph 1, further comprising at least one polynucleotide encoding 2A, delta 1D2A, or at least one other 2A-like translational interrupter, operatively linked to, or embedded within, the polynucleotide sequence encoding the engineered polypeptide of interest.

5. The polynucleotide of enumerated paragraph 1, wherein at least two protease cleavage site in the encoded engineered polypeptide of interest are cleaved by a potyvirus NIa protease.

6. The polynucleotide of enumerated paragraph 1, wherein the at least one cleavage site in the encoded engineered polypeptide of interest is cleaved by a potyvirus NIa protease of Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus.

7. The polynucleotide of enumerated paragraph 1, wherein the at least one potyvirus NIa protease cleavage site in the encoded engineered polypeptide of interest comprises at least one amino acid sequence selected from the group consisting of NVVVHQA (SEQ ID NO: 70), ETVRFQS (SEQ ID NO: 71), YEVHHQA (SEQ ID NO: 72), IVRHQS (SEQ ID NO: 73), IKVRLQA (SEQ ID NO: 74), XVRHQS, where X is Y/E/A/L or I (SEQ ID NO: 75), MLFVFQS (SEQ ID NO: 76), GGQVAHQA (SEQ ID NO: 77), GQVAHQA (SEQ ID NO: 78), EVRHQS (SEQ ID NO: 79), AVRHQS (SEQ ID NO: 80), LVRHQS (SEQ ID NO: 81), ENLYFQS (SEQ ID NO: 82), and ENLYFQG (SEQ ID NO: 83).

8. The polynucleotide of enumerated paragraph 1, wherein the at least one potyvirus NIa protease cleavage site in the encoded engineered polypeptide of interest is cleaved by the catalytic domain of Tobacco Etch virus NIa protease (SEQ ID NO: 26), hereinafter called TEV protease.

9. The polynucleotide of enumerated paragraph 8, wherein the at least one potyvirus NIa protease cleavage site in the engineered polypeptide of interest is a TEV protease cleavage site comprising the amino acid motif E1-X2-X3-Y4-X5-Q6-(G/S)7 (SEQ ID NO: 29) or E1-N2-L3-Y4-F5-Q6-S7 (SEQ ID NO: 30).

10. The polynucleotide of enumerated paragraph 8, wherein the at least one potyvirus NIa protease cleavage site in the engineered polypeptide is a TEV protease cleavage site comprising E1-D2-A3-Y4-T5-Q6-S7 (SEQ ID NO: 39), E1-F2-L3-Y4-K5-Q6-G7 (SEQ ID NO: 40), E1-D2-L3-Y4-F5-Q6-S7 (SEQ ID NO: 41), E1-K2-L3-Y4-K5-Q6-G7 (SEQ ID NO: 42), E1-L2-L3-Y4-K5-Q6-G7 (SEQ ID NO: 43) or E1-A2-L3-Y4-K5-Q6-S7 (SEQ ID NO: 44).

11. The polynucleotide of enumerated paragraph 8, further comprising at least one polynucleotide encoding 2A, delta 1D2A, or at least one other 2A-like translational interrupter, operatively linked to, or embedded within, the polynucleotide sequence encoding the engineered polypeptide of interest.

12. The polynucleotide of enumerated paragraph 1, wherein the at least one engineered polypeptide of interest comprises an engineered FMDV P1 precursor polypeptide that is at least 90% identical to at least one sequence of a FMDV P1 precursor polypeptide that has not been engineered selected from the group consisting of SEQ ID NOS: 22, 24, 124, 126, 128, 130, 132, 134 or 136 and comprises at least one potyvirus NIa protease cleavage site that is absent from a corresponding FMDV P1 precursor polypeptide that has not been engineered.

13. The polynucleotide of enumerated paragraph 12, wherein the at least one potyvirus NIa protease cleavage site in the engineered FMDV P1 precursor polypeptide is positioned at junction(s) that when cleaved by a potyvirus NIa protease produce VP0, VP3, and VP1.

14. The polynucleotide of enumerated paragraph 12, wherein at least one potyvirus NIa protease cleavage site in the engineered FMDV P1 precursor polypeptide is positioned at junction(s) that when cleaved by a potyvirus NIa protease produce VP4, VP2, VP3, and VP1.

15. The polynucleotide of enumerated paragraph 12, wherein the at least one potyvirus NIa protease cleavage site in the encoded engineered FMDV P1 precursor polypeptide is cleaved by a potyvirus NIa protease of Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus.

16. The polynucleotide of enumerated paragraph 12, wherein the at least one potyvirus NIa protease cleavage site in the engineered FMDV P1 precursor polypeptide is selected from the group consisting of NVVVHQA (SEQ ID NO: 70), ETVRFQS (SEQ ID NO: 71), YEVHHQA (SEQ ID NO: 72), IVRHQS (SEQ ID NO: 73), IKVRLQA (SEQ ID NO: 74), XVRHQS, where X is Y/E/A/L or I (SEQ ID NO: 75), MLFVFQS (SEQ ID NO: 76), GGQVAHQA (SEQ ID NO: 77), GQVAHQA (SEQ ID NO: 78), EVRHQS (SEQ ID NO: 79), AVRHQS (SEQ ID NO: 80), LVRHQS (SEQ ID NO: 81), ENLYFQS (SEQ ID NO: 82), and ENLYFQG (SEQ ID NO: 83).

17. The polynucleotide of enumerated paragraph 12, wherein the at least one potyvirus NIa protease cleavage site is a TEV protease cleavage site.

18. The polynucleotide of enumerated paragraph 17, wherein the at least one TEV protease cleavage site in the engineered FMDV P1 precursor polypeptide comprises E1-X2-X3-Y4-X5-Q6-(G/S)7 (SEQ ID NO: 29) in at least one junction between the VP4 and VP2, VP2 and VP3, VP3 and VP1, or VP1 and 2A components of the engineered FMDV P1 precursor polypeptide.

19. The polynucleotide of enumerated paragraph 17, wherein the at least one TEV protease cleavage site in the engineered FMDV P1 precursor polypeptide comprises E1-N2-L3-Y4-F5-Q6-S7 (SEQ ID NO: 30) in at least one junction between VP4 and VP2, VP2 and VP3, VP3 and VP1, or VP1 and 2A components of the engineered FMDV P1 precursor polypeptide.

20. The polynucleotide of enumerated paragraph 17, wherein the at least one TEV protease cleavage site in the engineered FMDV P1 precursor polypeptide comprises E1-D2-A3-Y4-T5-Q6-S7 (SEQ ID NO: 39), E1-F2-L3-Y4-K5-Q6-G7 (SEQ ID NO: 40), E1-D2-L3-Y4-F5-Q6-S7 (SEQ ID NO: 41), E1-K2-L3-Y4-K5-Q6-G7 (SEQ ID NO: 42), E1-L2-L3-Y4-K5-Q6-G7 (SEQ ID NO: 43) or E1-A2-L3-Y4-K5-Q6-S7 (SEQ ID NO: 44) in at least one junction between VP4 and VP2, VP2 and VP3, VP3 and VP1, or VP1 and 2A components of the engineered FMDV P1 precursor polypeptide.

21. The polynucleotide of enumerated paragraph 17, wherein the at least one TEV protease cleavage site in the engineered FMDV P1 precursor polypeptide is positioned at junction(s) that when cleaved by TEV protease produce VP0, VP3, and VP1.

22. The polynucleotide of enumerated paragraph 17, wherein the at least one TEV protease cleavage site in the engineered FMDV P1 precursor polypeptide is positioned at junction(s) that when cleaved by TEV protease produce VP2, VP4, VP3 and VP1.

23. The polynucleotide of enumerated paragraph 17, wherein the engineered FMDV P1 precursor polypeptide further comprises at least one protease cleavage site cleaved by FMDV 3C protease.

24. The polynucleotide of enumerated paragraph 17, further comprising a polynucleotide encoding at least one 2A, delta 1D2A or 2A-like translational interrupter operatively linked to, or embedded within, the polynucleotide sequence encoding the engineered FMDV P1 precursor polypeptide.

25. The polynucleotide of enumerated paragraph 1, further comprising a polynucleotide encoding at least one potyvirus NIa protease.

26. The polynucleotide of enumerated paragraph 1, further comprising a polynucleotide encoding at least one potyvirus NIa protease of Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus; or a protease that is at least 90% identical thereto.

27. The polynucleotide of enumerated paragraph 1, further comprising a polynucleotide encoding wild type TEV protease or a TEV protease that is at least 90% identical to the TEV protease sequence of SEQ ID NO: 26.

28. The polynucleotide of enumerated paragraph 1, further comprising a polynucleotide encoding at least one 2A, delta 1D2A, or 2A-like translational interrupter, operatively linked to, or embedded within, the polynucleotide sequence encoding the engineered polypeptide of interest.

29. The polynucleotide of enumerated paragraph 12, further comprising a polynucleotide encoding at least one potyvirus NIa protease.

30. The polynucleotide of enumerated paragraph 12, further comprising a polynucleotide encoding at least one potyvirus NIa protease of Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus; or a protease that is at least 90% identical thereto.

31. The polynucleotide of enumerated paragraph 12, further comprising a polynucleotide encoding wild type TEV protease or a TEV protease that is at least 90% identical to the TEV protease sequence of SEQ ID NO: 26.

32. The polynucleotide of enumerated paragraph 12, further comprising at least one polynucleotide encoding 2A, delta 1D2A, or 2A-like translational interrupter, operatively linked to, or embedded within, the polynucleotide sequence encoding the engineered polypeptide of interest.

33. The polynucleotide of enumerated paragraph 25, further comprising a polynucleotide encoding a wild type FMDV 3C protease, wherein said engineered polypeptide of interest comprises at least one protease cleavage site cleaved by FMDV 3C protease.

34. The polynucleotide of enumerated paragraph 25, further comprising a polynucleotide encoding a engineered FMDV 3C protease that is at least 90% identical to a FMDV 3C protease described by SEQ ID NO: 86, 88, 90 or 92, and that contains one or more amino acid substitutions within residues 26-35, 46, 80, 84, 125-134, 138-150, 163 or 181; and wherein said engineered polypeptide of interest comprises at least one protease cleavage site cleaved by FMDV 3C protease.

35. The polynucleotide of enumerated paragraph 34, wherein said encoded engineered FMDV 3C protease contains one or more amino acid substitutions within residues 125-134.

36. The polynucleotide of enumerated paragraph 34, wherein said encoded engineered FMDV 3C protease contains a L127P substitution.

37. The polynucleotide of enumerated paragraph 34, further comprising a polynucleotide encoding an engineered FMDV 3C protease containing one or more amino acid substitutions at residues 46, 80, 84, 163, or 181.

38. The polynucleotide of enumerated paragraph 34, wherein said encoded engineered FMDV 3C protease contains a C163A substitution.

39. The polynucleotide of enumerated paragraph 34, wherein said encoded engineered FMDV 3C protease contains a C163G substitution.

40. The polynucleotide of enumerated paragraph 34, wherein said encoded engineered FMDV 3C protease contains a C163S substitution.

41. The polynucleotide of enumerated paragraph 34, wherein said encoded engineered FMDV 3C protease contains a H46Y substitution.

42. The polynucleotide of enumerated paragraph 34, wherein said encoded engineered FMDV 3C protease contains a H181Y substitution.

43. The polynucleotide of enumerated paragraph 34, wherein said encoded engineered FMDV 3C protease contains a D80E substitution 44. The polynucleotide of enumerated paragraph 34, wherein said encoded engineered FMDV 3C protease contains a D84E substitution.

45. The polynucleotide of enumerated paragraph 34, wherein said encoded engineered FMDV 3C protease contains a D84N substitution.

46. The polynucleotide of enumerated paragraph 34, wherein said encoded engineered FMDV 3C protease contains a C163V substitution.

47. The polynucleotide of enumerated paragraph 34, wherein said encoded engineered FMDV 3C protease contains a C163I substitution.

48. The polynucleotide of enumerated paragraph 34, wherein said encoded engineered FMDV 3C protease contains a C163L substitution.

49. A vector comprising the polynucleotide according to enumerated paragraph 1, which encodes at least one engineered polypeptide of interest containing at least one potyvirus NIa protease cleavage site.

50. The vector of enumerated paragraph 49 that further encodes a potyvirus NIa protease.

51. The vector of enumerated paragraph 49 that further encodes a TEV protease.

52. The vector of enumerated paragraph 49 that further encodes at least one wild type or modified FMDV 3C protease that is at least 85% identical to a FMDV 3C protease described by SEQ ID NO: 86, 88, 90, or 92.

53. The vector of enumerated paragraph 49 that further encodes a modified FMDV 3C protease comprising one or more amino acid substitutions to residues 26-35, 125-134 or 138-150 described by SEQ ID NOS: 86, 88, 90 or 92, or to a 3C protease that is at least 95% identical to the amino acid sequence of SEQ ID NOS: 86, 88, 90 or 92.

54. The vector of enumerated paragraph 49 that comprises at least one 2A, 2A-like or other translation interrupter sequence.

55. A vector comprising the polynucleotide according to enumerated paragraph 1, which encodes at least one engineered FMDV P1 polypeptide that is at least 90% identical to a FMDV P1 precursor polypeptide having a sequence of SEQ ID NO: 22, 24, 124, 126, 128, 130, 132, 134 or 136 and that comprises at least one potyvirus NIa protease cleavage site.

56. The vector of enumerated paragraph 55 that further encodes a potyvirus NIa protease.

57. The vector of enumerated paragraph 55 that further encodes a TEV protease and wherein said FMDV P1 polypeptide comprises at least one TEV protease cleavage site.

58. The vector of enumerated paragraph 57 that further encodes at least one wild type or modified FMDV 3C protease that is at least 85% identical to a FMDV 3C protease described by SEQ ID NOS: 86, 88, 90, or 92.

59. The vector of enumerated paragraph 58 that further encodes a modified FMDV 3C protease comprising one or more amino acid substitutions to residues 26-35, 125-134 or 138-150 described by SEQ ID NOS: 86, 88, 90 or 92, or to a 3C protease that is at least 95% identical to the amino acid sequence of SEQ ID NOS: 86, 88, 90 or 92.

60. The vector of enumerated paragraph 55 that comprises at least one 2A, 2A-like or other translation interrupter sequence.

61. The vector of enumerated paragraph 55 that expresses the encoded engineered FMDV P1 precursor polypeptide in a eukaryotic cell.

62. The vector of enumerated paragraph 55 that expresses the encoded engineered FMDV P1 precursor polypeptide in *Saccharomyces cerevisiae, Pichia pastoris*, or another yeast or fungus cell.

63. The vector of enumerated paragraph 55 that expresses the encoded engineered FMDV P1 precursor polypeptide in *Arabidopsis thaliana, Chlamydomonas reinhardtii, Glycine max, Nicotiana benthamiana, Nicotiana tabacum, Oryza sativa, Zea mays* or another plant cell.

64. The vector of enumerated paragraph 55 that expresses the encoded engineered FMDV P1 precursor polypeptide in *Spodoptera frugiperda, Drosophila melanogaster*, Sf9, Sf21, or another insect cell.

65. The vector of enumerated paragraph 55 that expresses the encoded engineered FMDV P1 precursor polypeptide in a vertebrate cell.

66. The vector of enumerated paragraph 55 that expresses the encoded engineered FMDV P1 precursor polypeptide in HEK-293T (human kidney embryo) cell, LF-BK (porcine cell), LF-BK αV/β6 cell, CHO (Chinese hamster ovary) cell, or another mammalian cell.

67. The vector of enumerated paragraph 55 that expresses the encoded engineered FMDV P1 precursor polypeptide in a cell from a mammal or other animal susceptible to FMDV infection.

68. The vector of enumerated paragraph 55 that expresses the encoded engineered FMDV P1 precursor polypeptide in a prokaryotic cell.

69. The vector of enumerated paragraph 55 that expresses the encoded engineered FMDV P1 precursor polypeptide in *Bacillus, Lactococcus, Streptomyces, Rhodococcus, Corynebacterium, Mycobacterium* or in another gram-positive prokaryote.

70. The vector of enumerated paragraph 55 that expresses the encoded engineered FMDV P1 precursor polypeptide in *Escherichia, Pseudomonas* or in another gram-negative prokaryote.

71. The vector of enumerated paragraph 55 that is a minicircle vector, a replication deficient adenovirus vector, a vaccinia virus vector, or other viral vector that expresses the encoded engineered FMDV P1 precursor polypeptide in a host cell.

72. A composition comprising the vector according to enumerated paragraph 49 and at least one other vector encoding a potyvirus NIa protease and optionally a wild type or modified FMDV 3C protease that contains one or more amino acid substitutions to residues 26-35, 125-134 or 138-150 described by SEQ ID NOS: 86, 88, 90 or 92, or to a 3C protease that is at least 85% identical to the amino acid sequence of SEQ ID NOS: 86, 88, 90, or 92.

73. A composition comprising the vector according to enumerated paragraph 55 and at least one other vector encoding a TEV protease and optionally a wild type or modified FMDV 3C protease that contains one or more amino acid substitutions to residues 26-35, 125-134 or 138-150 described by SEQ ID NOS: 86, 88, 90, or 92, or to a 3C protease and that is at least 95% identical to the amino acid sequence of SEQ ID NOS: 86, 88, 90, or 92.

74. A host cell comprising the vector according to enumerated paragraph 49.

75. A host cell comprising the vector according to enumerated paragraph 50.

76. A host cell comprising the vector according to enumerated paragraph 51.

77. A host cell comprising the vector according to enumerated paragraph 52.

78. A host cell comprising the vector according to enumerated paragraph 53.

79. A host cell comprising the vector according to enumerated paragraph 54.

80. A host cell comprising the vector according to enumerated paragraph 55.

81. A host cell comprising the vector according to enumerated paragraph 56.

82. A host cell comprising the vector according to enumerated paragraph 57.

83. A host cell comprising the vector according to enumerated paragraph 58.

84. A host cell comprising the vector according to enumerated paragraph 59.

85. A host cell comprising the vector according to enumerated paragraph 60.

86. A host cell comprising the vector according to enumerated paragraph 49 and at least one other vector encoding a potyvirus NIa protease and optionally a wild type or modified FMDV 3C protease that contains one or more amino acid substitutions to residues 26-35, 125-134 or 138-150 described by SEQ ID NOS: 86, 88, 90, or 92, or to a 3C protease that is at least 85% identical to the amino acid sequence of SEQ ID NOS: 86, 88, 90, or 92.

87. A host cell comprising the vector according to enumerated paragraph 55 and at least one other vector encoding a TEV protease, and optionally a wild type or modified FMDV 3C protease that contains one or more amino acid substitutions to residues 26-35, 125-134 or 138-150 described by SEQ ID NOS: 86, 88, 90, or 92, or to a 3C protease that is at least 95% identical to the amino acid sequence of SEQ ID NOS: 86, 88, 90, or 92.

88. The host cell of enumerated paragraph 74 that is a eukaryotic cell.

89. The host cell of enumerated paragraph 74 that is *Saccharomyces cerevisiae, Pichia pastoris*, or another yeast or fungus cell.

90. The host cell of enumerated paragraph 74 that is *Arabidopsis thaliana, Chlamydomonas reinhardtii, Glycine max, Nicotiana benthamiana, Nicotiana tabacum, Oryza sativa, Zea mays* or another plant cell.

91. The host cell of enumerated paragraph 74 that is *Spodoptera frugiperda, Drosophila melanogaster*, Sf9, Sf21, or another insect cell.

92. The host cell of enumerated paragraph 74 that is a vertebrate cell.

93. The host cell of enumerated paragraph 74 that is a HEK-293T (human kidney embryo) cell, LF-BK (porcine cell), LF-BK αV/β6 cell, CHO (Chinese hamster ovary) cell, or another mammalian cell.

94. The host cell of enumerated paragraph 74 that is a cell from a mammal or other animal susceptible to FMDV infection.

95. The host cell of enumerated paragraph 74 that is a prokaryotic cell.

96. The host cell of enumerated paragraph 74 that is *Bacillus, Lactococcus, Streptomyces, Rhodococcus, Corynebacterium, Mycobacterium* or another gram-positive prokaryote.

97. The host cell of enumerated paragraph 74 that is *Escherichia, Pseudomonas* or another gram-negative prokaryote.

98. The host cell of enumerated paragraph 74, wherein said vector is a minicircle vector, a replication deficient adenovirus vector, a vaccinia virus vector, or another viral vector that encodes and expresses the engineered polypeptide of interest and, optionally, an engineered FMDV 3C protease.

99. The host cell of enumerated paragraph 74, wherein the at least one engineered polypeptide of interest comprises a 2A, delta 1D2A or at least one other 2A-like translational interrupter operatively linked to, or embedded within the at least one engineered polypeptide of interest.

100. The host cell of enumerated paragraph 74, wherein the at least one protease cleavage site is cleaved by the catalytic domain of a TEV protease and wherein the at least one engineered polypeptide of interest comprises a TEV protease, and a 2A, delta 1D2A or at least one other 2A-like translational interrupter operatively linked to, or embedded within the at least one engineered polypeptide of interest.

101. The host cell of enumerated paragraph 74, wherein the at least one engineered polypeptide of interest comprises a TEV protease, an engineered FMDV P1 precursor polypeptide that is at least 90% identical to a FMDV P1 precursor polypeptide having a sequence of SEQ ID NO: 22, 24, 124, 126, 128, 130, 132, 134 or 136 and a 2A, delta 1D2A or at least one other 2A-like translational interrupter operatively linked to, or embedded within the at least one engineered polypeptide of interest, wherein the engineered FMDV P1 precursor polypeptide further comprises at least one protease cleavage site that is cleaved by the catalytic domain of a TEV protease.

102. A method for proteolytically processing an engineered polypeptide of interest comprising culturing the host cell of enumerated paragraph 74 and recovering cleavage products of the at least one engineered polypeptide of interest produced by cleavage of the at least one protease cleavage site in the engineered polypeptide.

103. A method for proteolytically processing an engineered polypeptide of interest comprising culturing the host cell of enumerated paragraph 75 and recovering cleavage products of the at least one engineered polypeptide of interest produced by cleavage of the at least one protease cleavage site in the engineered polypeptide.

104. A method for proteolytically processing an engineered polypeptide of interest comprising culturing the host cell of enumerated paragraph 76 and recovering cleavage products of the at least one engineered polypeptide of interest produced by cleavage of the at least one protease cleavage site in the engineered polypeptide.

105. A method for proteolytically processing an engineered polypeptide of interest comprising culturing the host cell of enumerated paragraph 77 and recovering cleavage products of the at least one engineered polypeptide of interest produced by cleavage of the at least one protease cleavage site in the engineered polypeptide.

106. A method for proteolytically processing an engineered polypeptide of interest comprising culturing the host cell of enumerated paragraph 78 and recovering cleavage products of the at least one engineered polypeptide of interest produced by cleavage of the at least one protease cleavage site in the engineered polypeptide.

107. A method for proteolytically processing an engineered FMDV P1 precursor polypeptide comprising culturing the host cell of enumerated paragraph 79 and recovering cleavage products of the at least one engineered polypeptide of interest produced by cleavage of the at least one protease cleavage site in the engineered polypeptide.

108. A method for proteolytically processing an engineered FMDV P1 precursor polypeptide comprising culturing the host cell of enumerated paragraph 80 and recovering cleavage products of the at least one engineered polypeptide of interest produced by cleavage of the at least one TEV protease cleavage site in the engineered polypeptide.

109. A method for proteolytically processing an engineered FMDV P1 precursor polypeptide comprising culturing the host cell of enumerated paragraph 81 and recovering cleavage products of the at least one engineered polypeptide of interest produced by cleavage of the at least one potyvirus NIa protease cleavage site in the engineered polypeptide.

110. A method for proteolytically processing an engineered FMDV P1 precursor polypeptide comprising culturing the host cell of enumerated paragraph 82 and recovering cleavage products of the at least one engineered polypeptide of interest produced by cleavage of the at least one TEV protease cleavage site in the engineered polypeptide.

111. A method for proteolytically processing an engineered FMDV P1 precursor polypeptide comprising culturing the host cell of enumerated paragraph 83 and recovering cleavage products of the at least one engineered polypeptide of interest produced by cleavage of the at least one TEV protease cleavage site in the engineered polypeptide.

112. A method for proteolytically processing an engineered FMDV P1 precursor polypeptide comprising culturing the host cell of enumerated paragraph 84 and recovering cleavage products of the at least one engineered polypeptide of interest produced by cleavage of the at least one TEV protease cleavage site in the engineered polypeptide.

113. A method for proteolytically processing an engineered FMDV P1 precursor polypeptide comprising culturing the host cell of enumerated paragraph 85 and recovering cleavage products of the at least one engineered polypeptide of interest produced by cleavage of the at least one TEV protease cleavage site in the engineered polypeptide.

114. The method of enumerated paragraph 110, wherein the FMDV P1 precursor polypeptide contains a cleavage site cleaved by the catalytic domain of a TEV protease at junctions between VP0 and VP3; VP3 and VP1; or VP1 and 2A and said culturing produces VP0, VP3 and VP1.

115. The method of enumerated paragraph 110 comprising recovering VP0, VP3 and VP1 in the form of virus-like particles or VLPs.

116. The method of enumerated paragraph 110 comprising recovering VP0, VP3 and VP1 and assembling them into VLPs.

117. The method of enumerated paragraph 110, wherein the FMDV P1 precursor polypeptide contains a cleavage site cleaved by the catalytic domain of a TEV protease at junctions between VP4 and VP2; VP2, and VP3; VP3 and VP1; or VP1 and 2A and said culturing produces VP4, VP2, VP3 and VP1.

118. The method of enumerated paragraph 110 comprising recovering VP4, VP2, VP3 and VP1 in the form of virus-like particles or VLPs.

119. The method of enumerated paragraph 110 comprising recovering VP4, VP2, VP3 and VP1 and assembling them into VLPs.

120. The method of enumerated paragraph 110, wherein the host cells are cultured at a temperature at which the TEV protease is inactive, and then cultured or held at a temperature at which the TEV protease is active, and thereafter, optionally lysed and held at a temperature at which the TEV protease is active.

121. The method of enumerated paragraph 110, wherein the TEV protease is under the control of an inducible promoter, and the host cells are cultured in the absence of an inducer for the inducible promoter and then cultured in the presence of said inducer and thereafter, optionally lysed and held at a temperature at which TEV protease is active.

122. The method of enumerated paragraph 110, wherein said host cell further expresses a wild type FMDV 3C protease.

123. The method of enumerated paragraph 110, wherein said host cell further expresses an engineered FMDV 3C protease that is at least 85% identical to a FMDV 3C protease described by SEQ ID NOS: 86, 88, 90, or 92, and that contains one or more amino acid substitutions within residues 26-35, 46, 80, 84, 125-134, 138-150, 163 or 181.

124. The method of enumerated paragraph 110, wherein said host cell further expresses an engineered FMDV 3C protease that is at least 95% identical to a FMDV 3C protease described by SEQ ID NOS: 86, 88, 90, or 92, and that contains one or more amino acid substitutions within residues 125-134.

125. The method of enumerated paragraph 110, wherein said host cell further expresses an engineered FMDV 3C protease that is at least 85% identical to a FMDV 3C protease described by SEQ ID NOS: 86, 88, 90, or 92, and that contains substitution L127P.

126. The method of enumerated paragraph 110, wherein said host cell further expresses an engineered FMDV 3C protease that is at least 95% identical to a FMDV 3C protease described by SEQ ID NOS: 86, 88, 90, or 92, and that contains one or more amino acid substitutions at residues 46, 80, 84, 163, or 181.

127. A composition produced by the method of enumerated paragraph 102.

128. A composition produced by the method of enumerated paragraph 103.

129. A composition produced by the method of enumerated paragraph 104.

130. A composition produced by the method of enumerated paragraph 105.

131. A composition produced by the method of enumerated paragraph 106.

132. A composition produced by the method of enumerated paragraph 107.

133. A composition produced by the method of enumerated paragraph 108.

134. A composition produced by the method of enumerated paragraph 109.

135. A composition produced by the method of enumerated paragraph 110.

136. A composition produced by the method of enumerated paragraph 111.

137. A composition produced by the method of enumerated paragraph 112.

138. A composition produced by the method of enumerated paragraph 113.

139. A composition produced by the method of enumerated paragraph 114.

140. A composition produced by the method of enumerated paragraph 115.

141. A composition produced by the method of enumerated paragraph 116.

142. A composition produced by the method of enumerated paragraph 117.

143. A composition produced by the method of enumerated paragraph 118.

144. A composition produced by the method of enumerated paragraph 119.

145. A composition produced by the method of enumerated paragraph 120.

146. A composition produced by the method of enumerated paragraph 121.

147. A composition produced by the method of enumerated paragraph 122.

148. A composition produced by the method of enumerated paragraph 123.

149. A composition produced by the method of enumerated paragraph 124.

150. A composition produced by the method of enumerated paragraph 125.

151. A composition produced by the method of enumerated paragraph 126.

152. The composition of enumerated paragraph 127, further comprising a pharmaceutically acceptable adjuvant, buffer, carrier, solute or excipient.

153. The composition of enumerated paragraph 127, further comprising at least one other active immunogen, drug or antiviral agent.

154. The composition of enumerated paragraph 127, in a form suitable for parenteral administration.

155. The composition of enumerated paragraph 127, in a form suitable for intramuscular, intranasal, or intravenous administration.

156. The composition of enumerated paragraph 127, in a form suitable for administration orally or otherwise into the alimentary canal.

157. The composition of enumerated paragraph 127 that comprises VP0, VP1 and VP3.

158. The composition of enumerated paragraph 127 that comprises VP0, VP1 and VP3 in the form of virus-like particles, or VLPs, optionally as empty capsids not containing RNA.

159. The composition of enumerated paragraph 127 that comprises VP4, VP2, VP1 and VP3.

160. The composition of enumerated paragraph 127 that comprises VP4, VP2, VP1 and VP3 in the form of virus-like particles, or VLPs, optionally as empty capsids not containing RNA.

161. The composition of enumerated paragraph 135 that comprises VP0, VP1 and VP3.

162. The composition of enumerated paragraph 135 that comprises VP0, VP1 and VP3 in the form of virus-like particles, or VLPs, optionally as empty capsids not containing RNA.

163. The composition of enumerated paragraph 135 that comprises VP4, VP2, VP1 and VP3.

164. The composition of enumerated paragraph 135 that comprises VP4, VP2, VP1 and VP3 in the form of virus-like particles, or VLPs, optionally as empty capsids not containing RNA.

165. A method for preventing or treating FMDV infection comprising administering the composition of enumerated paragraph 110 to a subject in need thereof or at risk of FMDV infection.

166. The method of enumerated paragraph 165 comprising administering the composition to an uninfected subject.

167. The method of enumerated paragraph 165 comprising administering the composition to an infected subject.

168. The method of enumerated paragraph 165, wherein the subject is a cloven-footed animal.

169. The method of enumerated paragraph 165, wherein the subject is a bovine.

170. The method of enumerated paragraph 165, wherein the subject is a caprine.

171. The method of enumerated paragraph 165, wherein the subject is an ovine.

172. The method of enumerated paragraph 165, wherein the subject is a swine.

173. The method of enumerated paragraph 165, wherein the composition is administered parenterally.

174. The method of enumerated paragraph 165, wherein the composition is administered orally or otherwise into the alimentary canal.

175. The method of enumerated paragraph 165, wherein the composition is administered intranasally, intratracheally, intrapulmonarily or on to a mucous membrane.

176. A method for preventing or treating FMDV infection comprising administering a polynucleotide encoding an engineered FMDV P1 precursor protein containing one or more potyvirus NIa protease cleavage sites and encoding a potyvirus NIa protease.

177. The method for preventing or treating FMDV infection according to enumerated paragraph 176, wherein said one or more protease cleavage sites are cleaved by the catalytic domain of a TEV protease, and wherein said potyvirus NIa protease is TEV protease.

178. A method for preventing or treating FMDV infection comprising administering a host cell that expresses an engineered FMDV P1 precursor polypeptide containing one or more potyvirus NIa protease cleavage sites and a potyvirus NIa protease.

179. The method according to enumerated paragraph 178 comprising administering a host cell that expresses an engineered FMDV P1 precursor polypeptide containing one or more TEV protease cleavage sites and a TEV protease.

180. The method of enumerated paragraph 178, wherein the host cell is autologous.

181. An antigenic composition or diagnostic product comprising the composition obtained by proteolysis of the at least one engineered polypeptide of interest according to enumerated paragraph 102.

182. An antigenic composition or diagnostic product comprising the composition according to enumerated paragraph 109 which comprises cleavage products of a FMDV P1 precursor polypeptide.

183. An antigenic composition or diagnostic product comprising the composition according to enumerated paragraph 110 comprises cleavage products of a FMDV P1 precursor polypeptide.

184. A diagnostic chip or platform comprising the composition obtained by proteolysis of the at least one engineered polypeptide of interest according to enumerated paragraph 102.

185. A diagnostic chip or platform comprising the composition according to enumerated paragraph 109 which comprises cleavage products of a FMDV P1 precursor polypeptide.

186. A diagnostic chip or platform comprising the composition according to enumerated paragraph 110 which comprises cleavage products of a FMDV P1 precursor polypeptide.

187. A diagnostic kit or assay comprising the composition obtained by proteolysis of the engineered polypeptide of interest according to enumerated paragraph 102 and, optionally, at least one other reagent, test strip, plate, reaction container, package, bag, or instructions for use in written or computer readable form.

188. A diagnostic kit or assay comprising the composition obtained by proteolysis of the engineered polypeptide of interest according to enumerated paragraph 109 and, optionally, at least one other reagent, test strip, plate, reaction container, package, bag, or instructions for use in written or computer readable form.

189. A diagnostic kit or assay comprising the composition obtained by proteolysis of the engineered polypeptide of interest according to enumerated paragraph 110 and, optionally, at least one other reagent, test strip, plate, reaction container, package, bag, or instructions for use in written or computer readable form.

BRIEF DESCRIPTION OF THE DRAWINGS

An appreciation of the disclosure and many of the attendant advantages thereof may be understood by reference to the accompanying drawings.

FIG. 2A, first alignment at the VP4/VP2 junction (SEQ ID NO: 35), no matches with minimum TEV consensus sequence; FIG. 2A, $2^{nd}$ alignment at the VP2/VP3 junction (SEQ ID NO: 36), matches with minimum TEV consensus sequence shown in light gray in columns 1, 6 and 7. FIG. 2A, third alignment at the VP3/VP1 junction (SEQ ID NO: 37), matches with minimum TEV consensus sequence in column 6 shown in light gray; FIG. 2A, fourth alignment at the VP1/2A junction (SEQ ID NO: 38), matches with minimum TEV consensus sequence in column 6 shown in light gray. Aligned FMDV sequences for VP junctions are described as follows VP4/VP2 (SEQ ID NO: 35), VP2/VP3 (SEQ ID NO: 36), VP3/VP1 (SEQ ID NO: 37) and VP1/2A (SEQ ID NO: 38).

FIG. 8 describes the GI accession numbers for the whole genome assemblies of the enumerated viruses. The respective NIa proteins are encoded by the polynucleotides between the indicated start and end numbers. Any of these NIa proteases or their functional variants cleaving the corresponding NIa protease cleavage sequences may be incorporated into a platform according to the invention.

DETAILED DESCRIPTION OF THE INVENTION

In addition to its other benefits, the invention provides a new and advantageous way to produce FMDV capsid proteins from the FMDV P1 precursor polypeptide that is not hindered by toxic effects of the FMDV 3C protease conventionally used to process recombinantly-produced FMDV P1 precursor polypeptide. As mentioned above, conventional recombinant expression and recovery of the FMDV structural proteins that form viral capsids suffers from numerous drawbacks including the requirement for expression of host cell-toxic FMDV 3C protease and recovery of suboptimal amounts of viral proteins. Efficient recombinant production of FMDV viral proteins is highly desirable as it is not necessary to culture live, virulent virus to produce a vaccine.

Figure 1:
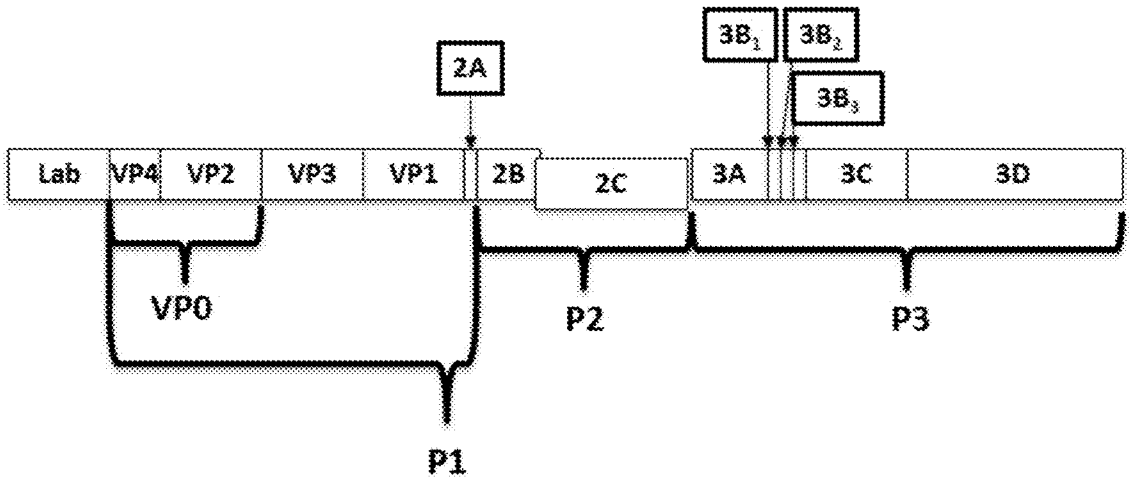
FIG. 1. Layout of the FMDV open reading frame (ORF). Primary processing of the FMDV ORF results in three large intermediate polyproteins: P1, P2 and P3. Separation of the P1 and P2 intermediate polyproteins is the result of translational interruption or "ribosomal skipping" induced by the 2A peptide sequence on the C-terminus of P1. Proteolytic cleavage by FMDV proteins Lpro and 3C produce smaller subproducts, like VP0, and mature proteins: Lpro (Lab, leader protein), VP4 (1A), VP2 (1B), VP3 (1C), VP1 (1D), 2A, 2B, 2C, 3A, $3B_1$, $3B_2$, $3B_3$, 3C and 3D.

Like the genome of other members of the Picornaviridae family, the FMDV genome encodes a single open reading frame (ORF) that is expressed and processed into precursor polypeptides, such as P1, P2 and P3, and then into individual viral peptides (VPs), FIG. 1. The 2A translational interrupter is responsible for the separation of the P1 and P2 polypeptides upon translation, FIG. 1. In some embodiments of the invention, a 2A or 2A-like translational interrupter is used to separate different segments of a precursor polypeptide, such as segments forming a NIa or TEV protease from segments forming an engineered polypeptide of interest.

The FMDV P1 precursor polypeptide encodes four structural proteins, VP4, VP2, VP3, and VP1 that comprise the FMDV capsid. Representative polynucleotide and amino acid sequences for FMDV P1 precursor proteins appear in SEQ ID NOS: 21-24 and 123-136. Upon translation, a native FMDV P1 precursor polypeptide is processed by the FMDV 3C protease into structural proteins VP0, VP3, and VP1. VP0 is a fusion of VP4 and VP2, FIG. 1. Cleavage of VP0 into VP4 and VP2 has been previously described to occur upon encapsulation.

In FMDV, processing and cleavage of VP0 occurs independently of viral RNA.

Conventional FMDV vaccine constructs utilize the 3C protease to process the P1 polypeptide into the individual VPs for assembly into virus like particles (VLPs). However, in host cells used to express FMDV proteins, the expression of the 3C protease has significant negative implications including Golgi fragmentation, loss of gamma-tubulin from microtubule organizing center, and processing of a number of host proteins including Histone H3, SAM68, NEMO, eIF4aI, and eIF4G.

The toxicity of the FMDV 3C protease to the host cell is detrimental to recombinant production of both individual FMDV VPs and VLPs (virus-like particles) that contain epitopes absent from individual or unassembled viral proteins.

The inventors have sought and found ways to avoid these problems. In U.S. Patent Application entitled "Modified Foot and Mouth Disease Virus Proteases, Compositions and Methods Thereof", U.S. Patent Application Publication US 2018/0066235 A1, which is hereby incorporated by reference in its entirety, the inventors disclose re-engineering of the FMDV 3C protease to be less toxic to host cells, for example, by providing a mutant FMDV 3C protease containing the V28K, L127P, V141T, C142T, or C163A substitutions to the 3C protease amino acid sequence. While the present invention is independently directed to use of the TEV protease instead of the 3C protease to process the FMDV P1 precursor polypeptide, in some embodiments both TEV and 3C proteases may be used in conjunction. For purposes of these embodiments of the invention, variants of the FMDV 3C protease amino acid sequence that retain proteolytic activity and are encoded by a polynucleotide having at least 70, 80, 90, 95, 99% sequence identity to SEQ ID NO: 85 (O1 Manissa FMDV 3C Protease), SEQ ID NO: 87 (Asia Lebanon 89 FMDV 3C Protease), SEQ ID NO: 89 (SAT 1 FMDV 3C Protease), or SEQ ID NO: 91 (SAT 2 Egypt FMDV 3C Protease) or which have at least 70, 80, 90, 95, 99% sequence similarity or identity to the amino acid sequence of SEQ ID NOS: 2, 4, 6, 8, 10, 12, 14, 16, 18, 20, 86, 88, 90, or 92 or which contain 1, 2, 3, 4, 5, 6, 7, 8, 9, 10, 15, 20 or more amino acid deletions, substitutions, or insertions to the amino acid sequence of SEQ ID NO: 2, 4, 6, 8, 10, 12, 14, 16, 18, 20, 86, 88, 90, or 92, may be employed. FMDV 3C proteases from other serotypes of FMDV as well as specific mutants of, and constructs containing, the FMDV 3C protease are incorporated by reference to U.S. Patent Application Publication US 2018/0066235 A1.

In the present application the inventors disclose an alternative approach that uses a potyvirus protease, such as TEV protease, that is not derived from FMDV. The toxic FMDV 3C protease is not needed to process a FMDV P1 precursor polypeptide, or other precursor polypeptide, using this new approach. FMDV capsid proteins VP0, VP1, VP2, VP3 and VP4 are efficiently expressed in the absence of FMDV 3C protease and expression of these proteins is not affected by the cytotoxic effects the FMDV 3C protease exerts on host cells.

The inventors have found that an FMDV P1 precursor protein expression system or platform using a TEV protease, instead of an FMDV 3C protease, effectively processes a recombinant FMDV P1 precursor protein that was engineered to contain TEV recognition sites. Surprisingly, this system produces satisfactory quantities of FMDV P1 precursor polypeptide and processes the P1 precursor polypeptide into antigenic viral proteins completely independently of the FMDV 3C protease and its toxic effects. This new expression platform or system completely avoids the host cell cytotoxicity associated with other systems that use the FMDV 3C protease.

The invention provides a valuable platform and foundation for the development and production of FMDV vaccines and other anti-FMDV biologics. Efficient recombinant production of FMDV viral antigens, immunogens, and virus-like particles contributes to meeting national defense objectives against bioterrorism, protecting critical farming and livestock infrastructure, and help respond to emergency situations involving FMDV.

Definitions

Potyvirus NIa Protease (Nuclear Inclusion a Protease)

The potyvirus NIa protein contains the following two domains; the VPg domain at the N-terminus and the NIa-pro domain at the C-terminus [PMID: 18024078, PMID: 9356344]. The ~250-amino acid NIa-pro domain adopts a characteristic two-domain antiparallel beta-barrel fold that is the hallmark of trypsin-like serine proteases, with the catalytic triad residues His, Asp, and Cys located at the interface between domains [PMID: 12377789]. There is only one proteolytic catalytic domain.

Potyvirus NIa proteases include those of Plum Pox Virus: (SEQ ID NO: 50), Tobacco vein mottling virus: (SEQ ID NO: 51), Potato Virus Y (SEQ ID NO: 52); Pea seed-borne mosaic virus (SEQ ID NO: 53); Turnip Mosaic Virus: (SEQ ID NO: 54); Clover Yellow Vein Virus (SEQ ID NO: 55); and Pepper Vein Banding Virus (SEQ ID NO: 56). Other NIa proteases are described by SEQ ID NOS: 57-67. NIa protease sequences are also incorporated by reference to the GI accession numbers described by FIG. 8 (last accessed Nov. 3, 2016). Additional information on Potyvirus NIa protease domain is available at: ebi.ac.uk/interpro/entry/IPR001730 the disclosure of which is incorporated by reference. Polynucleotide sequences encoding the NIa proteases disclosed herein may be deduced by the ordinary artisan based on the genetic code. Modified NIa proteases may have 70, 80, 90, 95, or 99% sequence identity or similarity to a NIa protease sequence described herein or have 1, 2, 3, 4, 5, 6, 7, 8, 9, 10 or more amino acid residue deletions, substitutions or additions to a native NIa protease sequence, and exhibit at least one activity of a corresponding native NIa protease.

Potyvirus NIa Protease Cleavage Recognition Sites

Recognition sites for potyviruses NIa proteases include: Plum Pox Virus: NVVVHQA (SEQ ID NO: 70), Tobacco vein mottling virus: ETVRFQS (SEQ ID NO: 71), Potato Virus Y: YEVHHQA (SEQ ID NO: 72), Pea seed-borne mosaic virus: IKVRLQA (SEQ ID NO: 74); Turnip Mosaic Virus: XVRHQS (SEQ ID NO: 75); where X=E/A/L/I; Clover Yellow Vein Virus: MLFVFQS (SEQ ID NO: 76); and Pepper Vein Banding Virus: GGQVAHQA (SEQ ID NO: 77). Other recognition sites are described by SEQ ID NOS: 78-83.

TEV Protease.

Figure 7:
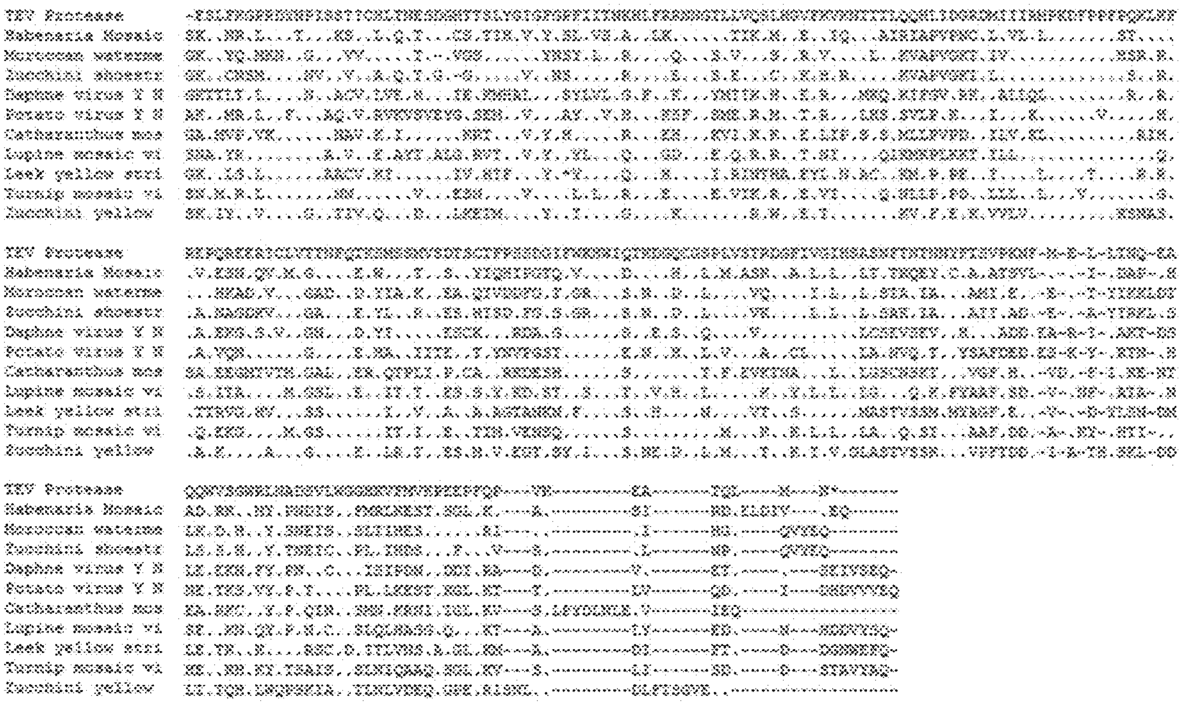
FIG. 7 is a sequence alignment of the TEV protease with other Potyvirus NIa proteases. The NIa protease according to one or more embodiments of the invention may comprise any of these sequences or fragments or variants thereof (e.g., variants with 70, 80, 90, 95% sequence identity to one of these sequences) exhibiting proteolytic activity, preferably on the same or similar substrates of for an intact native NIa protease. The sequentially aligned sequences respectively correspond to SEQ ID NOS: 26, 57, 58, 59, 60, 52, 61, 62, 63, 54, and 64.

Tobacco Etch Virus ("TEV") is a potyvirus. TEV encodes and expresses a NIa protein containing a 27 kDa catalytic proteolytic domain, hereinafter known as the "TEV protease". TEV protease has at least 41-52% sequence identity with other NIa proteases as can be shown by aligning the sequences described by FIG. 8 as shown in FIG. 7. Engineered NIa proteases having at least this degree of sequence identity with TEV protease and the ability to cleave a site recognized by the corresponding unmodified NIa protease may be employed in some embodiments of the invention. Such modified NIa protease includes those having 70, 80, 90, 95, or 99% sequence identity with TEV or NIa protease sequences described herein.

TEV protease recognizes and cleaves particular sites and the inventors have found that it can be effectively used to cleave engineered FMDV P1 precursor proteins engineered to contain TEV cleavage sites. Also, the inventors have found that TEV protease does not exhibit the cytotoxic effects that FMDV 3C protease does on host cells even though both TEV protease and FMDV 3C proteases are exogenous to most if not all host cells.

A modified TEV protease that comprises the amino acid sequence of SEQ ID NO: 26 is advantageously used as part of a platform according to the invention. This modified TEV protease contains the S219V mutation which has been previously shown to make it impervious to auto-inactivation thus providing a more efficient protease than the native TEV protease. However, the native TEV protease lacking the S219V mutation may be used or other engineered TEV protease variants may be employed in some embodiments of the invention. Such engineered TEV variants retain proteolytic activity and have at least 70, 80, 90, 95, 99% sequence identity to SEQ ID NO: 26, or may contain 1, 2, 3, 4, 5, 6, 7, 8, 9, 10, 15, 20 or more amino acid deletions, substitutions, or insertions to SEQ ID NO: 26.

TEV Cleavage Recognition Sites

TEV protease recognizes and processes amino acid sequences comprising $E_1$-$X_2$-$X_3$-$Y_4$-$X_5$-$Q_6$-$(G/S)_7$ (SEQ ID NO: 29) with cleavage occurring between amino acids six and seven of the recognition sequence. While the recognition domain of TEV protease does allow variability at the $P_2$, $P_3$, and/or $P_5$ amino acids, a preferred recognition sequence is $E_1$-$N_2$-$L_3$-$Y_4$-$F_5$-$Q_6$-$S_7$(SEQ ID NO: 30).

Foot and Mouth Disease Virus

Figure 2A:
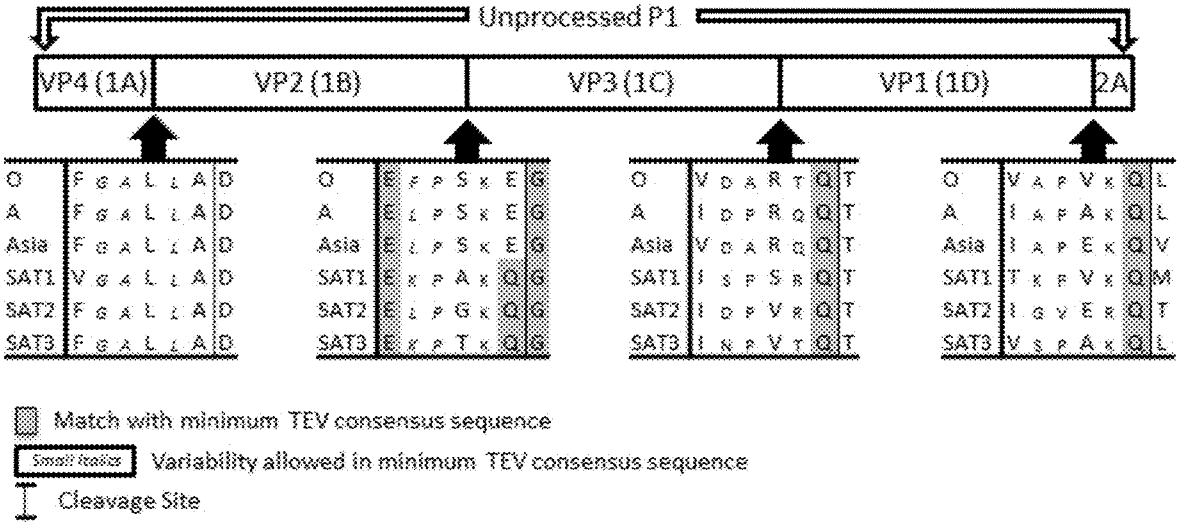
FIG. 2A. This figure compares the junctional amino acid sequences for FMDV serotypes O, A, Asia, SAT1, SAT2, and SAT3. Upward arrows indicate the positions of each junction within the unprocessed FMDV P1 precursor polypeptide. Residues with white backgrounds show matches with the minimum TEV protease cleavage consensus sequence E X X Y X Q G/S (SEQ ID NO 29). Residues in small italics denote allowed variability within the minimum TEV protease cleavage sequence.

A "foot-and-mouth-disease virus" or the acronym FMDV refers to, but is not limited to, any of the seven major FMDV antigenically distinct virus serotypes, for example serotypes A, O, C, Asia 1 and South African Territories (SAT) 1, 2 and 3 as well as the multiple subtypes or topotypes which exist within each serotype. The foot-and-mouth disease virus (FMDV) is a non-enveloped picornavirus, belonging to the genus Aphthovirus of the family Picornaviridae, with a single-stranded genomic RNA of between 7,500 to 8,000 nucleotides or approximately between 7,500 to 8,000 nucleotides, approximately 7,500 nucleotides, or approximately 8,000 nucleotides. Referring to FIGS. 1 and 2A, the FMDV RNA genome is translated in a single open reading frame as a single polypeptide precursor which must be cleaved into functional proteins by virally encoded proteases. Such cleavages take place at different stages as shown in FIGS. 1 and 2A, forming multiple intermediate polypeptide precursors and yielding the final protein products of capsid structural proteins VP1, VP2, VP3 and VP4, as well as non-structural proteins L, 2A, 2B, 2C, 3A, $3B_1$, $3B_2$, $3B_3$, 3C and 3D.

FMDV Hosts and Animals Susceptible to FMDV Infection.

The term "host" refers to a mammalian subject, especially but not limited to cloven-hooved livestock and wildlife (e.g. cattle, pigs, sheep, goats, water buffalos, yaks, reindeer, deer, elk, llamas, alpacas, bison, moose, camels, chamois, giraffes, hogs, warthogs, kudus, antelopes, gazelles, wildebeests) that are in need of treatment for foot-and-mouth disease (FMD). Hosts are in need of treatment for FMD when they are infected with one or more strains of the FMDV, have been diagnosed with FMD, or are otherwise at risk of contracting FMDV infection. Hosts that are "predisposed to" to FMD can be defined as hosts that do not exhibit overt symptoms of FMD but that are genetically, physiologically, or otherwise at risk of developing FMD. Cells of mammals may also host FMDV.

Mutants

The terms "wild-type" or its acronym "wt", and "native" refer to a biological molecule that has not been genetically engineered or otherwise modified, for example, a nucleotide sequence that encodes an FMDV P1 precursor polypeptide that exists in nature and has not been genetically engineered or modified, an FMDV P1 precursor polypeptide translated from a coding nucleotide sequence that exists in nature and has not been genetically engineered or modified, a transgene expression cassette containing a nucleotide sequence encoding for an FMDV P1 precursor polypeptide that exists in nature and has not been genetically modified, and a vector carrying a mutant nucleotide sequence encoding for an FMDV P1 precursor polypeptide that exists in nature and has not been genetically engineered or modified or a transgene expression cassette containing a mutant nucleotide sequence encoding for an FMDV P1 precursor polypeptide that exists in nature and has not been genetically engineered or otherwise modified.

The term "mutation" as used herein indicates any genetic modification of a nucleic acid and/or polypeptide which results in an altered nucleic acid or polypeptide. Mutations include, but are not limited to point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frameshift mutation, a nonsense mutation, an insertion, or a deletion of part or all of a gene. In addition, in some embodiments of the engineered or modified microorganism, a portion of the microorganism genome has been replaced with a heterologous polynucleotide. In some embodiments, the mutations or modifications are naturally-occurring. In other embodiments, the mutations are identified and/or enriched through artificial selection pressure. It must be noted that all the mutations, modifications or alterations described and exemplified in the present disclosure are the result of genetic engineering, and not naturally occurring mutations. However, some engineered constructs may comprise or make use of naturally-occurring mutations or modifications beyond those engineered by human intervention or selection.

The terms "mutated", "mutant", "modified", "altered", "variant", and "engineered" are used as adjectives describing a nucleotide sequence, a nucleic acid, a protein or a protease that differs from a native polynucleotide or amino acid sequence found in nature or from any prior sequence of interest. A prior sequence of interest includes a native polynucleotide or amino acid sequence, such as one isolated from a natural source, but also includes previously engineered polynucleotide or amino acid sequences that can be further engineered, mutated or otherwise modified. A native or unmodified FMDV P1 precursor polypeptide that is engineered to contain amino acid residues defining a potyvirus NIa protease site such as a TEV protease site is one example of a mutated, mutant, altered, variant or engineered polypeptide of interest. These terms may be similarly applied to a polynucleotide encoding mutated, mutant, altered, variant or engineered polypeptide of interest. The same terms apply to mutations to other polypeptide or nucleotide sequences, such as those constituting or encoding a previously engineered polypeptide of interest, a modified FMDV 3C protease, modified 2A or 2A-like polypeptide, luciferase or reporter protein, protein tag, or a modified NIa protease such as a modified TEV protease, as disclosed herein. A mutant may contain a single amino acid residue, nucleotide, or codon deletion, substitution, or insertion or multiple deletions, substitutions, or insertions compared to an unmodified, native or not mutated sequence, for example, 1, 2, 3, 4, 5, 6, 7, 8, 9, 10, 15, 20 or more of such deletions, substitutions, or insertions to residues, nucleotides or codons. Alternatively, a mutant or variant may be characterized by a degree of sequence identity or similarity to an unmodified, native or not mutated sequence or to an active portion of such a sequence (e.g., a catalytic site or domain or a nucleotide sequence encoding such), such as by a 60, 70, 80, 90, 95, 98, 99, 99.5, or <100% (or any intermediate value within this range) sequence identity or similarity to a sequence described herein or to an otherwise known sequence.

Polynucleotides, Vectors, Constructs, Recombinant or Genetic Expression

A "nucleotide" refers to an organic molecule that serves as a monomer, or a subunit of nucleic acids or polynucleotides like DNA and RNA. Nucleotides are building blocks of nucleic acids and are composed of a nitrogenous base, e.g., A (adenine), G (guanine), C (cytosine), T or U (thymine or uracil), a five-carbon sugar (ribose or deoxyribose), and at least one phosphate group. Thus, a nucleoside plus a phosphate group yields a nucleotide. Nucleotides in a nucleotide sequence are commonly indicated based on their nitrogenous bases.

A "nucleotide sequence" or a "nucleic acid sequence" is a succession of letters that indicate the order of nucleotides or nucleic acids within a DNA (using G, A, C, T) or RNA molecule (using G, A, C, U). A DNA or RNA molecule or polynucleotide may be single or double stranded and may be genomic, recombinant, synthetic, a transcript, a PCR- or amplification product, an mRNA or cDNA. It may optionally comprise modified bases or a modified backbone. It may comprise a sequence in either a sense or antisense orientation and it inherently describes its complement.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acids.

An "isolated polynucleotide" is a polynucleotide whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "coding region" or simply, a "region" of a gene consists of the nucleotide residues of the coding strand of the gene and the nucleotides of the non-coding strand of the gene which are homologous with or complementary to, respectively, the coding region of an mRNA molecule which is produced by transcription of the gene. A "coding region" of an mRNA molecule also consists of the nucleotide residues of the mRNA molecule which are matched with an anticodon region of a tRNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g. rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "transgene expression cassette", a "transgene expression construct", an "expression cassette", an "expression construct", a "construct", a "chimera", a "chimeric DNA", a "DNA chimera" or a "chimeric gene" is a nucleic acid sequence that has been artificially constructed to comprise one or more functional units, e.g. a promoter, control element, consensus sequence, translational frameshift sequence, or protein encoding gene not found together in nature, and is capable of directing the expression of any RNA transcript in an organism that the cassette has been transferred to, including gene encoding sequence(s) of interest as well as non-translated RNAs, such as shRNAs, microRNAs, siRNAs, or anti-sense RNAs. A transgene expression cassette may be single- or double-stranded and circular or linear. A transgene expression cassette can be constructed, inserted or cloned into a vector, which serves as a vehicle for transferring, replicating and/or expressing nucleic acid sequences in target cells.

A "promoter" is a region of DNA that initiates transcription of a particular gene or an expression cassette and is located near the transcription start sites of genes or expression cassettes, on the same strand and upstream on the DNA (towards the 5' region of the sense strand). A promoter can be about 100 to 1,000 base pairs long.

A "vector" is any means by which a nucleic acid can be propagated and/or transferred between organisms, cells, or cellular components. Vectors include viruses, bacteriophage, pro-viruses, plasmids, phagemids, transposons, cosmids, viral vectors, expression vectors, gene transfer vectors, minicircle vectors, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector typically contains at least an origin of replication, a cloning site and a selectable marker (e.g., antibiotic resistance). Natural versions of the foregoing non-limiting examples may be isolated, purified, and/or modified so the resultant natural version is differentiable from the material in its natural state. A vector can also be a naked RNA polynucleotide, a naked DNA polynucleotide, a polynucleotide composed of both DNA and RNA within the same strand, a polylysine-conjugated DNA or RNA, a peptide-conjugated DNA or RNA, a liposome-conjugated DNA, or the like, that are not episomal in nature, or it can be an organism which comprises one or more of the above polynucleotide constructs such as an *Agrobacterium* or a bacterium.

The term "recombinant vector" as used herein is defined as vector produced by joining pieces of nucleic acids from different sources or a copy thereof.

A "minicircle DNA vector" may be referred to as "minicircle vector" or "minicircle" is a small (usually in the range of 3-4 kb, approximately 3-4 kb or usually no larger than 10 kb) circular, episomal plasmid derivative wherein all prokaryotic vector parts (e.g., bacterial origin of replication, genes associated with bacterial propagation of plasmids) have been removed. Since minicircle vectors contain no prokaryotic DNA sequences, they are less likely to be perceived as foreign and destroyed when they are employed as vehicles for transferring transgenes into mammalian or other suitable target cells.

Transformation

"Transformation" refers to the process by which a vector or polynucleotide construct is introduced into a host cell. Transformation (or transduction, or transfection), can be achieved by any one of a number of means including chemical transformation (e.g., lithium acetate transformation), electroporation, microinjection, biolistics (or particle bombardment-mediated delivery), or *Agrobacterium* mediated transformation.

"Transfection" refers to the process by which a nucleic acid such as a gene cloned inside a vector (DNA or RNA) is delivered into a eukaryotic host cell.

Host Cells

The term "host cell" refers to a prokaryotic (e.g. bacterial) or a eukaryotic cell (e.g. mammalian, insect, yeast etc.) that is naturally infected or artificially transfected or transformed with a virus or a vector, for example, by vaccination. The virus introduced to the host cell may be live, inactivated, attenuated or modified, while the vector introduced carries a transgene expression cassette that, when expressed in the host cell, may produce viral structural proteins that self-assemble to form virus-like particles (VLPs). In some cases, a host cell may be inside of a host or subject and said host or subject may be treated by the administration of nucleic-acid-based vaccine encoding a modified FMDV P1 precursor polypeptide (or other modified polypeptide of interest) and at least one protease or polynucleotide sequence that cleaves or otherwise processes (e.g., via 2A transcription termination) an engineered FMDV P1 precursor polypeptide or other engineered polypeptide of interest. A host cell may contain a polynucleotide encoding a modified 3C protease in its genomic or episomal DNA. For example, a modified polynucleotide encoding a modified FMDV P1 precursor polypeptide may be incorporated into a host cell genome via recombination, by use of a transposon, or by other recombinant DNA methods well known in the art. Engineered proteins of interest and their cleavage or processed products as well as proteases that process them may also be expressed from the same or different plasmids, episomes, or other DNA or RNA constructs inside of a host cell.

A host cell for expression of an engineered polypeptide of interest or protease, such as FMDV P1 precursor protein or NIa protease, or other FMDV proteins or antigenic sequences and as other proteins of interest, may be a prokaryotic or eukaryotic cell. The term host cell includes yeast or fungal host cells, such as those of *Saccharomyces cerevisiae*, or *Pichia pastoris*; plant host cells, such as those of *Arabidopsis thaliana, Chlamydomonas reinhardtii, Glycine max, Nicotiana benthamiana, Nicotiana tabacum, Oryza sativa*, or *Zea mays*; insect cells or insect cell lines such as those of *Spodoptera frugiperda, Drosophila melanogaster*, Sf9, or Sf21; the cells of vertebrates or mammals or mammalian cell lines, such as HEK-239T (human kidney embryo) cell, LF-BK (porcine cell), LF-BK $\alpha V/\beta 6$, or cells of animals susceptible to FMDV infection; prokaryotic host cells such as those of gram-positive bacteria including cells of *Bacillus, Lactococcus, Streptomyces, Rhodococcus, Corynebacterium, Mycobacterium* or gram-negative bacteria such as *Escherichia* or *Pseudomonas.*

Amino Acids, Proteins, Polypeptide Structures

A "residue" or an "amino acid residue" refers to a specific amino acid within the polymeric chain of a peptide, a polypeptide or a protein. A residue may be one of the twenty-two conventional proteinogenic amino acid residues (which include selenocysteine and pyrrolysine), a modified proteinogenic amino acid residue, or a non-proteinogenic amino acid residue.

An "amino acid sequence", a "peptide sequence" or a "protein sequence" refers to the order in which amino acid residues, connected by peptide bonds, link in the chain in peptides and proteins. The sequence is generally reported from the N-terminal end containing a free amino group to the C-terminal end containing a free carboxyl group. Peptide sequence is often called protein sequence if it represents the primary structure of a protein. Throughout the present disclosure, an amino acid residue may be represented by a three-letter code or a single-letter code, including but not limited to Ala (A) for alanine, Arg (R) for arginine, Asn (N) for asparagine, Asp (D) for aspartic acid, Cys (C) for cysteine, Gln (Q) for glutamine, Glu (E) for glutamic acid, Gly (G) for glycine, His (H) for histidine, Ile (I) for isoleucine, Leu (L) for leucine, Lys (K) for lysine, Met (M) for methionine, Phe (F) for phenylalanine, Pro (P) for proline, Ser (S) for serine, Thr (T) for threonine, Trp (W) for tryptophan, Tyr (Y) for tyrosine, Val (V) for valine, Pyl (O) for pyrrolysine, Sec (U) for selenocysteine.

As used herein, a "non-coded amino acid", a "non-proteinogenic amino acid", a "synthetic amino acid" or an "unnatural amino acid" refers to an amino acid that is not naturally encoded or found in the genetic code (DNA or mRNA) of any organism, and may be synthesized in vitro or otherwise genetically engineered into a cell A "genetically coded amino acid", a "coded amino acid" or a "natural amino acid" refers to an amino acid that is naturally encoded by or found in the genetic code (DNA or mRNA) of an organism, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, pyrrolysine and selenocysteine.

The term "protein," "peptide," or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D- or L-optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide.

FMDV 3C protease. The FMDV 3C protease is a 213-amino acid, 23.1-kDa cysteine protease whose amino acid sequence is greater than 95% homologous across known serotypes and strains of the virus. The cysteine-histidine-aspartic acid catalytic triad at the active site of the FMDV 3C protease, which is conserved in cysteine proteases, is formed by the residues H46, D64 and C163. Proteolytic activity can be knocked out by substituting a residue in this active site, such as by the C163A substitution. The 3C protease cleaves the FMDV P1 precursor protein at the last three positions shown in FIG. 2A to produce viral proteins VP0, VP3 and VP1. Other activities of the native 3C protease include suppression of host cell protein production, processing of host cell proteins, fragmentation of the Golgi apparatus, induction of the loss of microtubule system integrity, and induction of the loss of gamma-tubulin from the microtubule organizing center. Further structural and functional characteristics of the FMDV 3C protease and modified forms of the FMDV 3C protease are described by U.S. Patent Application Publication US 2018/0066235 A1, which is hereby incorporated by reference.

FMDV P1 precursor polypeptide (or P1 precursor protein) is a polypeptide comprised of the FMDV structural proteins and/or precursors, VP0, VP1, VP2, VP3, and VP4, as well as the 2A translational interrupter, see FIG. 1. The FMDV P1 precursor is around 85 kDa in molecular weight. The P1 precursor is processed by the FMDV 3C protease into structural proteins forming VLPs and the FMDV capsid. Modified forms of FMDV P1 precursor polypeptide may contain protease cleavage sites, for example, for NIa proteases, such as TEV protease, or for other proteases, such as FMDV 3C protease. Polynucleotides encoding FMDV P1 precursor or modified forms thereof may incorporate other regulatory sequences, including 2A or 2A-like translation termination sequences, or sequences encoding protein tags or reporter proteins.

The FMDV VP0 protein is a precursor peptide comprised of the FMDV VP2 and VP4 structural proteins. The FMDV VP0 protein is also identified as the FMDV 1AB protein and is around 33 kDa in molecular weight. It is produced by the processing of the FMDV P1 precursor protein by the FMDV 3C protease. The FMDV VP0 protein is important in the formation of protomers along with FMDV proteins VP3 and VP1. Five of these protomers assemble into a pentamer and twelve pentamers can assemble into a FMDV capsid or VLP. Cleavage of VP0 into VP2 and VP4 occurs through an unknown mechanism. FMDV VP0 protein produced by cleavage of a NIa protease or TEV protease recognition site inserted into an engineered precursor polypeptide will generally be at least 90, 95 or 99% identical or similar to a native VP0 protein. Its terminal amino acid residues may be identical to a corresponding native VP0 protein and it may contain 1, 2, 3, 4, 5, 6, 7, 8, 9 or 10 variant amino acid residues, such as those forming a NIa or TEV cleavage site, proximal to its termini.

The FMDV VP1 protein is a structural protein which comprises the FMDV capsid and/or FMDV VLP. The FMDV VP1 protein is also identified as the FMDV 1D protein and is around 24 kDa in molecular weight. The FMDV VP1 protein contains a mobile loop structure, identified as the G-H loop, which emerges from the surface of the FMDV capsid and/or VLP. The FMDV VP1 protein can form a protomer along with VP0 and VP3. Five of these protomers assemble into a pentamer and twelve pentamers can assemble into a FMDV capsid or VLP. FMDV VP1 protein produced by cleavage of a NIa protease or TEV protease recognition site inserted into an engineered precursor polypeptide will generally be at least 90, 95 or 99% identical or similar to a native VP1 protein. Its terminal amino acid residues may be identical to a corresponding native VP1 protein and it may contain 1, 2, 3, 4, 5, 6, 7, 8, 9 or 10 variant amino acid residues, such as those forming a NIa or TEV cleavage site, proximal to its termini.

The FMDV VP2 protein is a structural protein which comprises the FMDV capsid and/or FMDV VLP. The FMDV VP2 protein is also identified as the FMDV 1B protein and is around 24 kDa in molecular weight. The FMDV VP2 protein, along with the FMDV VP4 protein, is part of the FMDV VP0 protein until the formation of FMDV capsids and/or VLPs at which point the VP0 protein is processed into VP2 and VP4. FMDV VP2 protein produced by cleavage of a NIa protease or TEV protease recognition site inserted into an engineered precursor polypeptide will generally be at least 90, 95 or 99% identical or similar to a native VP2 protein. Its terminal amino acid residues may be identical to a corresponding native VP2 protein and it may contain 1, 2, 3, 4, 5, 6, 7, 8, 9 or 10 variant amino acid residues, such as those forming a NIa or TEV cleavage site, proximal to its termini.

The FMDV VP3 protein is a structural protein which comprises the FMDV capsid and/or FMDV VLP. The FMDV VP3 protein is also identified as the FMDV 1C protein and is around 24 kDa in molecular weight. The FMDV VP3 protein can form a protomer along with VP0 and VP1. Five of these protomers assemble into a pentamer and twelve pentamers can assemble into a FMDV capsid or VLP. FMDV VP3 protein produced by cleavage of a NIa protease or TEV protease recognition site inserted into an engineered precursor polypeptide will generally be at least 90, 95 or 99% identical or similar to a native VP3 protein. Its terminal amino acid residues may be identical to a corresponding native VP3 protein and it may contain 1, 2, 3, 4, 5, 6, 7, 8, 9 or 10 variant amino acid residues, such as those forming a NIa or TEV cleavage site, proximal to its termini.

The FMDV VP4 protein is the smallest of the FMDV structural proteins and is part of the FMDV capsid and/or FMDV VLP. The FMDV VP4 protein is also identified as the FMDV 1A protein and is around 9 kDa in molecular weight. The FMDV VP4 protein, along with the FMDV VP2 protein, is part of the FMDV VP0 protein until the formation of FMDV capsids and/or VLPs at which point the VP0 protein is processed into VP2 and VP4. Unlike other FMDV proteins which comprise the capsid and/or VLP the VP4 protein is entirely located inside the capsid and/or VLP structure. FMDV VP4 protein produced by cleavage of a NIa protease or TEV protease recognition site inserted into an engineered precursor polypeptide will generally be at least 90, 95 or 99% identical or similar to a native VP4 protein. Its terminal amino acid residues may be identical to a corresponding native VP4 protein and it may contain 1, 2, 3, 4, 5, 6, 7, 8, 9 or 10 variant amino acid residues, such as those forming a NIa or TEV cleavage site, proximal to its termini.

"Virus-like particles" or "VLPs" resemble viruses, but are non-infectious because they do not contain any viral genetic material. The expression of viral structural proteins, such as envelope or capsid, can result in the self-assembly of VLPs that can stimulate an immune response in a mammalian organism. In other words, VLPs are often empty viral envelopes or empty viral capsids that are capable of stimulating an immune response like a full virus. Methods and problems associated with the production of VLPs in alternative systems include those described by Lee, et al., J. Biomed. Sci. 16:69 (Aug. 11, 2009), Srinivas, et al., Biologicals 44:64-68 (2016), Mayr, et al., Vaccine 19: 2152-2162 (2001) and Niborski, et al., Vaccine 24: 7204-7213 (2006) which are each incorporated by reference.

2A is an FMDV translation interrupter sequence, see Luke, et al, Biotech. Genetic Eng. Revs. 26:223-260 (2009) which is incorporated by reference. A 2A polynucleotide sequence is described by nucleotides 34-90 of SEQ ID NO: 111 and by the amino acid residues encoded thereby (SEQ ID NO: 112). Other 2A sequences may confirming to the 2A motif DXEXNPGP (SEQ ID NO: 113) described herein such as may be employed as well as translation interrupters from other Aphthoviruses such as but not limited to Bovine rhinitis A virus, Bovine rhinitis B virus, and Equine rhinitis A virus and Senecaviruses such as Senecavirus A.

Δ1D2A. A translation termination sequence that comprises FMDV 1D residues and the FMDV 2A amino acid residues. The polynucleotide sequence of SEQ ID NO: 109 encodes the Δ1D2A polypeptide of SEQ ID NO: 110. Other degenerate sequences encoding the polypeptide of SEQ ID NO: 110 may also be used. Polynucleotides 1-33 encode FMDV 1D residues, 34-87 encode the 2A amino acid residues, and 88-90 encode a C-terminal proline residue described by both SEQ ID NOS: 109 and 110. Other translation termination sequences similar to Δ1D2A may have fewer or more residues of the 1D protein than Δ1D2A or may contain 1, 2, 3 or more point mutations to the 2A sequence that do not affect its ability to act as a translation termination sequence. Δ1D2A will comprise the amino acid sequence PGP and may optionally comprise part or all of one of the following motifs:

```
                                        (SEQ ID NO: 114)
(H/R/Y/D)(K/R)(Q/T/F/V)(E/K/P/A/D)(I/P/L/A)(I/T/V)
(A/K/G/S)(P/V)(E/A/V)(K/R)Q(V/L/M/T)(L/C)(N/S)
FDLLKLAGDVESNPGP.

                                        (SEQ ID NO: 115)
(A/V/I/L/M/T)(T/S/L/C)(N/S)(F/K)(D/S/E)LL(K/Q/L)
(Q/R/L)AGD(V/I)E(T/C/S)NPGP

                                        (SEQ ID NO: 116)
AGD(V/I)E(T/C/S)NPGP

                                        (SEQ ID NO: 117)
LLXXAGDXEXNPGP

                                        (SEQ ID NO: 113)
DXEXNPGP
```

GLuc. *Gaussia* luciferase gene (GLuc) or a protein expressed therefrom, including variants that are luciferous, such as proteins having at least 90, 95, or 99% sequence identity with a native GLuc protein. GLuc is a small, naturally secreted luciferase of 185 amino acids (SEQ ID NOS: 118/119) useful for examination of low levels of protein expression.

Quaternary FMDV Protein structures. The FMDV VP1, VP0, and VP3 proteins can form a protomer structure consisting of a single copy of each protein. Five of these protomers, consisting of VP1, VP0, and VP3, can assemble into a pentamer structure.

Prophylaxis/Treatment

As used herein, the terms "prevent" and "preventing" include the prevention of the recurrence, spread or onset. It is not intended that the present disclosure be limited to complete prevention. In some embodiments, prevention delays disease onset, reduces severity, reduces contagion, or otherwise alters disease symptoms and presentation.

As used herein, the terms "treat" and "treating" are not limited to the case where the subject (e.g. cattle) is cured and the disease is eradicated. Rather, embodiments of the present disclosure also contemplate treatment that delays disease progression, decreases particular symptoms, reduces contagion, or otherwise reduces the severity of disease, disease presentation or its symptoms or progression. Prevention or treatment with proteins, such as FMDV viral proteins or VLPs according to the invention may induce cellular or humoral immune responses, for example, by priming or expanding T cells or B cells. The term "in vivo" refers to a reaction or interaction occurring inside the body, such as inside of the body of subject at risk or having a disease such as FMD.

The term "in vitro" referring to a reaction or interaction occurring outside of a host body or cell, including but not limited to tissue culture or other cultivation of host cells to produce FMDV viral proteins, NIa or TEV protease, or FMDV 3C proteases. Such processes may take place in a solution, a liquid culture medium, a liquid/solid or viscous medium, such as on agarose in a petri dish, test tube, flask, fermenter, or in an apparatus configured for production of large quantities of FMDV viral proteins or other proteins of interest.

Sequence Homology/Identity/Similarity

The term "homolog" used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes. Homologs include, but are not limited to, those of NIa proteases (e.g., TEV protease), FMDV P1 protein, FMDV viral proteins, and FMDV 3C proteases.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is defined to mean that the two proteins have similar amino acid sequences.

A mutant, variant or modified polypeptide may have 75, 80, 85, 90, 95, 97.5, 98, 99, or 100% sequence identity or sequence similarity with a known FMDV polynucleotide or polypeptide sequence, such as those described herein and in the sequence listing.

BLASTN may be used to identify a polynucleotide sequence having at least 70%, 75%, 80%, 85%, 87.5%, 90%, 92.5%, 95%, 97.5%, 98%, or 99% sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to blast.ncbi.nlm.nih.gov/_Blast.cgi?PROGRAM=blastn&BLAST_PROGRAMS=megaBlast&PAGE_TYPE=BlastSearch&SHOW_DEFAULTS=on&LINK_LOC=blasthome (last accessed Feb. 4, 2016).

BLASTP can be used to identify an amino acid sequence having at least 70%, 75%, 80%, 85%, 87.5%, 90%, 92.5%, 95%, 97.5%, 98%, or 99% sequence identity, or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/_Blast.cgi?PROGRAM=blastp&PAGE_TYPE=BlastSearch&LINK_LOC=blasthome (last accessed Jun. 29, 2016).

Codon Usage: Further modifications may be made to a polynucleotide sequence encoding a modified FMDV antigen, such as P1, VP0, VP1, VP2, VP3, VP4 or other proteins, such as the TEV or FMDV 3C proteases. For example, prior to the transformation of a host cell, codon frequency of a polynucleotide sequence encoding FMDV P1 precursor polypeptide, or other FMDV antigens may be modified to optimize expression or stability of a nucleic acid encoding FMDV P1 or other FMDV antigens. Software suitable for optimizing codon usage is known and may be used to optimize codon usage in nucleic acid encoding FMDV P1, or other FMDV antigens, see *Optimizer: A web server utility that optimize a DNA or Protein sequence*, created by P. Puigbo, Evolutionary Genomics Group Biochemistry and Biotechnology Department Universitat Rovira i Virgili (URV), Tarragona, Spain. Codon usage frequencies for various organisms are known and are also incorporated by reference to the Codon Usage Database, Kazusa DNA Research Institute, Chiba, Japan.

Not all amino acid codons are degenerate, for example, in the genetic code of most organisms, Met and Trp are encoded by single codons. However, for degenerate codons, frequency or average frequency of codon usage may be selected to range from 0% (no common degenerate codons) to 100% (same frequency of codon usage as host cell genome). This range includes all intermediate values include 0%, 10%, 20%, 30%, 40%, 50%, 60%, 70%, 80%, 90%, 95% and 100%. Similarly, G+C content of a nucleic acid encoding FMDV P1, other FMDV or picornavirus proteins, or NIa protease may be matched, moved closer or moved away from that of the host cell by selection of a degenerate codon with more or fewer G or C nucleotides. G+C content of exogenous nucleic acids encoding FMDV P1 precursor polypeptide or other FMDV antigens may range within 1, 2, 3, 4, 5, 6, 7, 8, 9, 10, 20, 30, 40, 50% more or less than the average G+C content of the host cell. Alternatively, codon usage may be modified to modulate or control the expression of NIa protease such as TEV protease, FMDV P1 or other FMDV or picornavirus polypeptides or to attenuate the expression of host cell proteins required for host cell viability, growth, or robustness; see for example, Kew, et al., U.S. Pat. No. 8,846,051 hereby incorporated by reference. In some embodiments, expression of TEV protease, 3C protease, 2A, GLuc, SGLuc, FMDV P1, other FMDV antigens or other proteins by a host cell may be limited or reduced by 5, 10, 20, 30, 40, 50, 60, 70, 80, 90, 95% or more compared to a maximum expression rate (e.g., where codon frequency is matched to the host cell) in order to permit aggregation of an antigen (e.g., into a quaternary structure) or a particular folding of an expressed protein (e.g., having a particular secondary or tertiary structure).

Polymerase Chain Reaction

A "polymerase chain reaction", or a "PCR", is a laboratory technique used to make multiple copies of a segment of DNA. PCR can be used to amplify, or copy, a specific DNA target from a mixture of DNA/mRNA/cDNA molecules. First, two short DNA/RNA sequences called primers are designed to bind to the start and end of the DNA target. Then, to perform PCR, the DNA/mRNA/cDNA template that contains the target is added to a tube that contains a formulated buffer, primers, free nucleotides, and an enzyme called DNA polymerase, and the mixture is placed in a PCR machine. The PCR machine increases and decreases the temperature of the sample in automatic, programmed steps. Initially, the mixture is heated to denature, or separate, the double-stranded DNA/mRNA/cDNA template into single strands. The mixture is then cooled so that the primers anneal, or bind, to the DNA template. At this point, some DNA polymerase are capable of synthesizing new strands of DNA starting from the primers at the same temperature as the annealing step. Other DNA polymerases require the temperature to be raised to a slightly higher temperature, but still below denaturation temperature. In either case this step is referred to as extension. Following extension and at the end of the first cycle, each double-stranded DNA molecule consists of one new and one old DNA strand. PCR then continues with additional cycles that repeat the aforementioned steps. The newly synthesized DNA segments serve as templates in later cycles, which allow the DNA target to be exponentially amplified millions of times. Thus, PCR can be used to detect, amplify, or mutate the polynucleotide constructs of the invention or their component parts. PCR can also be used to introduce one or more mutations and types of mutations to amplified copies of a DNA segment, such as but not limited to a site directed mutagenesis PCR. PCR may be used to modify proteins or proteases of interest, including FMDV P1 precursor protein, NIa/TEV proteases, and FMDV 3C proteases or to amplify polynucleotides expressing such proteins.

Embodiments

The invention includes the following, non-limited embodiments.

In one embodiment the invention involves a polynucleotide encoding an engineered substrate polypeptide recognized and cleaved by a NIa or by a NIa protease and FMDV 3C protease. A polypeptide of interest may be any polypeptide for which it is desired to introduce protease cleavage sites, such as a precursor polypeptide that to be processed into separate proteins. Such precursor polypeptides include but are not limited to FMDV P1 precursor polypeptide, as well as those of other viruses, including precursor polypeptides of other picornaviruses, especially those encompassing structural VPs that form capsids. The engineered, modified or mutated polypeptide of interest encoded by the polynucleotide sequence according to the invention will comprise at least one, two, three, four, five, six or more protease cleavage site(s) absent from a corresponding not engineered polypeptide of interest. The at least one protease cleavage site is recognized and cleaved by the catalytic domain of a potyvirus nuclear inclusion protein a, hereinafter called potyvirus NIa protease. A polypeptide of interest may also contain or be engineered to contain other protease sites, such as sites recognized and cleaved by the FMDV 3C protease or a modified or engineered variant thereof.

The polynucleotide of the invention as described above may further comprise at least one promoter or other transcription regulatory element, at least one prokaryotic or eukaryotic translation initiation sequence or other translation regulatory element, at least one translational interrupter sequence, or at least one reporter gene operatively linked to, or embedded within, the polynucleotide sequence encoding the engineered polypeptide of interest. Such sequences are known in the art and include, but are not limited to CMV (cytomegalovirus promoter), SV40 (simian virus 40 promoter), EF-1 (elongation factor 1 promoter), PGK1 (phosphoglycerate kinase 1 promoter), Ubc (ubiquitin C promoter), Beta Actin, CAG (combination of CMV enhancer, beta actin promoter, and rabbit beta-globin splice acceptor), TRE (Tetracycline response element promoter), UAS (*Drosophila* promoter), Ac5 (*Drosophila* Actin 5c gene promoter), Polyhedrin (baculovirus promoter), CaMKIIa ($Ca2+$/calmodulin-dependent protein kinase II promoter), GAL1 (Galactokinase promoter), GAL10 (Galactokinase promoter), TEF1 (Yeast transcription elongation factor promoter), GDS (Yeast Glyceraldehyde 3-phosphage dehydrogenase promoter), ADH1 (Yeast alcohol dehydrogenase I promoter), ADH2 (Yeast alcohol dehydrogenase 2 promoter), CaMV35S (Cauliflower Mosaic Virus promoter), Ubi (Maize ubiquitin gene promoter), H1 (human polymerase III RNA promoter), U6 (human U6 small nuclear promoter), T7 (T7 bacteriophage promoter), T7lac (T7 bacteriophage promoter with lac operators), Sp6 (Sp6 bacteriophage promoter), araBAD (arabinose metabolic operon promoter), trp (*E. coli* tryptophan operon promoter), lac (lac operon promoter), Ptac (hybrid promoter of lac and trp), pL (bacteriophage lambda promoter), CYC1/GRE, MFalpha1 (Mating Factor a 1 promoter), and PHO5 (Acid Phosphatase promoter).

The polynucleotide of the invention may further comprise a polynucleotide encoding a tag or reporter protein. Representative sequences include SEQ ID NO: 105 which encodes a FLAG or epitope tag (SEQ ID NO: 106), SEQ ID NO: 107 which encodes a His tag (SEQ ID NO: 108), SEQ ID NO: 118 encoding GLuc (SEQ ID NO: 119) and SEQ ID NO: 120 encoding SGLuc (SEQ ID NO: 121). Such tags may be used to monitor cleavage of a precursor polypeptide, to monitor intracellular trafficking or secretion of cleaved proteins linked to a tag or reporter, or for recovering or purifying a protein containing the tag.

A polynucleotide according to the invention may further comprise a polynucleotide sequence that represents a translation interrupter sequence, such as 2A, delta 1D2A, or at least one other 2A-like translational interrupter, operatively linked to, or embedded within, the polynucleotide sequence encoding the engineered polypeptide of interest. Translation interrupters other than the 2A interrupter from FMDV may be employed.

The polynucleotide of the invention may encode an engineered polypeptide of interest containing protease cleavage sites recognized or cleaved by a potyvirus NIa protease including, but not limited to those of Tobacco Etch Virus, Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus.

The protease recognition or cleavage sites engineered into and encoded by the polynucleotide of the invention may include one or more sites described by an amino acid sequence selected from the group consisting of NVVVHQA (SEQ ID NO: 70), ETVRFQS (SEQ ID NO: 71), YEVHHQA (SEQ ID NO: 72), IVRHQS (SEQ ID NO: 73), IKVRLQA (SEQ ID NO: 74), XVRHQS, where X is Y/E/A/L or I (SEQ ID NO: 75), MLFVFQS (SEQ ID NO: 76), GGQVAHQA (SEQ ID NO: 77), GQVAHQA (SEQ ID NO: 78), EVRHQS (SEQ ID NO: 79), AVRHQS (SEQ ID NO: 80), LVRHQS (SEQ ID NO: 81), ENLYFQS (SEQ ID NO: 82), and ENLYFQG (SEQ ID NO: 83).

In some preferred embodiments the polynucleotide of the invention will encode protease recognition or cleavage sites cleaved by the catalytic domain of Tobacco Etch virus NIa protease (SEQ ID NO: 26), hereinafter called TEV protease. Such a TEV protease recognition or cleavage site may comprise the amino acid motif $E_1$-$X_2$-$X_3$-$Y_4$-$X_5$-$Q_6$-$(G/S)_7$ (SEQ ID NO: 29) or $E_1$-$N_2$-$L_3$-$Y_4$-$F_5$-$Q_6$-$S_7$ (SEQ ID NO: 30) or may comprise a specific amino acid sequence such as EDAYTQS (SEQ ID NO: 39), EFLYKQG (SEQ ID NO: 40), EDLYFQS (SEQ ID NO: 41), EKLYKQG (SEQ ID NO: 42), ELLYKQG (SEQ ID NO: 43) or EALYKQS (SEQ ID NO: 44).

Embodiments of the polynucleotide according to the invention also include those encoding the TEV protease site(s) described above and also comprising polynucleotides representing 2A, delta 1D2A, or other 2A-like translational interrupters, operatively linked to, or embedded within, the polynucleotide sequence encoding the engineered polypeptide of interest having TEV protease site(s).

In one preferred embodiment, the polynucleotide of the invention will encode a FMDV P1 precursor polypeptide, which is engineered to contain NIa protease cleavage sites, that is at least 70, 75, 80, 85, 90, 95, 99% identical or similar to a FMDV P1 polypeptide described by SEQ ID NOS: 22, 24, 124, 126, 128, 130, 132, 134, and 136. Such NIa protease cleavage sites may be TEV protease cleavage sites. In such embodiments where an engineered FMDV P1 precursor polypeptide is encoded, the NIa or TEV protease recognition and cleavage sites or translation terminator sites are preferably position between at least one junction between VP4 and VP2, VP2 and VP3, VP3 and VP1, or VP1 so as to permit a P1 precursor polypeptide to be cleaved into separate viral proteins. Such cleavage or translation terminator sites may also be positioned at junctions producing other FMDV P1 cleavage products such as VP0, VP3 and VP1 or VP2, VP4, VP3 and VP1. Cleavage sites or translation terminators may also be engineered at junctions between other viral proteins derived from a precursor polypeptide besides those in the FMDV P1 precursor polypeptide or in non-FMDV precursor polypeptides, or at sites where cleavage or translation termination is desired in any protein of interest.

In addition to NIa protease and 2A-like translation interrupters, the polynucleotide of the invention may encode a polypeptide of interest containing sites recognized and cleaved by the FMDV 3C protease or an engineered variant of the FMDV 3C protease. Such sites may pre-exist in the engineered polypeptide or be engineered into it. Thus, in some embodiments the polynucleotide of the invention will encode an engineered polypeptide comprising at least one site recognized by the FMDV 3C protease or a variant thereof.

The polynucleotide of the invention may encode a 3C protease that is active or inactive and inactive proteases may function as scaffolds or accessories to cleavage of the engineered polypeptide of interest.

In another embodiment, the polynucleotide of the invention will encode at least one of a NIa, TEV or 3C protease in addition to an engineered polypeptide of interest containing NIa or TEV protease recognition and cleavage sites or 2A-like translation termination sites absent from the unmodified polypeptide of interest. It may encode at least one potyvirus NIa protease of Plum pox virus, Tobacco vein mottling virus, Potato virus Y, Pea seed-borne mosaic virus, Turnip mosaic virus, Clover Yellow vein virus, Pepper vein banding virus, Habenaria mosaic virus, Moroccan watermelon mosaic virus, Zucchini shoestring virus, Daphnea virus Y, or Catharanthus mosaic virus; or a protease that is at least 80%, 85%, 90%, 95%, or 99% identical or similar thereto and recognizes the same cleavage site as a reference NIa protease. For example, the polynucleotide of the invention may encode a TEV protease comprising the amino acid sequence of SEQ ID NO: 26 or a TEV protease that is at least 80, 85, 90, 95, or 99% identical or similar thereto and recognizes the same TEV protease cleavage sites as that described by SEQ ID NO: 26.

Such an embodiment may encode an FMDV 3C protease or a variant thereof that is at least 80%, 85%, 90%, 95%, or 99% identical or similar to a reference FMDV 3C protease, such as those encoded by or described by SEQ ID NOS: 1-20 or 85-92 or other FMDV strains. Modified FMDV 3C proteases include those that contain one or more amino acid substitutions within residues 26-35, 46, 80, 84, 125-134, 138-150, 163 or 181 of the FMDV 3C protease and that recognize and cleave at least one protease cleavage site recognized by the reference FMDV 3C protease. Such a modified FMDV 3C protease may contain one or more amino acid substitutions within residues 125-134, or preferably for purposes of reducing toxicity on host cells, the L127P substitution. A 3C protease cleavage site may be present in a precursor polypeptide such as a FMDV P1 precursor polypeptide naturally, or may be engineered into a P1 or other precursor polypeptide of interest.

A modified FMDV 3C protease encoded by a polynucleotide according to the invention may also contain one or more amino acid substitutions at residues 46, 80, 84, 163, or 181 of a reference FMDV 3C protease described herein. Specific substitutions to the encoded FMDV 3C protease include one or more of C163A, C163G, C163I, C163L, C163S, C163V, H46Y, H181Y, D80E, D84E, or D84N.

In one embodiment the polynucleotide of the invention will encode an engineered FMDV P1 polypeptide containing NIa or TEV protease cleavage sites and further comprise a polynucleotide encoding 2A, delta 1D2A or at least one other 2A-like translational interrupter operatively linked to, or embedded within, the polynucleotide sequence encoding the engineered FMDV P1 polypeptide; and encode a TEV protease that is at least 90, 95, or 99% identical or similar to the TEV protease of SEQ ID NO: 26; and optionally encode a FMDV 3C protease that is at least 90, 95 or 99% identical or similar to a FMDV 3C protease described by SEQ ID NOS: 2, 4, 6, 8, 10, 12, 14, 16, 18, 20, 86, 88, 90 or 92.

Another embodiment of the invention constitutes a vector, or one or more vectors, comprising the engineered polynucleotide(s) according to the invention. Suitable vectors for transformation into and expression in host cells that express the polynucleotides of the invention are known and include, but are not limited to plasmids such as pET, pLac-Z, pTac, pGEX, YIP (Yeast Integrative plasmids), TOPO, pUC, pBR322, pTarget, pCEP4, pBacPAK8, pCambia, pPZP, pGreen, pRI, pEarleyGate, pHELLSGATE, as well as vectors derived from pPZP such as the pPZP100, pPZP101, pPZP102, pPZP111, pPZP112, pPZP121, pPZP122, pPZP200, pPZP201, pPZP202, pPZP211, pPZP212, pPZP221, and pPZP222 vectors or vectors derived from the pET or pUC vector.

Polynucleotides according to the invention may also be incorporated into viral vectors such as Baculovirus, Adenovirus, Vaccinia Virus, Tobacco Mosaic Virus, Cowpea Mosaic Virus, Plum Pox Virus, Potato Virus X, and Tomato bushy stunt virus.

The polynucleotides according to the invention expressing an engineered polypeptide of interest and other components, such as NIa, TEV, or 3C proteases, or 3C polypeptides lacking protease activity, or 2A or 2A-like translation interrupters may be expressed on the same vector or different vectors. For example, a polynucleotide encoding an engineered FMDV P1 polypeptide comprising NIa or TEV protease cleavage sites as well as a NIa or TEV protease may be expressed on the same vector, or each may be expressed on a different vector. Preferably, they are both expressed on the same vector because this simplifies transformation of a host cell and expression of the encoded polypeptides. In some embodiments, the engineered polypeptide of interest and/or the NIa, TEV or 3C protease or polypeptide, may be incorporated into a host cell chromosome.

Examples of the vector according to the invention include these carrying a polynucleotide encoding an engineered polypeptide of interest, such as an engineered FMDV P1 precursor polypeptide, that comprise one or more potyvirus NIa or TEV sites, FMDV 3C protease sites, or 2A-like translation interrupter sequences, and that optionally encodes a NIa, TEV, or 3C protease that recognizes the protease sites in the engineered polypeptide of interest. A vector or vectors according to the invention may comprise any of the polynucleotides according to the invention disclosed herein or may comprise subparts of a polynucleotide of the invention, such as two vectors where one vector encodes an engineered polypeptide and the other a protease that cleaves the engineered polypeptide of interest.

A vector according to the invention may be selected to permit or facilitate expression in a particular kind of host cell, such as a vector suitable for transformation and expression in a eukaryotic cell or a prokaryotic cell. Such vectors include those transformable and expressible in yeasts or fungi, such as *Saccharomyces cerevisiae* or *Pichia pastoris*; in *Arabidopsis thaliana, Chlamydomonas reinhardtii, Glycine max, Nicotiana benthamiana, Nicotiana tabacum, Oryzas* encoded engineered FMDV P1 precursor polypeptide in *Spodoptera frugiperda, Drosophila melanogaster*, Sf9, Sf21, or another insect cell; in a vertebrate cell; in HEK-293T (human kidney embryo) cell, LF-BK (porcine cell), LF-BK $\alpha V/\beta 6$ cell, CHO (Chinese hamster ovary) cell, or another mammalian cell.

A vector according to the invention may transform and express in a host cell obtained or derived from a mammal or other animal susceptible to a viral infection, such as FMDV or other picornavirus.

Vectors transformable and expressible in prokaryotic cells include those for Gram-positive bacteria like *Bacillus, Lactococcus, Streptomyces, Rhodococcus, Corynebacterium, Mycobacterium*; or those transformable and expressible in Gram-negative bacteria such as *Escherichia, Salmonella*, or *Pseudomonas*.

Other vectors according to the invention may be minicircle vector, a replication deficient adenovirus vector, a vaccinia virus vector, or other viral vectors that express the encoded engineered FMDV P1 precursor polypeptide or other engineered polypeptide of interest in a host cell.

A vector according to the invention in addition to encoding one or more polypeptides of interest, which contain cleavage sites for TEV protease or one or more other NIa proteases, may further comprise a polynucleotide encoding 2A, delta 1D2A or at least one other 2A-like translational interrupter operatively linked to, or embedded within, a polynucleotide sequence encoding the engineered polypeptide of interest.

Other embodiments of the invention relate to vector composition(s) comprising (i) a vector encoding a potyvirus NIa protease and (ii) at least one other vector encoding an engineered polypeptide of interest that comprises at least one site cleaved by said potyvirus NIa protease. Such vector compositions may contain two or more vectors encoding the polypeptide(s) of interest, and separately, two or more vectors encoding at least one TEV or other NIa protease. Compositions containing multiple vectors may contain multiple vectors in a single composition or may constitute a kit comprising two or more compositions that can be combined, each of which contain a vector encoding a polypeptide of interest or a TEV or NIa protease. In specific embodiments, such a composition may comprise a vector that encodes TEV protease and (ii) the at least one other vector that encodes an engineered polypeptide of interest that comprises at least one site cleaved by TEV protease. Such a vector composition may contain a vector encoding at least one potyvirus NIa protease and a separate vector encoding at least one engineered polypeptide of interest that is a FMDV P1 precursor polypeptide that is at least 90% identical to a FMDV P1 precursor polypeptide having a sequence of SEQ ID NO: 22, 24, 124, 126, 128, 130, 132, 134, or 136 and that comprises at least one site cleaved by NIa protease. In another embodiment the vector composition may contain a vector encoding at least one TEV or other NIa protease and at least one other vector that encodes an engineered polypeptide of interest that is a FMDV P1 precursor polypeptide that is at least 90% identical to a FMDV P1 precursor polypeptide having a sequence of SEQ ID NO: 22, 24, 124, 126, 128, 130, 132, 134, or 136.

Another aspect of the invention is a host cell that comprises the engineered polynucleotide or vector according to the invention. Such a host cell may contain any of the vectors described herein, including those containing polynucleotides encoding engineered FMDV P1 polypeptides containing NIa or TEV protease cleavage sites, FMDV 3C proteases or modified proteases, a 2A or 2A-like translation interrupters. For example, the host cell may contain a vector that expresses an engineered FMDV P1 precursor polypeptide having a sequence that is at least 90% identical to the sequence described by SEQ ID NO: 22, 24, 124, 126, 128, 130, 132, 134, or 136 that contains one or more protease cleavage sites at junctions between viral proteins. The host cell may also contain, on the same vector or on a different vector, a 2A or 2A-like translation interrupter sequence and/or a sequence encoding a NIa, TEV, 3C or modified 3C protease that recognizes the protease cleavage sites on the engineered FMDV P1 polypeptide. When the host cell encodes a modified FMDV 3C protease the protease may contain one or more amino acid substitutions to residues 26-35, 125-134 or 138-150 of the native FMDV 3C protease sequence described by SEQ ID NOS: 2, 4, 6, 8, 10, 12, 14, 16, 18, 20, 86, 88, 90 or 92 or to a 3C protease that is least 85% identical to the amino acid sequence of SEQ ID NOS: 2, 4, 6, 8, 10, 12, 14, 16, 18, 20, 86, 88, 90 or 92.

A host cell according to the invention will generally express the engineered polypeptide or proteases encoded by the polynucleotides and vectors of the invention described herein. It may be a eukaryotic host cell or a prokaryotic host cell. Examples of such eukaryotic cells include those of fungi and yeasts including *Saccharomyces cerevisiae, Pichia pastoris*, or another yeast or fungus cell; *Arabidopsis thaliana, Chlamydomonas reinhardtii, Glycine max, Nicotiana benthamiana, Nicotiana tabacum, Oryza sativa, Zea mays* or another plant cell; *Spodoptera frugiperda, Drosophila melanogaster*, Sf9, Sf21, or another insect cell; a vertebrate cell; a mammalian cell, such as those from mammals or other animals susceptible to, or carriers of, FMDV infection, HEK-293T (human kidney embryo) cell, LF-BK (porcine cell), LF-BK $\alpha V/\beta 6$ cell, CHO (Chinese hamster ovary) cell, or another mammalian cell.

Alternatively, a host cell may be a prokaryotic cell. For example, a host cell may be selected from *Bacillus, Lactococcus, Streptomyces, Rhodococcus, Corynebacterium, Escherichia, Pseudomonas* or another gram-negative prokaryote.

A host cell may carry, or be capable of carrying, a vector that is minicircle vector, a replication deficient adenovirus vector, a vaccinia virus vector, or another viral vector that encodes and expresses the engineered polypeptide of interest and, optionally, an engineered FMDV 3C protease.

A host cell may also carry a vector or other nucleic acids that encode at least one engineered polypeptide of interest that comprises a 2A, delta 1D2A or at least one other 2A-like translational interrupter operatively linked to, or embedded within the at least one engineered polypeptide of interest.

Non-limited examples of host cells according to the invention include those carrying a polynucleotide or vector encoding FMDV P1 precursor polypeptide or another polypeptide of interest containing at least one protease cleavage site is cleaved by the catalytic domain of a TEV protease and wherein the at least one engineered polypeptide of interest comprises a TEV protease, and a 2A, delta 1D2A or at least one other 2A-like translational interrupter operatively linked to, or embedded within the at least one engineered polypeptide of interest; or a polynucleotide or vector encoding a TEV protease, an engineered FMDV P1 precursor polypeptide that is at least 90% identical to a P1 precursor polypeptide having a sequence of SEQ ID NO: 22, 24, 124, 126, 128, 130, 132, 134, or 136, and a 2A, delta 1D2A or at least one other 2A-like translational interrupter operatively linked to, or embedded within the at least one engineered polypeptide of interest, wherein the engineered FMDV P1 precursor polypeptide further comprises at least one protease cleavage site that is cleaved by the catalytic domain of a TEV protease.

Another aspect of the invention involves a method for proteolytically processing an engineered polypeptide of interest comprising culturing a host cell according to the invention and recovering cleavage products of the at least one engineered polypeptide of interest produced by cleavage of the at least one protease cleavage site in the engineered polypeptide or by producing shorter polypeptides from a longer precursor polypeptide by translation interruption via a 2A or 2A-like sequence.

Such a method may cultivate a host cell transformed or transfected with polynucleotide(s) encoding engineered FMDV P1 polypeptides containing NIa or TEV protease cleavage sites, FDMC 3C proteases or modified proteases, a 2A or 2A-like translation interrupters. For example, a host cell may be cultivated that contains a vector that expresses an engineered FMDV P1 precursor polypeptide having a sequence that is at least 90% identical to the sequence described by SEQ ID NO: 22, 24, 124, 126, 128, 130, 132, 134, or 136 that contains one or more protease cleavage sites at junctions between viral proteins. One may also cultivate a host cell containing, on the same vector or on a different vector, a 2A or 2A-like translation interrupter sequence and/or a sequence encoding a NIa, TEV, 3C or modified 3C protease that recognizes the protease cleavage sites on the engineered FMDV P1 polypeptide. When a host cell expressing a FMDV P1 precursor polypeptide that contains NIa, TEV, 3C or modified 3C proteases cleavage sites or 2A or 2A-like translation terminator sites at junctions between VP0 and VP3; VP3 and VP1; or VP1 and 2A and said culturing produces VP0, VP3 and VP1, then one may recover FMDV viral proteins VP0, VP1, VP2, VP3 and/or VP4 from the host cell culture as individual proteins or a higher order structures such as a quaternary structure of one or more viral proteins or as VLPs.

Those skilled in the art may further recover, concentrate or purify proteins produced by the methods according to the invention from the host cells per se (e.g., after cell lysis) or from culture medium. Proteins, such as individual FMDV viral proteins produced by cleavage of the P1 precursor polypeptide, may be further isolated on the basis of differences in protein size, physico-chemical properties, binding affinity or biologically activity, for example, by chromatographic separation or by affinity purification. In some embodiments viral proteins will be tagged, for example, with an epitope tag, a FLAG or His tag or a luminescent tag or reporter protein to facilitate recovery. Antibodies that recognize different FMDV proteins are known and may be used to selectively purify the proteins to which they bind using affinity purification.

Upon recovery, proteins such as FMDV viral proteins, may be allowed to assemble into higher order structures or assembled using methods known in the art into higher order structures such as VLPs. Higher order structures often contain structural epitopes absent from the individual proteins forming them. Examples of FMDV proteins that may be recovered include VP0, VP3 and VP1 as individual proteins or in the form of virus-like particles or VLPs; or VP4, VP2, VP3 and VP1 as individual proteins or in the form of virus-like particles or VLPs. Accordingly, some embodiments of this method according to the invention, include recovering VP0, VP3 and VP1 and assembling them into VLPs or recovering VP4, VP2, VP3 and VP1 and assembling them into VLPs. Such a method may advantageously be practiced by cultivating a host cell expressing an engineered FMDV P1 precursor polypeptide containing a cleavage site cleaved by the catalytic domain of a TEV protease at junctions between VP4 and VP2; VP2, and VP3; VP3 and VP1; or VP1 and 2A and said culturing produces VP4, VP2, VP3 and VP1; and then recovering and optionally assembling individual viral proteins into VLPs.

In some embodiments of this method the host cells are cultured at a temperature at which the TEV protease is inactive, and then cultured or held at a temperature at which the TEV protease is active, and thereafter, optionally lysed and held at a temperature at which the TEV protease is active so that cleavage of the engineered precursor polypeptide may occur. Alternatively, a host cell may express a NIa or TEV protease (or 3C or modified 3C protease) under the control of an inducible promoter. In this embodiment the host cells are cultured in the absence of an inducer for the inducible promoter and then cultured in the presence of said inducer and thereafter, optionally lysed and held at a temperature or under other conditions at which NIa, TEV, 3C and/or modified 3C protease is active.

Another embodiment of the invention constitutes a composition containing a modified polypeptide of interest, such as an engineered FMDV P1 precursor polypeptide containing NIa, TEV, 3C, or modified 3C cleavage sites, or polypeptide products produced by cleavage of such a polypeptide of interest by NIa, TEV, 3C and/or modified 3C proteases. For example, such a composition may contain an uncleaved engineered FMDV P1 polypeptide that can be admixed with a NIa, TEV, 3C or modified 3C protease, or may contain cleavage products of such a precursor polypeptide such as VP0, VP2 or VP3, or VP4, VP2, VP3 and VP1. Examples of composition containing cleavage products of an engineered FMDV P1 precursor polypeptide include those containing VP0, VP1 and VP3; VP0, VP1 and VP3 in the form of virus-like particles, or VLPs, optionally as empty capsids not containing RNA; VP4, VP2, VP1 and VP3; or VP4, VP2, VP1 and VP3 in the form of virus-like particles, or VLPs, optionally as empty capsids not containing RNA.

A composition according to the invention may comprise a suitable buffer for further processing the protein, for stabilizing the protein(s) for storage or for use in diagnostic procedures, or for administering the protein(s), such as a pharmaceutically acceptable adjuvant, buffer, carrier, solute or excipient. For therapeutic uses, the composition may further comprise at least one other active immunogen, drug or antiviral agent, such as immunogens for antiviral agents for FMDV or other picornavirus diseases.

In some embodiments a therapeutic composition will be formulated for parenteral administration, for intramuscular, intranasal, or intravenous administration, or for administration orally or otherwise into the alimentary canal.

Another aspect of the invention involves treatment of a subject at risk of or having a disease, such as FMD or another picornavirus disease, by administering polypeptides or cleavage products of polypeptides according to the invention. In one embodiment the invention is directed to a method for preventing or treating FMDV infection comprising administering a composition that contains FMDV viral proteins or VLPs to a subject in need thereof or at risk of FMDV infection. This method may comprise administering a FMDV viral protein composition according to the invention to an uninfected subject or to an infected subject. Suitable subjects include cloven-footed animals such as a bovine, caprine, ovine or swine. The composition may be administered to the subject parenterally, orally or otherwise into the alimentary canal, intranasally, intratracheally, intrapulmonarily or on to a mucous membrane.

In another embodiment, the invention is directed to a method for preventing or treating FMDV infection comprising administering at least one polynucleotide or vector encoding an engineered FMDV P1 precursor protein containing one or more potyvirus NIa, TEV, 3C, or modified 3C, protease cleavage sites and/or encoding a potyvirus NIa, TEV, 3C, or modified 3C protease. The engineered FMDV P1 polypeptide and protease may be encoded one polynucleotide or vector or on separate polynucleotides and vectors.

Another embodiment of the invention is directed to a method for preventing or treating FMDV infection comprising administering a host cell that expresses an engineered FMDV P1 precursor polypeptide containing one or more potyvirus NIa or TEV protease, and/or a 3C or modified 3C protease cleavage sites and a potyvirus NIa or TEV protease. Such a host cell may be autologous, syngeneic, or xenogeneic to the subject.

Other embodiments of the invention are directed to diagnostic products, assays and kits and include, but are not limited to, an antigenic composition or diagnostic product comprising the composition obtained by proteolysis of the at least one engineered polypeptide of interest according to the invention; an antigenic composition or diagnostic product comprising a composition that comprises cleavage products of a FMDV P1 precursor polypeptide; a diagnostic chip or platform comprising the composition obtained by proteolysis of the at least one engineered polypeptide of interest, such as but not limited to proteolysis of an engineered FMDV P1 precursor polypeptide; a diagnostic kit or assay comprising a composition according to the invention obtained by proteolysis of the engineered polypeptide of interest and, optionally, at least one other reagent, test strip, plate, reaction container, package, bag, or instructions for use in written or computer readable form; a diagnostic kit or assay comprising the composition according to the invention obtained by proteolysis of the engineered polypeptide of interest and, optionally, at least one other reagent, test strip, plate, reaction container, package, bag, or instructions for use in written or computer readable form.

EXAMPLES

To explore and evaluate whether it was practical and feasible to use a NIa protease (TEV protease) to process a FMDV P1 polypeptide modified to contain NIa protease cleavage sites, plasmids were constructed. These plasmids expressed a P1 polyprotein derived from FMDV O1 Manisa that was modified to have TEV protease recognition sequences at the junctions between segments of the P1 protein corresponding to individual FMDV VPs.

Plasmids encoding P1 polyprotein with either the minimum or optimum TEV recognition sequences were constructed and evaluated. This work showed that while TEV protease had some difficulty processing junctions modified to match the minimum recognition sequence, $E_1$-$X_2$-$X_3$-$Y_4$-$X_5$-$Q_6$-$(G/S)_7$ (SEQ ID NO: 29), it had no difficulty processing junctions modified to match the optimum recognition sequence, $E_1$-$N_2$-$L_3$-$Y_4$-$F_5$-$Q_6$-$S_7$ (SEQ ID NO: 30). These results showed that the TEV-based system produced fully processed VPs from the P1 polyprotein and subsequent work with immunoprecipitates of the processed VPs showed co-precipitation of different VPs suggesting that the VPs produced by this TEV-based system were able to interact.

Example 1

Engineering and Analysis of Constructs Expressing Engineered FMDV P1 Precursor Polypeptides Having Modified VP Junction Sites The amino acid sequences at the VP junction sites of the P1 precursor proteins of six FMDV serotypes were examined. Nucleic acid and amino sequences of the P1 precursor proteins were obtained from GenBank accessions as follows SAT 1 isolate KNP/196/91 (DQ009716.1)(SEQ ID NOS: 21 and 22), SAT 3 isolate ZIM/05/91/3 (DQ009740.1)(SEQ ID NOS: 23 and 24), O1 Manisa Iso87 (AY593823)(SEQ ID NOS: 123 and 124), O1 pan Asia (JX170747)(SEQ ID NOS: 125 and 126), A24 Cruzeiro iso71 (AY593768)(SEQ ID NOS: 127 and 128), A Turkey/2006 (JF749841)(SEQ ID NOS: 129 and 130), SAT2 Egypt 2010 (KC440884)(SEQ ID NO: 131 and 132), C3 indaial (AY593806)(SEQ ID NO: 133 and 134), Asia1 Shamir (JF739177)(SEQ ID NO: 135 and 136).

Constructs pMM and pOM were synthesized by Genscript and inserted into the mpTarget vector using cut sites BamHI and EcoRI. Vectors were propagated by transfecting NEB 5-alpha competent E. coli High Efficiency (New England Biolabs) as per manufacturer's instructions. Construct pV0J was created using construct pOM as a template.

A non-modified O1 Manisa template was used for PCR with primers mpTarget-F (GACATCCACTTTGCCTTTCTCTC)(SEQ ID NO: 100) and O1VP0-2j-R (TCCTCTAGAAGAGTGGT)(SEQ ID NO: 101) and OneTaq 2X Master Mix with Standard Buffer (New England Biolabs) as per manufacturer's instructions.

PCR product and pOM vector were digested with BamHI and XbaI (New England Biolabs) restriction enzymes as suggested by manufacturer.

Digested PCR product was ligated into digested pOM vector using a 3:1 insert to vector ratio with T4 DNA ligase (Roche) as per manufacturer's instructions.

Ligation reactions were transfected into NEB 5-alpha Competent *E. coli* High Efficiency (New England Biolabs) as per manufacturer's instructions and plated onto LB Agar plates with 100 µg/mL Carbenicillin, X-gal, and IPTG (Teknova) and incubated at 37° C. overnight.

Colonies were picked and grown in Terrific Broth with 100 ug/ml Carbenicillin overnight and plasmids isolated by using Qiagen plasmid mini-preps (Qiagen).

Construct expression sequences are described as follows: pMM (SEQ ID NO: 93), pOM (SEQ ID NO: 95) and pVOJ (SEQ ID NO: 97).

HEK293-T cells were transfected with constructs or controls using Lipofectamine 2000® (Life Technologies) as per manufacturer's instructions. Cells were placed at 30° C. for 48 hours to allow for expression and processing of transgene. Cells were removed from flasks by flushing media with a pipette. Media was then centrifuged at 500 rpm for 3 minutes to pellet cells. Supernatant was removed and the cell pellet dissolved in 500 µl of M-PER Mammalian Protein Extraction Reagent (Life Technologies).

For each lane on a protein gel 15 µl of cell lysate was mixed with 7.5 µl of 4× NuPage Loading Buffer and heated at 95° C. for 10 minutes prior to loading. NuPAGE protein gels (Invitrogen) were run for 35 minutes at 200V in running buffer. Samples were then transferred to membranes using the i-BLOT (Invitrogen) system as per manufacturer's instructions.

For western blotting, membranes were incubated in 5% milk blocking buffer at room temperature for 1 hour then washed three times with 1×PBS-T buffer for five minutes each time. Four different primary antibodies were diluted in 1×PBS-T and used for westerns F14 mouse monoclonal at 1:50 dilution, Anti-VP3 Rabbit polyclonal at 1:250 dilution, 12FE9 mouse monoclonal at 1:50 dilution, and an anti-DYKDDDDK (SEQ ID NO: 106) mouse monoclonal antibody (Clontech) at 1:1000 dilution. Primary antibodies were incubated on membranes for 1 hour at room temperature. After incubation, membranes were washed three times for five minutes each. Depending on the source of the primary antibody either a Goat anti-mouse-HRP conjugated antibody or Goat anti-rabbit-HRP conjugated antibody was used at 1:500 dilution. Membranes were incubated in secondary antibody for 1 hour at room temperature then washed three times for five minutes each. DAB stain packets (Sigma) were used as per manufacturer's instructions to visualize bands. After band visualization membranes were rinsed three times in $ddH_2O$.

Co-Immunoprecipitation was performed using Pierce Classic Magnetic IP/Co-IP Kit™ (Life Technologies) as per manufacturer's instructions using antibodies B473M anti-FMDV mouse monoclonal (ABCAM), 2D2 anti-FMDV mouse monoclonal (ABCAM), and G16 anti-Interferon alpha mouse monoclonal (ABCAM). Western blotting of elutions was performed as described previously with the same antibodies as described previously.

Example 2

Evaluation of VP Junction Sites in FMDV P1 Polypeptide Precursor

There are four points of cleavage in the FMDV P1 precursor polypeptide utilized to create the four fully processed VPs, FIG. 2A. The amino acids present for six of the seven FMDV serotypes at each point of cleavage within the P1 polypeptide were examined and compared to the seven amino acid sequence processed by TEV protease, see FIG. 2A. There was a small amount of overlap between the peptide sequence of three of the four cleavage sites and the TEV protease recognition sequence, FIG. 2A. The most prominent of these was the VP2/VP3 (1B/1C) junction in the three SAT serotypes which had three out of four matches with the minimum TEV recognition site, FIG. 2A. FMDV O1 Manisa has at least one conserved residue for three of four points of cleavage within the P1. While the three SAT strains had an additional amino acid conserved it was decided to proceed with a modified O1 Manisa P1 for this work due to availability of resources for evaluation, such as antibodies and the ability to screen for VLP arrays by electron microscopy.

To test the ability of TEV protease to process the P1 polypeptide the inventors examined its ability to process a modified P1 with the minimal number of mutations needed to generate the four separate VPs (pMM). It was decided not to induce cleavage between VP1 and 2A as a previous publication showed virus viability with VP1-2A fusions. This resulted in a total of 9 amino acids being altered at three VP junction sites, FIG. 2B, top panel, nine residues with white backgrounds.

Figure 3A:
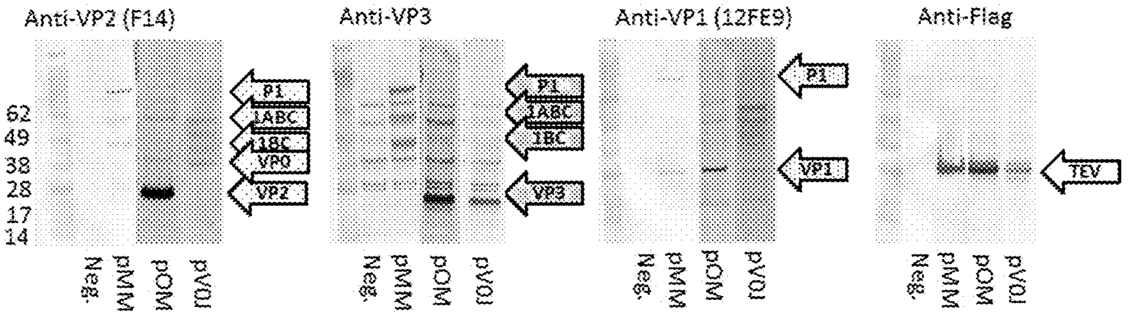
FIG. 3A. Western blots showing processing of engineered P1 precursor polypeptide constructs pMM. pOM and PVOJ described by FIG. 2B. The relative cleavage of the pMM, pOM, and pVOJ constructs by TEV protease (SEQ ID NO: 26) was determined by western blotting vs. anti-VP2, anti-VP3, anti-VP1 and anti-FLAG antibodies. FLAG sequences are described by SEQ ID NOS: 105 and 106. In the pMM construct, containing TEV sites conforming to the minimal cleavage motif, the TEV protease was able to process two of the three engineered junctions, VP4/VP2 and VP3/VP1. No fully processed VP2 or VP3 was observed suggesting that the TEV protease had difficulty processing the engineered VP2/VP3 site of $E_1$-$F_2$-$P_3$-$Y_4$-$K_5$-$Q_6$-$G_7$ (SEQ ID NO: 32). In the pOM construct, containing preferred TEV cleavage sites, the TEV protease was able to process all four junction sites. In the pVOJ construct containing preferred TEV protease cleavage sites at VP2/VP3, VP3/VP1 and VP1/2A junctions, but not at the VP4/VP2 junction, the TEV protease was able to process three junction sites with no fully processed VP2 being observed.

The pMM construct was able to provide expression of TEV protease unattached to the P1 polypeptide through usage of the 2A translational interrupter sequence, FIG. 3A, see arrow on last panel and successfully demonstrated that a FLAG-tagged TEV protease separated from the expression cassette by the FMDV 2A translational interrupter was able to cleave a precursor polypeptide modified to have minimal TEV protease target/recognition sites.

The TEV protease was able to process two of the three junctions in the engineered P1 polypeptide expressed by the pMM construct between VP4/VP2 and VP3/VP1. No fully processed VP2 or VP3 was observed suggesting that the TEV protease had difficulty processing the modified VP2/VP3 site of $E_1$-$F_2$-$P_3$-$Y_4$-$K_5$-$Q_6$-$G_7$ (SEQ ID NO: 32), FIG. 3A. The ability of the TEV protease to process other junctions of the pMM construct suggests that this is due to the influence of an un-mutated amino acid at the $P_2$, $P_3$, or $P_4$ positions.

Since the TEV protease was active but unable to fully process the engineered P1 polypeptide of the pMM construct which have $E_1$-$F_2$-$P_3$-$Y_4$-$K_5$-$Q_6$-$G_7$ (SEQ ID NO: 32) at the modified VP2/VP3 junction, the inventors examined the ability of the TEV protease to cleave a junction based on a preferred TEV consensus sequence. The pOM and pVOJ constructs were designed to have this preferred TEV protease target site present at all VP junction sites, see FIG. 2B, last two panels which describe the pOM and pVOJ constructs.

Figure 2B:
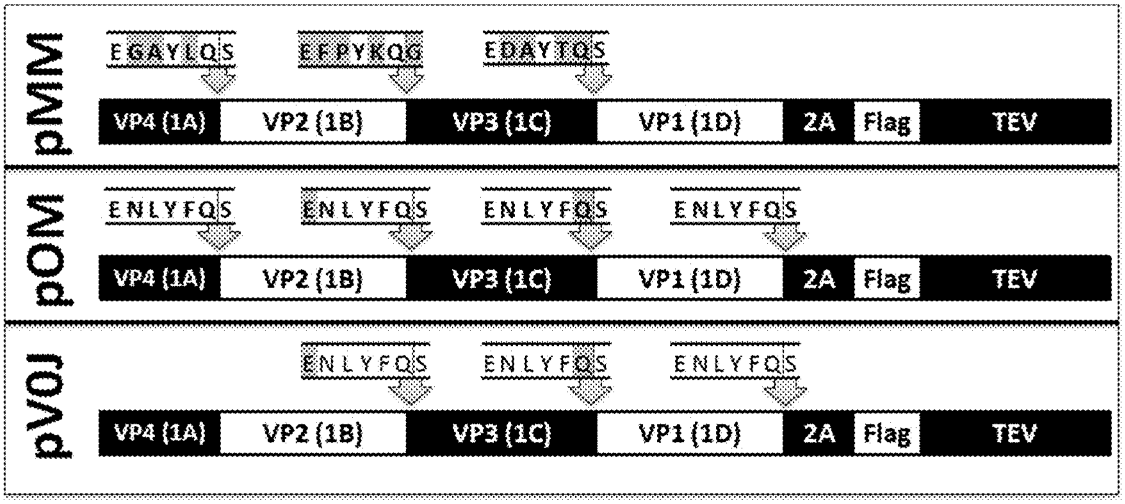
FIG. 2B. This figure maps and depicts junctional amino acid sequences for engineered FMDV P1 constructs pMM, pOM, and pVOJ. The junctional sequences of the pMM construct (top line) conform to the minimum TEV protease target sequence. The junctional sequences of pOM and pVOJ constructs (lower $2^{nd}$ and $3^{rd}$ panels) utilize the preferred TEV protease target sequence (SEQ ID NOS: 30 and 34). Amino acid sequences at junctions for pMM (FIG. 2B, first panel) are as follows: VP4/VP2 (SEQ ID NO: 31), VP2/VP3 (SEQ ID NO: 32) and VP3/VP1 (SEQ ID NO: 33).

In the pOM construct, all four points of cleavage needed to make fully processed VPs were modified to comprise the amino acid sequence $E_1$-$N_2$-$L_3$-$Y_4$-$F_5$-$Q_6$-$S_7$ (SEQ ID NO: 30), FIG. 2B.

In the pVOJ construct, there is no TEV protease target/recognition site at the VP4/VP2 junction, a junction that is not processed by the native FMDV 3C protease. VP4 and VP2 when uncleaved together form VP0. The process by which VP0 is separated into VP2 and VP4 is described in the literature as being independent from processing by the native FMDV 3C protease and as taking place upon encapsulation and not processed by the 3C protease. The inventors examined the pVOJ construct which had no TEV recognition sequence present within VP0 while retaining the preferred TEV consensus sequences at the other three VP junctions (pV0J), FIG. 2B. The pV0J construct allows TEV to process only the sites within the P1 processed by the 3C protease. This results in the expression of VP0, VP3, and VP1; see FIG. 3A.

Using the pOM construct, the inventors demonstrated that it is possible to obtain full processing of the engineered P1 precursor polypeptide into VPs using the TEV protease with only small amounts partially processed intermediates being present as shown by FIG. 3A.

The pV0J, which contains the preferred TEV protease target/recognition site at three of the found P1 junctions, closely mirrored the P1 processing products of the 3C protease and was able to produce fully processed VP0, VP3, and VP1; see FIG. 3A.

Example 3

Effects of Co-Expression of FMDV 3C Protease with Engineered FMDV P1 and TEV Protease The invention eliminates the requirement for native FMDV 3C protease to process FMDV P1 precursor polypeptide and thus avoids host cell toxicity associated with the 3C protease. However, it is unknown whether the FMDV 3C protease serves some other non-proteolytic function such as participation in post-translation modification of viral proteins or in their assembly into higher order structures such as viral capsids. For example, the 3C polypeptide could serve as a scaffolding protein to facilitate interactions amongst processed and/or unprocessed VPs.

Figure 2C:
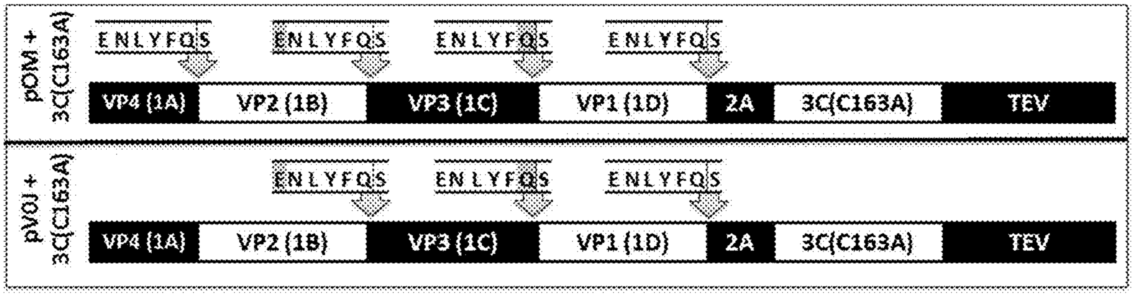
FIG. 2C. Two constructs were made and tested to evaluate the effect of fusing a modified FMDV 3C protease, containing a C163A mutation, to the N-terminus of TEV protease. The pOM 3C(C163A) and pVOJ 3C(C163A) constructs utilize the TEV protease preferred target sequence (SEQ ID NOS: 30 and 34) at the specified viral protein junctions as shown in this figure.
Figure 3B:
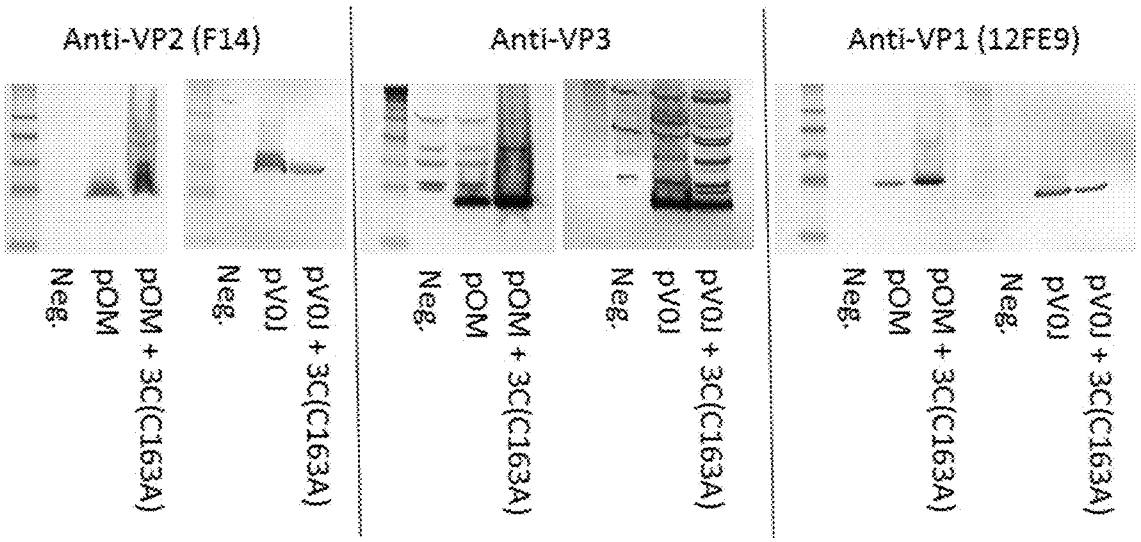
FIG. 3B. Western blots showing processing of engineered P1 precursor polypeptide constructs pOM, pOM+3C (C163A), pVOJ, and pVOJ+3C (C163A) described in FIG. 2C. TEV protease was able to process the engineered P1 polypeptide into individual VPs that were identified with antibodies to VP2, VP3 and VP1 with or without the modified FMDV 3C protease containing the C163A protease inactivating mutation fused to the N-terminus. Residue C163 in the FMDV 3C protease forms part of the catalytic triad. In FMDV 3C (C163A), the C163A substitution inactivates the FMDV 3C proteolytic catalytic site. These data show that the 3C protease is not required for processing of the FMDV P1 precursor polypeptide and that TEV protease activity was not inhibited by the presence of an engineered FMDV 3C protease containing an inactivated protease catalytic site.

To account for this possibility the inventors created two additional constructs based on the pOM and pV0J constructs that express an inactive FMDV 3C protease containing the C163A mutation which inactivates the FMDV 3C proteolytic catalytic site. These constructs are pOM+3C(C163A) and pV0J+3C(C163A) respectively, and are described by FIG. 2C. As shown by FIG. 3B, both pOM+3C(C163A) and pVPOJ+3C(C163A) constructs processed the engineered FMDV P1 precursor polypeptide in a similar manner to that of the pOM and pV0J constructs also depicted in the western blotting data in FIG. 3B. This shows that the presence of the FMDV 3C(C163A) sequence on the N-terminus of TEV protease did not inhibit processing of the polypeptide by TEV protease.

The pOM+3C(C163A) and pV0J+3C(C163A) constructs demonstrate that a fusion of the FMDV 3C(C163A) with the TEV protease retains the ability to process junctions on the FMDV P1 polypeptide modified to TEV protease recognition sequences; see FIG. 3B.

Example 4

Evaluation of Higher Order VP Structures Using Immunoprecipitation

For vaccine production, the assembly of tertiary or quaternary structures from individual FMDV VPs is desirable because these higher order structures contain unique or protective epitopes similar to those in the native virus. Since the pOM construct was able to produce fully processed VPs from the engineered FMDV P1 precursor polypeptide, the inventors further investigated protein interactions amongst these VPs. Co-immunoprecipitations were performed to look for protein interactions associated with the formation of the FMDV capsid or other higher order structures, FIG. 4.

Figure 4:
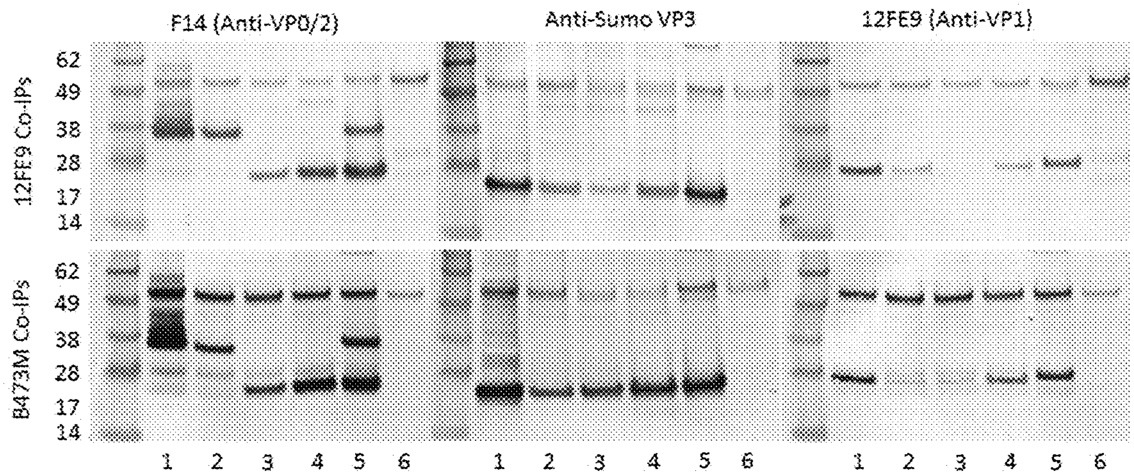
FIG. 4. Viral proteins expressed by engineered constructs pV0J, pVOJ+3C (C163A), pOM, and pOM+3C (C163A) were captured using either the anti-VP1 12FE9 monoclonal antibody or the B473M antibody. All the constructs contained the TEV protease cleavage site described by SEQ ID NOS: 30 and 34. However, pVOJ constructs do not contain a TEV protease cleavage site at the VP4/VP2 junction which is a junction that is not processed by the native FMDV 3C protease. As shown, Co-IPs using anti-FMDV antibodies 12FE9 and B473M were successful in pulling down fully processed VP2 and VP3. While these results do not confirm the presence of VLPs, they suggest at least that some capsid-like interactions are occurring amongst the VPs produced by these engineered constructs containing TEV protease cleavage sites at the P1 viral protein junctions. Lanes 5 and 6 in FIG. 4 are, respectively, positive and negative controls.

Co-IPs using anti-FMDV antibodies 12FE9 (anti-VP1) and B473M were successful in pulling down fully processed VP2 and VP3, FIG. 4. The successful capture of these VPs suggests capsid-like interactions amongst the VPs obtained by recombinant expression of processing of the engineered FMDV P1 precursor polypeptide.

Co-IPs using 12FE9 and B473M antibodies with the pV0J sample, which does not contain a TEV protease site between VP4/VP2, showed successful capture of VP0, VP3 and VP1 peptides, FIG. 4. The lack of capture of any significant amounts of VP2 suggests that while interactions amongst the processed VPs are taking place it is not inducing the reaction required to process VP0 into VP2 and VP4.

Co-IPs using 12FE9 (anti-VP1) and B473M antibodies with the pOM+3C(C163A) and pV0J+3C(C163A) samples showed successful capture of VP2, VP3 and VP1 peptides for only the pOM+3C(C163A) construct in the presence of modified 3C protease, FIG. 4.

The addition of the FMDV 3C(C163A) sequence on the N-terminus of the TEV protease enhanced the amount of VP2, VP3, and VP1 pulled down in both 12FE9 and B473M co-IPs when compared to the pOM construct alone suggesting the advantages of coexpressing a 3C or modified 3C protein. However, the lack of capture of any significant amounts of VP2 in the pVOJ+3C(C163A) construct suggests that while interactions amongst the processed VPs is taking place it is not inducing the reaction required to process VP0 into VP2 and VP4.

The Examples above demonstrate the feasibility of FMDV P1 processing using an alternative protease, specifically, the TEV protease, to reduce the negative effects on host cells caused by the FMDV 3C protease as well as the potential advantages of co-expressing a modified FMDV 3C protease.

Example 5

Prokaryotic Expression

Figure 5:
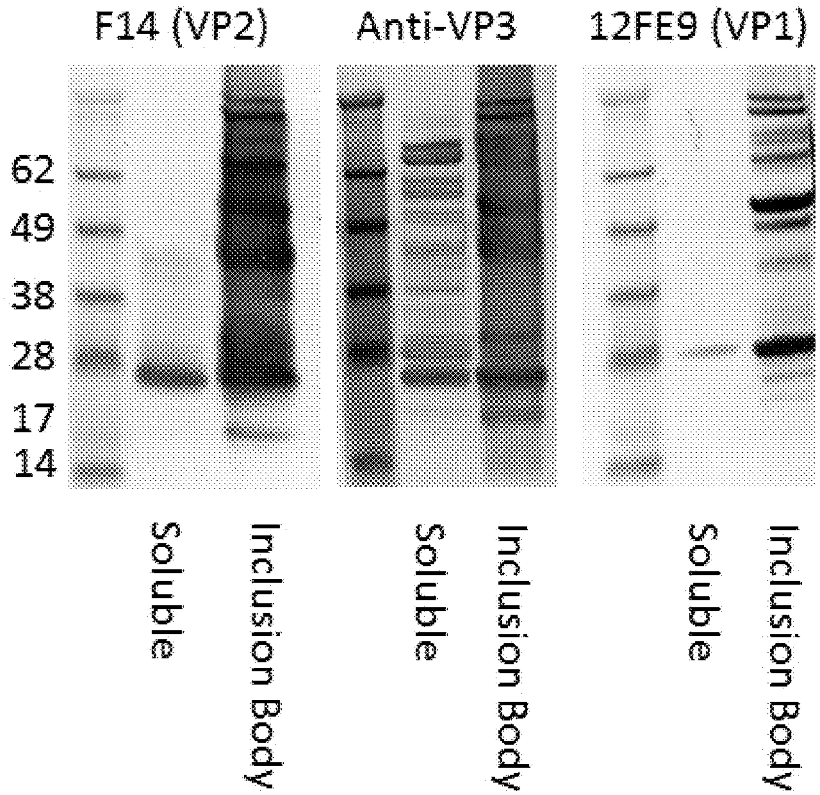
FIG. 5. Western blots of soluble and inclusion body fractions of bacterial cells expressing the pSNAP OM construct probed with anti-VP2 (monoclonal F14) antibody, anti-VP3 antibody, and anti-VP1 antibody 12FE9.
Figure 6A:
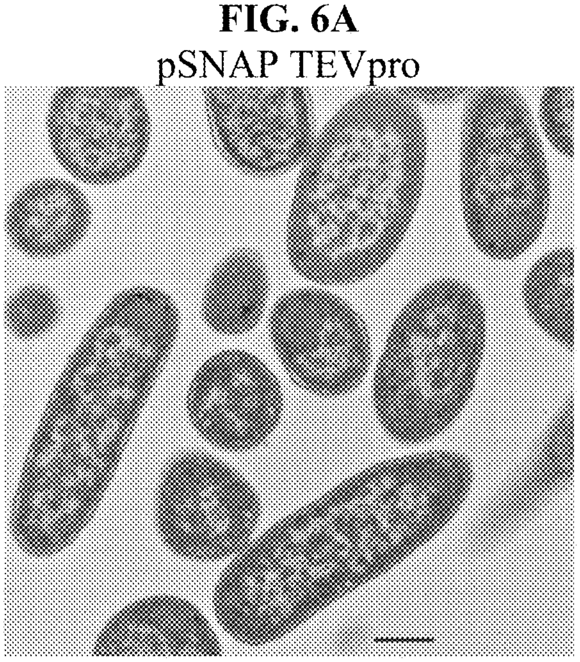
FIGS. 6A, 6B, 6C and 6D. These figures show electron micrographs comparing host cells expressing pSNAP TEVpro (FIG. 6A and FIG. 6C) and pSNAP OM (FIG. 6B and FIG. 6D). The scale bars represent 500 nm in FIG. 6A and FIG. 6B, and 100 nm in FIG. 6C and FIG. 6D. All images were taken on a Hitachi 7600 transmission electron microscope at 80 kV.
Figure 6B:
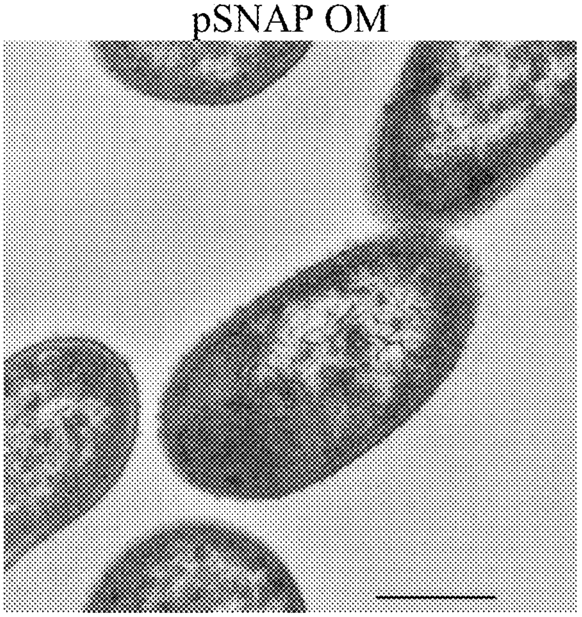
Figure 6C:
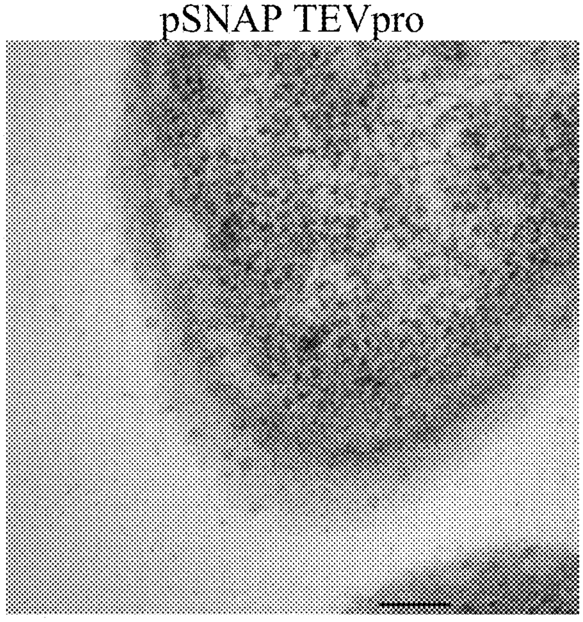
Figure 6D:
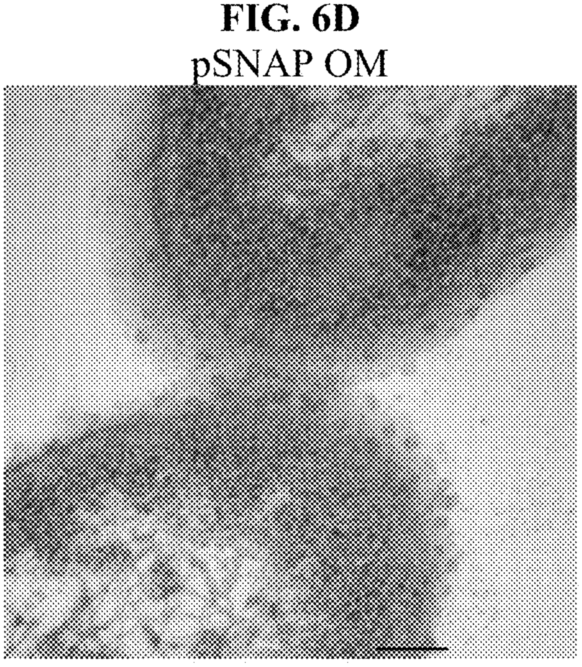

Bacterial Expression of DNA constructs encoding an engineered FMDV P1 protein and TEV Protease. A construct, pSNAP OM (SEQ ID NO: 122), which comprises DNA encoding the P1 precursor protein from FMDV serotype O and TEV protease. The pSNAP vector comprising this construct was transformed into prokaryotic (bacterial cells, *E. coli*). The western blot data in FIG. 5 shows that the TEV protease was active in bacterial cells and that individual FMDV viral proteins were produced. FIGS. 6A and 6B show that the recombinant host cells contained inclusion bodies which are shown in FIG. 5 to contain FMDV proteins. FIGS. 6C and 6D provide magnified views of inclusion bodies. FMDV VLPs were not observed.

These results in conjunction with data showing expression of FMDV and TEV in eukaryotic host cells suggest that other expression systems including other bacteria, yeasts, insect cells and plant cells will express functional TEV protease and permit processing of a protein expressed from a single open reading frame, such as an engineered FMDV P1 precursor polypeptide. Such expression systems are useful for production of vaccines, in biotherapies or in biomanufacturing where multiple proteins in stoichiometric amounts are desired. Moreover, expression of a single protein facilitates recombinant expression as only a single vector need be used.

The data herein show that FMDV P1 polypeptide can be altered in such a way to allow for processing by the TEV protease, a far more specific protease than the FMDV 3C protease. As shown, the TEV protease can be used to process a long single peptide into individual peptides which retain structural interactions similar to what occurs in nature using a single open reading frame in a plasmid system. The invention thus provides a safe and convenient way to produce larger amounts of FMDV proteins suitable for use in vaccines, diagnostic products, and other anti-FMDV biologics without the drawbacks of existing expression systems employing the FMDV 3C protease. The invention also provides a way that the TEV protease can be expressed within a single ORF along with a polypeptide for processing through utilization of the FMDV 2A translational interrupter sequence.

The foregoing disclosure provides examples of specific embodiments. As will be understood by those skilled in the art, the approaches, methods, techniques, materials, devices, and so forth disclosed herein may be embodied in additional embodiments as understood by those of skill in the art, it is the intention of this application to encompass and include such variations. Accordingly, this disclosure is illustrative and should not be taken as limiting the scope of the following claims.

What is claimed is:

1. A pharmaceutical composition, comprising:

at least one selected from the group consisting of VP0, VP1, VP2, VP3 and VP4, in the form of virus-like particles (VLPs); and a pharmaceutically acceptable buffer, wherein the VLPs are produced from proteolytic processing of at least one engineered Foot-and-mouth disease virus (FMDV) P1 precursor polypeptide that comprises at least one Tobacco etch virus (TEV) protease cleavage site, and wherein the at least one TEV protease cleavage site comprises $E_1$-$D_2$-$A_3$-$Y_4$-$T_5$-$Q_6$-$S_7$ (SEQ ID NO: 39), $E_1$-$F_2$-$L_3$-$Y_4$-$K_5$-$Q_6$-$G_7$ (SEQ ID NO: 40), $E_1$-$D_2$-$L_3$-$Y_4$-$F_5$-$Q_6$-$S_7$ (SEQ ID NO: 41), $E_1$-$K_2$-$L_3$-$Y_4$-$K_5$-$Q_6$-$G_7$ (SEQ ID NO: 42), $E_1$-$L_2$-$L_3$-$Y_4$-$K_5$-$Q_6$-$G_7$ (SEQ ID NO: 43) or $E_1$-$A_2$-$L_3$-$Y_4$-$K_5$-$Q_6$-$S_7$ (SEQ ID NO: 44) in at least one junction between VP4 and VP2, VP2 and VP3, VP3 and VP1, or VP1 and 2A components of the engineered FMDV P1 precursor polypeptide.

2. The pharmaceutical composition of claim 1, comprising VP0, VP1 and VP3 in the form of VLPs, or VP4, VP2, VP3 and VP1 in the form of VLPs.

3. The pharmaceutical composition of claim 1, wherein one or more of the VLPs comprise empty capsids not containing RNA.

4. The pharmaceutical composition of claim 1, comprising a pharmaceutically acceptable adjuvant.

5. The pharmaceutical composition of claim 1, further comprising at least one other active immunogen, drug or antiviral agent.

6. The pharmaceutical composition of claim 1, formulated for parenteral, intramuscular, intranasal, intravenous, intrapulmonary, intratracheal, oral, mucous membrane or alimentary canal administration.

7. The pharmaceutical composition of claim 1, wherein the composition is a vaccine.

8. The pharmaceutical composition of claim 1, wherein said proteolytic processing comprises:

culturing a host cell comprising a polynucleotide that encodes the at least one engineered FMDV P1 precursor polypeptide that comprises at least one Tobacco etch virus (TEV) protease cleavage site, and a polynucleotide encoding a TEV protease; and recovering cleavage products of the at least one engineered FMDV P1 precursor polypeptide produced by cleavage of the at least one TEV protease cleavage site.

9. A method for preventing or treating Foot-and-mouth disease virus (FMDV) infection in a subject, comprising administering to the subject an effective amount of a pharmaceutical composition comprising:

at least one selected from the group consisting of VP0, VP1, VP2, VP3 and VP4, in the form of virus-like particles (VLPs); and a pharmaceutically acceptable buffer, wherein the VLPs are produced from proteolytic processing of at least one engineered Foot-and-mouth disease virus (FMDV) P1 precursor polypeptide that comprises at least one Tobacco etch virus (TEV) protease cleavage site, and wherein the at least one TEV protease cleavage site comprises $E_1$-$D_2$-$A_3$-$Y_4$-$T_5$-$Q_6$-$S_7$ (SEQ ID NO: 39), $E_1$-$F_2$-$L_3$-$Y_4$-$K_5$-$Q_6$-$G_7$ (SEQ ID NO: 40), $E_1$-$D_2$-$L_3$-$Y_4$-$F_5$-$Q_6$-$S_7$ (SEQ ID NO: 41), $E_1$-$K_2$-$L_3$-$Y_4$-$K_5$-$Q_6$-$G_7$ (SEQ ID NO: 42), $E_1$-$L_2$-$L_3$-$Y_4$-$K_5$-$Q_6$-$G_7$ (SEQ ID NO: 43) or $E_1$-$A_2$-$L_3$-$Y_4$-$K_5$-$Q_6$-$S_7$ (SEQ ID NO: 44) in at least one junction between VP4 and VP2, VP2 and VP3, VP3 and VP1, or VP1 and 2A components of the engineered FMDV P1 precursor polypeptide.

10. The method of claim 9, wherein the subject is uninfected with FMDV.

11. The method of claim 9, wherein the subject is infected with FMDV.

12. The method of claim 9, wherein the subject is at risk of having foot-and-mouth disease (FMD).

13. The method of claim 9, wherein the subject has FMD.

14. The method of claim 9, wherein the subject is a bovine, caprine, ovine or swine.

15. The method of claim 9, wherein the pharmaceutical composition is administered parenterally, intramuscularly, intranasally, intravenously, intrapulmonarily, intratracheally, orally, on to a mucous membrane or into an alimentary canal.

16. A method for preventing or treating Foot-and-mouth disease virus (FMDV) infection in a subject, comprising administering to the subject an effective amount of a host cell that expresses:

an engineered FMDV P1 precursor polypeptide that comprises at least one Tobacco etch virus (TEV) protease cleavage site, wherein the at least one TEV protease cleavage site comprises $E_1$-$D_2$-$A_3$-$Y_4$-$T_5$-$Q_6$-$S_7$ (SEQ ID NO: 39), $E_1$-$F_2$-$L_3$-$Y_4$-$K_5$-$Q_6$-$G_7$ (SEQ ID NO: 40), $E_1$-$D_2$-$L_3$-$Y_4$-$F_5$-$Q_6$-$S_7$ (SEQ ID NO: 41), $E_1$-$K_2$-$L_3$-$Y_4$-$K_5$-$Q_6$-$G_7$ (SEQ ID NO: 42), $E_1$-$L_2$-$L_3$-$Y_4$-$K_5$-$Q_6$-$G_7$ (SEQ ID NO: 43) or $E_1$-$A_2$-$L_3$-$Y_4$-$K_5$-$Q_6$-$S_7$ (SEQ ID NO: 44) in at least one junction between VP4 and VP2, VP2 and VP3, VP3 and VP1, or VP1 and 2A components of the engineered FMDV P1 precursor polypeptide; and a TEV protease.

17. The method of claim 16, wherein the at least one TEV protease cleavage site in the engineered FMDV P1 precursor polypeptide is positioned at junction(s) that when cleaved by a TEV protease produce VP0, VP3, and VP1, or produce VP2, VP4, VP3 and VP1.

18. The method of claim 16, wherein the host cell is autologous.

19. The method of claim 16, wherein the host cell expresses a FMDV 3C protease.

20. The method of claim 19, wherein the FMDV 3C protease contains at least one of a V28K, L127P, V141T, C142T and C163A substitution.

* * * * *